US012098212B2

(12) United States Patent
Shang

(10) Patent No.: US 12,098,212 B2
(45) Date of Patent: Sep. 24, 2024

(54) METHODS AND COMPOSITIONS FOR PROMOTING AND POTENTIATING T-CELL MEDIATED IMMUNE RESPONSES THROUGH ADCC TARGETING OF CD39 EXPRESSING CELLS

(71) Applicant: Purinomia Biotech, Inc., Woburn, MA (US)

(72) Inventor: Yan Wu Shang, North Reading, MA (US)

(73) Assignee: Purinomia Biotech, Inc., Woburn, MA (US)

( * ) Notice: Subject to any disclaimer, the term of this patent is extended or adjusted under 35 U.S.C. 154(b) by 283 days.

(21) Appl. No.: 16/988,802

(22) Filed: Aug. 10, 2020

(65) Prior Publication Data

US 2021/0047425 A1 Feb. 18, 2021

Related U.S. Application Data

(60) Provisional application No. 62/885,509, filed on Aug. 12, 2019.

(51) Int. Cl.
*C07K 16/28* (2006.01)
*A61P 35/00* (2006.01)

(52) U.S. Cl.
CPC .......... *C07K 16/2896* (2013.01); *A61P 35/00* (2018.01); *C07K 16/2818* (2013.01); *C07K 16/2827* (2013.01)

(58) Field of Classification Search
CPC ............ C07K 16/2896; C07K 16/2818; C07K 16/2827; C07K 2317/41; C07K 2317/734;
(Continued)

(56) References Cited

U.S. PATENT DOCUMENTS

2021/0047425 A1* 2/2021 Shang .................. C07K 16/283

FOREIGN PATENT DOCUMENTS

WO WO-2017/089334 A1 6/2017
WO WO-2017/157948 A1 9/2017
(Continued)

OTHER PUBLICATIONS

Al-Lazikani, B. et al, Standard conformations for the canonical structures of immunoglobulins, 1997, Journal of Molecular Biology, vol. 273, 927-948. (Year: 1997).*
(Continued)

*Primary Examiner* — Joanne Hama
*Assistant Examiner* — Pratik Thapa
(74) *Attorney, Agent, or Firm* — Foley Hoag LLP; Philip S. Choi; David E. Shore

(57) ABSTRACT

In combination with conventional therapies (e.g. targeted therapy, chemotherapy, and angiogenesis inhibitors, etc.), immunotherapies targeting checkpoint molecules have shown promise in the treatment of solid or liquid tumors. However, the role of non-tumor cells in the intratumoral microenvironment has indicated that ablation of these cells may be a key to mounting an effective immune response against the tumor which includes tumor infiltration of cytotoxic T-cells and other anti-tumor cells of the immune system. Rather than focusing on trying to inhibit the ectonucleotidase activity of CD39 as an enzyme that generates adenosine, the present invention instead utilizes CD39 expression to bring about intratumoral cell ablation by CD39-depedent ADCC.

30 Claims, 35 Drawing Sheets

Specification includes a Sequence Listing.

(58) Field of Classification Search
CPC .............. C07K 2317/76; C07K 16/283; C07K 2317/732; C07K 2317/31; A61P 35/00; A61P 35/02; A61K 39/3955; A61K 45/06; A61K 2039/505
See application file for complete search history.

(56) References Cited

FOREIGN PATENT DOCUMENTS

| | | |
|---|---|---|
| WO | WO-2018/167267 A1 | 9/2018 |
| WO | WO-2019/027935 A1 | 2/2019 |
| WO | WO-2019/241707 A1 | 12/2019 |
| WO | WO-2021/030251 A1 | 2/2021 |

OTHER PUBLICATIONS

Junker, F. et al, Fc Gamma Receptors and Their Role in Antigen Uptake, Presentation, and T Cell Activation, 2020, Frontiers in Immunology, vol. 11, 1393. (Year: 2020).*
Hausler et al., "Anti-CD39 and anti-CD73 antibodies A1 and 7G2 improve targeted therapy in ovarian cancer by blocking adenosine-dependent immune evasion," Am J Transl Res, 6(2):129-139 (2014).
Invitation to Pay Additional Fees for International Application No. PCT/US2020/045589 dated Nov. 26, 2020.
International Preliminary Report on Patentability for International Application No. PCT/US2020/045589 mailed Feb. 24, 2022.
International Search Report and Written Opinion for International Application No. PCT/US2020/045589 dated Feb. 2, 2021.

* cited by examiner

Figure 33

| Clone number | Main epitope candidates |
|---|---|
| Ig39-21 | IYLTDCMERAR |
| 8C11 | LRMESEELADR |
| 8D8 | RVKGPGISKFV and/or DCMERAREVIPR |
| 9C10 | LTDCMERAREVIPR and/or SLSNYPFDFQGAR |
| 65H5 | CRVKGPGISKF and/or GAYGWITINYLLGKFSQK and/or ILRDPCFHPGYKK |

Representative reference CD39 extracellular domain sequence (aa38-478)

PROVIDED PROTEIN SEQUENCE

CD39 sequence.

UniprotKB-P49961(ENTPD1-HUMAN)

```
                              40         50
                         LAVGLTQN    KALPENVKYG
         60         70         80         90        100
IVLDAGSSHT SLYIYKWPAE KENDTGVVHQ VEECRVKGPG ISKFVQKVNE
        110        120        130        140        150
IGIYLTDCME RAREVIPRSQ HQETPVYLGA TAGMRLLRME SEELADRVLD
        160        170        180        190        200
VVERSLSNYP FDFQGARIIT GQEEGAYGWI TINYLLGKFS QKTRWFSIVP
        210        220        230        240        250
YETNNQETFG ALDLGGASTQ VTFVPQNQTI ESPDNALQFR LYGKDYNVYT
        260        270        280        290        300
HSFLCYGKDQ ALWQKLAKDI QVASNEILRD PCFHPGYKKV VNVSDLYKTP
        310        320        330        340        350
CTKRFEMTLP FQQFEIQGIG NYQQCHQSIL ELFNTSYCPY SQCAFNGIFL
        360        370        380        390        400
PPLQGDFGAF SAFYFVMKFL NLTSEKVSQE KVTEMMKKFC AQPWEEIKTS
        410        420        430        440        450
YAGVKEKYLS EYCFSGTYIL SLLLQGYHFT ADSWEHIHFI GKIQGSDAGW
        460        470        480
TLGYMLNLTN MIPAEQPLST PLSHSTYV
```

*For the purpose of this report, the sequence listed here is renumbered from 1.*

Rendering of homology model of a dimer of human CD39 based on 3ZX3.pdb.

SEQUENCE LISTING

```
<160> NUMBER OF SEQ ID NOS: 66

<210> SEQ ID NO 1
<211> LENGTH: 357
<212> TYPE: DNA
<213> ORGANISM: Artificial Sequence
<220> FEATURE:
<223> OTHER INFORMATION: derived from human variable chain library
<220> FEATURE:
<221> NAME/KEY: CDS
<222> LOCATION: (1)..(357)

<400> SEQUENCE: 1 gag gtg caa ctg gtg gag tct ggg gga ggt gtg gta agg cct ggg ggg      48
Glu Val Gln Leu Val Glu Ser Gly Gly Gly Val Val Arg Pro Gly Gly
1               5                   10                  15 tcc ctg aga ctc tcc tgt gca gcc tct gga ttc acc ttc agt agc tat      96
Ser Leu Arg Leu Ser Cys Ala Ala Ser Gly Phe Thr Phe Ser Ser Tyr
            20                  25                  30 gct atg cac tgg gtc cgc cag gct cca ggc aag ggg ctg gag tgg gtg     144
Ala Met His Trp Val Arg Gln Ala Pro Gly Lys Gly Leu Glu Trp Val
        35                  40                  45 gca gtt ata tca tat gat gta agc aat aaa tac tac gca gac tcc gtg     192
Ala Val Ile Ser Tyr Asp Val Ser Asn Lys Tyr Tyr Ala Asp Ser Val
    50                  55                  60
```

```
aag ggc cga ttc acc atc tcc aga gac aat tcc aag aac acg ctg tat      240
Lys Gly Arg Phe Thr Ile Ser Arg Asp Asn Ser Lys Asn Thr Leu Tyr
 65                  70                  75                  80 ctg caa atg aac agc ctg aga gct gag gac acg gct gtg tat tac tgt      288
Leu Gln Met Asn Ser Leu Arg Ala Glu Asp Thr Ala Val Tyr Tyr Cys
                 85                  90                  95 gcg aga tct tac tac tac tac tac ggt atg gac gtc tgg ggc caa ggg      336
Ala Arg Ser Tyr Tyr Tyr Tyr Tyr Gly Met Asp Val Trp Gly Gln Gly
            100                 105                 110 acc acg gtc acc gtc tcc tca                                          357
Thr Thr Val Thr Val Ser Ser
        115

<210> SEQ ID NO 2
<211> LENGTH: 119
<212> TYPE: PRT
<213> ORGANISM: Artificial Sequence
<220> FEATURE:
<223> OTHER INFORMATION: Synthetic Construct

<400> SEQUENCE: 2

Glu Val Gln Leu Val Glu Ser Gly Gly Gly Val Val Arg Pro Gly Gly
 1               5                  10                  15

Ser Leu Arg Leu Ser Cys Ala Ala Ser Gly Phe Thr Phe Ser Ser Tyr
                 20                  25                  30

Ala Met His Trp Val Arg Gln Ala Pro Gly Lys Gly Leu Glu Trp Val
            35                  40                  45

Ala Val Ile Ser Tyr Asp Val Ser Asn Lys Tyr Tyr Ala Asp Ser Val
        50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Arg Ser Tyr Tyr Tyr Tyr Tyr Gly Met Asp Val Trp Gly Gln Gly
            100                 105                 110

Thr Thr Val Thr Val Ser Ser
        115

<210> SEQ ID NO 3
<211> LENGTH: 321
<212> TYPE: DNA
<213> ORGANISM: Artificial Sequence
<220> FEATURE:
<223> OTHER INFORMATION: Derived from human variable chain library
<220> FEATURE:
<221> NAME/KEY: CDS
<222> LOCATION: (1)..(321)

<400> SEQUENCE: 3 gat gtt gtg atg acc cag tct cca tcc tcc ctg tct gca tct gta gga       48
Asp Val Val Met Thr Gln Ser Pro Ser Ser Leu Ser Ala Ser Val Gly
 1               5                  10                  15 gac aga gtc acc atc act tgc cgg gca agt cag agc att agc agg tac       96
Asp Arg Val Thr Ile Thr Cys Arg Ala Ser Gln Ser Ile Ser Arg Tyr
                 20                  25                  30 tta gcc tgg tac caa cag aaa cct ggc cag gct ccc agg ctc ctc atc      144
Leu Ala Trp Tyr Gln Gln Lys Pro Gly Gln Ala Pro Arg Leu Leu Ile
            35                  40                  45 tat gat gca tcc aac agg gcc act ggc atc cca gtc agg ttc agt ggc      192
Tyr Asp Ala Ser Asn Arg Ala Thr Gly Ile Pro Val Arg Phe Ser Gly
        50                  55                  60
```

```
agt ggg tct ggg aca gac ttc act ctc acc atc agc aga ctg gag cca    240
Ser Gly Ser Gly Thr Asp Phe Thr Leu Thr Ile Ser Arg Leu Glu Pro
 65                  70                  75                  80 gaa gat ttt gca gtg tat tac tgt cag cag ttt ggt agg tca cct cgg    288
Glu Asp Phe Ala Val Tyr Tyr Cys Gln Gln Phe Gly Arg Ser Pro Arg
                 85                  90                  95 acg ttc ggc caa ggg aca cga ctg gag att aaa                        321
Thr Phe Gly Gln Gly Thr Arg Leu Glu Ile Lys
            100                 105

<210> SEQ ID NO 4
<211> LENGTH: 107
<212> TYPE: PRT
<213> ORGANISM: Artificial Sequence
<220> FEATURE:
<223> OTHER INFORMATION: Synthetic Construct

<400> SEQUENCE: 4

Asp Val Val Met Thr Gln Ser Pro Ser Ser Leu Ser Ala Ser Val Gly
 1               5                  10                  15

Asp Arg Val Thr Ile Thr Cys Arg Ala Ser Gln Ser Ile Ser Arg Tyr
                20                  25                  30

Leu Ala Trp Tyr Gln Gln Lys Pro Gly Gln Ala Pro Arg Leu Leu Ile
            35                  40                  45

Tyr Asp Ala Ser Asn Arg Ala Thr Gly Ile Pro Val Arg Phe Ser Gly
    50                  55                  60

Ser Gly Ser Gly Thr Asp Phe Thr Leu Thr Ile Ser Arg Leu Glu Pro
 65                  70                  75                  80

Glu Asp Phe Ala Val Tyr Tyr Cys Gln Gln Phe Gly Arg Ser Pro Arg
                 85                  90                  95

Thr Phe Gly Gln Gly Thr Arg Leu Glu Ile Lys
            100                 105

<210> SEQ ID NO 5
<211> LENGTH: 357
<212> TYPE: DNA
<213> ORGANISM: Artificial Sequence
<220> FEATURE:
<223> OTHER INFORMATION: derived from rabbit monoclonal
<220> FEATURE:
<221> NAME/KEY: CDS
<222> LOCATION: (1)..(357)

<400> SEQUENCE: 5 cag tca gtg aag gag gcc ggg ggt cgc ctg gta acg cct gga gga tcc     48
Gln Ser Val Lys Glu Ala Gly Gly Arg Leu Val Thr Pro Gly Gly Ser
 1               5                  10                  15 ctg aca ctc acc tgc aca gtc tct gga ttc tcc ctc agt gcg tat gga     96
Leu Thr Leu Thr Cys Thr Val Ser Gly Phe Ser Leu Ser Ala Tyr Gly
                20                  25                  30 ata agt tgg gtc cgc cag gct cca ggg aag gga ctg gaa tgg atc gga    144
Ile Ser Trp Val Arg Gln Ala Pro Gly Lys Gly Leu Glu Trp Ile Gly
            35                  40                  45 atc att tat agt agt ggt agg act tac tac gcg aac tgg gcg aaa ggc    192
Ile Ile Tyr Ser Ser Gly Arg Thr Tyr Tyr Ala Asn Trp Ala Lys Gly
    50                  55                  60 cga ttc acc atc tcc aaa acc tcg tcg acc acg gtg gat ctg aaa atg    240
Arg Phe Thr Ile Ser Lys Thr Ser Ser Thr Thr Val Asp Leu Lys Met
 65                  70                  75                  80 acc agt ctg aca acc gag gac acg gcc gcc tat ttc tgt gcc aga tca    288
Thr Ser Leu Thr Thr Glu Asp Thr Ala Ala Tyr Phe Cys Ala Arg Ser
                 85                  90                  95
```

-continued

```
cgg gct ggt att agt agt ggt gat ggt ttt gat tcc tgg ggc cca ggc      336
Arg Ala Gly Ile Ser Ser Gly Asp Gly Phe Asp Ser Trp Gly Pro Gly
        100                 105                 110 acc ctg gtc acc gtc tcc tca                                          357
Thr Leu Val Thr Val Ser Ser
        115
```

<210> SEQ ID NO 6
<211> LENGTH: 119
<212> TYPE: PRT
<213> ORGANISM: Artificial Sequence
<220> FEATURE:
<223> OTHER INFORMATION: Synthetic Construct

<400> SEQUENCE: 6

```
Gln Ser Val Lys Glu Gly Gly Arg Leu Val Thr Pro Gly Gly Ser
1               5                   10                  15

Leu Thr Leu Thr Cys Thr Val Ser Gly Phe Ser Leu Ser Ala Tyr Gly
            20                  25                  30

Ile Ser Trp Val Arg Gln Ala Pro Gly Lys Gly Leu Glu Trp Ile Gly
        35                  40                  45

Ile Ile Tyr Ser Ser Gly Arg Thr Tyr Tyr Ala Asn Trp Ala Lys Gly
    50                  55                  60

Arg Phe Thr Ile Ser Lys Thr Ser Ser Thr Thr Val Asp Leu Lys Met
65                  70                  75                  80

Thr Ser Leu Thr Thr Glu Asp Thr Ala Ala Tyr Phe Cys Ala Arg Ser
                85                  90                  95

Arg Ala Gly Ile Ser Ser Gly Asp Gly Phe Asp Ser Trp Gly Pro Gly
            100                 105                 110

Thr Leu Val Thr Val Ser Ser
        115
```

<210> SEQ ID NO 7
<211> LENGTH: 339
<212> TYPE: DNA
<213> ORGANISM: Artificial Sequence
<220> FEATURE:
<223> OTHER INFORMATION: derived from rabbit monoclonal
<220> FEATURE:
<221> NAME/KEY: CDS
<222> LOCATION: (1)..(339)

<400> SEQUENCE: 7

```
gcc aga tgt gcc ctt gtg atg acc cag act cca tcc tcc gtg tct gca      48
Ala Arg Cys Ala Leu Val Met Thr Gln Thr Pro Ser Ser Val Ser Ala
1               5                   10                  15 gct gtg gga ggc aca gtc acc atc aat tgc cag gcc agt cag aac att      96
Ala Val Gly Gly Thr Val Thr Ile Asn Cys Gln Ala Ser Gln Asn Ile
            20                  25                  30 tac agc aat tta gcc tgg tat cag cag aaa cca ggg cag cgt ccc cag     144
Tyr Ser Asn Leu Ala Trp Tyr Gln Gln Lys Pro Gly Gln Arg Pro Gln
        35                  40                  45 ctc ctg atc tac agg gca tcc act ctg gca tct ggg gtc cca tcg cgg     192
Leu Leu Ile Tyr Arg Ala Ser Thr Leu Ala Ser Gly Val Pro Ser Arg
    50                  55                  60 ttc aaa ggc agt gca tct ggg aca gaa tac act ctc acc atc agc ggt     240
Phe Lys Gly Ser Ala Ser Gly Thr Glu Tyr Thr Leu Thr Ile Ser Gly
65                  70                  75                  80 gtg cag tgt gac gat gct gcc act tac tat tgt caa cag ggt ttt gat     288
Val Gln Cys Asp Asp Ala Ala Thr Tyr Tyr Cys Gln Gln Gly Phe Asp
                85                  90                  95
```

```
agt agt aac att gat aat act ttc ggc gga ggg acc gag gtg gtg gtc     336
Ser Ser Asn Ile Asp Asn Thr Phe Gly Gly Gly Thr Glu Val Val Val
            100                 105                 110 aca                                                                 339
Thr

<210> SEQ ID NO 8
<211> LENGTH: 113
<212> TYPE: PRT
<213> ORGANISM: Artificial Sequence
<220> FEATURE:
<223> OTHER INFORMATION: Synthetic Construct

<400> SEQUENCE: 8

Ala Arg Cys Ala Leu Val Met Thr Gln Thr Pro Ser Ser Val Ser Ala
1               5                   10                  15

Ala Val Gly Gly Thr Val Thr Ile Asn Cys Gln Ala Ser Gln Asn Ile
            20                  25                  30

Tyr Ser Asn Leu Ala Trp Tyr Gln Gln Lys Pro Gly Gln Arg Pro Gln
        35                  40                  45

Leu Leu Ile Tyr Arg Ala Ser Thr Leu Ala Ser Gly Val Pro Ser Arg
50                  55                  60

Phe Lys Gly Ser Ala Ser Gly Thr Glu Tyr Thr Leu Thr Ile Ser Gly
65                  70                  75                  80

Val Gln Cys Asp Asp Ala Ala Thr Tyr Tyr Cys Gln Gln Gly Phe Asp
                85                  90                  95

Ser Ser Asn Ile Asp Asn Thr Phe Gly Gly Gly Thr Glu Val Val Val
            100                 105                 110

Thr

<210> SEQ ID NO 9
<211> LENGTH: 345
<212> TYPE: DNA
<213> ORGANISM: Artificial Sequence
<220> FEATURE:
<223> OTHER INFORMATION: derived from rabbit monoclonal
<220> FEATURE:
<221> NAME/KEY: CDS
<222> LOCATION: (1)..(345)

<400> SEQUENCE: 9 cag tcg gtg gag gag tcc ggg ggt cgc ctg gtc acg cct ggg aca cac     48
Gln Ser Val Glu Glu Ser Gly Gly Arg Leu Val Thr Pro Gly Thr His
1               5                   10                  15 ctg aca ctc acc tgc aca gtc tct gga ttc tcc ctc agt aag agt ata     96
Leu Thr Leu Thr Cys Thr Val Ser Gly Phe Ser Leu Ser Lys Ser Ile
            20                  25                  30 ata agt tgg gtc cgc cag gct cca ggg aag ggg ctg gaa tac atc gga    144
Ile Ser Trp Val Arg Gln Ala Pro Gly Lys Gly Leu Glu Tyr Ile Gly
        35                  40                  45 atc att ggt agt agt ggt agc aca tac tac gcg aac tgg gcg aaa ggc    192
Ile Ile Gly Ser Ser Gly Ser Thr Tyr Tyr Ala Asn Trp Ala Lys Gly
    50                  55                  60 cga ttc acc atc tcc aaa acc tcg tcg acc acg gtg gat ctg aga atg    240
Arg Phe Thr Ile Ser Lys Thr Ser Ser Thr Thr Val Asp Leu Arg Met
65                  70                  75                  80 acc agt ctg aca ccc gag gac acg gcc act tat ttc tgt gcc aga gga    288
Thr Ser Leu Thr Pro Glu Asp Thr Ala Thr Tyr Phe Cys Ala Arg Gly
                85                  90                  95 ctt ctt tat tct ggt aat aaa tcg tgg ggc ccg ggc acc ctg gtc acc    336
```

```
Leu Leu Tyr Ser Gly Asn Lys Ser Trp Gly Pro Gly Thr Leu Val Thr
            100                 105                 110 gtc tcc tca                                                           345
Val Ser Ser
        115

<210> SEQ ID NO 10
<211> LENGTH: 115
<212> TYPE: PRT
<213> ORGANISM: Artificial Sequence
<220> FEATURE:
<223> OTHER INFORMATION: Synthetic Construct

<400> SEQUENCE: 10

Gln Ser Val Glu Glu Ser Gly Gly Arg Leu Val Thr Pro Gly Thr His
1               5                   10                  15

Leu Thr Leu Thr Cys Thr Val Ser Gly Phe Ser Leu Ser Lys Ser Ile
            20                  25                  30

Ile Ser Trp Val Arg Gln Ala Pro Gly Lys Gly Leu Glu Tyr Ile Gly
        35                  40                  45

Ile Ile Gly Ser Ser Gly Ser Thr Tyr Tyr Ala Asn Trp Ala Lys Gly
    50                  55                  60

Arg Phe Thr Ile Ser Lys Thr Ser Ser Thr Thr Val Asp Leu Arg Met
65                  70                  75                  80

Thr Ser Leu Thr Pro Glu Asp Thr Ala Thr Tyr Phe Cys Ala Arg Gly
                85                  90                  95

Leu Leu Tyr Ser Gly Asn Lys Ser Trp Gly Pro Gly Thr Leu Val Thr
            100                 105                 110

Val Ser Ser
        115

<210> SEQ ID NO 11
<211> LENGTH: 339
<212> TYPE: DNA
<213> ORGANISM: Artificial Sequence
<220> FEATURE:
<223> OTHER INFORMATION: derived from rabbit monoclonal
<220> FEATURE:
<221> NAME/KEY: CDS
<222> LOCATION: (1)..(339)

<400> SEQUENCE: 11 gcc aca ttt gcc att gat atg acc cag act cca tcc tcc gtg tct gca    48
Ala Thr Phe Ala Ile Asp Met Thr Gln Thr Pro Ser Ser Val Ser Ala
1               5                   10                  15 gct gtg gga ggc aca gtc acc atc aac tgc cag tcc agt cag agt gtt    96
Ala Val Gly Gly Thr Val Thr Ile Asn Cys Gln Ser Ser Gln Ser Val
            20                  25                  30 tta ctg aac aac caa tta tcc tgg ttt cag cag aaa cca ggg cag cct   144
Leu Leu Asn Asn Gln Leu Ser Trp Phe Gln Gln Lys Pro Gly Gln Pro
        35                  40                  45 ccc aag ctc ctg atc tat gat gca tcc act ctg gaa tct ggg gtc cca   192
Pro Lys Leu Leu Ile Tyr Asp Ala Ser Thr Leu Glu Ser Gly Val Pro
    50                  55                  60 tct cgg ttc aca ggc agt gga tct ggg aca cag ttc act ctc acc atc   240
Ser Arg Phe Thr Gly Ser Gly Ser Gly Thr Gln Phe Thr Leu Thr Ile
65                  70                  75                  80 agc gac ctg gag tgt gac gat gct gcc act tac tat tgt tta ggc ggt   288
Ser Asp Leu Glu Cys Asp Asp Ala Ala Thr Tyr Tyr Cys Leu Gly Gly
                85                  90                  95 tat agt ggg aac ctt tat gct ttc ggc gga ggg acc gag gtg cta gtc   336
```

```
Tyr Ser Gly Asn Leu Tyr Ala Phe Gly Gly Gly Thr Glu Val Leu Val
            100                 105                 110 aaa                                                                    339
Lys

<210> SEQ ID NO 12
<211> LENGTH: 113
<212> TYPE: PRT
<213> ORGANISM: Artificial Sequence
<220> FEATURE:
<223> OTHER INFORMATION: Synthetic Construct

<400> SEQUENCE: 12

Ala Thr Phe Ala Ile Asp Met Thr Gln Thr Pro Ser Ser Val Ser Ala
1               5                   10                  15

Ala Val Gly Gly Thr Val Thr Ile Asn Cys Gln Ser Ser Gln Ser Val
            20                  25                  30

Leu Leu Asn Asn Gln Leu Ser Trp Phe Gln Gln Lys Pro Gly Gln Pro
        35                  40                  45

Pro Lys Leu Leu Ile Tyr Asp Ala Ser Thr Leu Glu Ser Gly Val Pro
    50                  55                  60

Ser Arg Phe Thr Gly Ser Gly Ser Gly Thr Gln Phe Thr Leu Thr Ile
65                  70                  75                  80

Ser Asp Leu Glu Cys Asp Asp Ala Ala Thr Tyr Tyr Cys Leu Gly Gly
                85                  90                  95

Tyr Ser Gly Asn Leu Tyr Ala Phe Gly Gly Gly Thr Glu Val Leu Val
            100                 105                 110

Lys

<210> SEQ ID NO 13
<211> LENGTH: 351
<212> TYPE: DNA
<213> ORGANISM: Artificial Sequence
<220> FEATURE:
<223> OTHER INFORMATION: derived from rabbit monoclonal
<220> FEATURE:
<221> NAME/KEY: CDS
<222> LOCATION: (1)..(351)

<400> SEQUENCE: 13 cag tcg gtg gag gag tcc ggg ggt cgc ctg gtc acg cct ggg aca ccc      48
Gln Ser Val Glu Glu Ser Gly Gly Arg Leu Val Thr Pro Gly Thr Pro
1               5                   10                  15 ctg aca ctc acc tgc aca gtc tct gga ttc tcc ctc agt agc tat gca      96
Leu Thr Leu Thr Cys Thr Val Ser Gly Phe Ser Leu Ser Ser Tyr Ala
            20                  25                  30 ata agt tgg gtc cgc cag gct cca ggg aag ggg ctc gaa tat atc gcg     144
Ile Ser Trp Val Arg Gln Ala Pro Gly Lys Gly Leu Glu Tyr Ile Ala
        35                  40                  45 atc att aat agt tat ggt acc aca tac tac gcg agc tgg gcg aaa ggc     192
Ile Ile Asn Ser Tyr Gly Thr Thr Tyr Tyr Ala Ser Trp Ala Lys Gly
    50                  55                  60 cga gtc acc atc tcc aaa acc tcg agc acg gtg gat ctg aaa atc tcc     240
Arg Val Thr Ile Ser Lys Thr Ser Ser Thr Val Asp Leu Lys Ile Ser
65                  70                  75                  80 agt ccg aca acc gag gac acg gcc acc tat ttc tgt gcc aga ggc gat     288
Ser Pro Thr Thr Glu Asp Thr Ala Thr Tyr Phe Cys Ala Arg Gly Asp
                85                  90                  95 agt tat ggt agt ggt gtt ggt ttg ggc ttg tgg ggc cca ggc acc ctg     336
Ser Tyr Gly Ser Gly Val Gly Leu Gly Leu Trp Gly Pro Gly Thr Leu
            100                 105                 110
```

```
gtc acc gtc tcc tca                                                   351
Val Thr Val Ser Ser
        115

<210> SEQ ID NO 14
<211> LENGTH: 117
<212> TYPE: PRT
<213> ORGANISM: Artificial Sequence
<220> FEATURE:
<223> OTHER INFORMATION: Synthetic Construct

<400> SEQUENCE: 14

Gln Ser Val Glu Glu Ser Gly Gly Arg Leu Val Thr Pro Gly Thr Pro
1               5                   10                  15

Leu Thr Leu Thr Cys Thr Val Ser Gly Phe Ser Leu Ser Ser Tyr Ala
            20                  25                  30

Ile Ser Trp Val Arg Gln Ala Pro Gly Lys Gly Leu Glu Tyr Ile Ala
        35                  40                  45

Ile Ile Asn Ser Tyr Gly Thr Thr Tyr Tyr Ala Ser Trp Ala Lys Gly
    50                  55                  60

Arg Val Thr Ile Ser Lys Thr Ser Thr Val Asp Leu Lys Ile Ser
65                  70                  75                  80

Ser Pro Thr Thr Glu Asp Thr Ala Thr Tyr Phe Cys Ala Arg Gly Asp
                85                  90                  95

Ser Tyr Gly Ser Gly Val Gly Leu Gly Leu Trp Gly Pro Gly Thr Leu
            100                 105                 110

Val Thr Val Ser Ser
        115

<210> SEQ ID NO 15
<211> LENGTH: 339
<212> TYPE: DNA
<213> ORGANISM: Artificial Sequence
<220> FEATURE:
<223> OTHER INFORMATION: derived from rabbit monoclonal
<220> FEATURE:
<221> NAME/KEY: CDS
<222> LOCATION: (1)..(339)

<400> SEQUENCE: 15 gcc aga tgt gcc tat gat atg acc cag act cca gcc tct gtg gag gta      48
Ala Arg Cys Ala Tyr Asp Met Thr Gln Thr Pro Ala Ser Val Glu Val
1               5                   10                  15 gct gtg gga ggc aca gtc acc atc aag tgc cag gcc agt cag aac att      96
Ala Val Gly Gly Thr Val Thr Ile Lys Cys Gln Ala Ser Gln Asn Ile
            20                  25                  30 tac agc aat tta gcc tgg tat cag cag aaa cca ggg cag cgt ccc aag     144
Tyr Ser Asn Leu Ala Trp Tyr Gln Gln Lys Pro Gly Gln Arg Pro Lys
        35                  40                  45 ctc ctg atc tac agg gca tcc agt ctg gca tct ggg gtc ccg tcg cgg     192
Leu Leu Ile Tyr Arg Ala Ser Ser Leu Ala Ser Gly Val Pro Ser Arg
    50                  55                  60 ttc agt ggc agt gga tct ggg aca gag ttc act ctc acc atc agc ggt     240
Phe Ser Gly Ser Gly Ser Gly Thr Glu Phe Thr Leu Thr Ile Ser Gly
65                  70                  75                  80 gtg cag tgt gac gat gct gcc act tac tac tgt caa cag ggt ttt agt     288
Val Gln Cys Asp Asp Ala Ala Thr Tyr Tyr Cys Gln Gln Gly Phe Ser
                85                  90                  95 agt aat aat gtt gat aat act ttc ggc gga ggg acc gag gtg gtg gtc     336
Ser Asn Asn Val Asp Asn Thr Phe Gly Gly Gly Thr Glu Val Val Val
            100                 105                 110
```

```
aaa                                                                              339
Lys <210> SEQ ID NO 16
<211> LENGTH: 113
<212> TYPE: PRT
<213> ORGANISM: Artificial Sequence
<220> FEATURE:
<223> OTHER INFORMATION: Synthetic Construct

<400> SEQUENCE: 16

Ala Arg Cys Ala Tyr Asp Met Thr Gln Thr Pro Ala Ser Val Glu Val
1               5                   10                  15

Ala Val Gly Gly Thr Val Thr Ile Lys Cys Gln Ala Ser Gln Asn Ile
            20                  25                  30

Tyr Ser Asn Leu Ala Trp Tyr Gln Gln Lys Pro Gly Gln Arg Pro Lys
        35                  40                  45

Leu Leu Ile Tyr Arg Ala Ser Ser Leu Ala Ser Gly Val Pro Ser Arg
50                  55                  60

Phe Ser Gly Ser Gly Ser Gly Thr Glu Phe Thr Leu Thr Ile Ser Gly
65                  70                  75                  80

Val Gln Cys Asp Asp Ala Ala Thr Tyr Tyr Cys Gln Gln Gly Phe Ser
                85                  90                  95

Ser Asn Asn Val Asp Asn Thr Phe Gly Gly Gly Thr Glu Val Val Val
            100                 105                 110

Lys

<210> SEQ ID NO 17
<211> LENGTH: 357
<212> TYPE: DNA
<213> ORGANISM: Artificial Sequence
<220> FEATURE:
<223> OTHER INFORMATION: derived from rabbit monoclonal
<220> FEATURE:
<221> NAME/KEY: CDS
<222> LOCATION: (1)..(357)

<400> SEQUENCE: 17 cag tcg gtg gag gag tcc ggg ggt cgc ctg gtc acg cct ggg aca ccc     48
Gln Ser Val Glu Glu Ser Gly Gly Arg Leu Val Thr Pro Gly Thr Pro
1               5                   10                  15 ctg aca ctc acc tgc acc gtc tcc gga ttc tcc ctc agt agc tat gca     96
Leu Thr Leu Thr Cys Thr Val Ser Gly Phe Ser Leu Ser Ser Tyr Ala
            20                  25                  30 atg agc tgg gtc cgc cag gct cca ggg aag ggg ctg gaa tac atc gga    144
Met Ser Trp Val Arg Gln Ala Pro Gly Lys Gly Leu Glu Tyr Ile Gly
        35                  40                  45 atc att agt agt agt ggt agc aca tac tac gcg agc tgg gcg aaa ggc    192
Ile Ile Ser Ser Ser Gly Ser Thr Tyr Tyr Ala Ser Trp Ala Lys Gly
50                  55                  60 cga ttc acc atc tcc aaa acc tcg acc acg gtg gat ctg aaa atc tcc    240
Arg Phe Thr Ile Ser Lys Thr Ser Thr Thr Val Asp Leu Lys Ile Ser
65                  70                  75                  80 agt ccg aca acc gag gac acg gcc acc tat ttc tgt gcc aga gat cgt    288
Ser Pro Thr Thr Glu Asp Thr Ala Thr Tyr Phe Cys Ala Arg Asp Arg
                85                  90                  95 gtt att tat agt att ggt ccg tat tat ttt aat ttg tgg ggc cca ggc    336
Val Ile Tyr Ser Ile Gly Pro Tyr Tyr Phe Asn Leu Trp Gly Pro Gly
            100                 105                 110 acc ctg gtc acc gtc tcc tca                                        357
```

```
Thr Leu Val Thr Val Ser Ser
        115

<210> SEQ ID NO 18
<211> LENGTH: 119
<212> TYPE: PRT
<213> ORGANISM: Artificial Sequence
<220> FEATURE:
<223> OTHER INFORMATION: Synthetic Construct

<400> SEQUENCE: 18

Gln Ser Val Glu Glu Ser Gly Gly Arg Leu Val Thr Pro Gly Thr Pro
1               5                   10                  15

Leu Thr Leu Thr Cys Thr Val Ser Gly Phe Ser Leu Ser Ser Tyr Ala
                20                  25                  30

Met Ser Trp Val Arg Gln Ala Pro Gly Lys Gly Leu Glu Tyr Ile Gly
            35                  40                  45

Ile Ile Ser Ser Ser Gly Ser Thr Tyr Tyr Ala Ser Trp Ala Lys Gly
        50                  55                  60

Arg Phe Thr Ile Ser Lys Thr Ser Thr Thr Val Asp Leu Lys Ile Ser
65                  70                  75                  80

Ser Pro Thr Thr Glu Asp Thr Ala Thr Tyr Phe Cys Ala Arg Asp Arg
                85                  90                  95

Val Ile Tyr Ser Ile Gly Pro Tyr Tyr Phe Asn Leu Trp Gly Pro Gly
            100                 105                 110

Thr Leu Val Thr Val Ser Ser
        115

<210> SEQ ID NO 19
<211> LENGTH: 339
<212> TYPE: DNA
<213> ORGANISM: Artificial Sequence
<220> FEATURE:
<223> OTHER INFORMATION: derived from rabbit monoclonal
<220> FEATURE:
<221> NAME/KEY: CDS
<222> LOCATION: (1)..(339)

<400> SEQUENCE: 19 gcc aga tgt gcc tat gat atg acc cag act cca tcc tcc gtg tct gca      48
Ala Arg Cys Ala Tyr Asp Met Thr Gln Thr Pro Ser Ser Val Ser Ala
1               5                   10                  15 act gtg gga ggc aca gtc acc atc aat tgc cag gcc agt gag atc att      96
Thr Val Gly Gly Thr Val Thr Ile Asn Cys Gln Ala Ser Glu Ile Ile
                20                  25                  30 tat agc aat tta gcc tgg tat cag cag aaa cca ggg cag cct ccc aag     144
Tyr Ser Asn Leu Ala Trp Tyr Gln Gln Lys Pro Gly Gln Pro Pro Lys
            35                  40                  45 ctc ctg atc tat ggt gca tcc act ctg gca tct ggg gtc cca tcg cgg     192
Leu Leu Ile Tyr Gly Ala Ser Thr Leu Ala Ser Gly Val Pro Ser Arg
        50                  55                  60 ttc aaa ggc agt gga tct ggg aca gag tac act ctc acc atc agc gac     240
Phe Lys Gly Ser Gly Ser Gly Thr Glu Tyr Thr Leu Thr Ile Ser Asp
65                  70                  75                  80 ctg cag tgt gac gat gct gcc act tac tac tgt caa cag agt ttt agt     288
Leu Gln Cys Asp Asp Ala Ala Thr Tyr Tyr Cys Gln Gln Ser Phe Ser
                85                  90                  95 agt aat aat gtt ggg aat att ttc ggc gga ggg acc gag gtg gtg gtc     336
Ser Asn Asn Val Gly Asn Ile Phe Gly Gly Gly Thr Glu Val Val Val
            100                 105                 110 aaa                                                                  339
```

Lys

<210> SEQ ID NO 20
<211> LENGTH: 113
<212> TYPE: PRT
<213> ORGANISM: Artificial Sequence
<220> FEATURE:
<223> OTHER INFORMATION: Synthetic Construct

<400> SEQUENCE: 20

```
Ala Arg Cys Ala Tyr Asp Met Thr Gln Thr Pro Ser Ser Val Ser Ala
1               5                   10                  15

Thr Val Gly Gly Thr Val Thr Ile Asn Cys Gln Ala Ser Glu Ile Ile
            20                  25                  30

Tyr Ser Asn Leu Ala Trp Tyr Gln Gln Lys Pro Gly Gln Pro Pro Lys
        35                  40                  45

Leu Leu Ile Tyr Gly Ala Ser Thr Leu Ala Ser Gly Val Pro Ser Arg
    50                  55                  60

Phe Lys Gly Ser Gly Ser Gly Thr Glu Tyr Thr Leu Thr Ile Ser Asp
65                  70                  75                  80

Leu Gln Cys Asp Asp Ala Ala Thr Tyr Tyr Cys Gln Gln Ser Phe Ser
                85                  90                  95

Ser Asn Asn Val Gly Asn Ile Phe Gly Gly Gly Thr Glu Val Val Val
            100                 105                 110
```

Lys

<210> SEQ ID NO 21
<211> LENGTH: 351
<212> TYPE: DNA
<213> ORGANISM: Artificial Sequence
<220> FEATURE:
<223> OTHER INFORMATION: derived from rabbit monoclonal
<220> FEATURE:
<221> NAME/KEY: CDS
<222> LOCATION: (1)..(351)

<400> SEQUENCE: 21

```
cag tcg gtg gag gag tcc ggg ggt cgc ctg gtc acg cct ggg aca ccc      48
Gln Ser Val Glu Glu Ser Gly Gly Arg Leu Val Thr Pro Gly Thr Pro
1               5                   10                  15 ctg aca ctc acc tgc aca gcc tct gga ttc tcc ctc agt acc cat gca      96
Leu Thr Leu Thr Cys Thr Ala Ser Gly Phe Ser Leu Ser Thr His Ala
            20                  25                  30 ata aac tgg gtc cgc cag gct cca ggg aag ggg ctg gaa tgg atc ggg     144
Ile Asn Trp Val Arg Gln Ala Pro Gly Lys Gly Leu Glu Trp Ile Gly
        35                  40                  45 atc act tat gct agt ggt agg aca tat tac gcg agc tgg gcg aaa ggc     192
Ile Thr Tyr Ala Ser Gly Arg Thr Tyr Tyr Ala Ser Trp Ala Lys Gly
    50                  55                  60 cga ttc acc atc tcc aaa acc tcg acc acg gtg gat ctg aaa atc acc     240
Arg Phe Thr Ile Ser Lys Thr Ser Thr Thr Val Asp Leu Lys Ile Thr
65                  70                  75                  80 agt ccg aca acc gag gac acg gcc acc tat ttc tgt gcc aga aat ggg     288
Ser Pro Thr Thr Glu Asp Thr Ala Thr Tyr Phe Cys Ala Arg Asn Gly
                85                  90                  95 gct gat gaa aca ttt tac tac ttt gac ttg tgg ggc cca ggc acc ctg     336
Ala Asp Glu Thr Phe Tyr Tyr Phe Asp Leu Trp Gly Pro Gly Thr Leu
            100                 105                 110 gtc acc gtc tcc tca                                                 351
Val Thr Val Ser Ser
            115
```

<210> SEQ ID NO 22
<211> LENGTH: 117
<212> TYPE: PRT
<213> ORGANISM: Artificial Sequence
<220> FEATURE:
<223> OTHER INFORMATION: Synthetic Construct

<400> SEQUENCE: 22

Gln Ser Val Glu Glu Ser Gly Gly Arg Leu Val Thr Pro Gly Thr Pro
1               5                   10                  15

Leu Thr Leu Thr Cys Thr Ala Ser Gly Phe Ser Leu Ser Thr His Ala
            20                  25                  30

Ile Asn Trp Val Arg Gln Ala Pro Gly Lys Gly Leu Glu Trp Ile Gly
        35                  40                  45

Ile Thr Tyr Ala Ser Gly Arg Thr Tyr Tyr Ala Ser Trp Ala Lys Gly
    50                  55                  60

Arg Phe Thr Ile Ser Lys Thr Ser Thr Thr Val Asp Leu Lys Ile Thr
65                  70                  75                  80

Ser Pro Thr Thr Glu Asp Thr Ala Thr Tyr Phe Cys Ala Arg Asn Gly
                85                  90                  95

Ala Asp Glu Thr Phe Tyr Tyr Phe Asp Leu Trp Gly Pro Gly Thr Leu
            100                 105                 110

Val Thr Val Ser Ser
        115

<210> SEQ ID NO 23
<211> LENGTH: 339
<212> TYPE: DNA
<213> ORGANISM: Artificial Sequence
<220> FEATURE:
<223> OTHER INFORMATION: derived from rabbit monoclonal
<220> FEATURE:
<221> NAME/KEY: CDS
<222> LOCATION: (1)..(339)

<400> SEQUENCE: 23 gcc aga tgt gcc tat gat atg acc cag act cca gcc tcc gtg gag gca      48
Ala Arg Cys Ala Tyr Asp Met Thr Gln Thr Pro Ala Ser Val Glu Ala
1               5                   10                  15 gct gtg gga ggc aca gtc acc atc aag tgc cag gcc agt cag aat att      96
Ala Val Gly Gly Thr Val Thr Ile Lys Cys Gln Ala Ser Gln Asn Ile
            20                  25                  30 aat act tgg tta tcc tgg tat cag cag aag gca ggg cag cct ccc aag     144
Asn Thr Trp Leu Ser Trp Tyr Gln Gln Lys Ala Gly Gln Pro Pro Lys
        35                  40                  45 ctc ctg atc tac agg gca tcc act ctg gca tct ggg gtc tca tcg cgg     192
Leu Leu Ile Tyr Arg Ala Ser Thr Leu Ala Ser Gly Val Ser Ser Arg
    50                  55                  60 ttc aaa ggc agt gga tct ggg aca cag ttc act ctc acc atc agc ggc     240
Phe Lys Gly Ser Gly Ser Gly Thr Gln Phe Thr Leu Thr Ile Ser Gly
65                  70                  75                  80 gtg gag tgt gcc gat gct gcc act tac tac tgt caa caa tat gat gct     288
Val Glu Cys Ala Asp Ala Ala Thr Tyr Tyr Cys Gln Gln Tyr Asp Ala
                85                  90                  95 agt att aat att gat aat gct ttc ggc gga ggg acc gag gtg gtg gtc     336
Ser Ile Asn Ile Asp Asn Ala Phe Gly Gly Gly Thr Glu Val Val Val
            100                 105                 110 aaa                                                                  339
Lys

<210> SEQ ID NO 24
<211> LENGTH: 113
<212> TYPE: PRT
<213> ORGANISM: Artificial Sequence
<220> FEATURE:
<223> OTHER INFORMATION: Synthetic Construct

<400> SEQUENCE: 24

```
Ala Arg Cys Ala Tyr Asp Met Thr Gln Thr Pro Ala Ser Val Glu Ala
1               5                   10                  15

Ala Val Gly Gly Thr Val Thr Ile Lys Cys Gln Ala Ser Gln Asn Ile
            20                  25                  30

Asn Thr Trp Leu Ser Trp Tyr Gln Gln Lys Ala Gly Gln Pro Pro Lys
        35                  40                  45

Leu Leu Ile Tyr Arg Ala Ser Thr Leu Ala Ser Gly Val Ser Ser Arg
    50                  55                  60

Phe Lys Gly Ser Gly Ser Gly Thr Gln Phe Thr Leu Thr Ile Ser Gly
65                  70                  75                  80

Val Glu Cys Ala Asp Ala Ala Thr Tyr Tyr Cys Gln Gln Tyr Asp Ala
                85                  90                  95

Ser Ile Asn Ile Asp Asn Ala Phe Gly Gly Gly Thr Glu Val Val Val
            100                 105                 110

Lys
```

<210> SEQ ID NO 25
<211> LENGTH: 351
<212> TYPE: DNA
<213> ORGANISM: Artificial Sequence
<220> FEATURE:
<223> OTHER INFORMATION: derived from rabbit monoclonal
<220> FEATURE:
<221> NAME/KEY: CDS
<222> LOCATION: (1)..(351)

<400> SEQUENCE: 25

```
cag tcg gtg gag gag tcc ggg ggt cgc ctg gtc acg cct ggg aca ccc       48
Gln Ser Val Glu Glu Ser Gly Gly Arg Leu Val Thr Pro Gly Thr Pro
1               5                   10                  15 ctg aca ctc acc tgc aca gtc tct gga atc gac ctc agt agc aat gca       96
Leu Thr Leu Thr Cys Thr Val Ser Gly Ile Asp Leu Ser Ser Asn Ala
            20                  25                  30 atg agc tgg gtc cgc cag gct cca ggg aag ggg ctg gaa tat atc gga      144
Met Ser Trp Val Arg Gln Ala Pro Gly Lys Gly Leu Glu Tyr Ile Gly
        35                  40                  45 att att agg aat aat gat atc aca tac tac gcg agc tgg gcg aaa ggc      192
Ile Ile Arg Asn Asn Asp Ile Thr Tyr Tyr Ala Ser Trp Ala Lys Gly
    50                  55                  60 cga ttc acc atc tcc aaa acc tcg acc acg gtg gat ctg ata atc acc      240
Arg Phe Thr Ile Ser Lys Thr Ser Thr Thr Val Asp Leu Ile Ile Thr
65                  70                  75                  80 agt ccg aca acc gag gac acg gcc acc tat ttc tgt gcc aga ggg ggt      288
Ser Pro Thr Thr Glu Asp Thr Ala Thr Tyr Phe Cys Ala Arg Gly Gly
                85                  90                  95 ggt tct tac agt att gtc ttc tgg aac tta tgg ggc cca ggc acc ctg      336
Gly Ser Tyr Ser Ile Val Phe Trp Asn Leu Trp Gly Pro Gly Thr Leu
            100                 105                 110 gtc acc gtc tcc tca                                                  351
Val Thr Val Ser Ser
        115
```

```
<210> SEQ ID NO 26
<211> LENGTH: 117
<212> TYPE: PRT
<213> ORGANISM: Artificial Sequence
<220> FEATURE:
<223> OTHER INFORMATION: Synthetic Construct

<400> SEQUENCE: 26
```

Gln Ser Val Glu Glu Ser Gly Gly Arg Leu Val Thr Pro Gly Thr Pro
1               5                   10                  15

Leu Thr Leu Thr Cys Thr Val Ser Gly Ile Asp Leu Ser Ser Asn Ala
            20                  25                  30

Met Ser Trp Val Arg Gln Ala Pro Gly Lys Gly Leu Glu Tyr Ile Gly
        35                  40                  45

Ile Ile Arg Asn Asn Asp Ile Thr Tyr Tyr Ala Ser Trp Ala Lys Gly
    50                  55                  60

Arg Phe Thr Ile Ser Lys Thr Ser Thr Thr Val Asp Leu Ile Ile Thr
65                  70                  75                  80

Ser Pro Thr Thr Glu Asp Thr Ala Thr Tyr Phe Cys Ala Arg Gly Gly
                85                  90                  95

Gly Ser Tyr Ser Ile Val Phe Trp Asn Leu Trp Gly Pro Gly Thr Leu
            100                 105                 110

Val Thr Val Ser Ser
        115

```
<210> SEQ ID NO 27
<211> LENGTH: 339
<212> TYPE: DNA
<213> ORGANISM: Artificial Sequence
<220> FEATURE:
<223> OTHER INFORMATION: derived from rabbit monoclonal
<220> FEATURE:
<221> NAME/KEY: CDS
<222> LOCATION: (1)..(339)

<400> SEQUENCE: 27
```

| | | | | | | | | | | | | | | | | |
|---|---|---|---|---|---|---|---|---|---|---|---|---|---|---|---|---|
| gcc | aga | tgt | gcc | tat | gat | atg | acc | cag | act | cca | gcc | tct | gtg | gag | gta | 48 |
| Ala | Arg | Cys | Ala | Tyr | Asp | Met | Thr | Gln | Thr | Pro | Ala | Ser | Val | Glu | Val | |
| 1 | | | | 5 | | | | 10 | | | | 15 | | | | | gct gtg gga ggc aca gtc acc atc aat tgc cag gcc agt gag agg att     96
Ala Val Gly Gly Thr Val Thr Ile Asn Cys Gln Ala Ser Glu Arg Ile
            20                  25                  30 tat agc aat tta gcc tgg tat cag cag aaa cca ggg cag cgt ccc aaa    144
Tyr Ser Asn Leu Ala Trp Tyr Gln Gln Lys Pro Gly Gln Arg Pro Lys
        35                  40                  45 ctc ctg atc tat tat gca tcc act ctg gca tct ggg gtc tca tcg cgg    192
Leu Leu Ile Tyr Tyr Ala Ser Thr Leu Ala Ser Gly Val Ser Ser Arg
    50                  55                  60 ttc aaa ggc agt gga tct ggg aca cag ttc act ctc acc atc agc ggc    240
Phe Lys Gly Ser Gly Ser Gly Thr Gln Phe Thr Leu Thr Ile Ser Gly
65                  70                  75                  80 gtg cag tgt gcc gat gct gcc act tac tac tgt cag cag ggt tat agt    288
Val Gln Cys Ala Asp Ala Ala Thr Tyr Tyr Cys Gln Gln Gly Tyr Ser
                85                  90                  95 aat aat aat gtt gac aat act ttc ggc gga ggg acc gag gtg gtg gtc    336
Asn Asn Asn Val Asp Asn Thr Phe Gly Gly Gly Thr Glu Val Val Val
            100                 105                 110 aga                                                                 339
Arg

```
<210> SEQ ID NO 28
```

```
<211> LENGTH: 113
<212> TYPE: PRT
<213> ORGANISM: Artificial Sequence
<220> FEATURE:
<223> OTHER INFORMATION: Synthetic Construct

<400> SEQUENCE: 28

Ala Arg Cys Ala Tyr Asp Met Thr Gln Thr Pro Ala Ser Val Glu Val
1               5                   10                  15

Ala Val Gly Gly Thr Val Thr Ile Asn Cys Gln Ala Ser Glu Arg Ile
            20                  25                  30

Tyr Ser Asn Leu Ala Trp Tyr Gln Gln Lys Pro Gly Gln Arg Pro Lys
        35                  40                  45

Leu Leu Ile Tyr Tyr Ala Ser Thr Leu Ala Ser Gly Val Ser Ser Arg
    50                  55                  60

Phe Lys Gly Ser Gly Ser Gly Thr Gln Phe Thr Leu Thr Ile Ser Gly
65                  70                  75                  80

Val Gln Cys Ala Asp Ala Ala Thr Tyr Tyr Cys Gln Gln Gly Tyr Ser
                85                  90                  95

Asn Asn Asn Val Asp Asn Thr Phe Gly Gly Gly Thr Glu Val Val Val
            100                 105                 110

Arg

<210> SEQ ID NO 29
<211> LENGTH: 8
<212> TYPE: PRT
<213> ORGANISM: Artificial Sequence
<220> FEATURE:
<223> OTHER INFORMATION: Derived from human VH domain

<400> SEQUENCE: 29

Gly Phe Thr Phe Ser Ser Tyr Ala
1               5

<210> SEQ ID NO 30
<211> LENGTH: 8
<212> TYPE: PRT
<213> ORGANISM: Artificial Sequence
<220> FEATURE:
<223> OTHER INFORMATION: Derived from human VH domain

<400> SEQUENCE: 30

Ile Ser Tyr Asp Val Ser Asn Lys
1               5

<210> SEQ ID NO 31
<211> LENGTH: 12
<212> TYPE: PRT
<213> ORGANISM: Artificial Sequence
<220> FEATURE:
<223> OTHER INFORMATION: Derived from human VH domain

<400> SEQUENCE: 31

Ala Arg Ser Tyr Tyr Tyr Tyr Gly Met Asp Val
1               5                   10

<210> SEQ ID NO 32
<211> LENGTH: 6
<212> TYPE: PRT
<213> ORGANISM: Artificial Sequence
<220> FEATURE:
<223> OTHER INFORMATION: Derived from human VL domain

<400> SEQUENCE: 32
```

```
Gln Ser Ile Ser Arg Tyr
1               5

<210> SEQ ID NO 33
<211> LENGTH: 3
<212> TYPE: PRT
<213> ORGANISM: Artificial Sequence
<220> FEATURE:
<223> OTHER INFORMATION: Derived from human VL domain

<400> SEQUENCE: 33

Asp Ala Ser
1

<210> SEQ ID NO 34
<211> LENGTH: 9
<212> TYPE: PRT
<213> ORGANISM: Artificial Sequence
<220> FEATURE:
<223> OTHER INFORMATION: Derived from human VL domain

<400> SEQUENCE: 34

Gln Gln Phe Gly Arg Ser Pro Arg Thr
1               5

<210> SEQ ID NO 35
<211> LENGTH: 1350
<212> TYPE: DNA
<213> ORGANISM: Artificial Sequence
<220> FEATURE:
<223> OTHER INFORMATION: Derived from human variable domain and human Ig
      domain
<220> FEATURE:
<221> NAME/KEY: CDS
<222> LOCATION: (1)..(1350)

<400> SEQUENCE: 35 gag gtg caa ctg gtg gag tct ggg gga ggt gtg gta agg cct ggg ggg        48
Glu Val Gln Leu Val Glu Ser Gly Gly Gly Val Val Arg Pro Gly Gly
1               5                   10                  15 tcc ctg aga ctc tcc tgt gca gcc tct gga ttc acc ttc agt agc tat        96
Ser Leu Arg Leu Ser Cys Ala Ala Ser Gly Phe Thr Phe Ser Ser Tyr
            20                  25                  30 gct atg cac tgg gtc cgc cag gct cca ggc aag ggg ctg gag tgg gtg       144
Ala Met His Trp Val Arg Gln Ala Pro Gly Lys Gly Leu Glu Trp Val
        35                  40                  45 gca gtt ata tca tat gat gta agc aat aaa tac tac gca gac tcc gtg       192
Ala Val Ile Ser Tyr Asp Val Ser Asn Lys Tyr Tyr Ala Asp Ser Val
    50                  55                  60 aag ggc cga ttc acc atc tcc aga gac aat tcc aag aac acg ctg tat       240
Lys Gly Arg Phe Thr Ile Ser Arg Asp Asn Ser Lys Asn Thr Leu Tyr
65                  70                  75                  80 ctg caa atg aac agc ctg aga gct gag gac acg gct gtg tat tac tgt       288
Leu Gln Met Asn Ser Leu Arg Ala Glu Asp Thr Ala Val Tyr Tyr Cys
                85                  90                  95 gcg aga tct tac tac tac tac tac ggt atg gac gtc tgg ggc caa ggg       336
Ala Arg Ser Tyr Tyr Tyr Tyr Tyr Gly Met Asp Val Trp Gly Gln Gly
            100                 105                 110 acc acg gtc acc gtc tcc tca gcc tcc act aag ggc cca tcc gtg ttc       384
Thr Thr Val Thr Val Ser Ser Ala Ser Thr Lys Gly Pro Ser Val Phe
        115                 120                 125 cca ctg gca ccc tct agt aag agc aca tct ggg ggt act gcc gct ctg       432
Pro Leu Ala Pro Ser Ser Lys Ser Thr Ser Gly Gly Thr Ala Ala Leu
    130                 135                 140
```

| | | |
|---|---|---|
| gga tgt ctg gtg aag gat tac ttc cca gag cca gtc acc gtg tcc tgg<br>Gly Cys Leu Val Lys Asp Tyr Phe Pro Glu Pro Val Thr Val Ser Trp<br>145 150 155 160 | | 480 |
| aac agc ggg gcc ctg act tcc ggt gtc cat acc ttt cca gct gtg ctg<br>Asn Ser Gly Ala Leu Thr Ser Gly Val His Thr Phe Pro Ala Val Leu<br>165 170 175 | | 528 |
| cag tca tcc ggc ctg tac agc ctg agc tct gtg gtc acc gtc ccc agt<br>Gln Ser Ser Gly Leu Tyr Ser Leu Ser Ser Val Val Thr Val Pro Ser<br>180 185 190 | | 576 |
| tca tcc ctg gga aca cag act tat atc tgc aac gtg aat cac aag cca<br>Ser Ser Leu Gly Thr Gln Thr Tyr Ile Cys Asn Val Asn His Lys Pro<br>195 200 205 | | 624 |
| tcc aat aca aaa gtc gac aag aaa gtg gaa ccc aag agc tgt gat aaa<br>Ser Asn Thr Lys Val Asp Lys Lys Val Glu Pro Lys Ser Cys Asp Lys<br>210 215 220 | | 672 |
| acc cat aca tgc ccc cct tgt cct gct cca gag ctg ctg gga gga cca<br>Thr His Thr Cys Pro Pro Cys Pro Ala Pro Glu Leu Leu Gly Gly Pro<br>225 230 235 240 | | 720 |
| tcc gtg ttc ctg ttt cca ccc aag cct aaa gac act ctg atg att tct<br>Ser Val Phe Leu Phe Pro Pro Lys Pro Lys Asp Thr Leu Met Ile Ser<br>245 250 255 | | 768 |
| cga acc ccc gaa gtc aca tgc gtg gtc gtg gac gtg tcc cac gag gat<br>Arg Thr Pro Glu Val Thr Cys Val Val Val Asp Val Ser His Glu Asp<br>260 265 270 | | 816 |
| cct gaa gtc aag ttc aac tgg tac gtg gat ggc gtc gag gtg cat aat<br>Pro Glu Val Lys Phe Asn Trp Tyr Val Asp Gly Val Glu Val His Asn<br>275 280 285 | | 864 |
| gcc aag aca aaa cca cga gag gaa cag tac aac agt acc tat cgt gtc<br>Ala Lys Thr Lys Pro Arg Glu Glu Gln Tyr Asn Ser Thr Tyr Arg Val<br>290 295 300 | | 912 |
| gtg tca gtc ctg aca gtg ctg cac cag gac tgg ctg aac ggg aag gaa<br>Val Ser Val Leu Thr Val Leu His Gln Asp Trp Leu Asn Gly Lys Glu<br>305 310 315 320 | | 960 |
| tat aag tgc aaa gtg agc aat aag gca ctg ccc gcc cct atc gag aaa<br>Tyr Lys Cys Lys Val Ser Asn Lys Ala Leu Pro Ala Pro Ile Glu Lys<br>325 330 335 | | 1008 |
| aca att tct aag gct aaa gga cag cct agg gaa cca cag gtg tac act<br>Thr Ile Ser Lys Ala Lys Gly Gln Pro Arg Glu Pro Gln Val Tyr Thr<br>340 345 350 | | 1056 |
| ctg cct cca tca cgg gac gag ctg aca aag aac cag gtc agt ctg act<br>Leu Pro Pro Ser Arg Asp Glu Leu Thr Lys Asn Gln Val Ser Leu Thr<br>355 360 365 | | 1104 |
| tgt ctg gtg aaa ggg ttc tat cct tct gat atc gcc gtg gag tgg gaa<br>Cys Leu Val Lys Gly Phe Tyr Pro Ser Asp Ile Ala Val Glu Trp Glu<br>370 375 380 | | 1152 |
| agt aat ggt cag cca gag aac aat tac aag acc aca ccc cct gtc ctg<br>Ser Asn Gly Gln Pro Glu Asn Asn Tyr Lys Thr Thr Pro Pro Val Leu<br>385 390 395 400 | | 1200 |
| gac tct gat ggg agt ttc ttt ctg tat tcc aag ctg acc gtg gat aaa<br>Asp Ser Asp Gly Ser Phe Phe Leu Tyr Ser Lys Leu Thr Val Asp Lys<br>405 410 415 | | 1248 |
| agc cgg tgg cag cag ggt aat gtc ttt agt tgt tca gtg atg cac gag<br>Ser Arg Trp Gln Gln Gly Asn Val Phe Ser Cys Ser Val Met His Glu<br>420 425 430 | | 1296 |
| gca ctg cac aat cac tac acc cag aaa tca ctg tca ctg tca cca ggt<br>Ala Leu His Asn His Tyr Thr Gln Lys Ser Leu Ser Leu Ser Pro Gly<br>435 440 445 | | 1344 |
| aaa tga<br>Lys | | 1350 |

```
<210> SEQ ID NO 36
<211> LENGTH: 449
<212> TYPE: PRT
<213> ORGANISM: Artificial Sequence
<220> FEATURE:
<223> OTHER INFORMATION: Synthetic Construct

<400> SEQUENCE: 36

Glu Val Gln Leu Val Glu Ser Gly Gly Gly Val Val Arg Pro Gly Gly
1               5                   10                  15

Ser Leu Arg Leu Ser Cys Ala Ala Ser Gly Phe Thr Phe Ser Ser Tyr
            20                  25                  30

Ala Met His Trp Val Arg Gln Ala Pro Gly Lys Gly Leu Glu Trp Val
        35                  40                  45

Ala Val Ile Ser Tyr Asp Val Ser Asn Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Ser Tyr Tyr Tyr Tyr Gly Met Asp Val Trp Gly Gln Gly
            100                 105                 110

Thr Thr Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Lys Val Glu Pro Lys Ser Cys Asp Lys
    210                 215                 220

Thr His Thr Cys Pro Pro Cys Pro Ala Pro Glu Leu Leu Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
        275                 280                 285

Ala Lys Thr Lys Pro Arg Glu Glu Gln Tyr Asn Ser Thr Tyr Arg Val
    290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Arg Asp Glu Leu Thr Lys Asn Gln Val Ser Leu Thr
        355                 360                 365
```

```
Cys Leu Val Lys Gly Phe Tyr Pro Ser Asp Ile Ala Val Glu Trp Glu
        370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
            420                 425                 430

Ala Leu His Asn His Tyr Thr Gln Lys Ser Leu Ser Leu Ser Pro Gly
        435                 440                 445

Lys

<210> SEQ ID NO 37
<211> LENGTH: 645
<212> TYPE: DNA
<213> ORGANISM: Artificial Sequence
<220> FEATURE:
<223> OTHER INFORMATION: Derived from human variable domain and human Ig
      domain
<220> FEATURE:
<221> NAME/KEY: CDS
<222> LOCATION: (1)..(645)

<400> SEQUENCE: 37 gat gtt gtg atg acc cag tct cca tcc tcc ctg tct gca tct gta gga        48
Asp Val Val Met Thr Gln Ser Pro Ser Ser Leu Ser Ala Ser Val Gly
1               5                   10                  15 gac aga gtc acc atc act tgc cgg gca agt cag agc att agc agg tac        96
Asp Arg Val Thr Ile Thr Cys Arg Ala Ser Gln Ser Ile Ser Arg Tyr
            20                  25                  30 tta gcc tgg tac caa cag aaa cct ggc cag gct ccc agg ctc ctc atc       144
Leu Ala Trp Tyr Gln Gln Lys Pro Gly Gln Ala Pro Arg Leu Leu Ile
        35                  40                  45 tat gat gca tcc aac agg gcc act ggc atc cca gtc agg ttc agt ggc       192
Tyr Asp Ala Ser Asn Arg Ala Thr Gly Ile Pro Val Arg Phe Ser Gly
    50                  55                  60 agt ggg tct ggg aca gac ttc act ctc acc atc agc aga ctg gag cca       240
Ser Gly Ser Gly Thr Asp Phe Thr Leu Thr Ile Ser Arg Leu Glu Pro
65                  70                  75                  80 gaa gat ttt gca gtg tat tac tgt cag cag ttt ggt agg tca cct cgg       288
Glu Asp Phe Ala Val Tyr Tyr Cys Gln Gln Phe Gly Arg Ser Pro Arg
                85                  90                  95 acg ttc ggc caa ggg aca cga ctg gag att aaa cga act gtg gct gca       336
Thr Phe Gly Gln Gly Thr Arg Leu Glu Ile Lys Arg Thr Val Ala Ala
            100                 105                 110 cca tct gtc ttc atc ttc ccg cca tct gat gag cag ttg aaa tct gga       384
Pro Ser Val Phe Ile Phe Pro Pro Ser Asp Glu Gln Leu Lys Ser Gly
        115                 120                 125 act gcc tct gtt gtg tgc ctg ctg aat aac ttc tat ccc aga gag gcc       432
Thr Ala Ser Val Val Cys Leu Leu Asn Asn Phe Tyr Pro Arg Glu Ala
    130                 135                 140 aaa gta cag tgg aag gtg gat aac gcc ctc caa tcg ggt aac tcc cag       480
Lys Val Gln Trp Lys Val Asp Asn Ala Leu Gln Ser Gly Asn Ser Gln
145                 150                 155                 160 gag agt gtc aca gag cag gac agc aag gac agc acc tac agc ctc agc       528
Glu Ser Val Thr Glu Gln Asp Ser Lys Asp Ser Thr Tyr Ser Leu Ser
                165                 170                 175 agc acc ctg acg ctg agc aaa gca gac tac gag aaa cac aaa gtc tac       576
Ser Thr Leu Thr Leu Ser Lys Ala Asp Tyr Glu Lys His Lys Val Tyr
            180                 185                 190
```

```
gcc tgc gaa gtc acc cat cag ggc ctg agc tcg ccc gtc aca aag agc      624
Ala Cys Glu Val Thr His Gln Gly Leu Ser Ser Pro Val Thr Lys Ser
            195                 200                 205 ttc aac agg gga gag tgt tag                                           645
Phe Asn Arg Gly Glu Cys
    210
```

<210> SEQ ID NO 38
<211> LENGTH: 214
<212> TYPE: PRT
<213> ORGANISM: Artificial Sequence
<220> FEATURE:
<223> OTHER INFORMATION: Synthetic Construct

<400> SEQUENCE: 38

```
Asp Val Val Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Arg Tyr
            20                  25                  30

Leu Ala Trp Tyr Gln Gln Lys Pro Gly Gln Ala Pro Arg Leu Leu Ile
        35                  40                  45

Tyr Asp Ala Ser Asn Arg Ala Thr Gly Ile Pro Val Arg Phe Ser Gly
    50                  55                  60

Ser Gly Ser Gly Thr Asp Phe Thr Leu Thr Ile Ser Arg Leu Glu Pro
65                  70                  75                  80

Glu Asp Phe Ala Val Tyr Tyr Cys Gln Gln Phe Gly Arg Ser Pro Arg
                85                  90                  95

Thr Phe Gly Gln Gly Thr Arg Leu Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210
```

<210> SEQ ID NO 39
<211> LENGTH: 732
<212> TYPE: DNA
<213> ORGANISM: Artificial Sequence
<220> FEATURE:
<223> OTHER INFORMATION: Derived from human variable domains
<220> FEATURE:
<221> NAME/KEY: CDS
<222> LOCATION: (1)..(732)

<400> SEQUENCE: 39

```
gat gtt gtg atg acc cag tct cca tcc tcc ctg tct gca tct gta gga       48
Asp Val Val Met Thr Gln Ser Pro Ser Ser Leu Ser Ala Ser Val Gly
1               5                   10                  15 gac aga gtc acc atc act tgc cgg gca agt cag agc att agc agg tac       96
Asp Arg Val Thr Ile Thr Cys Arg Ala Ser Gln Ser Ile Ser Arg Tyr
```

```
                Asp Arg Val Thr Ile Thr Cys Arg Ala Ser Gln Ser Ile Ser Arg Tyr
                            20                  25                  30 tta gcc tgg tac caa cag aaa cct ggc cag gct ccc agg ctc ctc atc         144
Leu Ala Trp Tyr Gln Gln Lys Pro Gly Gln Ala Pro Arg Leu Leu Ile
            35                  40                  45 tat gat gca tcc aac agg gcc act ggc atc cca gtc agg ttc agt ggc         192
Tyr Asp Ala Ser Asn Arg Ala Thr Gly Ile Pro Val Arg Phe Ser Gly
 50                  55                  60 agt ggg tct ggg aca gac ttc act ctc acc atc agc aga ctg gag cca         240
Ser Gly Ser Gly Thr Asp Phe Thr Leu Thr Ile Ser Arg Leu Glu Pro
 65                  70                  75                  80 gaa gat ttt gca gtg tat tac tgt cag cag ttt ggt agg tca cct cgg         288
Glu Asp Phe Ala Val Tyr Tyr Cys Gln Gln Phe Gly Arg Ser Pro Arg
                 85                  90                  95 acg ttc ggc caa ggg aca cga ctg gag att aaa ggc gga tcc tct agg         336
Thr Phe Gly Gln Gly Thr Arg Leu Glu Ile Lys Gly Gly Ser Ser Arg
            100                 105                 110 tca agt tcc agc ggc ggc ggt ggc agc gga ggc ggc ggt gag gtg caa         384
Ser Ser Ser Ser Gly Gly Gly Gly Ser Gly Gly Gly Gly Glu Val Gln
        115                 120                 125 ctg gtg gag tct ggg gga ggt gtg gta agg cct ggg ggg tcc ctg aga         432
Leu Val Glu Ser Gly Gly Gly Val Val Arg Pro Gly Gly Ser Leu Arg
130                 135                 140 ctc tcc tgt gca gcc tct gga ttc acc ttc agt agc tat gct atg cac         480
Leu Ser Cys Ala Ala Ser Gly Phe Thr Phe Ser Ser Tyr Ala Met His
145                 150                 155                 160 tgg gtc cgc cag gct cca ggc aag ggg ctg gag tgg gtg gca gtt ata         528
Trp Val Arg Gln Ala Pro Gly Lys Gly Leu Glu Trp Val Ala Val Ile
                165                 170                 175 tca tat gat gta agc aat aaa tac tac gca gac tcc gtg aag ggc cga         576
Ser Tyr Asp Val Ser Asn Lys Tyr Tyr Ala Asp Ser Val Lys Gly Arg
            180                 185                 190 ttc acc atc tcc aga gac aat tcc aag aac acg ctg tat ctg caa atg         624
Phe Thr Ile Ser Arg Asp Asn Ser Lys Asn Thr Leu Tyr Leu Gln Met
        195                 200                 205 aac agc ctg aga gct gag gac acg gct gtg tat tac tgt gcg aga tct         672
Asn Ser Leu Arg Ala Glu Asp Thr Ala Val Tyr Tyr Cys Ala Arg Ser
210                 215                 220 tac tac tac tac tac ggt atg gac gtc tgg ggc caa ggg acc acg gtc         720
Tyr Tyr Tyr Tyr Tyr Gly Met Asp Val Trp Gly Gln Gly Thr Thr Val
225                 230                 235                 240 acc gtc tcc tca                                                         732
Thr Val Ser Ser <210> SEQ ID NO 40
<211> LENGTH: 244
<212> TYPE: PRT
<213> ORGANISM: Artificial Sequence
<220> FEATURE:
<223> OTHER INFORMATION: Synthetic Construct

<400> SEQUENCE: 40

Asp Val Val Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Arg Tyr
            20                  25                  30

Leu Ala Trp Tyr Gln Gln Lys Pro Gly Gln Ala Pro Arg Leu Leu Ile
        35                  40                  45

Tyr Asp Ala Ser Asn Arg Ala Thr Gly Ile Pro Val Arg Phe Ser Gly
    50                  55                  60
```

```
Ser Gly Ser Gly Thr Asp Phe Thr Leu Thr Ile Ser Arg Leu Glu Pro
 65                  70                  75                  80

Glu Asp Phe Ala Val Tyr Tyr Cys Gln Gln Phe Gly Arg Ser Pro Arg
             85                   90                   95

Thr Phe Gly Gln Gly Thr Arg Leu Glu Ile Lys Gly Gly Ser Ser Arg
            100                 105                 110

Ser Ser Ser Ser Gly Gly Gly Ser Gly Gly Gly Glu Val Gln
            115                 120                 125

Leu Val Glu Ser Gly Gly Val Arg Pro Gly Gly Ser Leu Arg
130             135                 140

Leu Ser Cys Ala Ala Ser Gly Phe Thr Phe Ser Ser Tyr Ala Met His
145                 150                 155                 160

Trp Val Arg Gln Ala Pro Gly Lys Gly Leu Glu Trp Val Ala Val Ile
                165                 170                 175

Ser Tyr Asp Val Ser Asn Lys Tyr Tyr Ala Asp Ser Val Lys Gly Arg
            180                 185                 190

Phe Thr Ile Ser Arg Asp Asn Ser Lys Asn Thr Leu Tyr Leu Gln Met
            195                 200                 205

Asn Ser Leu Arg Ala Glu Asp Thr Ala Val Tyr Tyr Cys Ala Arg Ser
210                 215                 220

Tyr Tyr Tyr Tyr Gly Met Asp Val Trp Gly Gln Gly Thr Thr Val
225                 230                 235                 240

Thr Val Ser Ser
```

<210> SEQ ID NO 41
<211> LENGTH: 351
<212> TYPE: DNA
<213> ORGANISM: Artificial Sequence
<220> FEATURE:
<223> OTHER INFORMATION: chimeric sequences
<220> FEATURE:
<221> NAME/KEY: CDS
<222> LOCATION: (1)..(351)

<400> SEQUENCE: 41

```
cag tcg gtg gag gag tcc ggg ggt cgc ctg gtc acg cct ggg aca ccc      48
Gln Ser Val Glu Glu Ser Gly Gly Arg Leu Val Thr Pro Gly Thr Pro
 1               5                  10                  15 ctg aca ctc acc tgc aca gtc tct gga atc gac ctc agt aac aat gca      96
Leu Thr Leu Thr Cys Thr Val Ser Gly Ile Asp Leu Ser Asn Asn Ala
             20                  25                  30 atg agc tgg gtc cgc cag gct cca ggg aag ggg ctg gaa tat atc gga     144
Met Ser Trp Val Arg Gln Ala Pro Gly Lys Gly Leu Glu Tyr Ile Gly
         35                  40                  45 atc att agg agt agt ggt agt aca tat tac gcg aac tgg gca aaa ggc     192
Ile Ile Arg Ser Ser Gly Ser Thr Tyr Tyr Ala Asn Trp Ala Lys Gly
 50                  55                  60 cgg ttc acc atc tcc aaa acc tcg acc acg gtg gat ctg ata atc acc     240
Arg Phe Thr Ile Ser Lys Thr Ser Thr Thr Val Asp Leu Ile Ile Thr
 65                  70                  75                  80 agt ccg aca acc gag gac acg gcc acc tat ttc tgt gcc aga ggg ggt     288
Ser Pro Thr Thr Glu Asp Thr Ala Thr Tyr Phe Cys Ala Arg Gly Gly
                 85                  90                  95 ggt tct tac agt att gtc ttc tgg aac ttg tgg ggc cca ggc acc ctg     336
Gly Ser Tyr Ser Ile Val Phe Trp Asn Leu Trp Gly Pro Gly Thr Leu
            100                 105                 110 gtc acc gtc tcc tca                                                  351
Val Thr Val Ser Ser
```

<210> SEQ ID NO 42
<211> LENGTH: 117
<212> TYPE: PRT
<213> ORGANISM: Artificial Sequence
<220> FEATURE:
<223> OTHER INFORMATION: Synthetic Construct

<400> SEQUENCE: 42

```
Gln Ser Val Glu Glu Ser Gly Gly Arg Leu Val Thr Pro Gly Thr Pro
1               5                   10                  15

Leu Thr Leu Thr Cys Thr Val Ser Gly Ile Asp Leu Ser Asn Asn Ala
            20                  25                  30

Met Ser Trp Val Arg Gln Ala Pro Gly Lys Gly Leu Glu Tyr Ile Gly
        35                  40                  45

Ile Ile Arg Ser Ser Gly Ser Thr Tyr Tyr Ala Asn Trp Ala Lys Gly
    50                  55                  60

Arg Phe Thr Ile Ser Lys Thr Ser Thr Thr Val Asp Leu Ile Ile Thr
65                  70                  75                  80

Ser Pro Thr Thr Glu Asp Thr Ala Thr Tyr Phe Cys Ala Arg Gly Gly
                85                  90                  95

Gly Ser Tyr Ser Ile Val Phe Trp Asn Leu Trp Gly Pro Gly Thr Leu
            100                 105                 110

Val Thr Val Ser Ser
            115
```

<210> SEQ ID NO 43
<211> LENGTH: 342
<212> TYPE: DNA
<213> ORGANISM: Artificial Sequence
<220> FEATURE:
<223> OTHER INFORMATION: chimeric sequences
<220> FEATURE:
<221> NAME/KEY: CDS
<222> LOCATION: (1)..(342)

<400> SEQUENCE: 43

```
gcc aga tgt gcc tat gat atg acc cag act cca gcc tct gtg gag gta      48
Ala Arg Cys Ala Tyr Asp Met Thr Gln Thr Pro Ala Ser Val Glu Val
1               5                   10                  15 gct gtg gga ggc aca gtc acc atc aat tgc cag gcc agt gag agg att      96
Ala Val Gly Gly Thr Val Thr Ile Asn Cys Gln Ala Ser Glu Arg Ile
            20                  25                  30 tat agc aat tta gcc tgg tat cag cag aaa cca ggg cag cgt ccc aag     144
Tyr Ser Asn Leu Ala Trp Tyr Gln Gln Lys Pro Gly Gln Arg Pro Lys
        35                  40                  45 ctc ctg atc tat tat aca tcc act ctg gca tct ggg gtc tca tcg cgg     192
Leu Leu Ile Tyr Tyr Thr Ser Thr Leu Ala Ser Gly Val Ser Ser Arg
    50                  55                  60 ttc aaa ggc agt gga tct ggg aca cag ttc act ctc acc atc agc ggc     240
Phe Lys Gly Ser Gly Ser Gly Thr Gln Phe Thr Leu Thr Ile Ser Gly
65                  70                  75                  80 gtg gag tgt gcc gat gct gcc act tac tac tgt caa cag ggt tat agt     288
Val Glu Cys Ala Asp Ala Ala Thr Tyr Tyr Cys Gln Gln Gly Tyr Ser
                85                  90                  95 agt agt aat gtt gac aat act ttc ggc gga ggg acc gag gtg gtg gtc     336
Ser Ser Asn Val Asp Asn Thr Phe Gly Gly Gly Thr Glu Val Val Val
            100                 105                 110 aaa ggt                                                             342
Lys Gly
```

<210> SEQ ID NO 44
<211> LENGTH: 114
<212> TYPE: PRT
<213> ORGANISM: Artificial Sequence
<220> FEATURE:
<223> OTHER INFORMATION: Synthetic Construct

<400> SEQUENCE: 44

Ala Arg Cys Ala Tyr Asp Met Thr Gln Thr Pro Ala Ser Val Glu Val
1               5                   10                  15

Ala Val Gly Gly Thr Val Thr Ile Asn Cys Gln Ala Ser Glu Arg Ile
            20                  25                  30

Tyr Ser Asn Leu Ala Trp Tyr Gln Gln Lys Pro Gly Gln Arg Pro Lys
        35                  40                  45

Leu Leu Ile Tyr Tyr Thr Ser Thr Leu Ala Ser Gly Val Ser Ser Arg
    50                  55                  60

Phe Lys Gly Ser Gly Ser Gly Thr Gln Phe Thr Leu Thr Ile Ser Gly
65                  70                  75                  80

Val Glu Cys Ala Asp Ala Ala Thr Tyr Tyr Cys Gln Gln Gly Tyr Ser
                85                  90                  95

Ser Ser Asn Val Asp Asn Thr Phe Gly Gly Gly Thr Glu Val Val Val
            100                 105                 110

Lys Gly

<210> SEQ ID NO 45
<211> LENGTH: 363
<212> TYPE: DNA
<213> ORGANISM: Artificial Sequence
<220> FEATURE:
<223> OTHER INFORMATION: chimeric sequences
<220> FEATURE:
<221> NAME/KEY: CDS
<222> LOCATION: (1)..(363)

<400> SEQUENCE: 45 ggc gag cag cag ctg gtg gag agc ggc gga ggc ctg gtg cag cct gga      48
Gly Glu Gln Gln Leu Val Glu Ser Gly Gly Gly Leu Val Gln Pro Gly
1               5                   10                  15 gga agc ctg agg ctg agc tgc gcc gtg tcc ggc ttc agc ctg agc agc      96
Gly Ser Leu Arg Leu Ser Cys Ala Val Ser Gly Phe Ser Leu Ser Ser
            20                  25                  30 tac gcc atc agc tgg gtg agg cag gcc ccc gga aag ggc ctg gag tac     144
Tyr Ala Ile Ser Trp Val Arg Gln Ala Pro Gly Lys Gly Leu Glu Tyr
        35                  40                  45 atc gcc atc atc aac agc tac ggc acc acc tac tac gcc agc tgg gcc     192
Ile Ala Ile Ile Asn Ser Tyr Gly Thr Thr Tyr Tyr Ala Ser Trp Ala
    50                  55                  60 aag ggc aga gtg acc atc tcc aag gat tcc tcc aag aac acc gtg tac     240
Lys Gly Arg Val Thr Ile Ser Lys Asp Ser Ser Lys Asn Thr Val Tyr
65                  70                  75                  80 ctg cag atg ggc tcc ctg aga gcc gag gat atg gcc gtg tac ttt tgc     288
Leu Gln Met Gly Ser Leu Arg Ala Glu Asp Met Ala Val Tyr Phe Cys
                85                  90                  95 gcc aga ggc gat tcc tac ggc tcc ggc gtg ggc ctg ggc ctg tgg gga     336
Ala Arg Gly Asp Ser Tyr Gly Ser Gly Val Gly Leu Gly Leu Trp Gly
            100                 105                 110 cct gga acc ctg gtg aca gtg tcc tcc                                 363
Pro Gly Thr Leu Val Thr Val Ser Ser
        115                 120

<210> SEQ ID NO 46
<211> LENGTH: 121
<212> TYPE: PRT
<213> ORGANISM: Artificial Sequence
<220> FEATURE:
<223> OTHER INFORMATION: Synthetic Construct

<400> SEQUENCE: 46

```
Gly Glu Gln Gln Leu Val Glu Ser Gly Gly Gly Leu Val Gln Pro Gly
1               5                   10                  15

Gly Ser Leu Arg Leu Ser Cys Ala Val Ser Gly Phe Ser Leu Ser Ser
            20                  25                  30

Tyr Ala Ile Ser Trp Val Arg Gln Ala Pro Gly Lys Gly Leu Glu Tyr
        35                  40                  45

Ile Ala Ile Ile Asn Ser Tyr Gly Thr Thr Tyr Tyr Ala Ser Trp Ala
    50                  55                  60

Lys Gly Arg Val Thr Ile Ser Lys Asp Ser Lys Asn Thr Val Tyr
65                  70                  75                  80

Leu Gln Met Gly Ser Leu Arg Ala Glu Asp Met Ala Val Tyr Phe Cys
                85                  90                  95

Ala Arg Gly Asp Ser Tyr Gly Ser Gly Val Leu Gly Leu Trp Gly
            100                 105                 110

Pro Gly Thr Leu Val Thr Val Ser Ser
        115                 120
```

<210> SEQ ID NO 47
<211> LENGTH: 333
<212> TYPE: DNA
<213> ORGANISM: Artificial Sequence
<220> FEATURE:
<223> OTHER INFORMATION: chimeric sequences
<220> FEATURE:
<221> NAME/KEY: CDS
<222> LOCATION: (1)..(333)

<400> SEQUENCE: 47

```
gga gac tac cag atg aca cag tcc cct agc acc ctg tcc gcc tcc gtg    48
Gly Asp Tyr Gln Met Thr Gln Ser Pro Ser Thr Leu Ser Ala Ser Val
1               5                   10                  15 ggc gac aga gtg aca atc acc tgt cag gcc tcc cag aat atc tac agc    96
Gly Asp Arg Val Thr Ile Thr Cys Gln Ala Ser Gln Asn Ile Tyr Ser
            20                  25                  30 aat ctg gcc tgg tac cag cag aag cct ggc aag agg ccc aag ctg ctg   144
Asn Leu Ala Trp Tyr Gln Gln Lys Pro Gly Lys Arg Pro Lys Leu Leu
        35                  40                  45 atc tac aga gcc agc tcc ctg gcc tcc ggc gtg cca tct aga ttt tcc   192
Ile Tyr Arg Ala Ser Ser Leu Ala Ser Gly Val Pro Ser Arg Phe Ser
    50                  55                  60 ggc tcc ggc agc ggc aca gag ttt acc ctg aca atc agc agc ctg cag   240
Gly Ser Gly Ser Gly Thr Glu Phe Thr Leu Thr Ile Ser Ser Leu Gln
65                  70                  75                  80 ccc gat gat ttc gcc acc tac tac tgt cag cag ggc ttc agc agc aat   288
Pro Asp Asp Phe Ala Thr Tyr Tyr Cys Gln Gln Gly Phe Ser Ser Asn
                85                  90                  95 aat gtg gac aat aca ttt ggc ggc ggc aca aag gtg gag atc aag       333
Asn Val Asp Asn Thr Phe Gly Gly Gly Thr Lys Val Glu Ile Lys
            100                 105                 110
```

<210> SEQ ID NO 48
<211> LENGTH: 111
<212> TYPE: PRT

```
<213> ORGANISM: Artificial Sequence
<220> FEATURE:
<223> OTHER INFORMATION: Synthetic Construct

<400> SEQUENCE: 48

Gly Asp Tyr Gln Met Thr Gln Ser Pro Ser Thr Leu Ser Ala Ser Val
1               5                   10                  15

Gly Asp Arg Val Thr Ile Thr Cys Gln Ala Ser Gln Asn Ile Tyr Ser
                20                  25                  30

Asn Leu Ala Trp Tyr Gln Gln Lys Pro Gly Lys Arg Pro Lys Leu Leu
            35                  40                  45

Ile Tyr Arg Ala Ser Ser Leu Ala Ser Gly Val Pro Ser Arg Phe Ser
50                  55                  60

Gly Ser Gly Ser Gly Thr Glu Phe Thr Leu Thr Ile Ser Ser Leu Gln
65                  70                  75                  80

Pro Asp Asp Phe Ala Thr Tyr Tyr Cys Gln Gln Gly Phe Ser Ser Asn
                85                  90                  95

Asn Val Asp Asn Thr Phe Gly Gly Gly Thr Lys Val Glu Ile Lys
                100                 105                 110

<210> SEQ ID NO 49
<211> LENGTH: 354
<212> TYPE: DNA
<213> ORGANISM: Artificial Sequence
<220> FEATURE:
<223> OTHER INFORMATION: chimeric sequences
<220> FEATURE:
<221> NAME/KEY: CDS
<222> LOCATION: (1)..(354)

<400> SEQUENCE: 49 ggc gag cag cag ctg gtg gag agc ggc gga ggc ctg gtg cag cct gga    48
Gly Glu Gln Gln Leu Val Glu Ser Gly Gly Gly Leu Val Gln Pro Gly
1               5                   10                  15 gga agc ctg agg ctg agc tgc gcc gtg tcc ggc ttt tcc ctg agc aag    96
Gly Ser Leu Arg Leu Ser Cys Ala Val Ser Gly Phe Ser Leu Ser Lys
                20                  25                  30 agc atc atc agc tgg gtg agg cag gcc cct ggc aag ggc ctg gag tac   144
Ser Ile Ile Ser Trp Val Arg Gln Ala Pro Gly Lys Gly Leu Glu Tyr
            35                  40                  45 atc ggc atc atc ggc agc agc ggc tcc acc tac tac gcc aac tgg gcc   192
Ile Gly Ile Ile Gly Ser Ser Gly Ser Thr Tyr Tyr Ala Asn Trp Ala
50                  55                  60 aag ggc aga ttc aca atc tcc aag gac tcc tcc aag aat acc gtg tac   240
Lys Gly Arg Phe Thr Ile Ser Lys Asp Ser Ser Lys Asn Thr Val Tyr
65                  70                  75                  80 ctg cag atg ggc tcc ctg agg gcc gag gat atg gcc gtg tac ttt tgt   288
Leu Gln Met Gly Ser Leu Arg Ala Glu Asp Met Ala Val Tyr Phe Cys
                85                  90                  95 gcc aga ggc ctg ctg tac tcc ggc aat aag tcc tgg ggc ccc ggc aca   336
Ala Arg Gly Leu Leu Tyr Ser Gly Asn Lys Ser Trp Gly Pro Gly Thr
                100                 105                 110 ctg gtg acc gtg agc tcc                                            354
Leu Val Thr Val Ser Ser
        115

<210> SEQ ID NO 50
<211> LENGTH: 118
<212> TYPE: PRT
<213> ORGANISM: Artificial Sequence
<220> FEATURE:
<223> OTHER INFORMATION: Synthetic Construct
```

<400> SEQUENCE: 50

Gly Glu Gln Gln Leu Val Glu Ser Gly Gly Leu Val Gln Pro Gly
1               5                   10                  15

Gly Ser Leu Arg Leu Ser Cys Ala Val Ser Gly Phe Ser Leu Ser Lys
            20                  25                  30

Ser Ile Ile Ser Trp Val Arg Gln Ala Pro Gly Lys Gly Leu Glu Tyr
        35                  40                  45

Ile Gly Ile Ile Gly Ser Ser Gly Ser Thr Tyr Tyr Ala Asn Trp Ala
    50                  55                  60

Lys Gly Arg Phe Thr Ile Ser Lys Asp Ser Ser Lys Asn Thr Val Tyr
65                  70                  75                  80

Leu Gln Met Gly Ser Leu Arg Ala Glu Asp Met Ala Val Tyr Phe Cys
                85                  90                  95

Ala Arg Gly Leu Leu Tyr Ser Gly Asn Lys Ser Trp Gly Pro Gly Thr
            100                 105                 110

Leu Val Thr Val Ser Ser
            115

<210> SEQ ID NO 51
<211> LENGTH: 333
<212> TYPE: DNA
<213> ORGANISM: Artificial Sequence
<220> FEATURE:
<223> OTHER INFORMATION: chimeric sequences
<220> FEATURE:
<221> NAME/KEY: CDS
<222> LOCATION: (1)..(333)

<400> SEQUENCE: 51

```
ggc gac atc gtg atg acc cag tcc ccc gat tcc ctg gcc gtg tcc ctg     48
Gly Asp Ile Val Met Thr Gln Ser Pro Asp Ser Leu Ala Val Ser Leu
1               5                   10                  15 ggc gag aga gcc aca atc aat tgt cag tcc tcc cag agc gtg ctg ctg     96
Gly Glu Arg Ala Thr Ile Asn Cys Gln Ser Ser Gln Ser Val Leu Leu
            20                  25                  30 aac aat cag ctg tcc tgg ttc cag cag aag cct ggc cag cct ccc aag    144
Asn Asn Gln Leu Ser Trp Phe Gln Gln Lys Pro Gly Gln Pro Pro Lys
        35                  40                  45 ctg ctg atc tac gac gcc tcc aca ctg gag tcc ggc gtg ccc gat agg    192
Leu Leu Ile Tyr Asp Ala Ser Thr Leu Glu Ser Gly Val Pro Asp Arg
    50                  55                  60 ttc agc ggc tcc ggc agc ggc acc gac ttt acc ctg acc atc tcc agc    240
Phe Ser Gly Ser Gly Ser Gly Thr Asp Phe Thr Leu Thr Ile Ser Ser
65                  70                  75                  80 ctg cag gcc gag gat gtg gcc gtg tac tac tgc ctg ggc ggc tac agc    288
Leu Gln Ala Glu Asp Val Ala Val Tyr Tyr Cys Leu Gly Gly Tyr Ser
                85                  90                  95 ggc aac ctg tac gcc ttt ggc ggc ggc acc aag gtg gag atc aag        333
Gly Asn Leu Tyr Ala Phe Gly Gly Gly Thr Lys Val Glu Ile Lys
            100                 105                 110
```

<210> SEQ ID NO 52
<211> LENGTH: 111
<212> TYPE: PRT
<213> ORGANISM: Artificial Sequence
<220> FEATURE:
<223> OTHER INFORMATION: Synthetic Construct

<400> SEQUENCE: 52

Gly Asp Ile Val Met Thr Gln Ser Pro Asp Ser Leu Ala Val Ser Leu

```
1               5                   10                  15
Gly Glu Arg Ala Thr Ile Asn Cys Gln Ser Ser Gln Ser Val Leu Leu
                20                  25                  30

Asn Asn Gln Leu Ser Trp Phe Gln Gln Lys Pro Gly Gln Pro Pro Lys
                35                  40                  45

Leu Leu Ile Tyr Asp Ala Ser Thr Leu Glu Ser Gly Val Pro Asp Arg
            50                  55                  60

Phe Ser Gly Ser Gly Ser Gly Thr Asp Phe Thr Leu Thr Ile Ser Ser
65                  70                  75                  80

Leu Gln Ala Glu Asp Val Ala Val Tyr Tyr Cys Leu Gly Gly Tyr Ser
                85                  90                  95

Gly Asn Leu Tyr Ala Phe Gly Gly Gly Thr Lys Val Glu Ile Lys
                100                 105                 110
```

<210> SEQ ID NO 53
<211> LENGTH: 369
<212> TYPE: DNA
<213> ORGANISM: Artificial Sequence
<220> FEATURE:
<223> OTHER INFORMATION: chimeric sequences
<220> FEATURE:
<221> NAME/KEY: CDS
<222> LOCATION: (1)..(369)

<400> SEQUENCE: 53

```
ggc gag cag cag ctg gtg gag tcc ggc gga ggc ctg gtg cag cca gga      48
Gly Glu Gln Gln Leu Val Glu Ser Gly Gly Gly Leu Val Gln Pro Gly
1               5                   10                  15 gga agc ctg agg ctg tcc tgt gcc gtg agc ggc ttc tcc ctg agc tcc      96
Gly Ser Leu Arg Leu Ser Cys Ala Val Ser Gly Phe Ser Leu Ser Ser
                20                  25                  30 tac gcc atg agc tgg gtg agg cag gcc ccc gga aag ggc ctg gag tac     144
Tyr Ala Met Ser Trp Val Arg Gln Ala Pro Gly Lys Gly Leu Glu Tyr
            35                  40                  45 atc ggc atc atc agc agc agc ggc agc aca tac tac gcc agc tgg gcc     192
Ile Gly Ile Ile Ser Ser Ser Gly Ser Thr Tyr Tyr Ala Ser Trp Ala
        50                  55                  60 aag ggc agg ttc aca atc agc aag gat tcc tcc aag aat aca gtg tac     240
Lys Gly Arg Phe Thr Ile Ser Lys Asp Ser Ser Lys Asn Thr Val Tyr
65                  70                  75                  80 ctg cag atg ggc tcc ctg agg gcc gag gac atg gcc gtg tac ttc tgt     288
Leu Gln Met Gly Ser Leu Arg Ala Glu Asp Met Ala Val Tyr Phe Cys
                85                  90                  95 gcc aga gac agg gtc atc tat tcc atc ggc cct tac tac ttc aac ctg     336
Ala Arg Asp Arg Val Ile Tyr Ser Ile Gly Pro Tyr Tyr Phe Asn Leu
                100                 105                 110 tgg ggc ccc ggc aca ctg gtg aca gtg tcc agc                         369
Trp Gly Pro Gly Thr Leu Val Thr Val Ser Ser
            115                 120
```

<210> SEQ ID NO 54
<211> LENGTH: 123
<212> TYPE: PRT
<213> ORGANISM: Artificial Sequence
<220> FEATURE:
<223> OTHER INFORMATION: Synthetic Construct

<400> SEQUENCE: 54

```
Gly Glu Gln Gln Leu Val Glu Ser Gly Gly Gly Leu Val Gln Pro Gly
1               5                   10                  15

Gly Ser Leu Arg Leu Ser Cys Ala Val Ser Gly Phe Ser Leu Ser Ser
```

```
                20                  25                  30
Tyr Ala Met Ser Trp Val Arg Gln Ala Pro Gly Lys Gly Leu Glu Tyr
            35                  40                  45
Ile Gly Ile Ile Ser Ser Gly Ser Thr Tyr Tyr Ala Ser Trp Ala
         50                  55                  60
Lys Gly Arg Phe Thr Ile Ser Lys Asp Ser Lys Asn Thr Val Tyr
 65                  70                  75                  80
Leu Gln Met Gly Ser Leu Arg Ala Glu Asp Met Ala Val Tyr Phe Cys
                 85                  90                  95
Ala Arg Asp Arg Val Ile Tyr Ser Ile Gly Pro Tyr Tyr Phe Asn Leu
             100                 105                 110
Trp Gly Pro Gly Thr Leu Val Thr Val Ser Ser
             115                 120
```

<210> SEQ ID NO 55
<211> LENGTH: 333
<212> TYPE: DNA
<213> ORGANISM: Artificial Sequence
<220> FEATURE:
<223> OTHER INFORMATION: chimeric sequences
<220> FEATURE:
<221> NAME/KEY: CDS
<222> LOCATION: (1)..(333)

<400> SEQUENCE: 55

```
ggc gat tac cag atg aca cag tcc ccc tcc tcc ctg agc gcc tcc gtg    48
Gly Asp Tyr Gln Met Thr Gln Ser Pro Ser Ser Leu Ser Ala Ser Val
 1               5                  10                  15 gga gat agg gtg acc atc aca tgc cag gcc agc gag atc atc tac agc    96
Gly Asp Arg Val Thr Ile Thr Cys Gln Ala Ser Glu Ile Ile Tyr Ser
             20                  25                  30 aat ctg gcc tgg tac cag cag aag ccc ggc aag ccc ccc aag ctg ctg   144
Asn Leu Ala Trp Tyr Gln Gln Lys Pro Gly Lys Pro Pro Lys Leu Leu
         35                  40                  45 atc tac ggc gcc tcc aca ctg gcc agc ggc gtg cct agc aga ttc agc   192
Ile Tyr Gly Ala Ser Thr Leu Ala Ser Gly Val Pro Ser Arg Phe Ser
     50                  55                  60 ggc agc ggc tcc ggc acc gat tac acc ctg aca atc tcc agc ctg cag   240
Gly Ser Gly Ser Gly Thr Asp Tyr Thr Leu Thr Ile Ser Ser Leu Gln
 65                  70                  75                  80 cct gag gat ttt gcc aca tac tac tgt cag cag tcc ttc agc tcc aat   288
Pro Glu Asp Phe Ala Thr Tyr Tyr Cys Gln Gln Ser Phe Ser Ser Asn
                 85                  90                  95 aac gtg ggc aac atc ttc ggc ggc gga aca aag gtg gag atc aag       333
Asn Val Gly Asn Ile Phe Gly Gly Gly Thr Lys Val Glu Ile Lys
             100                 105                 110
```

<210> SEQ ID NO 56
<211> LENGTH: 111
<212> TYPE: PRT
<213> ORGANISM: Artificial Sequence
<220> FEATURE:
<223> OTHER INFORMATION: Synthetic Construct

<400> SEQUENCE: 56

```
Gly Asp Tyr Gln Met Thr Gln Ser Pro Ser Ser Leu Ser Ala Ser Val
 1               5                  10                  15

Gly Asp Arg Val Thr Ile Thr Cys Gln Ala Ser Glu Ile Ile Tyr Ser
             20                  25                  30

Asn Leu Ala Trp Tyr Gln Gln Lys Pro Gly Lys Pro Pro Lys Leu Leu
         35                  40                  45
```

```
Ile Tyr Gly Ala Ser Thr Leu Ala Ser Gly Val Pro Ser Arg Phe Ser
    50                  55                  60

Gly Ser Gly Ser Gly Thr Asp Tyr Thr Leu Thr Ile Ser Ser Leu Gln
65                  70                  75                  80

Pro Glu Asp Phe Ala Thr Tyr Tyr Cys Gln Gln Ser Phe Ser Ser Asn
                85                  90                  95

Asn Val Gly Asn Ile Phe Gly Gly Gly Thr Lys Val Glu Ile Lys
            100                 105                 110
```

<210> SEQ ID NO 57
<211> LENGTH: 11
<212> TYPE: PRT
<213> ORGANISM: Artificial Sequence
<220> FEATURE:
<223> OTHER INFORMATION: Derived from CD39

<400> SEQUENCE: 57

```
Ile Tyr Leu Thr Asp Cys Met Glu Arg Ala Arg
1               5                   10
```

<210> SEQ ID NO 58
<211> LENGTH: 11
<212> TYPE: PRT
<213> ORGANISM: Artificial Sequence
<220> FEATURE:
<223> OTHER INFORMATION: Derived from CD39

<400> SEQUENCE: 58

```
Leu Arg Met Glu Ser Glu Glu Leu Ala Asp Arg
1               5                   10
```

<210> SEQ ID NO 59
<211> LENGTH: 11
<212> TYPE: PRT
<213> ORGANISM: Artificial Sequence
<220> FEATURE:
<223> OTHER INFORMATION: Derived from CD39.

<400> SEQUENCE: 59

```
Arg Val Lys Gly Pro Gly Ile Ser Lys Phe Val
1               5                   10
```

<210> SEQ ID NO 60
<211> LENGTH: 12
<212> TYPE: PRT
<213> ORGANISM: Artificial Sequence
<220> FEATURE:
<223> OTHER INFORMATION: Derived from CD39

<400> SEQUENCE: 60

```
Asp Cys Met Glu Arg Ala Arg Glu Val Ile Pro Arg
1               5                   10
```

<210> SEQ ID NO 61
<211> LENGTH: 14
<212> TYPE: PRT
<213> ORGANISM: Artificial Sequence
<220> FEATURE:
<223> OTHER INFORMATION: Derived from CD39

<400> SEQUENCE: 61

```
Leu Thr Asp Cys Met Glu Arg Ala Arg Glu Val Ile Pro Arg
1               5                   10
```

```
<210> SEQ ID NO 62
<211> LENGTH: 13
<212> TYPE: PRT
<213> ORGANISM: Artificial Sequence
<220> FEATURE:
<223> OTHER INFORMATION: Derived from CD39

<400> SEQUENCE: 62

Ser Leu Ser Asn Tyr Pro Phe Asp Phe Gln Gly Ala Arg
1               5                   10

<210> SEQ ID NO 63
<211> LENGTH: 11
<212> TYPE: PRT
<213> ORGANISM: Artificial Sequence
<220> FEATURE:
<223> OTHER INFORMATION: Derived from CD39

<400> SEQUENCE: 63

Cys Arg Val Lys Gly Pro Gly Ile Ser Lys Phe
1               5                   10

<210> SEQ ID NO 64
<211> LENGTH: 18
<212> TYPE: PRT
<213> ORGANISM: Artificial Sequence
<220> FEATURE:
<223> OTHER INFORMATION: Derived from CD39

<400> SEQUENCE: 64

Gly Ala Tyr Gly Trp Ile Thr Ile Asn Tyr Leu Leu Gly Lys Phe Ser
1               5                   10                  15

Gln Lys

<210> SEQ ID NO 65
<211> LENGTH: 13
<212> TYPE: PRT
<213> ORGANISM: Artificial Sequence
<220> FEATURE:
<223> OTHER INFORMATION: Derived from CD39

<400> SEQUENCE: 65

Ile Leu Arg Asp Pro Cys Phe His Pro Gly Tyr Lys Lys
1               5                   10

<210> SEQ ID NO 66
<211> LENGTH: 446
<212> TYPE: PRT
<213> ORGANISM: Homo sapiens

<400> SEQUENCE: 66

Leu Ala Val Gly Leu Thr Gln Asn Lys Ala Leu Pro Glu Asn Val Lys
1               5                   10                  15

Tyr Gly Ile Val Leu Asp Ala Gly Ser Ser His Thr Ser Leu Tyr Ile
                20                  25                  30

Tyr Lys Trp Pro Ala Glu Lys Glu Asn Asp Thr Gly Val Val His Gln
            35                  40                  45

Val Glu Glu Cys Arg Val Lys Gly Pro Gly Ile Ser Lys Phe Val Gln
        50                  55                  60

Lys Val Asn Glu Ile Gly Ile Tyr Leu Thr Asp Cys Met Glu Arg Ala
65                  70                  75                  80

Arg Glu Val Ile Pro Arg Ser Gln His Gln Glu Thr Pro Val Tyr Leu
                85                  90                  95
```

```
Gly Ala Thr Ala Gly Met Arg Leu Leu Arg Met Glu Ser Glu Leu
            100                 105                 110

Ala Asp Arg Val Leu Asp Val Val Glu Arg Ser Leu Ser Asn Tyr Pro
        115                 120                 125

Phe Asp Phe Gln Gly Ala Arg Ile Ile Thr Gly Gln Glu Gly Ala
    130                 135                 140

Tyr Gly Trp Ile Thr Ile Asn Tyr Leu Leu Gly Lys Phe Ser Gln Lys
145                 150                 155                 160

Thr Arg Trp Phe Ser Ile Val Pro Tyr Glu Thr Asn Asn Gln Glu Thr
                165                 170                 175

Phe Gly Ala Leu Asp Leu Gly Gly Ala Ser Thr Gln Val Thr Phe Val
                180                 185                 190

Pro Gln Asn Gln Thr Ile Glu Ser Pro Asp Asn Ala Leu Gln Phe Arg
                195                 200                 205

Leu Tyr Gly Lys Asp Tyr Asn Val Tyr Thr His Ser Phe Leu Cys Tyr
    210                 215                 220

Gly Lys Asp Gln Ala Leu Trp Gln Lys Leu Ala Lys Asp Ile Gln Val
225                 230                 235                 240

Ala Ser Asn Glu Ile Leu Arg Asp Pro Cys Phe His Pro Gly Tyr Lys
                245                 250                 255

Lys Val Val Asn Val Ser Asp Leu Tyr Lys Thr Pro Cys Thr Lys Arg
                260                 265                 270

Phe Glu Met Thr Leu Pro Phe Gln Gln Phe Glu Ile Gln Gly Ile Gly
            275                 280                 285

Asn Tyr Gln Gln Cys His Gln Ser Ile Leu Glu Leu Phe Asn Thr Ser
    290                 295                 300

Tyr Cys Pro Tyr Ser Gln Cys Ala Phe Asn Gly Ile Phe Leu Pro Pro
305                 310                 315                 320

Leu Gln Gly Asp Phe Gly Ala Phe Ser Ala Phe Tyr Phe Val Met Lys
                325                 330                 335

Phe Leu Asn Leu Thr Ser Glu Lys Val Ser Gln Glu Lys Val Thr Glu
            340                 345                 350

Met Met Lys Lys Phe Cys Ala Gln Pro Trp Glu Glu Ile Lys Thr Ser
            355                 360                 365

Tyr Ala Gly Val Lys Glu Lys Tyr Leu Ser Glu Tyr Cys Phe Ser Gly
370                 375                 380

Thr Tyr Ile Leu Ser Leu Leu Leu Gln Gly Tyr His Phe Thr Ala Asp
385                 390                 395                 400

Ser Trp Glu His Ile His Phe Ile Gly Lys Ile Gln Gly Ser Asp Ala
                405                 410                 415

Gly Trp Thr Leu Gly Tyr Met Leu Asn Leu Thr Asn Met Ile Pro Ala
                420                 425                 430

Glu Gln Pro Leu Ser Thr Pro Leu Ser His Ser Thr Tyr Val
            435                 440                 445
```

METHODS AND COMPOSITIONS FOR PROMOTING AND POTENTIATING T-CELL MEDIATED IMMUNE RESPONSES THROUGH ADCC TARGETING OF CD39 EXPRESSING CELLS

CROSS-REFERENCE TO RELATED APPLICATIONS

This application claims the benefit of priority to U.S. Provisional Application Ser. No. 62/885,509, filed on 12 Aug. 2019; the entire contents of said application are incorporated herein in their entirety by this reference.

REFERENCE TO A SEQUENCE LISTING

This application contains a Sequence Listing in computer readable form. The computer readable form is incorporated herein by reference. Said ASCII copy, created on May 19, 2023, is named PNC-00101_SL and is 96,965 bytes in size.

BACKGROUND OF THE INVENTION

For people with advanced cancers, hope can be a valuable but rare commodity. In recent years, a new class of drugs called immune checkpoint inhibitors has shown remarkable promise, keeping tumors at bay and preventing them from growing, and allowing some people who receive the treatments to essentially be cured. But these groundbreaking therapies have a substantial challenge. Despite the success of immunotherapies in advanced cancers based on inhibitory antibodies to programmed cell death protein 1(PD1), PD1 ligand 1 (PDL1) and cytotoxic T lymphocyte antigen 4 (CTLA4) therapies in advanced cancer, a considerable proportion of patients remain unresponsive to these treatments. With increasing attention on the immunosuppressive tumor microenvironment as a major driver of resistance, and characterization of "hot" and "cold" tumors depending on the level of immune cell infiltration, researchers have found several different mechanisms underlying the lack of efficacious responses to checkpoint monotherapies. Immunologically "hot" tumors contain high levels of infiltrating T cells and more antigens, making them more recognizable by the immune system and more likely to trigger a strong immune response. Among the cancers considered to be immunologically hot are bladder, head and neck, kidney, melanoma, and non-small cell lung cancers. However, even within these immunologically "hot" cancers, it is still only the minority of patients who derive benefit from immunotherapy. In contrast, immunologically "cold" tumors are cancers that for various reasons contain few infiltrating T cells, do not appear to be recognized as foreign and do not provoke a strong response by the immune system, making these cancers difficult to treat with current immunotherapies. Cancers that are classically immunologically "cold" include glioblastomas, as well as ovarian, prostate, pancreatic, and most breast cancers.

The microenvironment of tumors contains numerous cell types in addition to cancer cells, which include bone marrow-derived inflammatory cells, lymphocytes, blood vessels, fibroblastic cells, and the extracellular matrix (ECM) composed of collagen and proteoglycans. Indeed, tumor drug responses are not exclusively determined by the tumor cell's intrinsic characteristics because tumor-associated stromal cells, including fibroblasts, mesenchymal stromal cells (MSCs), immuno-inflammatory cells, vascular endothelial cells and the ECM combine in response to anti-cancer treatment. In many instances, whether the tumor has T-cell infiltration or lacks T-cell infiltration, the resistance or unresponsiveness to checkpoint therapy is the consequence of suppressive effects of other cells present in the tumor—the suppressive effects ranging from intratumoral signaling that results in downregulation or inhibition of cytotoxic T-cells already present in the tumor to developing a tumor microenvironment that excludes cytotoxic T-cells altogether by reducing the ability of those cells to extravasate into the tumor from the surrounding vascular.

Accordingly, there is a great need in the art to identify alternative mechanisms for potentiating T-cell responses.

SUMMARY OF THE INVENTION

The ectonucleotidase CD39 has been targeted to produce a decrease in the intratumoral level of the enzymatic activity associated with that protein, and, in doing so, reduce the intratumoral levels of the immunosuppressive agent, adenosine. The present invention is based, at least in part, on the additional discovery that CD39 is expressed by a range of cells in the tumor microenvironment, such as stromal cells, type II NKT cells and tumor-associated macrophages (TAMs) that serve to produce an immunosuppressive or immune exclusionary environment, and that targeting those cells for ablation in the tumor using certain antibody-dependent cellular cytotoxicity (ADCC) competent anti-CD39 antibodies can be used to increase infiltration of cytotoxic T-cells and, in effect, convert "cold" tumors into immunologically "hot" ones.

For example, in one aspect, an anti-CD39 antibody, or antigen-binding fragment thereof, comprising (i) at least one antigen binding domain that binds ectonucleoside triphosphate diphosphohydrolase-1 (CD39) at a site such that the anti-CD39 antibody forms a stable immune complex, and (ii) an FcγRIIIa binding moiety that binds FcγRIIIa receptor and confers ADCC activity against CD39+ cells to the anti-CD39 antibody, is provided.

Numerous embodiments are further provided that may be applied to any aspect of the present invention and/or combined with any other embodiment described herein. For example, in one embodiment, the anti-CD39 antibody, or antigen-binding fragment thereof, promotes: (i) stable immune complex formation when incubated with HCC1739BL cells as characterized by loss of less than 40% of the immune complex after 24 hours, or less than 35%, less than 30%, less than 25%, less than 20%, less than 15% or even less than 10% after 24 hours, optionally wherein the immune complex formation is detected by fluorescent intensity using a fluorescently labeled secondary antibody (e.g., merely to illustrate, the stability of an immune complex formed with an anti-CD39 antibody can be determined by incubating anti-CD39 monoclonal antibodies (mAbs) (e.g., at 2 μg/ml or greater) with HCC1739BL cells for different times and then detecting the presence of immune complex by fluorescent conjugated secondary antibody); (ii) complement dependent cytotoxicity (CDC) activity against CD39+ cells; (iii) antibody-mediated target cytosis of CD39 on CD45+ immune cells; (iv) antibody-mediated target cytosis of CD39 from tumor vascular endothelium disruption or vasculature network collapse in a tumor; (v) binding to a CD39 epitope having a sequence selected from the group of CD39 amino acid epitope sequence listed in FIG. 33; and/or (vi) binding to CD39 in a manner that is non-competitive or only partially competitive with monoclonal antibody clone A1 binding to CD39.

In another embodiment, the FcγRIIIa binding moiety is selected from the group consisting of an Fc domain, an antibody or fragment thereof that binds to FcγRIIIa, and an FcγRIIIa binding peptide. In still another embodiment, the antigen binding domain is selected from the group consisting of a Fab, Fab', F(ab')$_2$, Fv or single chain Fv (scFv), Fav, dsFv, sc(Fv)2, Fde, sdFv, single domain antibody (dAb), and diabodies fragments and/or wherein the anti-CD39 antibody, or antigen-binding fragment, is monoclonal. In yet another embodiment, the anti-CD39 antibody, or antigen-binding fragment thereof, is conjugated to an agent, optionally wherein the agent is selected from the group consisting of a binding protein, an enzyme, a drug, a chemotherapeutic agent, a biologic agent, a toxin, a radionuclide, an immunomodulatory agent, a detectable moiety, and a tag. In another embodiment, the anti-CD39 antibody, or antigen-binding fragment thereof, has a VH domain with an amino acid sequence that can be encoded by the nucleic acid sequence of or a nucleic acid that hybridizes under stringent conditions to the nucleic acid of SEQ ID No. 1 and a VL domain with an amino acid sequence that can be encoded by the nucleic acid sequence of or a nucleic acid that hybridizes under stringent conditions to the nucleic acid of SEQ ID No. 3 (such as hybrididzation under 6× sodium chloride/sodium citrate (SSC) at 45° C., and washing in 0.2×SSC/0.1% SDS at 50-65° C.). In still another embodiment, the anti-CD39 antibody, or antigen-binding fragment thereof, comprises a heavy chain having CDRs at least 60% identical (e.g., at least 65%, 70%, 75%, 80%, 81%, 82%, 83%, 84%, 85%, 86%, 87%, 88%, 89%, 90%, 91%, 92%, 93%, 94%, 95%, 96%, 97%, 98%, 99%, or greater) to the CDRs of SEQ ID No. 2, 6, 10, 14, 18, 22, 26, 42, 46, 50, or 54, and a light chain having CDRs at least 60% identical (e.g., at least 65%, 70%, 75%, 80%, 81%, 82%, 83%, 84%, 85%, 86%, 87%, 88%, 89%, 90%, 91%, 92%, 93%, 94%, 95%, 96%, 97%, 98%, 99%, or greater) to the CDRs of SEQ ID No. 4, 8, 12, 16, 20, 24, 28, 44, 48, 52, or 56. In yet another embodiment, the anti-CD39 antibody, or antigen-binding fragment thereof, comprises a variable heavy (VH) chain at least 60% identical (e.g., at least 65%, 70%, 75%, 80%, 81%, 82%, 83%, 84%, 85%, 86%, 87%, 88%, 89%, 90%, 91%, 92%, 93%, 94%, 95%, 96%, 97%, 98%, 99%, or greater) to SEQ ID No. 2, 6, 10, 14, 18, 22, 26, 42, 46, 50, or 54, and a variable light (VL) chain at least 60% identical (e.g., at least 65%, 70%, 75%, 80%, 81%, 82%, 83%, 84%, 85%, 86%, 87%, 88%, 89%, 90%, 91%, 92%, 93%, 94%, 95%, 96%, 97%, 98%, 99%, or greater) to SEQ ID No. 4, 8, 12, 16, 20, 24, 28, 44, 48, 52, or 56. In another embodiment, the anti-CD39 antibody, or antigen-binding fragment thereof, comprises: (i) a heavy chain having a CDR1 amino acid sequence at least 80% identical (e.g., at least 81%, 82%, 83%, 84%, 85%, 86%, 87%, 88%, 89%, 90%, 91%, 92%, 93%, 94%, 95%, 96%, 97%, 98%, 99%, or greater) to SEQ ID No. 29, a CDR2 amino acid sequence at least 80% (e.g., at least 81%, 82%, 83%, 84%, 85%, 86%, 87%, 88%, 89%, 90%, 91%, 92%, 93%, 94%, 95%, 96%, 97%, 98%, 99%, or greater) identical to SEQ ID No. 30, and a CDR3 amino acid sequence at least 80% identical (e.g., at least 81%, 82%, 83%, 84%, 85%, 86%, 87%, 88%, 89%, 90%, 91%, 92%, 93%, 94%, 95%, 96%, 97%, 98%, 99%, or greater) to SEQ ID No. 31; and (ii) a light chain having a CDR1 amino acid sequence at least 80% identical (e.g., at least 81%, 82%, 83%, 84%, 85%, 86%, 87%, 88%, 89%, 90%, 91%, 92%, 93%, 94%, 95%, 96%, 97%, 98%, 99%, or greater) to SEQ ID No. 32, a CDR2 amino acid sequence at least 80% identical (e.g., at least 81%, 82%, 83%, 84%, 85%, 86%, 87%, 88%, 89%, 90%, 91%, 92%, 93%, 94%, 95%, 96%, 97%, 98%, 99%, or greater) to SEQ ID No. 33, and a CDR3 amino acid sequence at least 80% identical (e.g., at least 81%, 82%, 83%, 84%, 85%, 86%, 87%, 88%, 89%, 90%, 91%, 92%, 93%, 94%, 95%, 96%, 97%, 98%, 99%, or greater) to SEQ ID No. 34. In still another embodiment, the anti-CD39 antibody, or antigen-binding fragment thereof, comprises a heavy chain having CDRs selected from the group consisting of CDRs of SEQ ID No. 6, 10, 14, 18, 22, 26, 42, 46, 50, and 54, and a light chain having CDRs selected from the group consisting of CDRs of SEQ ID No. 8, 12, 16, 20, 24, 28, 44, 48, 52, or 56, and human framework sequences to form humanized heavy and light chains with an antigen binding site able to specifically bind human CD39. In yet another embodiment, the anti-CD39 antibody, or antigen-binding fragment thereof, comprises an Fc domain of an IgG1 or IgG3 isotype, optionally wherein the Fc domain is human. In another embodiment, the anti-CD39 antibody, or antigen-binding fragment thereof, is hypofucosylated or afucosylated. In still another embodiment, the anti-CD39 antibody, or antigen-binding fragment thereof, is human or is humanized. In yet another embodiment, the anti-CD39 antibody, or antigen-binding fragment thereof, is a bispecific including at least one additional antigen binding site for a tumor antigen, immune checkpoint, or costimulatory receptor, wherein if the additional antigen binding site is for an immune checkpoint it functions as a checkpoint inhibitor and wherein if the additional antigen binding site is for a costimulatory receptor it functions as a costimulatory agonist. In another embodiment, the additional antigen binding site binds to a checkpoint protein selected from the group consisting of PD-1, PD-L1, CTLA-4/B7-1/B7-2, PD-L2, NKG2A, KIR, LAG-3, TIM-3, CD96, VISTA, TIGIT and Siglec-15. In still another embodiment, the additional antigen binding site binds a checkpoint protein upregulated on T-cells and associated with T-cell exhaustion. In yet another embodiment, the additional antigen binding site binds to an immune costimulatory receptors selected from the group consisting of MHCI molecules, BTLA receptor, OX40, CD27, CD28, CDS, ICAM-1, LFA-1 (CD11a/CD18), ICOS (CD278) and 4-1BB (CD137). In another embodiment, the additional antigen binding site binds to CD47, SIRPM, CD24 or Siglec-10.

In another aspect, a pharmaceutical preparation comprising a therapeutically effective amount of at least one anti-CD39 antibody, or antigen-binding fragment thereof, described herein, and one or more pharmaceutically acceptable excipients, buffers or solutions, is provided. For example, the pharmaceutical preparation can be for improving anti-tumor T cell immunity and suitable for administration to a subject having a tumor, comprising an effective amount of the anti-CD39 antibody, or antigen-binding fragment thereof, and one or more pharmaceutically acceptable excipients, buffers or solutions, wherein administration of the anti-CD39 antibody to the subject results in a reduction in numbers of intratumoral CD39$^{high}$ cells and enhances T-cell infiltration into the tumor or decreases T-cell exhaustion in the tumor or both.

In still another aspect, an isolated nucleic acid molecule that i) hybridizes, under stringent conditions, with the complement of a nucleic acid encoding an immunoglobulin heavy and/or light chain polypeptide of an anti-CD39 antibody, or antigen-binding fragment thereof, described herein; ii) has a sequence with at least about 90% identity across its full length to a nucleic acid encoding an immunoglobulin heavy and/or light chain polypeptide of an anti-CD39 antibody, or antigen-binding fragment thereof, described herein; or iii) encodes an immunoglobulin heavy and/or light chain polypeptide of an anti-CD39 antibody, or antigen-binding fragment thereof, described herein, is provided.

In yet another aspect, an isolated immunoglobulin heavy and/or light chain polypeptide encoded by a nucleic acid descried herein, is provided.

In another aspect, a vector comprising an isolated nucleic acid described herein, is provided, optionally wherein the vector is an expression vector.

In still another aspect, a host cell which comprises an isolated nucleic acid described herein, that: a) expresses an anti-CD39 antibody, or antigen-binding fragment thereof, described herein; b) comprises the immunoglobulin heavy and/or light chain polypeptide of a polypeptide described herein; or c) comprises a vector described herein, is provided.

In yet another aspect, a device or kit comprising at least one anti-CD39 antibody, or antigen-binding fragment thereof, described herein is provided. The device or kit optionally comprises a label to detect at least one anti-CD39 antibody, or antigen-binding fragment thereof, or a complex comprising the anti-CD39 antibody, or antigen-binding fragment thereof.

In another aspect, a device or kit comprising a pharmaceutical composition, isolated nucleic acid molecule, isolated immunoglobulin heavy and/or light chain polypeptide, vector, and/or host cell described herein, is provided.

In still another aspect, a method of producing at least one anti-CD39 antibody, or antigen-binding fragment thereof, of any one of claims 1-18, which method comprises the steps of: (i) culturing a transformed host cell which has been transformed by a nucleic acid comprising a sequence encoding at least one anti-CD39 antibody, or antigen-binding fragment thereof, under conditions suitable to allow expression of said anti-CD39 antibody, or antigen-binding fragment thereof; and (ii) recovering the expressed anti-CD39 antibody, or antigen-binding fragment thereof.

In yet another aspect, a method of detecting the presence or level of CD39 polypeptide comprising obtaining a sample and detecting said polypeptide in the sample by use of at least one anti-CD39 antibody, or antigen-binding fragment thereof, described herein, is provided. For example, the at least one anti-CD39 antibody, or antigen-binding fragment thereof, can form a complex with the CD39 polypeptide and the complex can be detected in the form of an enzyme linked immunosorbent assay (ELISA), radioimmune assay (RIA), immunochemical assay, Western blot, mass spectrometry assay, nuclear magnetic resonance assay, or using an intracellular flow assay.

In another aspect, a method for improving anti-tumor T cell immunity by depleting intratumoral $CD39^{high}$ cells, comprising administering to a subject having a tumor an effective amount of a pharmaceutical composition of an anti-CD39 antibody, or antigen-binding fragment thereof, described herein, wherein administration of the anti-CD39 antibody, or antigen-binding fragment thereof, results in a reduction in numbers of intratumoral $CD39^{high}$ cells and enhances T-cell infiltration into the tumor or decreases T-cell exhaustion in the tumor or both, is provided.

In still another aspect, a method for promoting immune cell infiltration into tumors, comprising administering to a subject having a tumor an effective amount of a pharmaceutical composition of an anti-CD39 antibody, or antigen-binding fragment thereof, described herein, wherein administration of the anti-CD39 antibody, or antigen-binding fragment thereof, results in ablation and reduction of CD39+ CD45− SCA-1+ stromal cells in the tumor and increased infiltration of the tumor with cytotoxic T-cells, is provided.

In yet another aspect, a method for reducing type II NKT cells suppression of intratumoral immune cell function, comprising administering to a subject having a tumor an effective amount of a pharmaceutical composition of an anti-CD39 antibody, or antigen-binding fragment thereof, described herein, wherein administration of the anti-CD39 antibody, or antigen-binding fragment thereof, results in ablation and reduction of type II NKT cells cell in the tumor, is provided.

In another aspect, a method for reducing regulatory T cells (Treg) suppression of intratumoral immune cell function, comprising administering to a subject having a tumor an effective amount of a pharmaceutical composition of an anti-CD39 antibody, or antigen-binding fragment thereof, described herein, wherein administration of the anti-CD39 antibody, or antigen-binding fragment thereof, results in ablation and reduction of $CD39^{high}$ Tregs in the tumor, is provided.

In yet another aspect, a method for reducing tumor-associated macrophages (TAMs) suppression of intratumoral immune cell function, comprising administering to a subject having a tumor an effective amount of a pharmaceutical composition of an anti-CD39 antibody, or antigen-binding fragment thereof, described herein, wherein administration of the anti-CD39 antibody, or antigen-binding fragment thereof, results in ablation and reduction of $CD39^{high}$ TAMs in the tumor, is provided.

In still another aspect, a method for promoting an anti-tumor immune response comprising administering to a subject having a tumor an anti-CD39 antibody, or antigen-binding fragment thereof, described herein, in an amount sufficient to result in a reduction of CD39 expressing cells in the tumor, is provided.

In yet another aspect, a method for promoting T-cell mediated immune function in a tumor of a subject, comprising (i) identifying a cancer subject having a degree of tumor infiltrated tumor-reactive lymphocytes that is below a predetermined threshold so as to be characterized as being a non-infiltrated or under-infiltrated tumor phenotype; and (ii) administering to the subject an anti-CD39 antibody, or antigen-binding fragment thereof, described herein in an amount that increases tumor infiltration by tumor-reactive T-cells, is provided.

As described above, numerous embodiments are further provided that may be applied to any aspect of the present invention and/or combined with any other embodiment described herein.

For example, in one embodiment, the intratumoral $CD39^{high}$ cells are selected from hematopoietic stem or progenitor cells (CD45-Sca-1+), CD39+ NKT cells, CD39+ macrophages, CD39+ cancer cells, CD39+ endothelial cells or a combination thereof. In another embodiment, the anti-CD39 antibody, or antigen-binding fragment thereof, reduces levels of $CD39^{high}$ cells occurring within one or more hematopoietic compartments, optionally wherein the one or more hematopoietic compartments is selected from the group consisting of blood, spleen and liver. In still another embodiment, the anti-CD39 antibody, or antigen-binding fragment thereof, is administered as part of an antitumor therapy. In yet another embodiment, the anti-CD39 antibody, or antigen-binding fragment thereof, is administered as part of an anti-infective therapy, optionally wherein the anti-infect therapy is antiviral therapy (including treatment of HIV and HBV infection as well as COVID-19 infection), treatment for *Mycobacterium tuberculosis*, and treatment for visceral leishmaniasis. In another embodiment, the anti-CD39 antibody, or antigen-binding fragment thereof, is administered as part of an antitumor therapy for treating a solid tumor, optionally wherein the solid tumor is pancreatic cancer, liver cancer, lung cancer, stomach cancer, esophageal cancer, head and neck squamous cell carcinoma, prostate cancer, colon cancer, breast cancer, lymphoma, gallbladder cancer, renal cancer, multiple myeloma, ovarian cancer, cervical cancer or glioma. In still another embodiment, the anti-CD39 antibody, or antigen-binding fragment thereof, is administered as part of an antitumor therapy for treating a liquid tumor, optionally wherein the liquid tumor is a leukemia. In yet another embodiment, the anti-CD39 antibody, or antigen-binding fragment thereof, is administered as part of a therapy involving one or more chemotherapeutic agents, anti-angiogenetic agents, immuno-oncology agents and/or radiation. In another embodiment, the therapy includes administering one or more inhibitors (antagonists) of one or more checkpoint molecules, optionally wherein the one or more checkpoint molecules is selected from the group consisting of a PD-1 antagonists, a CTLA-4 antagonist, a LAG-3 antagonist, a TIM-3 antagonist, a TIGIT antagonist and a Siglec-15 antagonist. In still another embodiment, the therapy includes administering one or more activators (agonists) of one or more costimulatory molecules, optionally wherein the one or more costimulatory molecules is selected from the group consisting of a GITR agonist, a CD27 agonist, a 4-1BB agonist, an OX40 agonist, a CD137 agonist, an ICOS agonist and a CD28 agonist. In yet another embodiment, the therapy includes administering one or more of a VEGFR or VEGF antagonist, an EGFR or EGF antagonist, an IDO inhibitor, an IDO1 inhibitor, an HDAC inhibitor, a PI3K delta inhibitor, an IL-15 agonist, a CXCR4 antagonist, a CXCL12 antagonist, a DNMT inhibitor, interleukin-21, an anti-KIR antibody, an anti-CSF-1R antibody, an anti-CCR4 antibody, GMCSF, an anti-PS antibody, an anti-CD30 antibody-aurstatin E conjugate, an anti-CD19 antibody, an anti-CEA IL-2 antibody, an anti-NY-ESO-1 antibody, an anti-NKG2A antibody, a STING agonist, a TRL7/8 agonist, a RIG-1 agonist and/or NRLP3 inhibitor, an anti-CD73 antibody (such as MED19447), a P2X7 antagonist or an adenosine A2A receptor antagonist. In another embodiment, the therapy includes administering one or more innate immune inducers, optionally wherein the one or more innate immune inducers is selected from the group consisting of an inhibitor of the CD47-SIRPα axis (e.g., antibodies or other binding moieties that bind to CD47 or SIRPα and inhibit the interaction of the two molecules), an inhibitor of the CD24-Siglec-10 axis (e.g., antibodies or other binding moieties that bind to CD24 or Siglec-10 and inhibit the interaction of the two molecules), an NGK2A checkpoint inhibitor that blocks HLA-E driven inhibition of NK and CD8+ cells, a STING agonist, a TLR7/8 agonist and an RIG-1 agonist. In still another embodiment, the anti-CD39 antibody, or antigen-binding fragment thereof, is administered as a part of therapy including a tumor vaccine, adoptive cell therapy (including CAR-T and ACTR therapy), antitumor gene therapy, inhibitory nucleic acid therapy (such as siRNA, shRNA, antisense, CRISPR and TALEN therapy) and/or oncolytic viral therapy. In yet another embodiment, the subject is an animal model of cancer. In another embodiment, the subject is a mammal, optionally wherein the mammal is a human or a rodent.

DETAILED DESCRIPTION OF THE INVENTION

I. Overview

Figure 1:
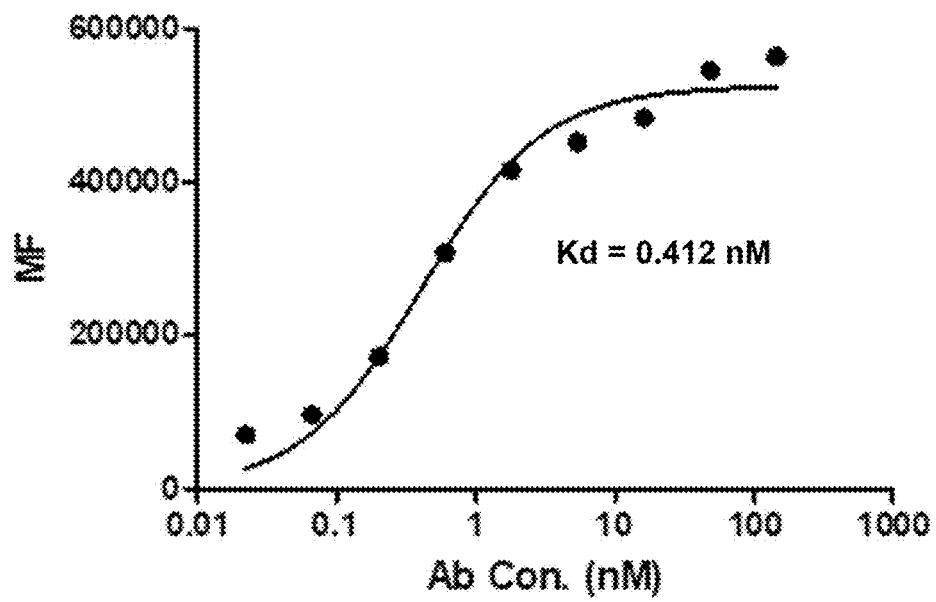
FIG. 1. Affinity of Ig39-21 measured by flow cytometry using human CD39hi human B lymphoblastoid (HCC1739BL) cells. Our fully human anti-CD39 antibody clone Ig39-21 produced by transient transfection was serially diluted as indicated and incubated with HCC1739BL cells for 30 minutes at 4° C., followed by flow cytometric analysis. Kd was calculated as 0.412 nM.
Figure 2:
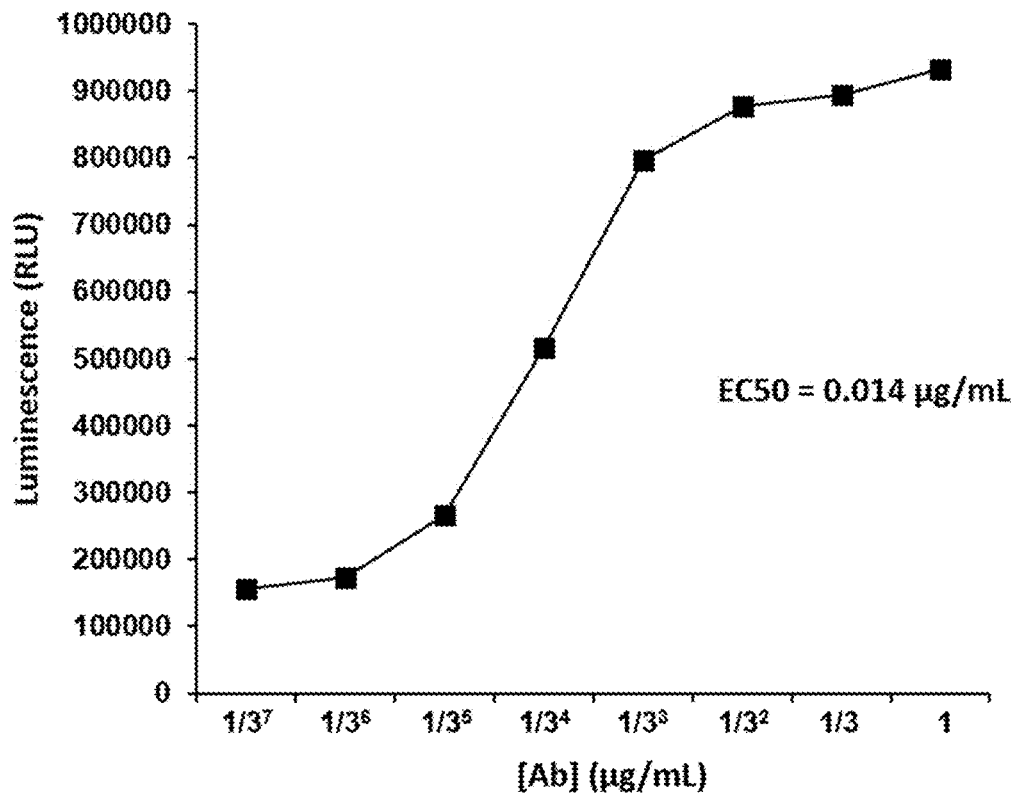
FIG. 2. Ig39-21 demonstrates ADCC activity against HCC1739BL cells: Luc-reporter assay. HCC1739BL cells were used as target cells. Jurkat cells stably expressing luciferase and hCD16a-158V were used as effector cells. Target cells were pre-incubated with serially diluted Ig39-21 as indicated for 30 minutes at 37° C. in 5% $CO_2$, followed by co-culture with effector cells (T:E=1:6) for 6 hours. ADCC activity was indicated by an increase of luciferase activity over background. RLU: Relative Luminescence Unit. EC50 was calculated as 0.014 μg/mL.

Extracellular adenosine has been known as an inhibitor of immune functions. While intracellular adenosine is involved in energy metabolism, nucleic acid metabolism, and the methionine cycle, in the tumor microenvironment extracellular adenosine plays an important role in suppressing immune signaling. Immunosuppressive adenosine 3'5'-monophosphate (cAMP)-mediated pathway, signaling through adenosine A2A receptor (A2AR), can inhibit T lymphocytes and natural killer (NK) cells in hypoxic, inflamed, and cancerous microenvironment (Ohta et al. (2006) $Proc\ Natl\ Acad\ Sci\ USA$, 103:13132-7). Preclinical proof, along with recent and evolving positive clinical trial data, demonstrates that the administration of A2AR inhibitors can be a potential novel strategy for immunotherapy. In addition, blocking the adenosine-generating pathway involving CD39/CD73 also induces regression of breast cancer, colorectal cancer and melanoma in experimental animal models. In the case of anti-CD39 and anti-CD73 antibody therapies, the focus is predominantly on the inhibition or reduction of ATP and derivative nucleotide catabolism, ultimately to adenosine through binding to these cell surface adenosine generating enzymes ("ectonucleotidases") and inhibiting the enzymatic activity or removing the enzymatic activity from the cell surface.

The present invention is based at least in part on the discovery that certain antibodies to CD39 are capable of selectively targeting and ablating, such as by antibody-dependent cellular cytotoxicity, CD39 expressing cells in the tumor microenvironment—more efficiently than anti-CD39 antibodies in the prior art—including CD39+ CD45– SCA-1+ stromal cells (such as hematopoietic progenitor cells), CD39+ NKT cells, CD39+ macrophages, and CD39+ endothelial cells, as well as CD39+ cancer cells. The resulting reduction in numbers of intratumoral CD39$^{high}$ cells can lead to such changes in the inflammatory phenotype of the tumor as enhanced T-cell infiltration into the tumor, decreased T-cell exhaustion in the tumor, reduced type II NKT cells suppression of intratumoral immune cell function, and/or reduced regulatory T cells (Treg) suppression of intratumoral immune cell function, and/or reduced tumor-associated macrophages (TAMs) suppression of intratumoral immune cell function.

While not wishing to be bound by any particular theory, certain of the antibodies generated by the inventors are capable of forming more stable immune complexes with CD39 in order to produce a more potent ADCC killing efficacy. Antibodies that are not able to form as stable an immune complex with CD39 as those encompassed by the present invention, inventors have observed, result in reduction of CD39 from the surface but through a mechanism of increased shedding of CD39 or cytosis (internalization) and not have the same efficacy in terms of being able to ablate the CD39 expressing cells by antibody-dependent cellular cytotoxicity. In certain embodiments, certain antibodies encompassed by the present invention have been shown to bind to epitopes on CD39 that are non-competitive with or only partially competitive with the binding of the monoclonal antibody clone A1 to CD39.

As described in greater detail in the Exemplary Methods and illustrated in the Figures, rather than direct inhibition of CD39 NTPase activity, e.g. by all anti-CD39 therapeutic antibodies in the prior art (Perrot et al., 2019, $Cell\ Reports$ 27:2411-2425; Li et al., 2020, $Cancer\ Discovery$ 9(12):CD-19-0541; and PCT Publ. WO 2017/089334), our anti-CD39 antibodies were specifically designed to have human constant regions with an IgG1 Fc domain. This design confers FcγRIIIa receptor-dependent cellular activities e.g. antibody-dependent cellular cytotoxicity (ADCC) and complement dependent cytotoxicity (CDC) against CD39+ cells, and/or antibody-mediated target cytosis of intratumoral CD39+ cells, to the anti-CD39 antibodies of the instant invention. Consequently, such cellular activities result in ablation and reduction of CD39$^{high}$ cells in the tumor.

Exemplary features of the subject anti-CD39 monoclonal antibodies, features which are taught away from for use in therapeutic anti-CD39 antibodies described in the literature, are summarized as below.

The subject antibodies target CD39+ cells in the tumor through FcγRIIIa receptor-dependent activity e.g. ADCC.

Figure 13:
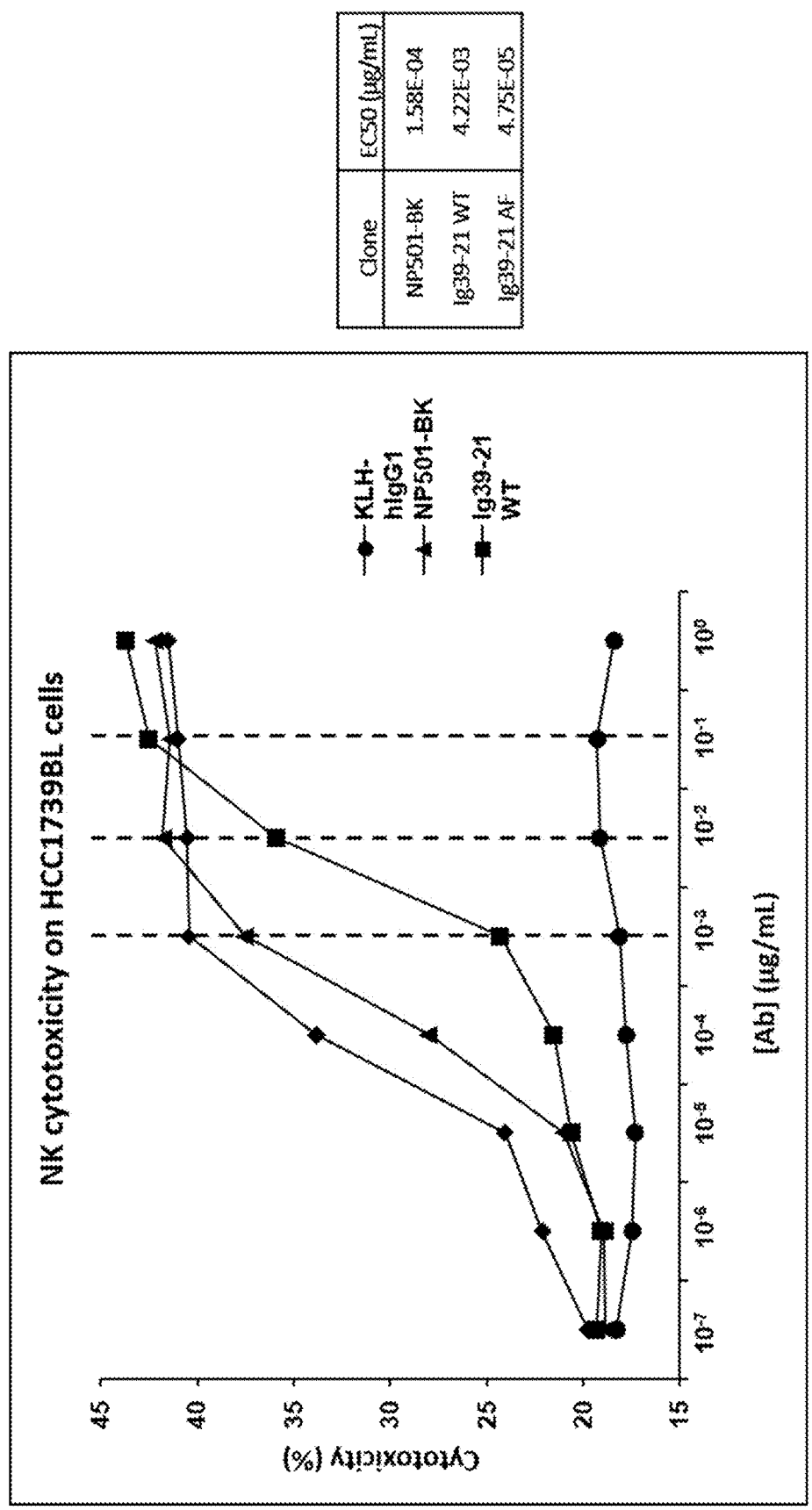
FIG. 13. NP501-BK and Ig39-21 AF exert much higher ADCC activity than Ig39-21 WT: NK cytotoxicity toward HCC1739BL cells. CFSE-labeled HCC1739BL target cells were incubated with serially diluted human IgG1 isotype control antibody (KLH-hIgG1) or fully human anti-CD39 monoclonal antibodies (Ig39-21 WT, Ig39-21 AF or NP501-BK) as indicated for 30 minutes at 37° C. in 5% $CO_2$. Cells were then co-cultured with NK-92-CD16 V/V effector cells (E:T=1:8) for 6 hours at 37° C. Target cell death was analyzed by flow cytometry and % of CFSE$^+$P/I$^+$ cells (% of cytotoxicity) was calculated. EC50 was calculated as 1.58E-04 µg/mL (NP501-BK), 4.22E-03 µg/mL (Ig39-21 WT) and 4.75E-05 µg/mL (Ig39-21 AF).
Figure 14:
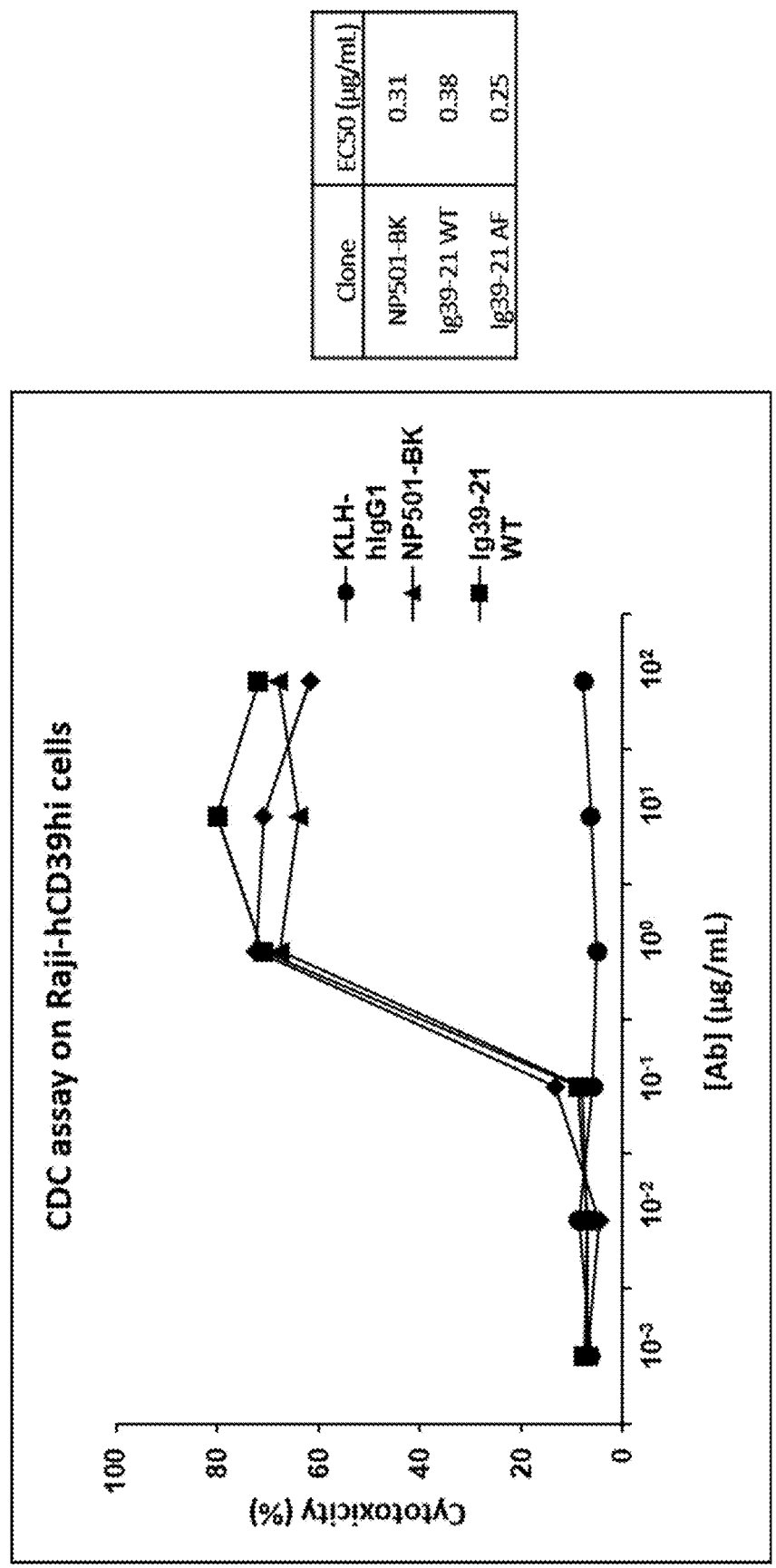
FIG. 14. Fully human anti-CD39 antibodies exhibit similar CDC activity toward Raji-hCD39hi cells. Raji-hCD39hi target cells were pre-incubated with serially diluted human IgG1 isotype control (KLH-hIgG1) or fully human anti-CD39 monoclonal antibodies (Ig39-21 WT, Ig39-21 AF or NP501-BK) for 30 minutes at 37° C. and further exposed to 10% Normal Human Serum (NHS) for 2 hours. Target cell lysis was analyzed by flow cytometry and % P/I$^+$ cells (% of cytotoxicity) was calculated. EC50 was calculated as 0.31 µg/mL (NP501-BK), 0.38 µg/mL (Ig39-21 WT) and 0.25 µg/mL (Ig39-21 AF)
Figure 15:
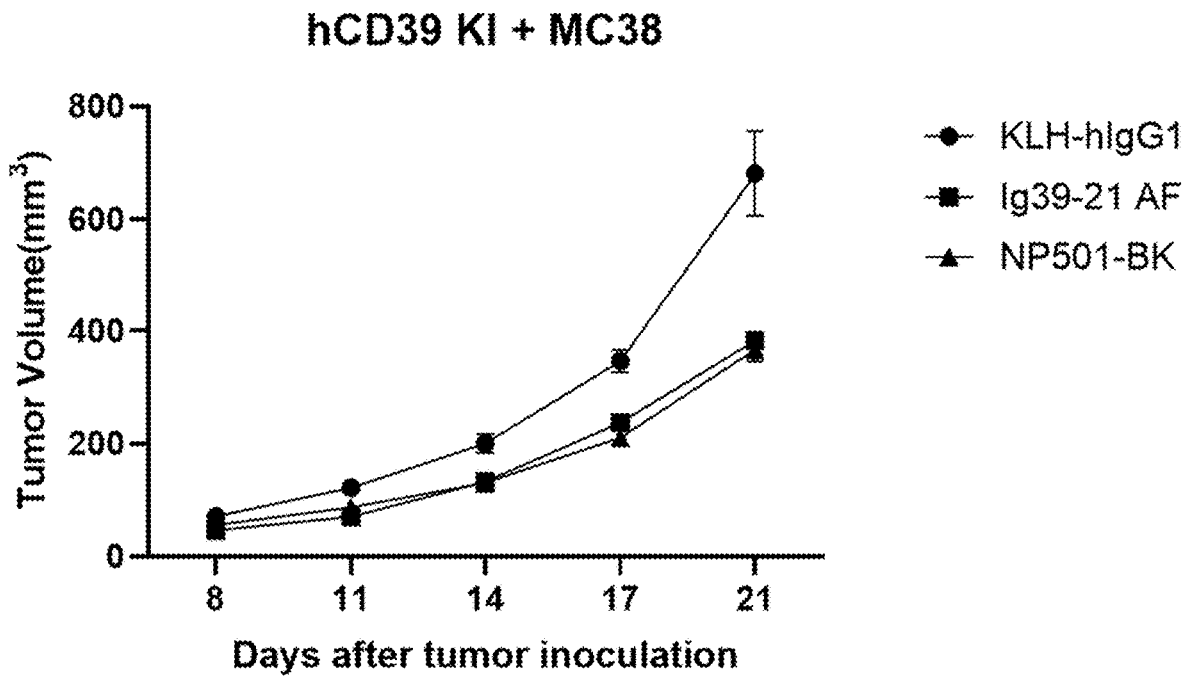
FIG. 15. NP501-BK and Ig39-21 AF exert similar anti-tumor efficacy in vivo. C57BL6 humanized CD39 mice (hCD39 KI) subcutaneously implanted with MC38 cells were treated with 5 mg/kg of human IgG1 isotype control antibody (KLH-hIgG1), or fully human anti-CD39 monoclonal antibodies (Ig39-21 AF or NP501-BK) on days 8, 11, 14 and 17 after tumor challenge. Tumor length (L) and width (W) were measured using a digital caliper twice weekly. Tumor volume (mm$^3$) was determined as L*W*W*0.52. n=5 per group.
Figure 26:
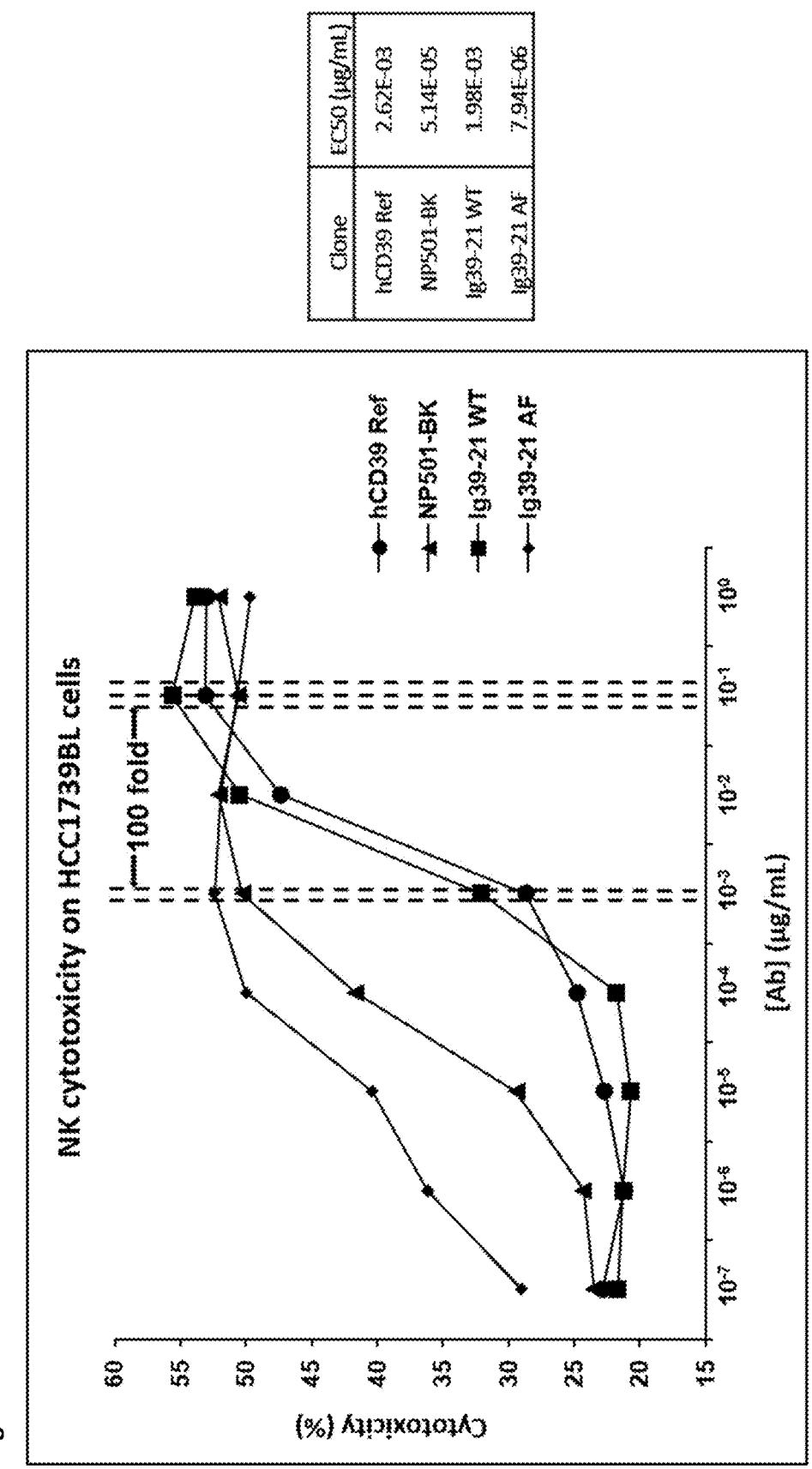
FIG. 26. Reference antibody (hCD39 Ref) and Ig39-21 WT containing the same human IgG1 Fc fraction exert similar ADCC activity: NK cytotoxicity toward HCC1739BL cells. CFSE-labeled HCC1739BL target cells were incubated with serially diluted anti-hCD39 monoclonal antibodies (hCD39 Ref, NP501-BK, Ig39-21 WT or Ig39-21 AF) as indicated for 30 minutes at 37° C. in 5% $CO_2$. Cells were then co-cultured with NK-92-CD16 V/V effector cells (E:T=1:8) for 6 hours at 37° C. Target cell death was analyzed by flow cytometry and % of $CFSE^+P/I^+$ cells (% of cytotoxicity) was calculated. EC50 was calculated as 2.62E-03 µg/mL (hCD39 Ref), 5.14E-05 µg/mL (NP501-BK), 1.98E-03 µg/mL (Ig39-21 WT) and 7.94E-06 µg/mL (Ig39-21 AF).

As examples, FIGS. 13 & 26 show that decreased fucosylation (aka hypo-fucosylation or afucosylation) of our lead clone Ig39-21, a fully human anti-CD39 monoclonal antibody, either by using a fucosylation inhibitor (Ig39-21 AF) or by optimizing the production process (NP501-BK), dramatically boosts its ADCC activity against CD39+ cells in vitro. This is concurrent with enhancement of anti-tumor activity of these afucosylated antibodies in vivo (FIG. 15), whereas the fully glycosylated format (Ig39-21 WT) does not show anti-tumor activity in the same tumor model (data not shown).

The in vitro maximum effective dose (MaxED) of these differently fucosylated Ig39-21 antibodies, as projected by NK cytotoxicity assay in FIGS. 13 & 26, further explains their differential in vivo anti-tumor activities. For example, afucosylation enhances Ig39-21 WT's MaxED from 0.1 µg/ml up to 0.001 µg/ml. Such 100-fold increase, when translated into the clinic, would be high efficacy, favorable safety profile, good tolerability and low cost.

In comparison, the reference hCD39 antibody (hCD39 Ref) used herein shares the antigen binding sites with an antibody in the art. However, that prior art antibody, in contrast to the Ref antibody used in the current examples, was generated with an Fc portion specifically designed to have an abrogated ADCC function (i.e., was taught to have been generated specifically to bind CD39 and inhibit NTPase activity without invoking CD39 dependent ADCC cell killing).

ADCC activity of the subject anti-CD39 antibodies is selectively toward CD39$^{high}$ cells.

Figure 3:
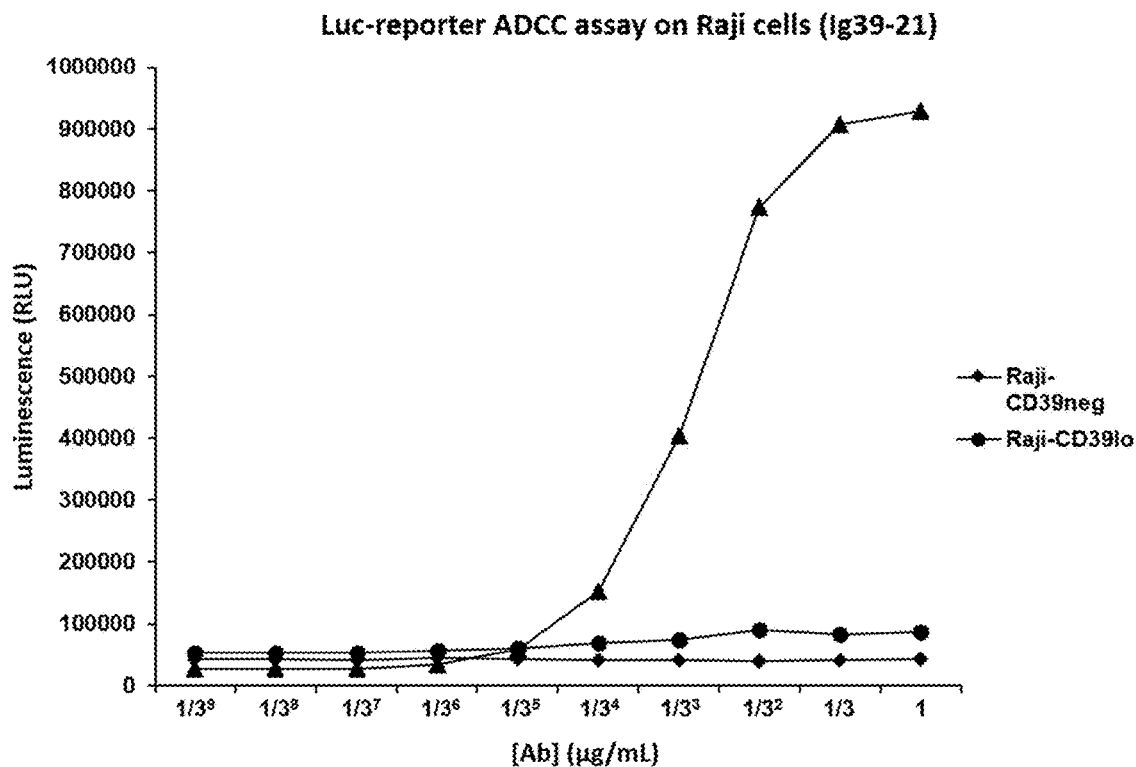
FIG. 3. Ig39-21 demonstrates ADCC activity selectively toward human CD39hi Raji cells: Luc-reporter assay. Various Raji cell lines with different human CD39-expression levels including Raji cells (Raji-hCD39neg), hCD39-transfected Raji cells that highly express human CD39 (Raji-hCD39hi) or hCD39-transfected Raji cells that express low level of human CD39 (Raji-hCD39lo) were used as target cells. Jurkat cells stably expressing luciferase and hCD16a-158V were used as effector cells. Target cells were pre-incubated with serially diluted Ig39-21 as indicated for 30 minutes at 37° C. in 5% $CO_2$, followed by co-culture with effector cells (T:E=1:6) for 6 hours. ADCC activity was indicated by an increase of luciferase activity over background (RLU). RLU: Relative Luminescence Unit.
Figure 4:
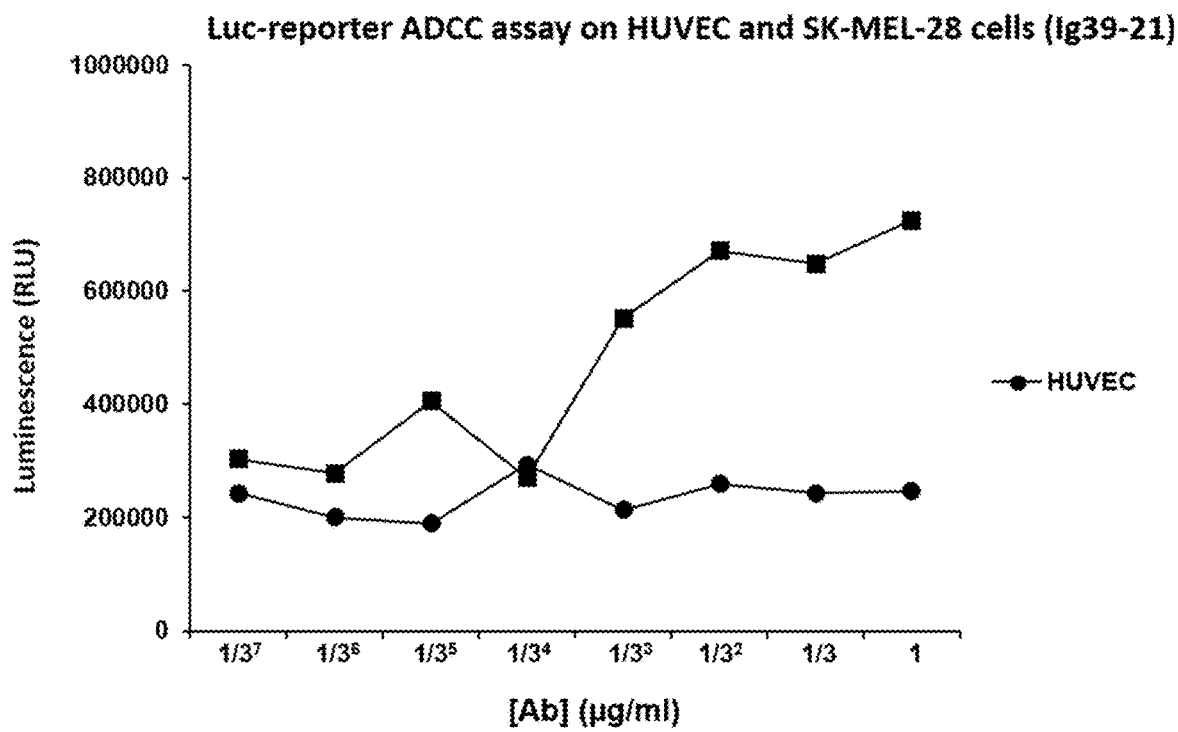
FIG. 4. Ig39-21 does not exert ADCC activity toward CD39low normal endothelial cells, HUVEC. Both human melanoma cells (SK-MEL-28) and human umbilical vein endothelial cells (HUVEC) were used as target cells. Jurkat cells stably expressing luciferase and hCD16a-158V were used as effector cells. Target cells were pre-incubated with serially diluted Ig39-21 as indicated for 30 minutes at 37° C. in 5% $CO_2$, followed by co-culture with effector cells (T:E=1:6) for 6 hours. ADCC activity was indicated by an increase of luciferase activity over background. RLU: Relative Luminescence Unit. This data is indicative of the safety of Ig39-21 avoiding potential systemic side-effects.
Figure 5:
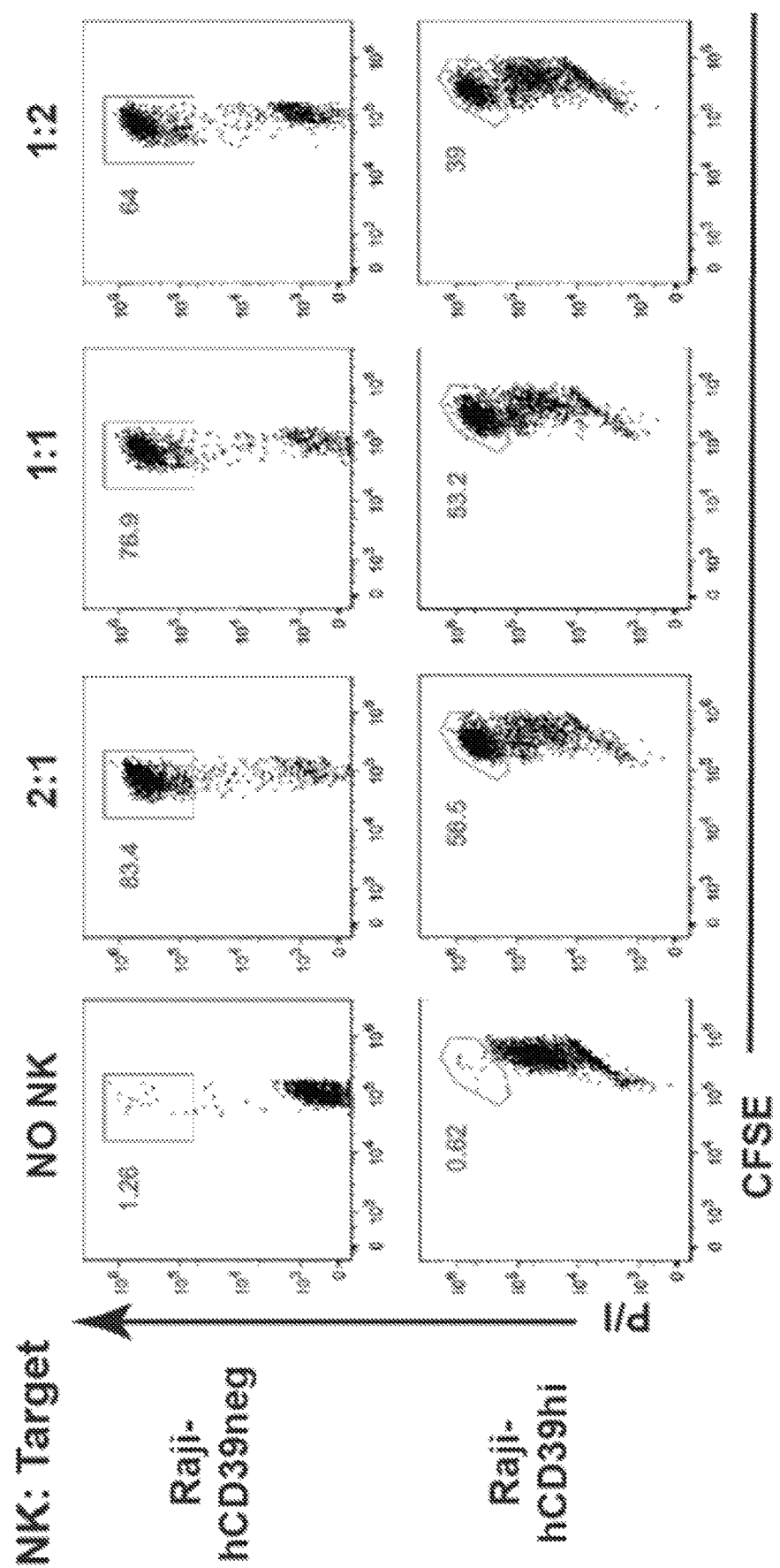
FIG. 5. CD39 confers resistance of target Raji-hCD39hi cells to NK cytotoxicity. CFSE-labeled Raji-hCD39neg or Raji-hCD39hi cells were used as target cells and were co-cultured with NK-92-CD16 V/V effector cells in different proportions (as indicated) for 6 hours at 37° C. in 5% $CO_2$. Target cell death was then analyzed by Propidium Iodide (P/I) uptake by flow cytometry. Results were expressed as % of $CFSE^+P/I^+$ cells.
Figure 5:
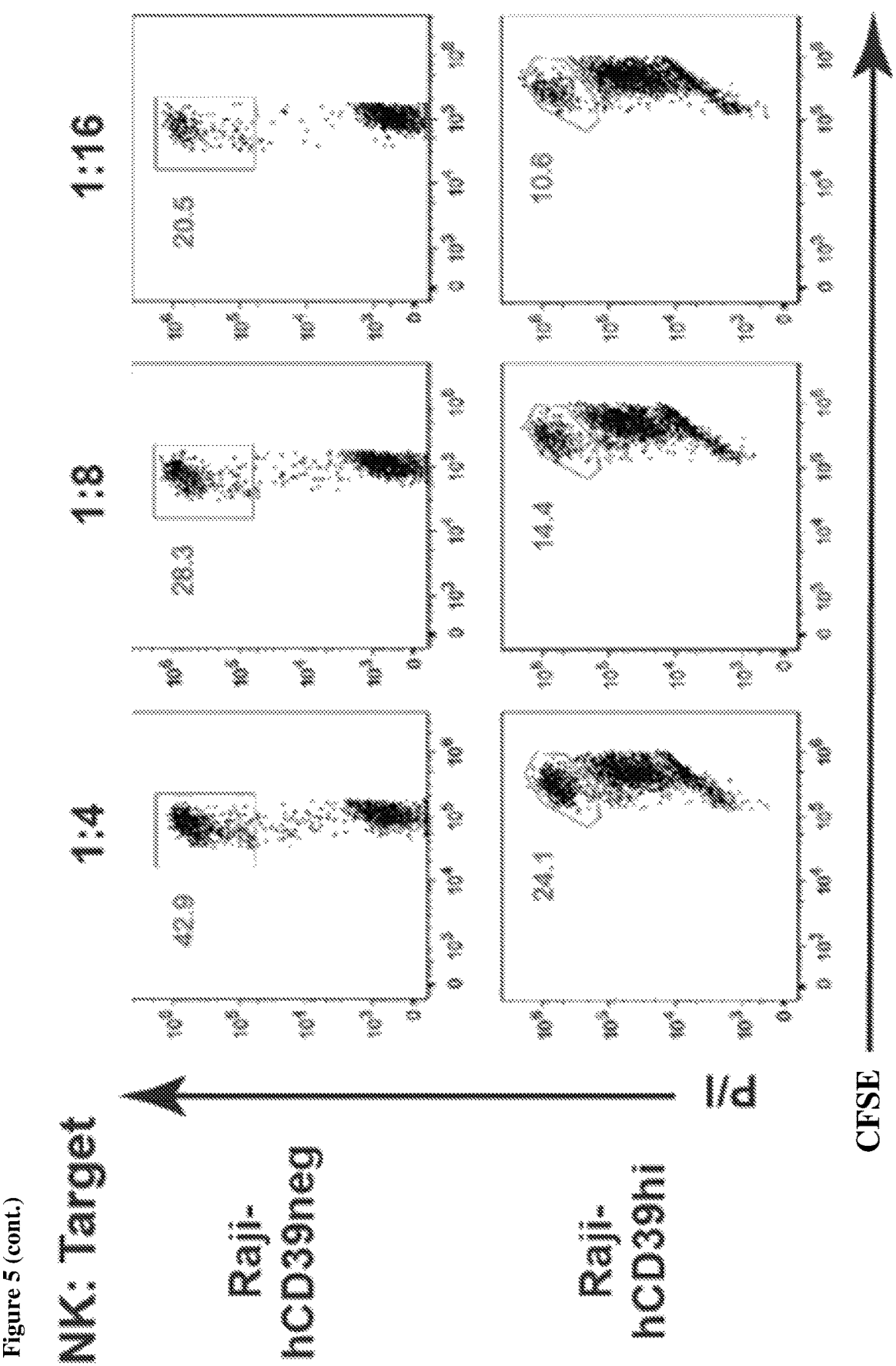
Figure 6:
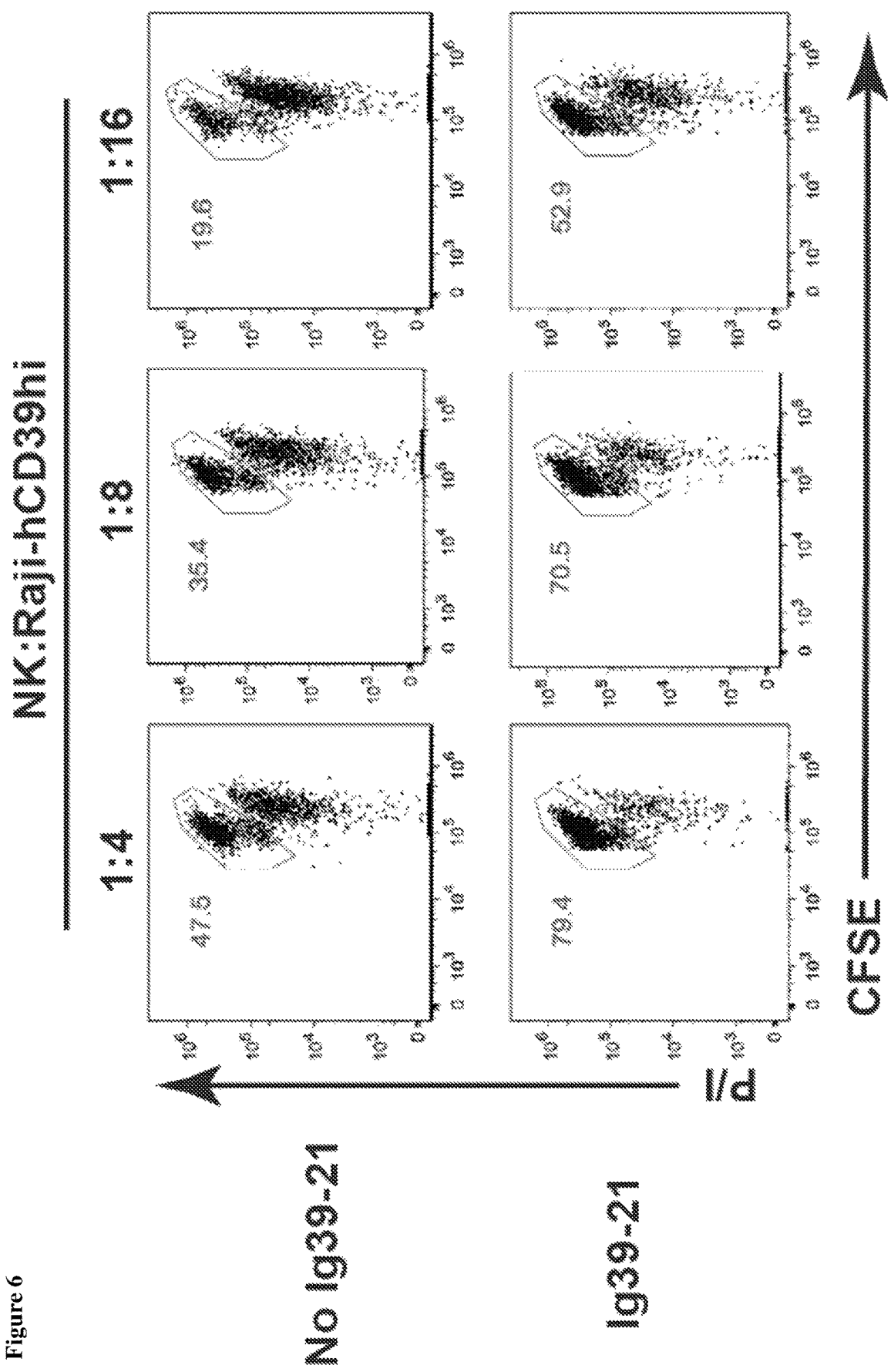
FIG. 6. Ig39-21 potentiates NK cytotoxicity toward Raji-hCD39hi cells. CFSE-labeled Raji-hCD39hi target cells were incubated with or without Ig39-21 antibody (10 μg/mL) for 30 minutes at 37° C. in 5% $CO_2$, followed by co-culture with NK-92-CD16 V/V effector cells in different proportions (as indicated) for 6 hours at 37° C. Target cell death was analyzed by flow cytometry, and % of $CFSE^+P/I^+$ cells was calculated.
Figure 7:
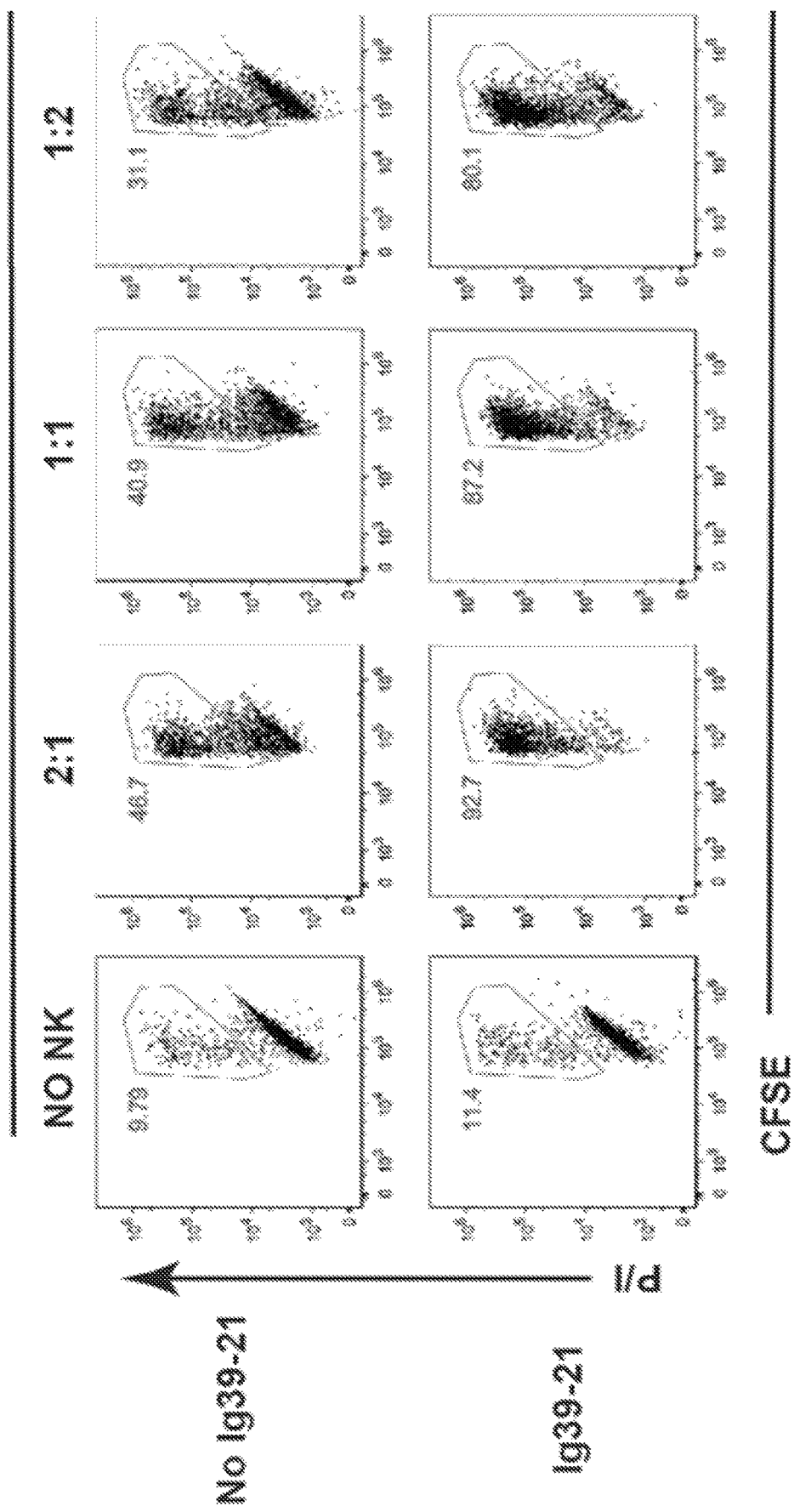
FIG. 7. Ig39-21 potentiates NK cytotoxicity toward hCD39hi human B lymphoblastoid (HCC1739BL) cells. CFSE-labeled HCC1739BL target cells were incubated with or without Ig39-21 antibody (10 μg/mL) for 30 minutes at 37° C. in 5% $CO_2$, followed by co-culture with NK-92-CD16 V/V effector cells in different proportions (as indicated) for 6 hours at 37° C. Target cell death was analyzed by flow cytometry, and % of $CFSE^+P/I^+$ cells was calculated.
Figure 7:
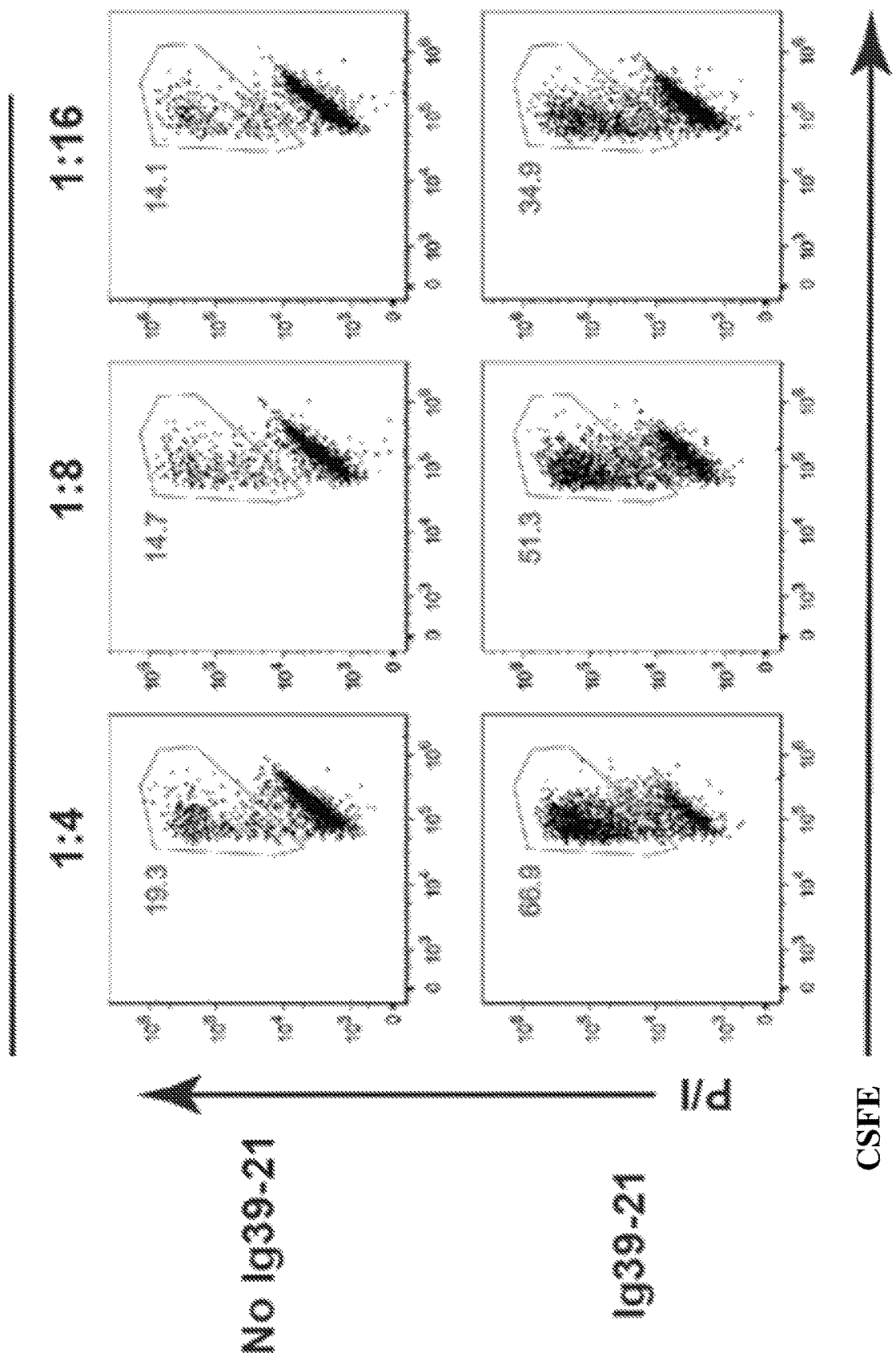
Figure 8:
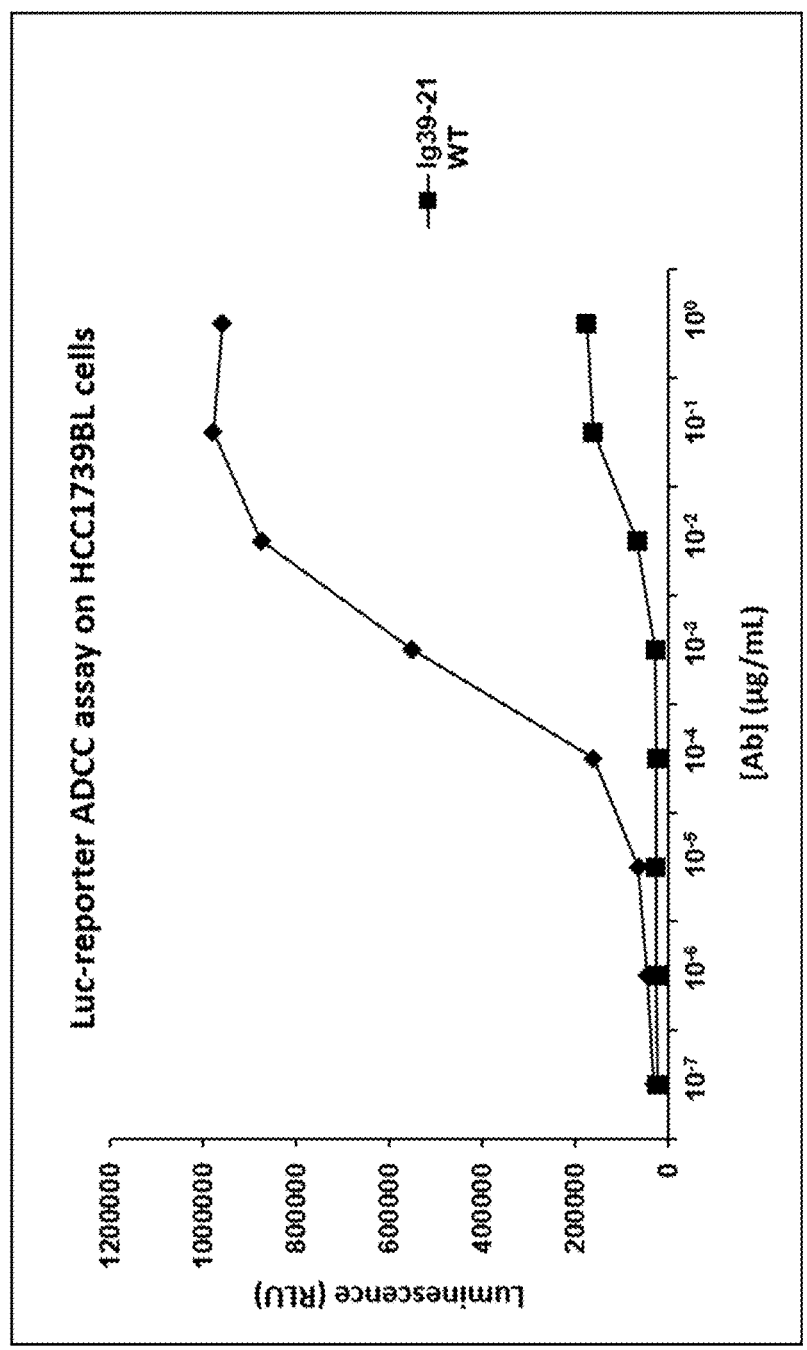
FIG. 8. Afucosylation boosts Ig39-21 mediated ADCC against HCC1739BL cells: Luc-reporter assay. HCC1739BL target cells were pre-incubated with serially diluted Ig39-21 produced by transient transfection in the absence (Ig39-21 WT) or presence of fucosylation inhibitor (Ig39-21 AF) for 30 minutes at 37° C. and further co-cultured with Jurkat effector cells (T:E=1:6) for 6 hours. ADCC activity was indicated by an increase of luciferase activity over background. RLU: Relative Luminescence Unit. EC50 was calculated as 0.02 µg/mL (Ig39-21 WT) and 0.0008 µg/mL (Ig39-21 AF) FIG. 9. Afucosylation boosts Ig39-21 mediated ADCC against HCC1739BL cells: NK cytotoxicity assay. CFSE-labeled HCC1739BL target cells were incubated with serially diluted Ig39-21 WT or Ig39-21 AF as indicated for 30 minutes at 37° C. in 5% $CO_2$. Cells were then co-cultured with NK-92-CD16 V/V effector cells (E:T=1:8) for 6 hours at 37° C. Target cell death was analyzed by flow cytometry and % of CFSE$^+$P/I$^+$ cells (% of cytotoxicity) was calculated. EC50 was calculated as 0.04 µg/mL (Ig39-21 WT) and 0.0006 µg/mL (Ig39-21 AF).
Figure 9:
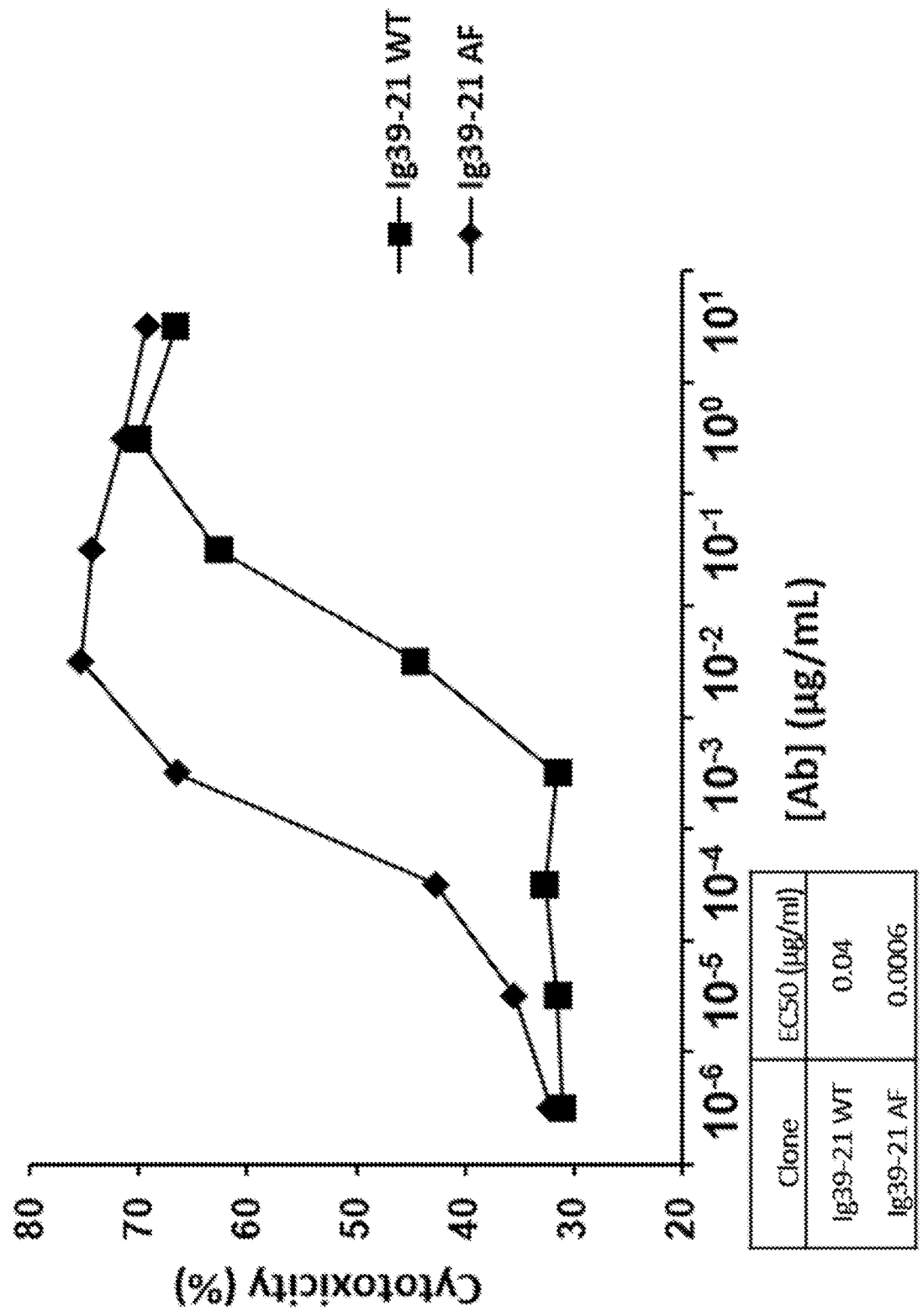
Figure 10:
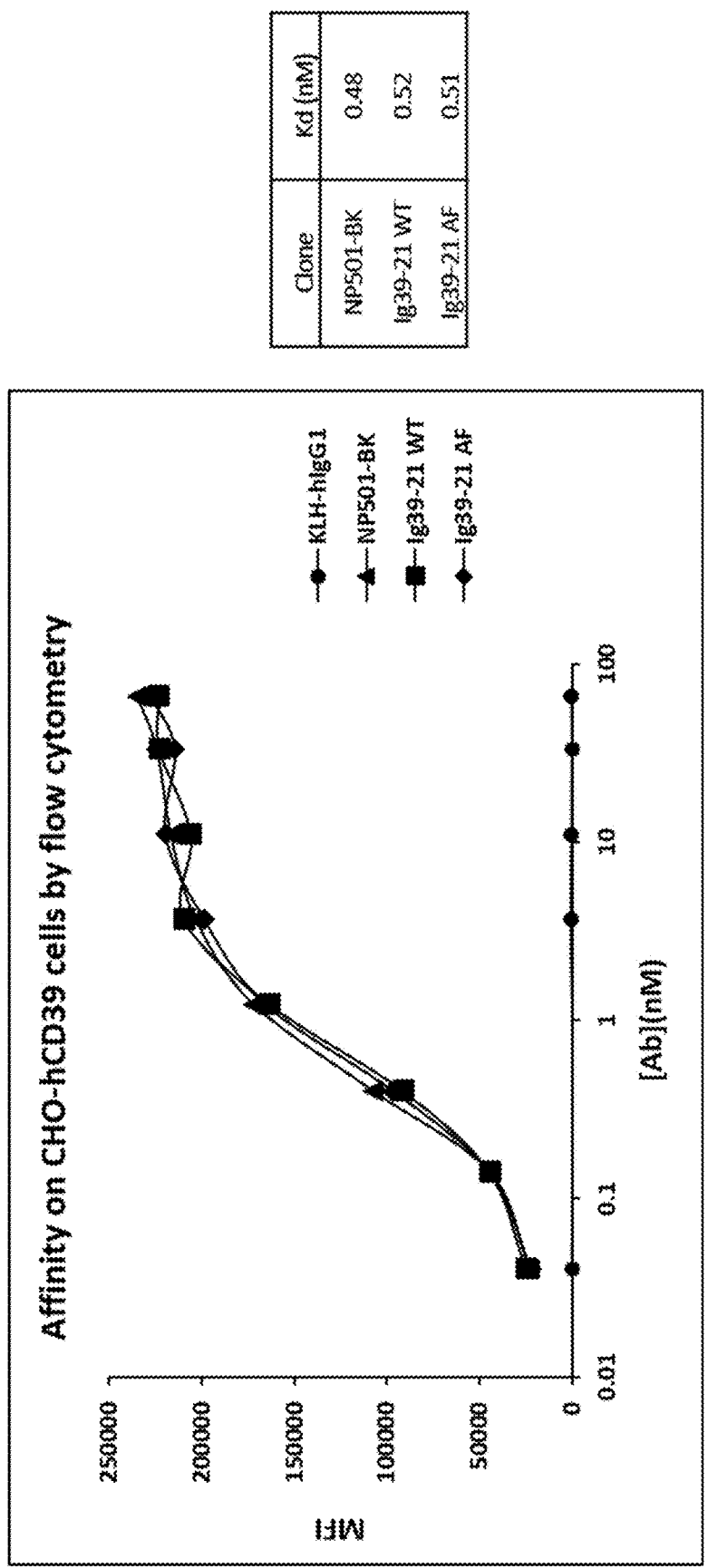
FIG. 10. Optimized Ig39-21 (NP501-BK), Ig39-21 WT and Ig39-21 AF exhibit similar binding affinity using human CD39 positive CHO cells (CHO-hCD39). Ig39-21 WT, Ig39-21 AF or NP501-BK (an optimized version of Ig39-21 by production using stably transfected cells) were serially diluted as indicated and incubated with CHO-hCD39 cells for 30 minutes at 4° C. Cells were then stained with secondary antibody (anti-human IgG (Fc specific), Alexa Fluor® 488) for 30 minutes at 4° C. and analyzed by flow cytometry. Human IgG1 isotype control antibody (KLH-hIgG1) was used in parallel. Kd was calculated as 0.48 nM (NP501-BK), 0.52 nM (Ig39-21 WT) and 0.51 nM (Ig39-21AF).
Figure 11:
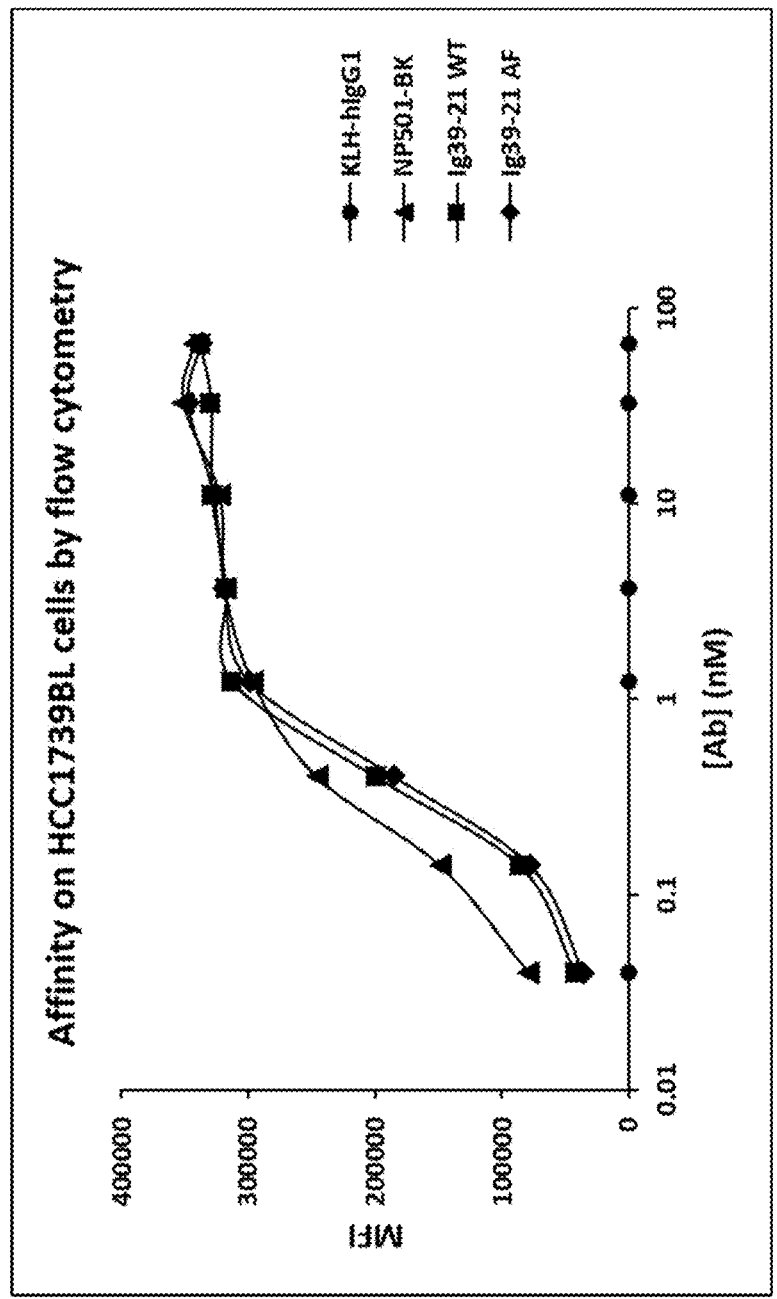
FIG. 11. NP501-BK, Ig39-21 WT and Ig39-21 AF exhibit similar binding affinity using CD39 expressing HCC1739BL cells. Ig39-21 WT, Ig39-21 AF or NP501-BK were serially diluted as indicated and incubated with HCC1739BL cells for 30 minutes at 4° C. Afterwards, cells were stained with secondary antibody (anti-human IgG (Fc specific), Alexa Fluor® 488) for 30 minutes at 4° C. and analyzed by flow cytometry. Human IgG1 isotype control antibody (KLH-hIgG1) was used in parallel. Kd was calculated as 0.16 nM (NP501-BK), 0.29 nM (Ig39-21 WT) and 0.35 nM (Ig39-21 AF).
Figure 12:
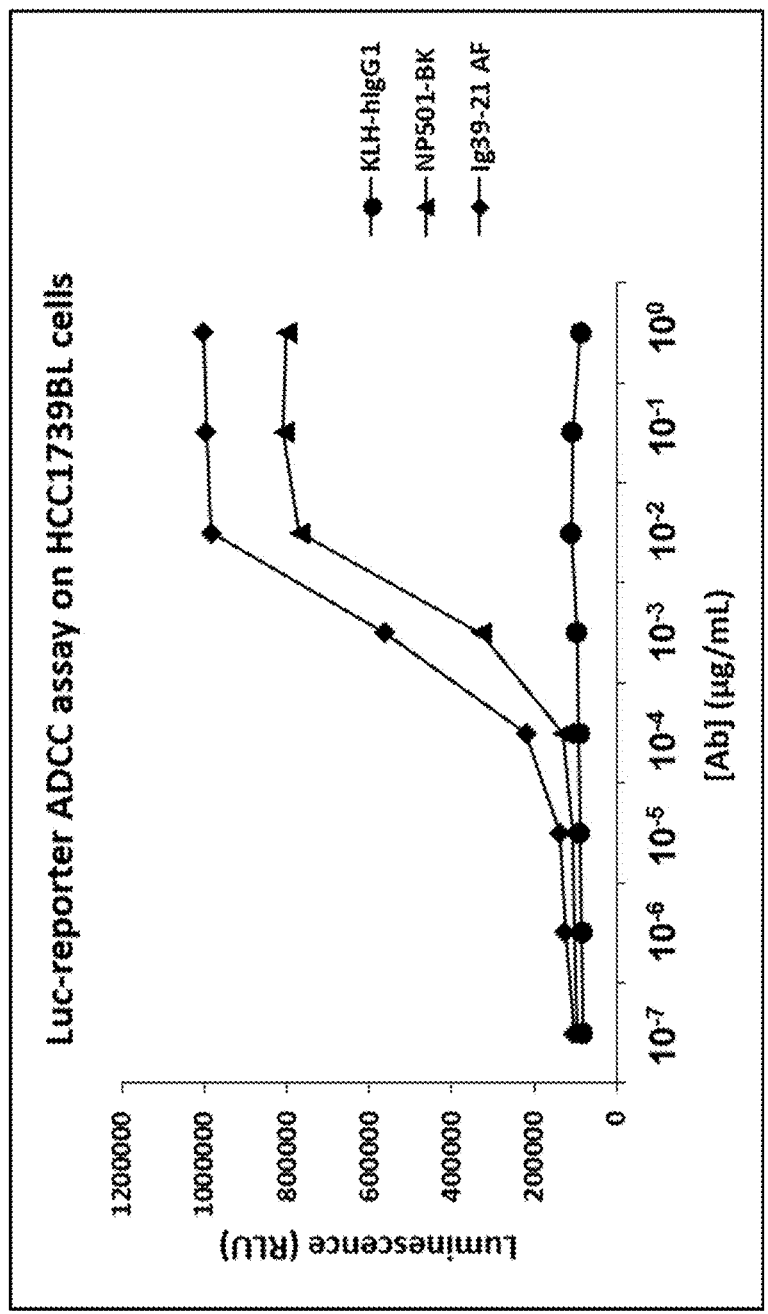
FIG. 12. Optimized Ig39-21 (NP501-BK) and afucosylated Ig39-21 exert similar ADCC activity: Luc-reporter assay using HCC1739BL cells. HCC1739BL target cells were pre-incubated with serially diluted human IgG1 isotype control antibody (KLH-hIgG1) or fully human anti-CD39 monoclonal antibodies (Ig39-21 AF or NP501-BK) for 30 minutes at 37° C. and further co-cultured with Jurkat effector cells (T:E=1:6) for 6 hours. ADCC activity was indicated by an increase of luciferase activity over background. RLU: Relative Luminescence Unit. EC50 was calculated as 0.0017 µg/mL (NP501-BK) and 0.00086 µg/mL (Ig39-21 AF).

As examples, FIGS. 3 & 4 show that ADCC activity of Ig39-21 is selectively against CD39$^{high}$ cells (i.e. Raji-hCD39hi cells in FIG. 3 and SK-MEL-28 cells in FIG. 4).

Figure 16:
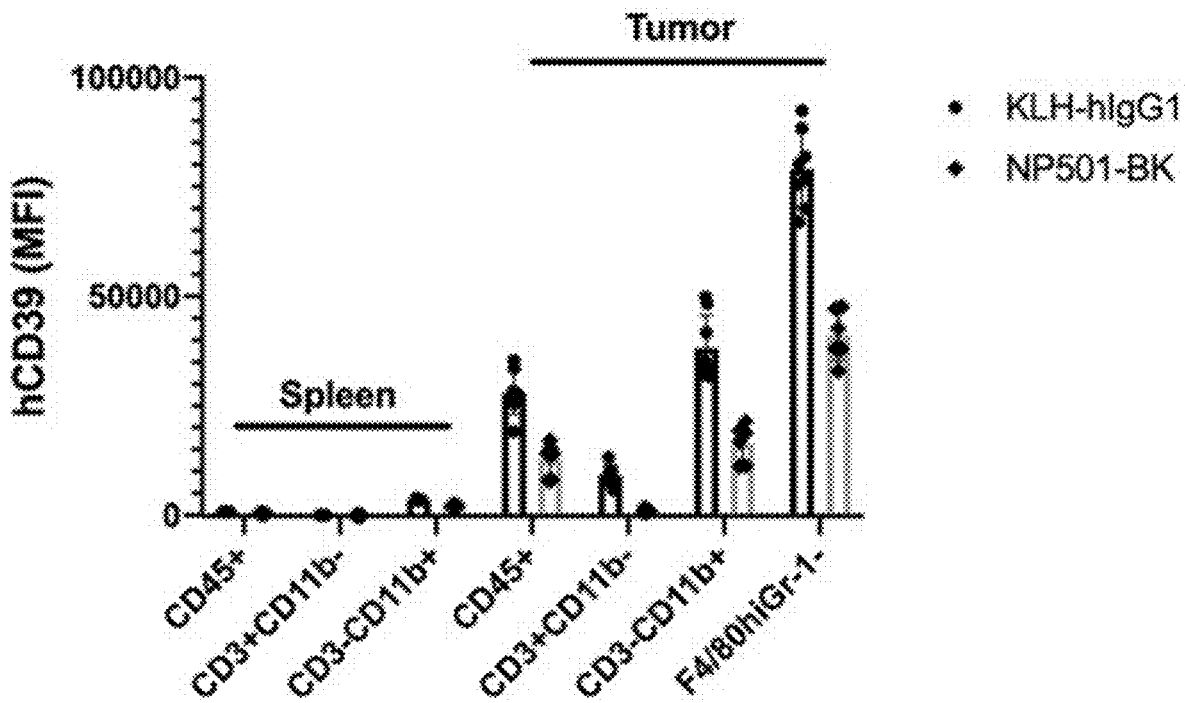
FIG. 16. NP501-BK treatment results in reduction of hCD39 expression on CD39hi tumor-infiltrating lymphocytes. MC38 tumor-bearing hCD39 KI mice were treated with three doses of KLH-hIgG1 (5 mg/kg) or NP501-BK (5 mg/kg) on days 8, 11 and 14 after tumor inoculation. On day 15, splenocytes and tumor-infiltrating lymphocytes were purified from these mice, stained with indicated cell surface markers, and analyzed by flow cytometry as described in Materials and Methods. n=6-8 per group.

The relevance of these in vitro data to the in vivo tumor microenvironment: FIG. 16 demonstrates that hCD39 is highly upregulated inside the tumor of MC38-bearing hCD39 KI mice, including CD45+ tumor-infiltrating lymphocytes (i.e. CD3+CD11b– T cells, CD3–CD11b+ myeloid cells and F4/80hiGr-1–tumor-associated macrophages) and tumor-associated vascular endothelial cells (data not shown). NP501-BK treatment results in ablation and reduction of CD39$^{high}$ cells in the tumor (FIG. 16 & data not shown).

This functional trait should confer tumor specificity to the antibodies, avoiding systemic side-effects which should result in a safer anti-CD39 antibody.

Formation of a stable immune complex of anti-CD39 antibodies with the antigen on target cell membrane confers high ADCC activity to the antibodies.

Figure 29:
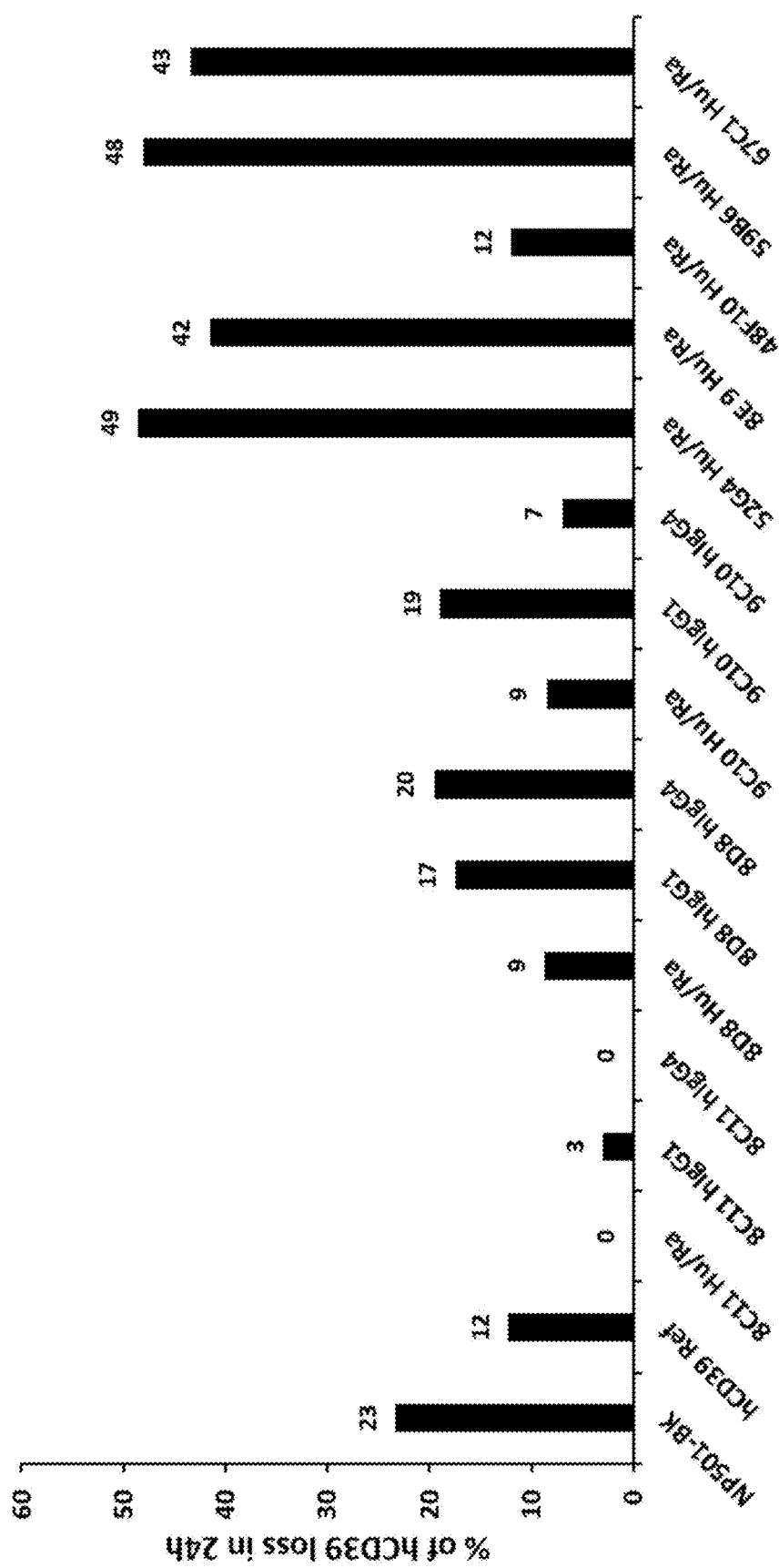
FIG. 29. Stability of antibody:antigen immune complex on HCC1739BL cells. Anti-human CD39 antibodies (2 µg/ml) were incubated with HCC1739BL cells for 24 hours at 37° C. in 5% $CO_2$ or 20 min at 4° C., followed by secondary antibody staining (anti-human IgG (Fc specific), Alexa Fluor® 488) for 30 minutes at 4° C. Cells were then washed and analyzed by flow cytometry. The difference in AF488 MFI between 20 minutes and 24 hours treatment represents the loss of human CD39 on cell membrane that was calculated as described in Materials and Methods. Exemplary chimeric clones from the luc-reporter ADCC-negative group (8E9, 59B6 and 67C1) and ADCC-low group (52G4) do not form stable immune complex on cell membrane after 24 hours (e.g. the loss of CD39 is greater than 40%). Hu/Ra: Human/Rabbit chimeric antibody; hIgG1: humanized rabbit antibody, IgG1 isotype; hIgG4: humanized rabbit antibody, IgG4 isotype.
Figure 30:
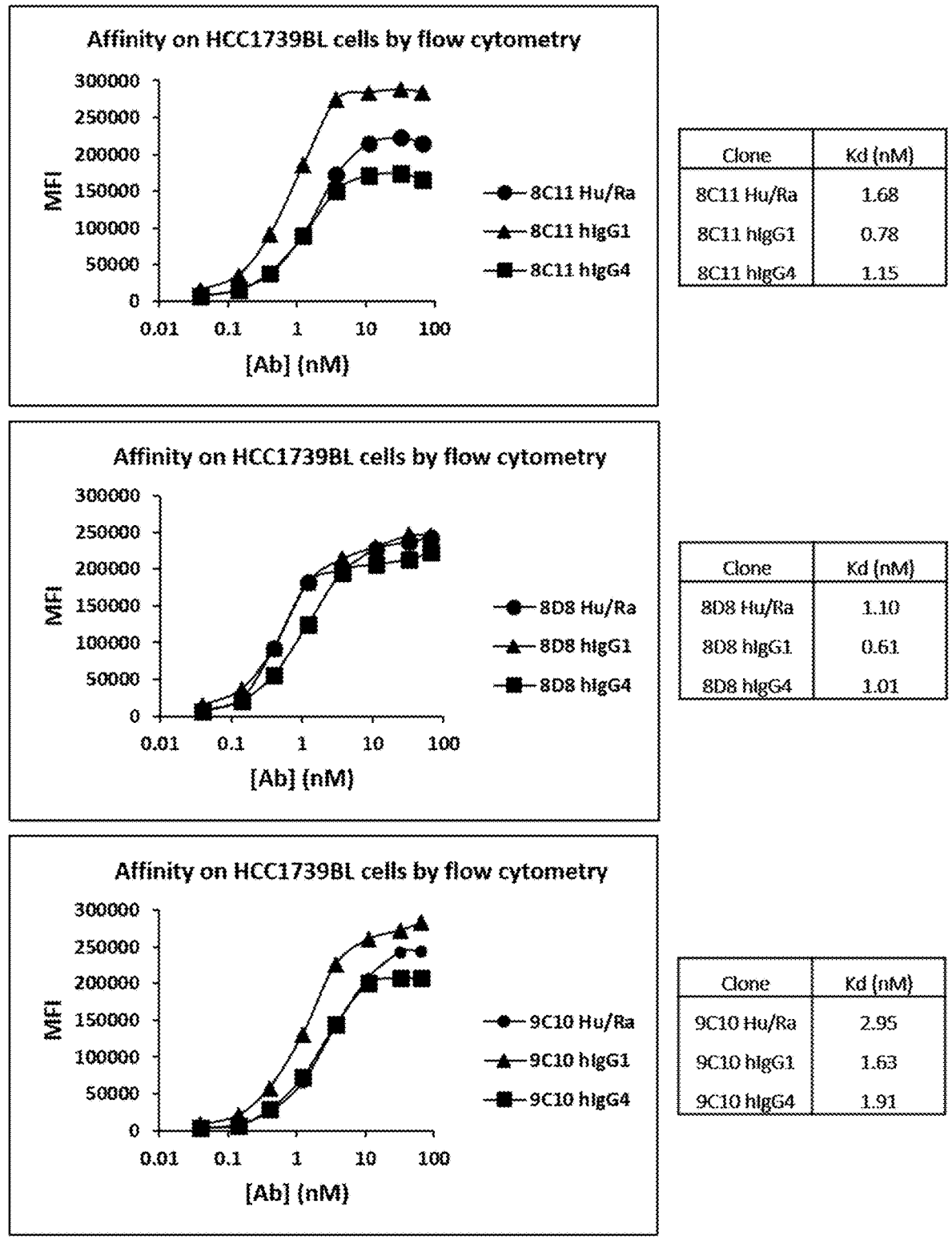
FIG. 30. Affinity of humanized rabbit antibodies measured by flow cytometry using HCC1739BL cells. Human/Rabbit chimeric clones (Hu/Ra 8C11, 8D8 and 9C10) and their respective humanized clones (IgG1 or IgG4 isotype) were serially diluted as indicated and incubated with HCC1739BL cells for 30 minutes at 4° C. Cells were then stained with secondary antibody (anti-human IgG (Fc specific), Alexa Fluor® 488) for 30 minutes at 4° C. and analyzed by flow cytometry. Kd was calculated and indicated beside the graphics.
Figure 31:
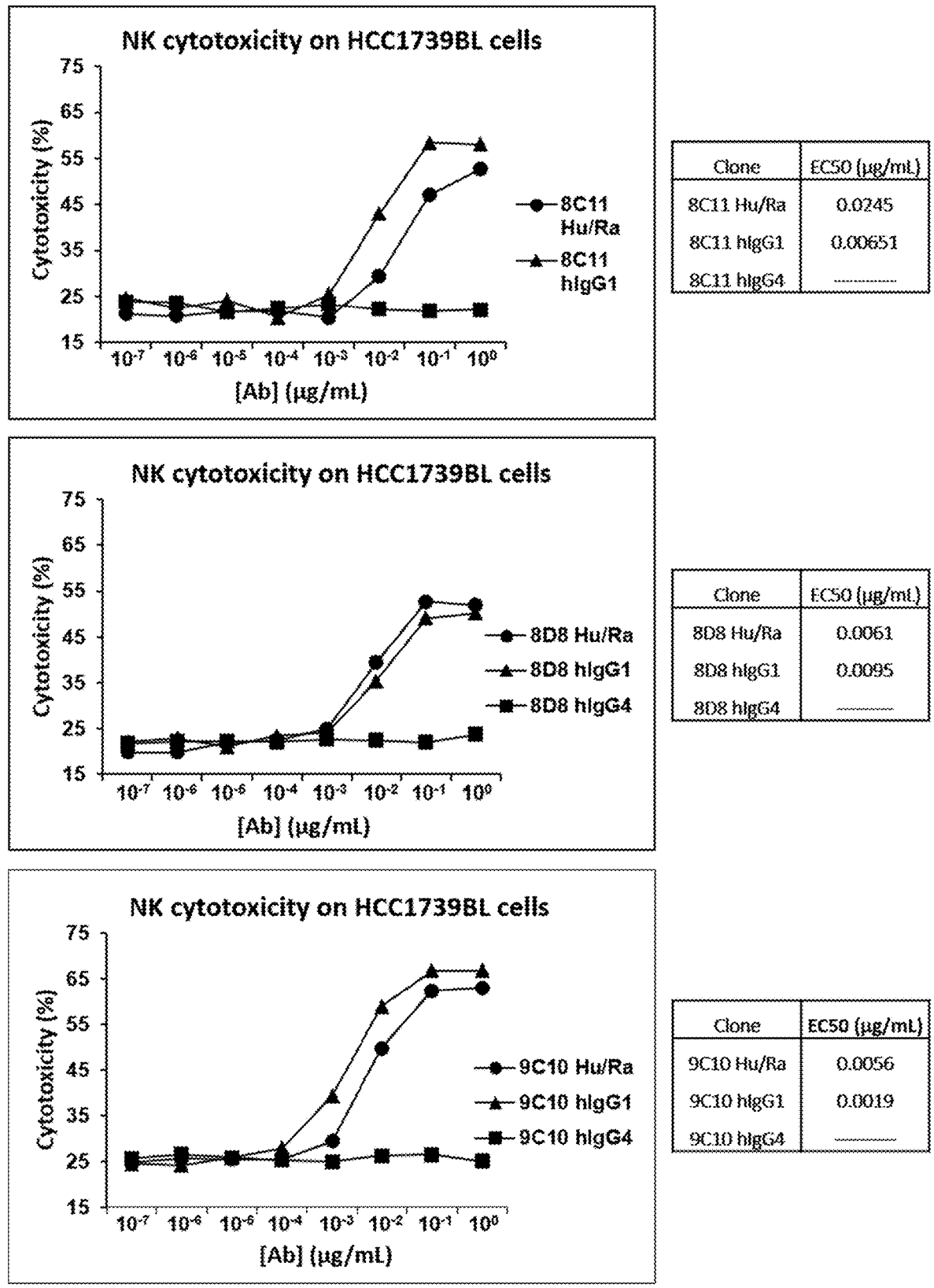
FIG. 31. NK cytotoxicity of humanized rabbit antibodies toward HCC1739BL cells. Human/Rabbit chimeric clones (Hu/Ra 8C11, 8D8 and 9C10) and their respective humanized clones (IgG1 or IgG4 isotype) were serially diluted as indicated and incubated with CFSE-labeled HCC1739BL target cells for 30 minutes at 37° C. in 5% $CO_2$. Cells were then co-cultured with NK-92-CD16 V/V effector cells (E:T=1:8) for 6 hours at 37° C. Target cell death was analyzed by flow cytometry and % of CFSE⁺P/I⁺ cells (% of cytotoxicity) was calculated. Calculated EC50 was listed.
Figure 32:
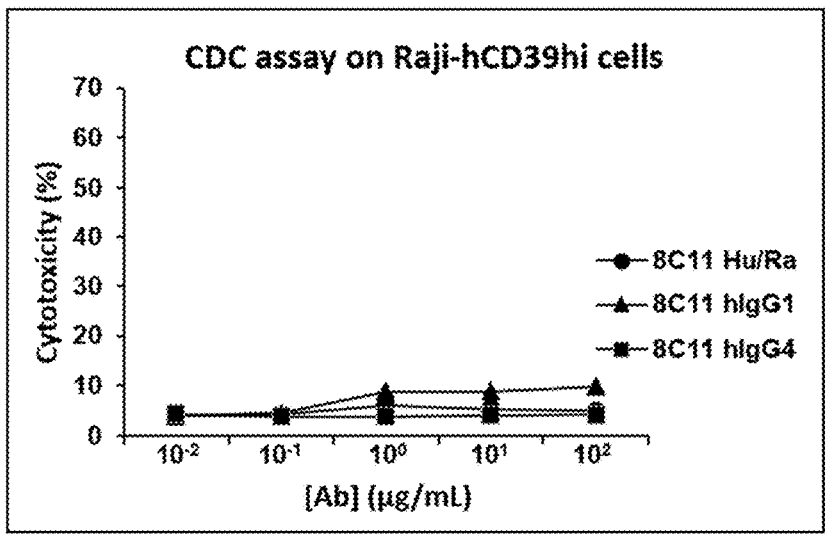
FIG. 32. CDC activity of humanized rabbit antibodies toward Raji-hCD39hi cells. Human/Rabbit chimeric clones (Hu/Ra 8C11, 8D8 and 9C10) and their respective humanized clones (IgG1 or IgG4 isotype) were serially diluted as indicated and pre-incubated with Raji-hCD39hi target cells for 30 minutes at 37° C., followed by incubation with 10% Normal Human Serum (NHS) for 2 hours. Target cell lysis was analyzed by flow cytometry and % P/I⁺ cells (% of cytotoxicity) was calculated. Calculated EC50 was listed.
Figure 32:
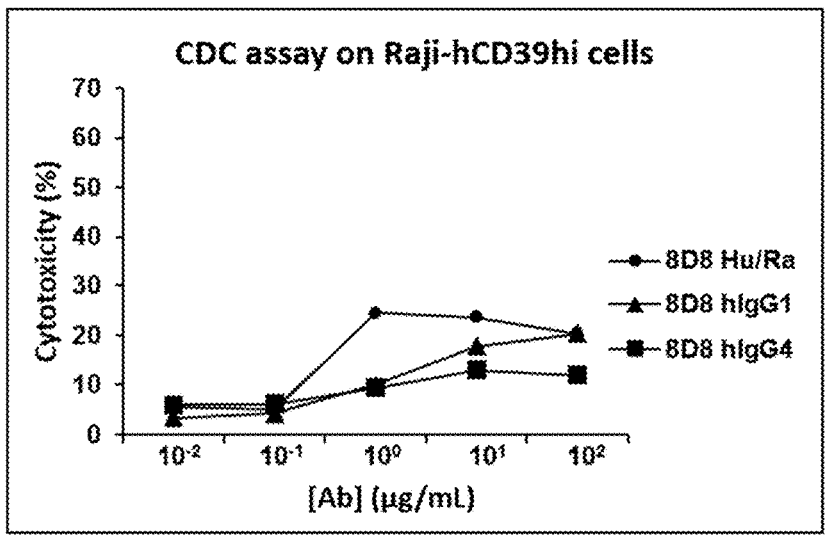
Figure 32:
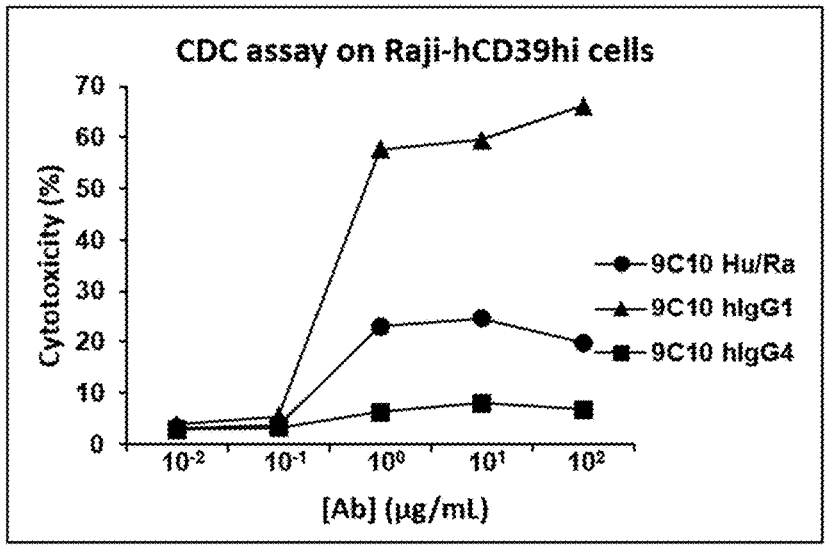

As an example shown in FIG. 29, the stability of the antibody:antigen immune complex on target cell surface was examined using antibodies selected from three groups: ADCC-high (i.e. NP501-BK, hCD39 Ref, and Human/Rabbit chimeric clones 8C11, 8D8, 9C10 and 48F10), ADCC-low (Human/Rabbit chimeric clone 52G4), or ADCC-negative (Human/Rabbit chimeric clones 8E9, 59B6 and 67C1). A strong and positive correlation between the stability of such immune complex and the antibody's ADCC activity is clearly seen viz. the more stable the antibody:antigen immune complex is, the higher the antibody's ADCC activity.

Different epitopes of anti-CD39 antibodies directly link to antibodies' ADCC activity.

Figure 21:
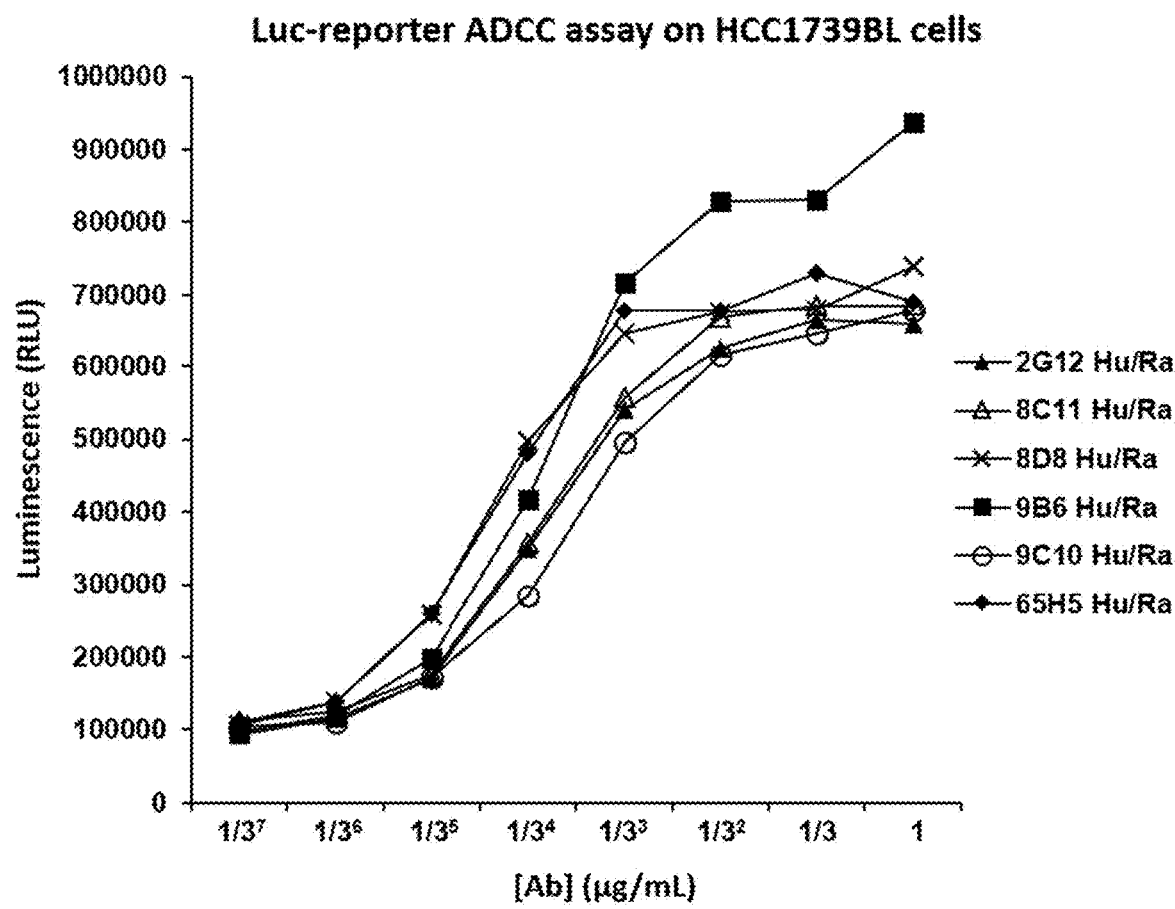
FIG. 21. Human/Rabbit chimeric antibodies with high ADCC activity: Luc-reporter assay using HCC1739BL cells. Luc-reporter ADCC assay were performed as described above in FIG. 20. Six clones with high ADCC activity were summarized. Five out of six clones (except for 65H5) do not compete with the epitope of Clone A1 (See FIG. 18).
Figure 22:
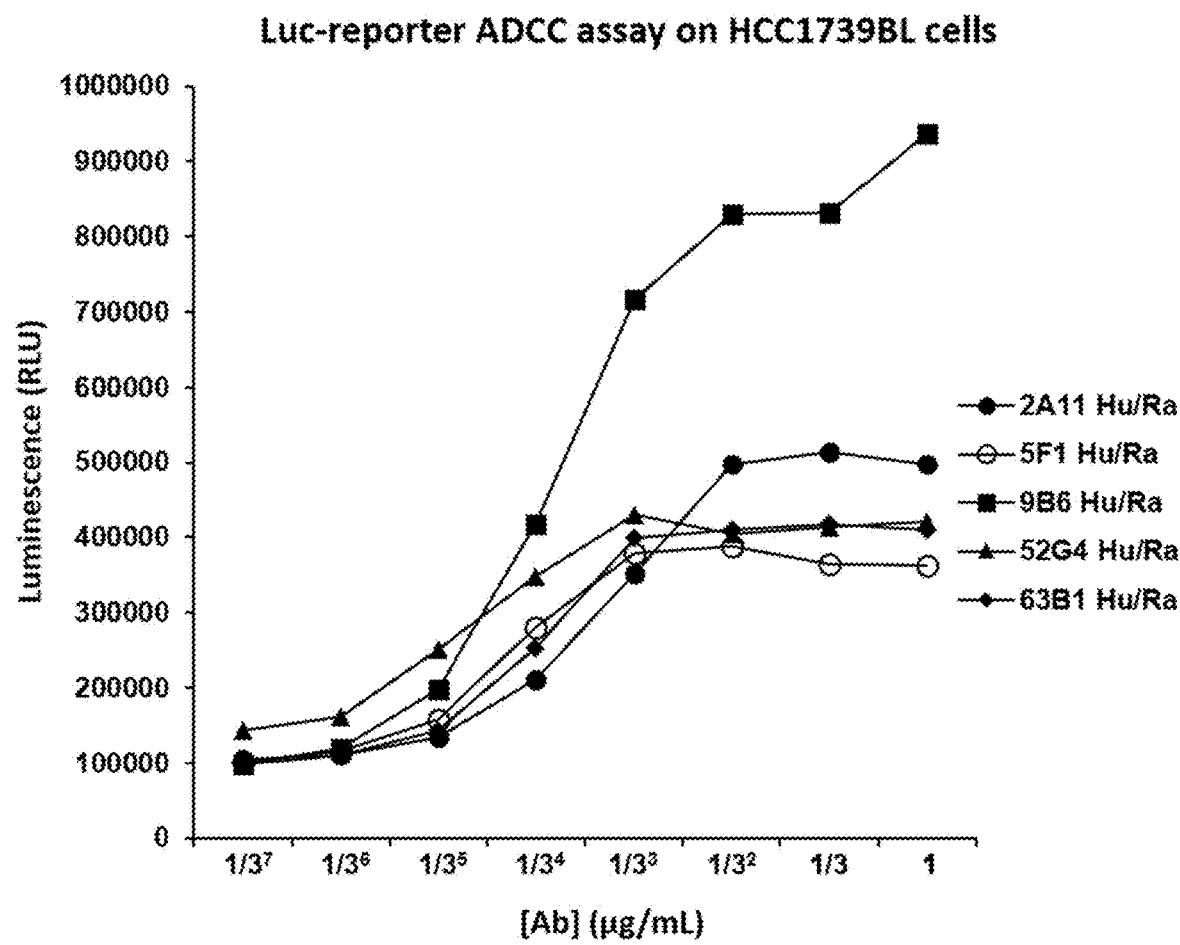
FIG. 22. Human/Rabbit chimeric clones with low ADCC activity: Luc-reporter assay using HCC1739BL cells. Luc-reporter ADCC assay were performed as described above in FIG. 20. Four clones with low ADCC activity were summarized, all of which completely compete with the epitope of Clone A1 (See FIG. 18). 9B6 serves as a positive control.
Figure 23:
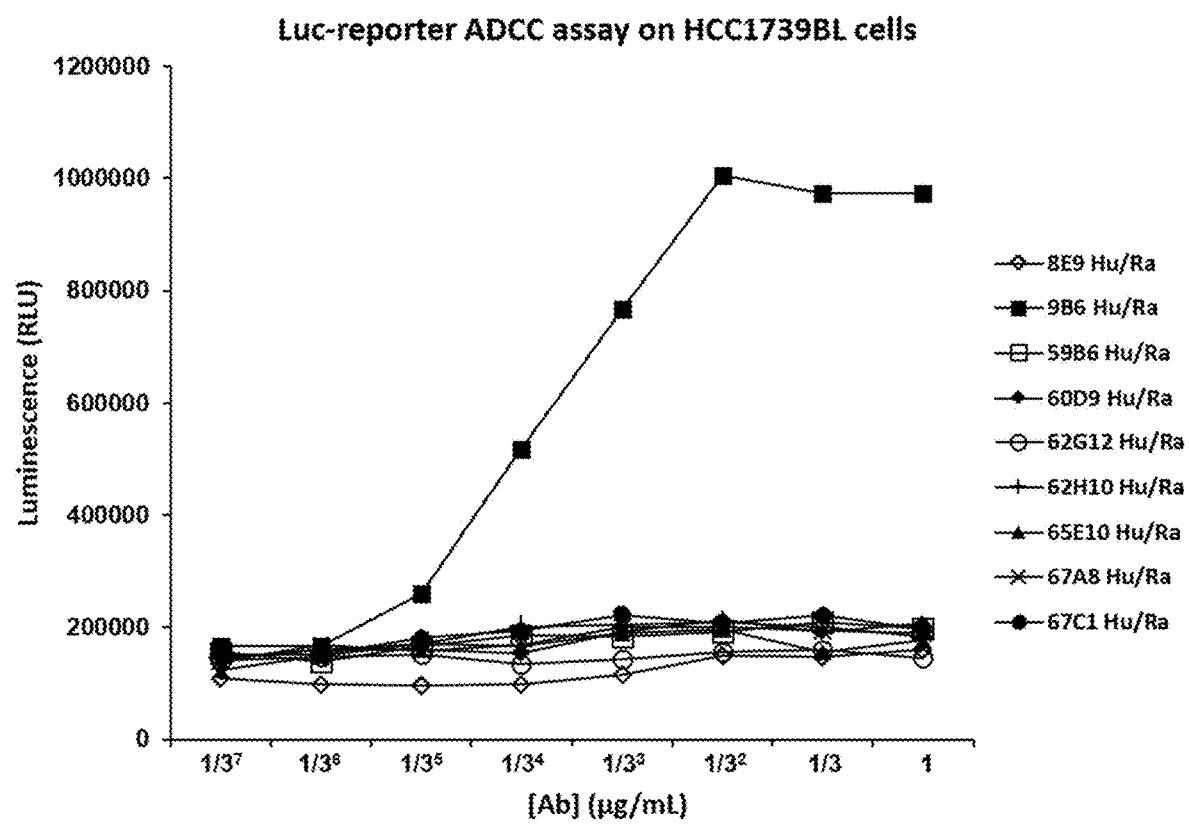
FIG. 23. Human/Rabbit chimeric antibodies without ADCC activity: Luc-reporter assay using HCC1739BL cells. Luc-reporter ADCC assay were performed as described above in FIG. 20. Eight clones without ADCC activity were summarized, all of which completely compete with the epitope of Clone A1 (See FIG. 18). 9B6 serves as a positive control.
Figure 24:
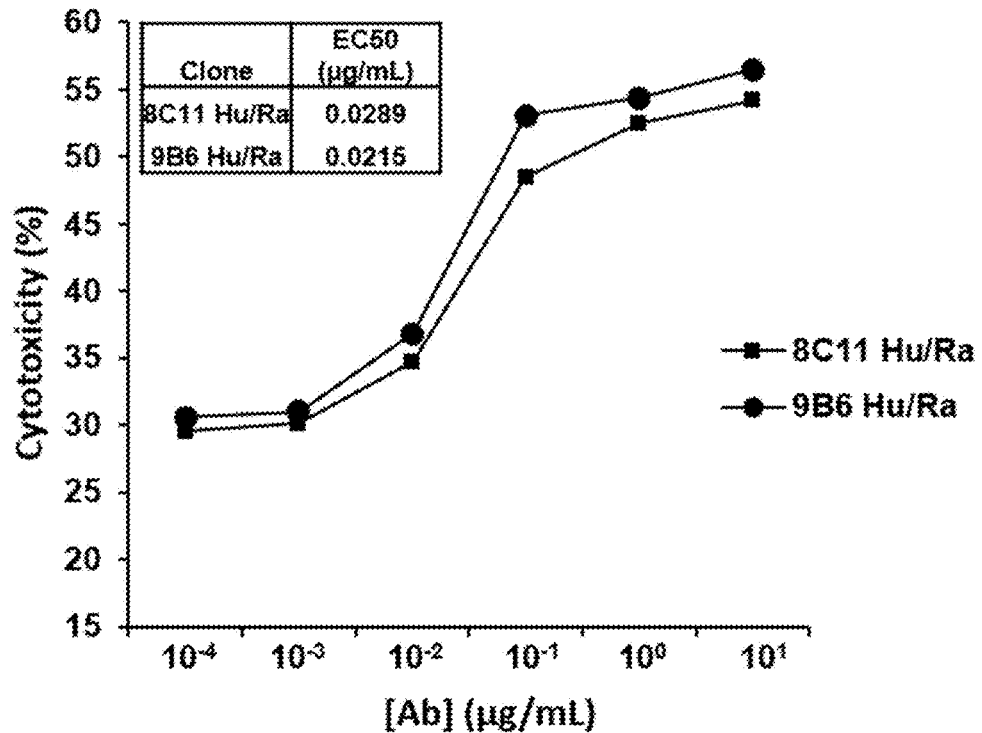
FIG. 24. NK cytotoxicity of select Human/Rabbit chimeric antibodies toward HCC1739BL cells. CFSE-labeled HCC1739BL target cells were incubated with serially diluted Human/Rabbit chimeric clones as indicated for 30 minutes at 37° C. in 5% $CO_2$. Cells were then co-cultured with NK-92-CD16 V/V effector cells (E:T=1:8) for 6 hours at 37° C. Target cell death was analyzed by flow cytometry and % of $CFSE^+P/I^+$ cells (% of cytotoxicity) was calculated. Calculated EC50 was listed. % of maximal cytotoxicity over background was determined as: % of maximal cytotoxicity at 1 µg/mL–% of background cytotoxicity (at $10^{-4}$ µg/mL) for each clone. Exemplary chimeric clones from the luc-reporter ADCC-high group (8C11, 8D8, 9B6, 9C10, 48F10 and 65H5) exhibit high NK killing activity. In contrast, chimeric clones from the luc-reporter ADCC-negative group (59B6, 60D9, 62G12 and 62H10) display low NK killing activity.
Figure 24:
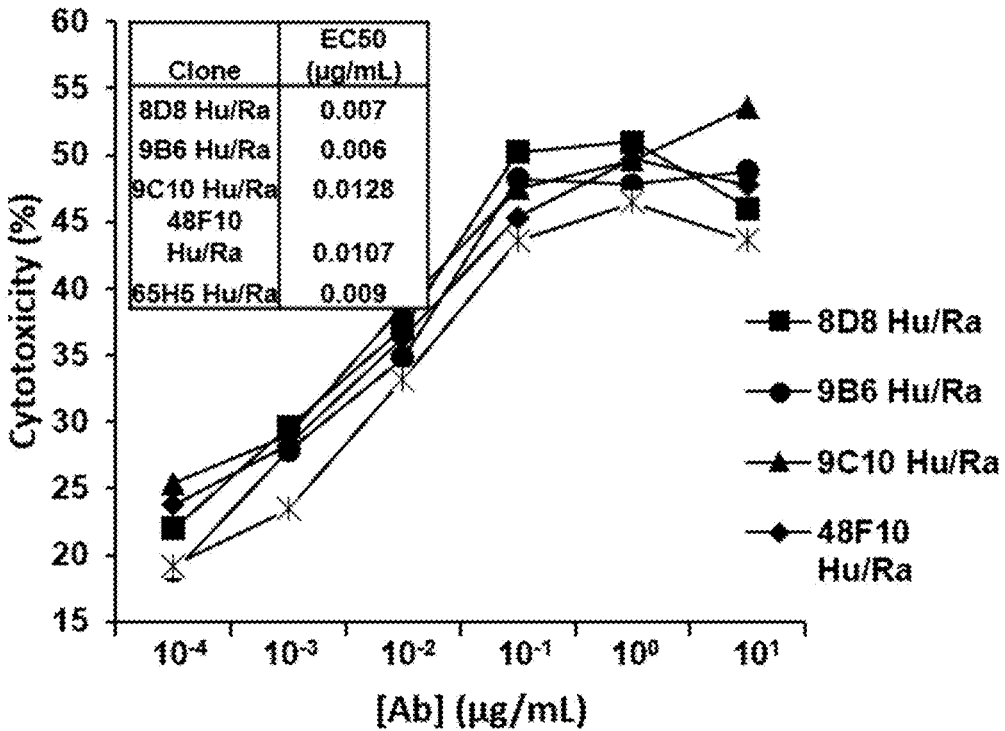
Figure 24:
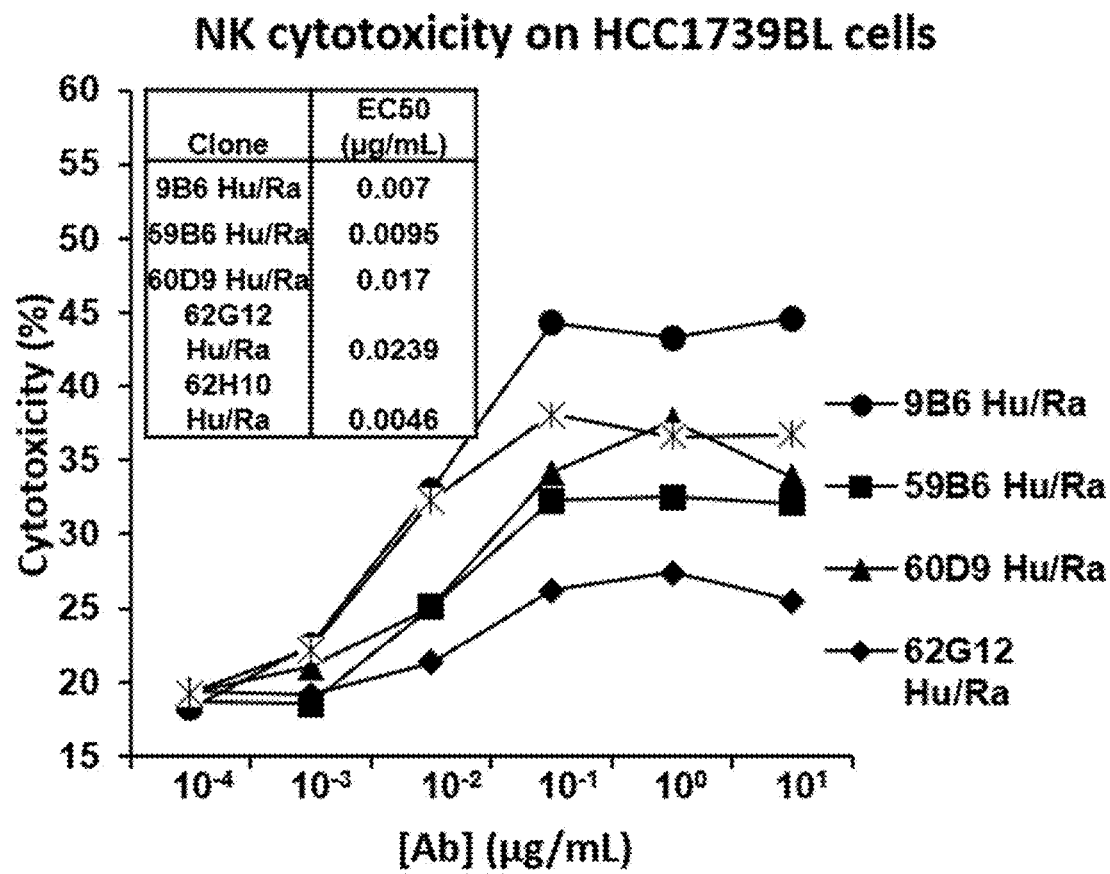
Figure 24:
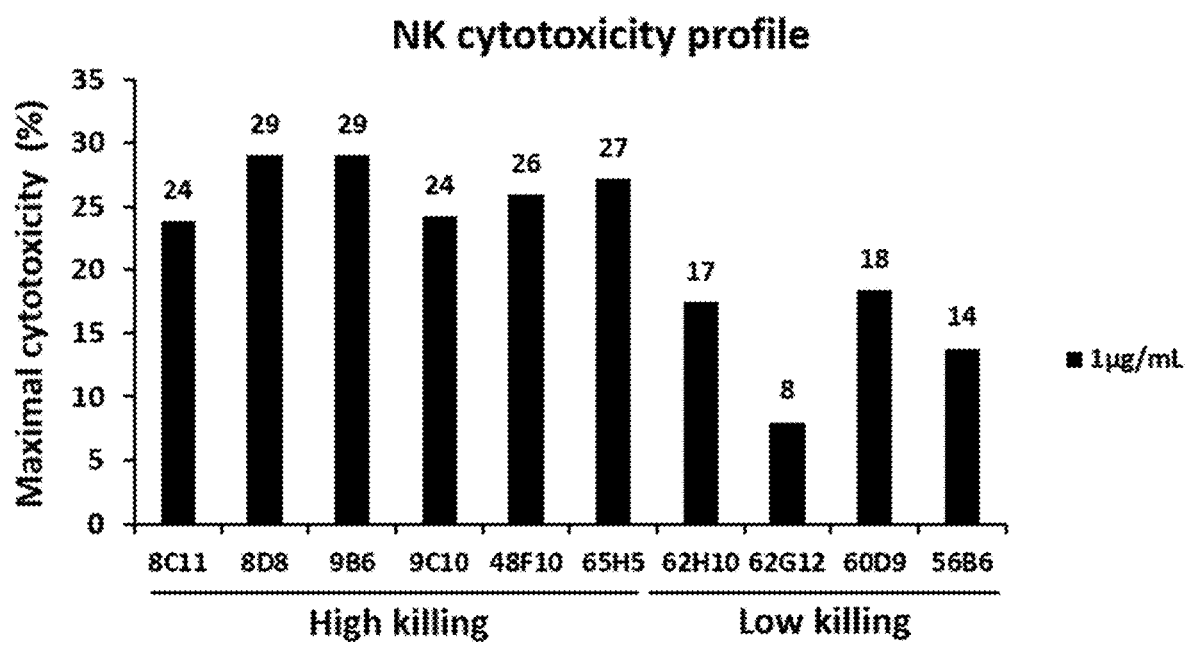
Figure 25:
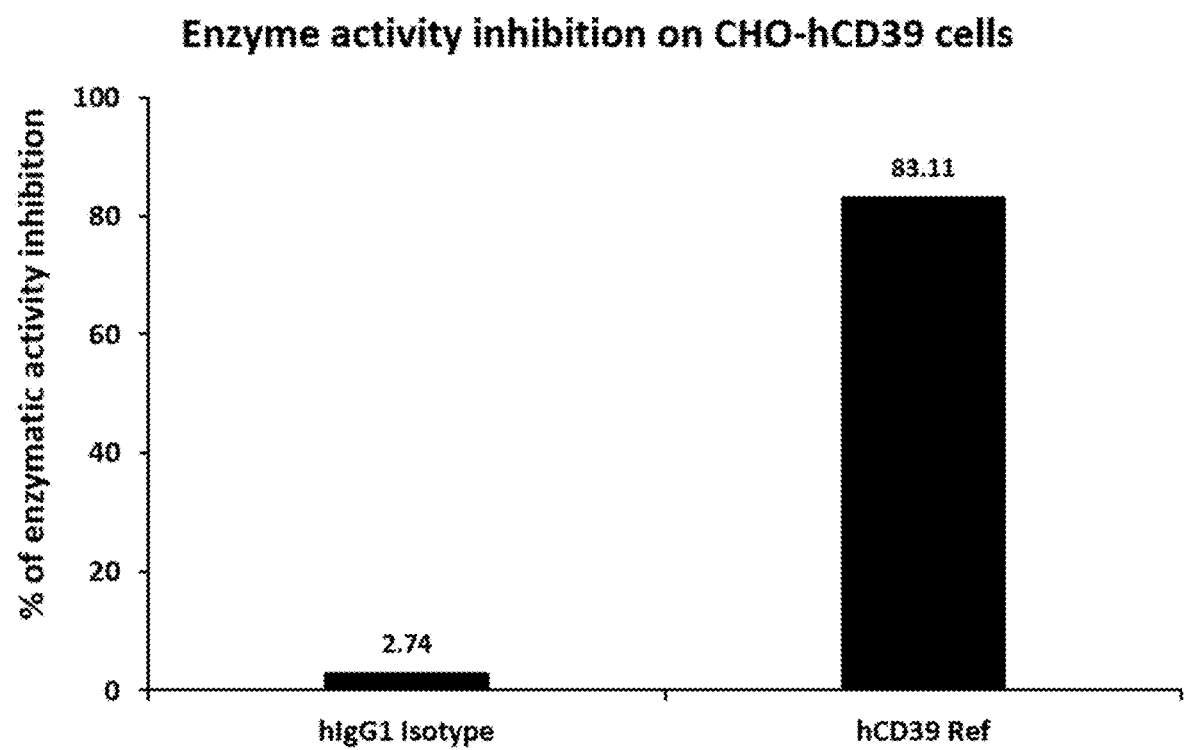
FIG. 25. Reference anti-human CD39 monoclonal antibody (hCD39 Ref) inhibits hCD39 ATPase activity on CHO cell membrane. CHO-hCD39 cells were incubated with 10 µg/mL of human IgG1 isotype Ultra-LEAF antibody or anti-hCD39 Ref antibody (hCD39 Ref) for 30 minutes at 37° C., followed by incubation with ATP (250 µM) for 15 minutes at room temperature. Supernatants were then collected, and ATP levels were detected by luminescence using CellTiter-Glo®. Cells with no antibody (Cells+ ATP) or ATP alone in the absence of cells were also detected in parallel to calculate the % of enzyme activity inhibition as described in Materials and Methods.

As an example, by comparing epitopes of the subject Human/Rabbit chimeric anti-hCD39 antibodies against the commercially available anti-hCD39 monoclonal antibody Clone A1, FIGS. 18 and 21-23 show anti-CD39 antibodies that bind to CD39 in a manner that is non-competitive or only partially competitive with Clone A1 binding to CD39 have a high likelihood of containing high ADCC activity, i.e. five (2G12, 8C11, 8D8, 9B6 and 9C10) out of six ADCC-high antibodies, except 65H5, display such trait (FIG. 21). In contrast, all antibodies in the ADCC-low (2A11, 5F1, 52G4 and 63B1) and ADCC-negative (8E9, 59B6, 60D9, 62G12, 62H10, 65E10, 67A8 and 67C1) groups display epitopes that completely overlap with Clone A1's (FIGS. 22 & 23).

Multiple CD39high cellular targets of the subject anti-CD39 antibodies in the tumor.

As an example, a CD39-MC38 colorectal cancer model in hCD39 KI mice (FIGS. 15 & 16) was employed. Anti-tumor activity by NP501-BK in this model is a consequence of its targeted effects on CD39$^{high}$ tumor-infiltrating lymphocytes and tumor-associated vascular endothelial cells (data not shown).

Figure 17:
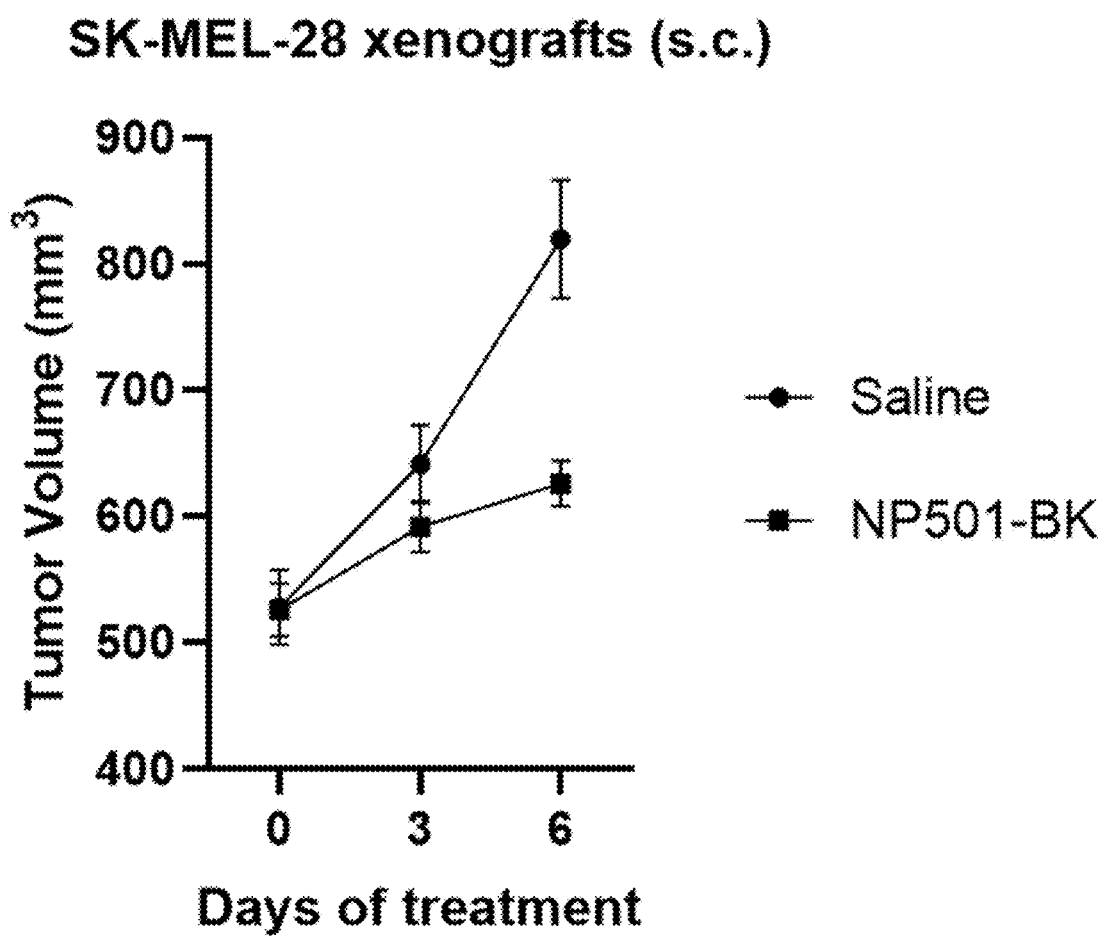
FIG. 17. NP501-BK exerts anti-tumor activity in the CD39+SK-MEL-28 xenograft model. NU/J nude mice subcutaneously implanted with SK-MEL-28 xenografts were used for evaluation of in vivo efficacy of NP501-BK. When tumors reached an average volume of approximately 500 mm$^3$ (considered as day 0 of treatment), mice were treated with two doses of 300 µl of saline or 10 mg/kg of NP501-BK on days 0 and 3 via i.p. Tumor length (L) and width (W) were measured using a digital caliper every three days. Tumor volume (mm$^3$) was determined as L*W*W*0.52. n=6-7 per group.
Figure 18:
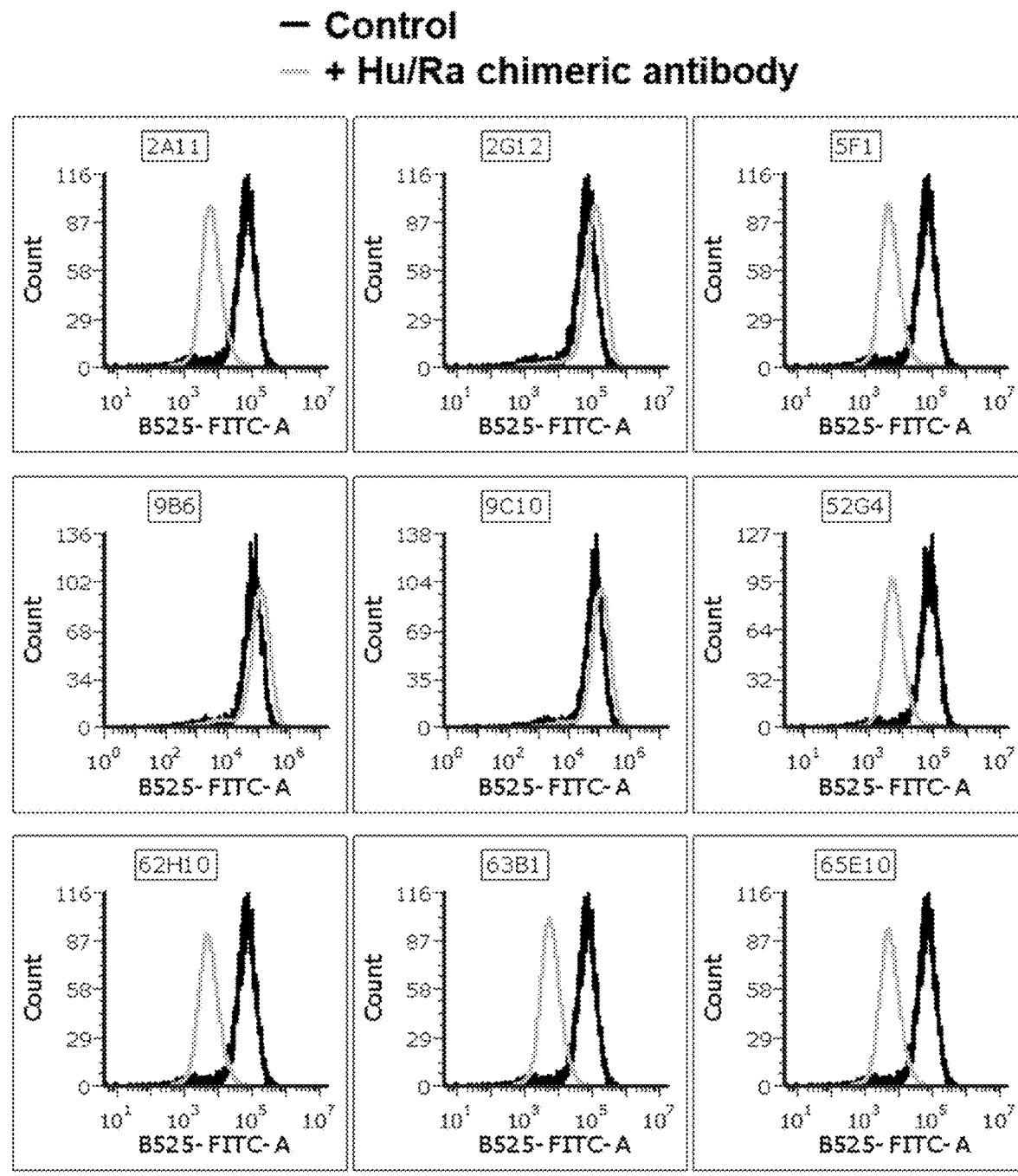
FIG. 18. Epitope competition assay of 18 Human/Rabbit chimeric anti-human CD39 monoclonal antibodies against reference anti-hCD39 monoclonal antibody Clone A1 on HCC1739BL cells. HCC1739BL cells were incubated with a panel of 18 anti-hCD39 monoclonal antibodies (Human/Rabbit chimeric clones; unconjugated, 2 µg/ml) at 4° C. for 30 minutes. Cells were then washed twice and stained with mouse anti-hCD39 monoclonal antibody Clone A1 conjugated with PE for 30 minutes at 4° C., followed by flow cytometry analysis. Cells without chimeric antibody incubation were used as a control.
Figure 18:
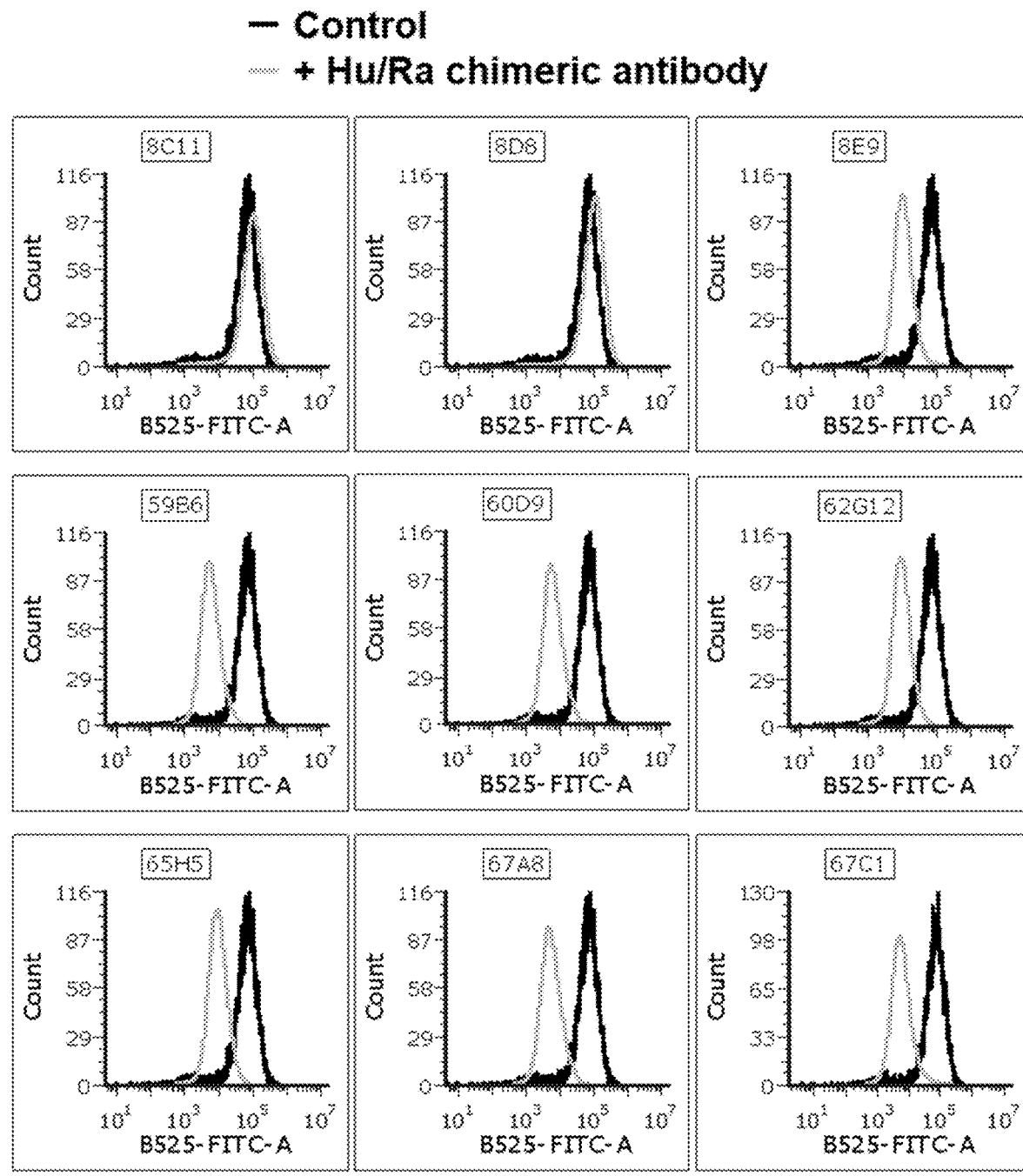
Figure 19:
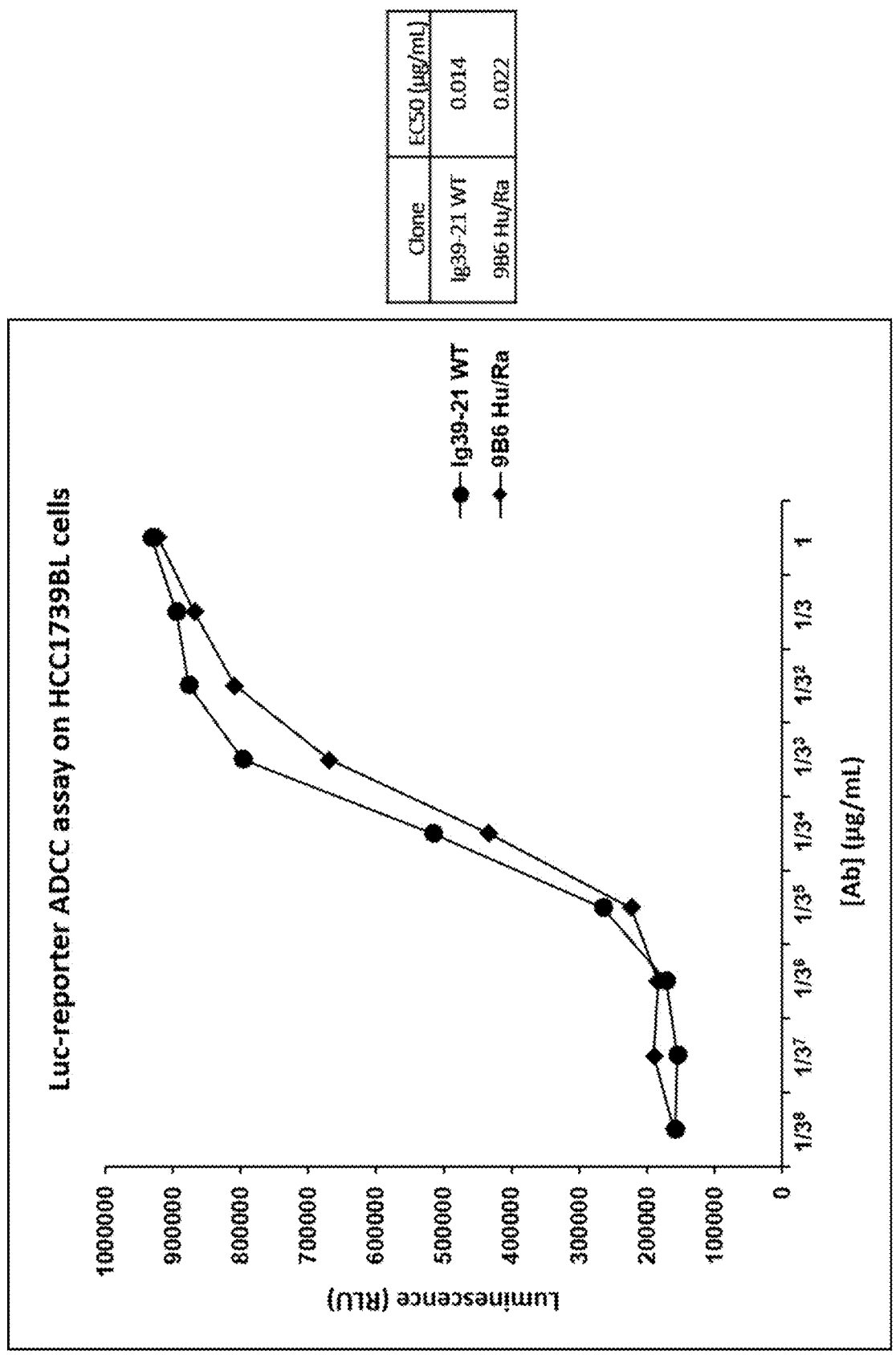
FIG. 19. Human/Rabbit chimeric clone 9B6 and Ig39-21 exert similar ADCC activity: Luc-reporter assay using HCC1739BL cells. HCC1739BL cells were used as target cells. Jurkat cells stably expressing luciferase and hCD16a-158V were used as effector cells. Target cells were pre-incubated with serially diluted Ig39-21 WT or Human/Rabbit chimeric clone 9B6 (Hu/Ra 9B6; a rabbit anti-hCD39 monoclonal antibody chimerized with a human IgG1 Fc having the highest ADCC activity among all chimeric clones) for 30 minutes at 37° C. and further co-cultured with Jurkat effector cells (T:E=1:6) for 6 hours. ADCC activity was indicated by an increase of luciferase activity over background (RLU). RLU: Relative Luminescence Unit. EC50 was calculated as 0.014 µg/mL (Ig39-21 WT) and 0.022 µg/mL (Hu/Ra 9B6).
Figure 20:
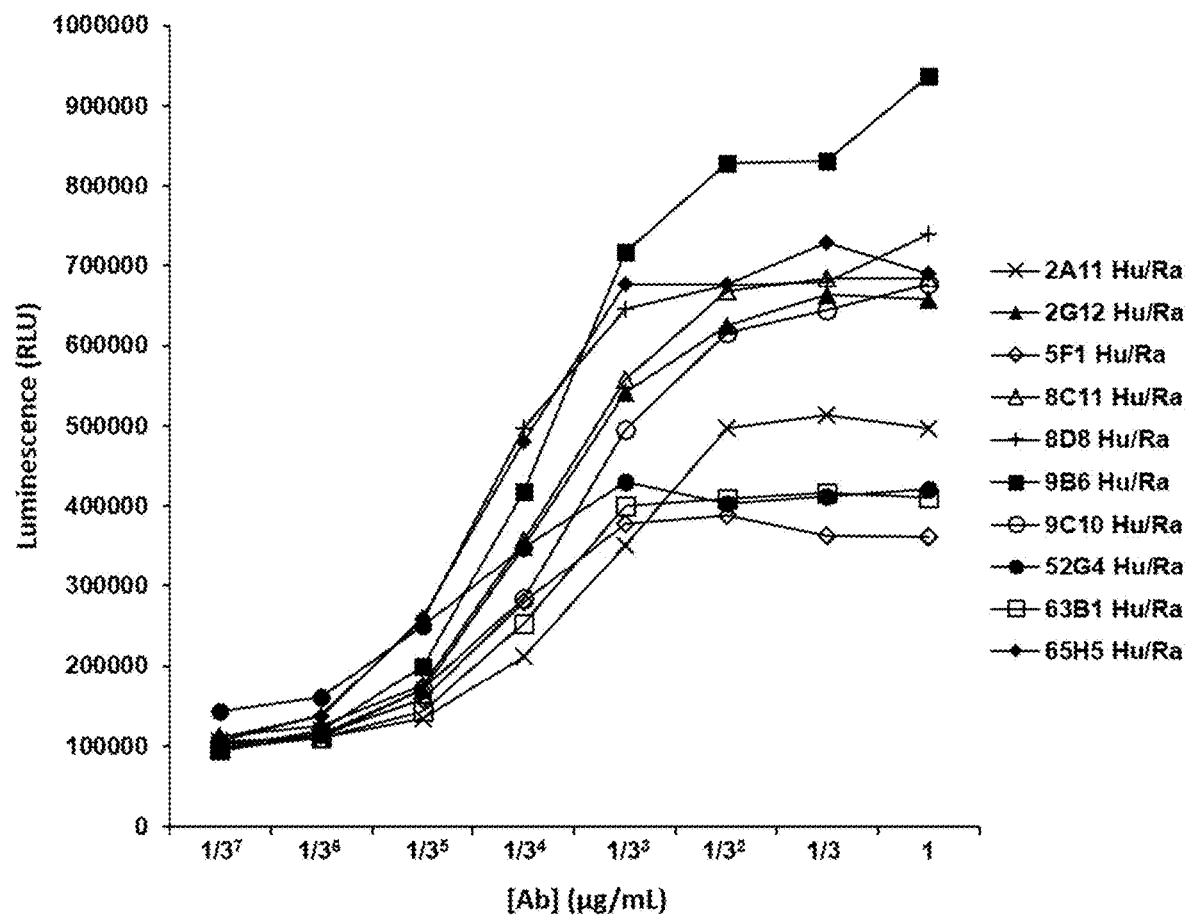
FIG. 20. ADCC activities of 18 Human/Rabbit chimeric antibodies: Luc-reporter assay using HCC1739BL cells. HCC1739BL cells were used as target cells. Jurkat cells stably expressing luciferase and hCD16a-158V were used as effector cells. A panel of 18 Human/Rabbit chimeric antibodies was examined for ADCC activity, as described above. Briefly, target cells were pre-incubated with serially diluted antibodies for 30 minutes at 37° C. and further co-cultured with Jurkat effector cells (T:E=1:6) for 6 hours. ADCC activity was indicated by an increase of luciferase activity over background (RLU). RLU: Relative Luminescence Unit. Ten out of 18 clones show positive ADCC activity.

Another example is the xenograft tumor model using NU/J nude mice implanted with CD39+ human SK-MEL-28 melanoma cells (FIG. 17). These homozygous athymic nude mice lack T cells with also a partial defect in B cell development, whereas their NK cells are functionally competent. Therefore, the target cells of NP501-BK-mediated ADCC killing in this xenograft tumor model are CD39+SK-MEL-28 tumor cells, which is in line with the antibody's in vitro ADCC activity toward SK-MEL-28 cells (FIG. 4).

II. Definitions

To facilitate an understanding of the present invention, a number of terms and phrases are defined below.

"CD39", also referred to as "Cluster of Differentiation 39", "ectonucleoside triphosphate diphosphohydrolase-1" or (gene) "ENTPD1" and (protein) "NTPDase1" is a cell surface-located ectonucleotidase with an extracellularly facing catalytic site that catalyse the hydrolysis of γ- and β-phosphate residues of triphospho- and diphosphonucleosides to the monophosphonucleoside derivative (ENZYME entry: EC 3.6.1.5), such as to hydrolyzes P2 receptor ligands such as ATP, ADP, UTP and UDP (Junger et al. (2011) *Nat. Rev. Immunol.* 11:201-212). A representative human NTPDase1 protein sequence is provided in the UniProtKB entry "P49961 (ENTP1_HUMAN)", and a representative human coding sequence for the enzyme is provided in GenBank Accession S73813. Pericellular adenosine can modulate proinflammatory or proinhibitory signals in immune cells by binding various adenosine receptors (Ernst et al. (2010) *J. Immunol.* 185:1993-1998; Antonioli et al. (2013) *Trends Mol. Med.* 19:355-367; Parodi et al. (2013) *Cancer Immunol. Immunother.* 62:851-862; Boer et al. (2013) *Eur. J. Immunol.* 43:1925-1932; Xu et al. (2013) *Neuro-Oncol.* 15:1160-1172; U.S. Pat. Publ. 2013/0123345). For example, adenosine binds to A2A receptors expressed by lymphocytes causing accumulation of intracellular cAMP, preventing T cell activation and NK cytotoxicity (Zarek et al. (2008) *Blood* 111:251-259; Lokshin et al. (2006) *Canc. Res.* 66:7758-7765). CD39 was originally identified as an activation marker on human lymphocytes, but has subsequently been shown to be a hallmark feature of regulatory T cells (Kansas et al. (1991) *J. Immunol.* 146:2235-2244; Deaglio et al. (2007) *J. Exp. Med.* 204:1257-1265; Borsellino et al. (2007) *Blood* 110:1225-1232). Loss of CD39 in Tregs markedly impairs their ability to suppress T cell activation, suggesting that the juxtacrine activity of CD39 serves to negatively regulate T cell function (Deaglio et al. (2007) *J. Exp. Med.* 204:1257-1265). CD8+ T cells have generally been reported to be CD39$^-$ (Kansas et al. (1991) *J. Immunol.* 146:2235-2244; Moncrieffe et al. (2010) *J. Immunol.* 185: 134-143; Pulte et al. (2011) *Clin. Lymph. Myeloma Leuk.* 11:367-372; Boer et al. (2013) *Eur. J. Immunol.* 43:1925-1932). However, upregulation of this marker on exhausted T cells has recently been noted in the settings of tumor and chronic viral infections (e.g. HCV and HIV, as well as coronaviridae such as SARS-COV2 (COVID-19)) (Canale et al. (2017) *Cancer Res.* 78(1):115-28; Gupta et al. (2015) *PLoS Pathog.* 11(10):e1005177; Mathew et al. (2020) *Science* 10.1126/science.abc8511).

The structure-function relationship of CD39 proteins is well known in the art (reviewed, for example, by Antonioli et al. (2013) *Trends Mol. Med.* 19:355-367; Wang and Guidotti (1996) *J. Biol. Chem.* 271:9898-9901; Kaczmarek et al. (1996) *J. Biol. Chem.* 271:33116-33122). For example, human CD39 is an approximately 500-amino acid protein with approximately seven potential N-linked glycosylation sites, eleven Cys residues, and two transmembrane regions (Maliszewski et al. (1994) *J. Immunol.* 153:3574-3583) organized in the form of two transmembrane domains, a small cytoplasmic domain comprising the N- and C-terminal segments, and a large extracellular hydrophobic domain consisting of five highly conserved domains, known as apyrase conserved regions (ACR) 1-5, which are required for the enzyme's catabolic activity (Heine et al. (2001) *Eur. J. Biochem.* 268:364-373). The amino acid sequences of ACR 1 and ACR 5 contain a phosphate-binding motif (DXG), which is important for stabilizing the interaction between the enzyme and its nucleotide substrate during phosphate cleavage. In addition, two ACR residues, Glu 174 in ACR 3 and Ser 218 of ACR 4 are also required for enzymatic activity (Heine et al. (2001) *Eur. J. Biochem.* 268:364-373; Smith et al. (1998) *Biochim. Biophys.* Acta 1386:65-78). Upon cell surface expression, CD39 becomes catalytically active (Smith et al. (1998) *Biochim. Biophys. Acta* 1386:65-78).

Representative human CD39 cDNA and protein sequences are well-known in the art and are publicly available from the National Center for Biotechnology Information (NCBI). For example, at least seven human CD39 transcript variants are known encoding six different human CD39 isoforms. Human CD39 isoform 1 is available under accession numbers NM_001776.5 and NP_001767.3. The transcript variant represents the longest transcript and encodes isoform 1. Human CD39 isoform 2, available under accession numbers NM_001098175.1 and NP_001091645.1, uses an alternate 5' exon than transcript variant 1 that results in a distinct 5' untranslated region (UTR) and causes translation initiation at an alternate start codon leading to a longer and distinct N-terminus. Human CD39 isoform 3, available under accession numbers NM_001164178.1 and NP_001157650.1, uses an alternate 5' exon than transcript variant 1 that results in a distinct 5' UTR and causes translation initiation at an alternate start codon leading to a longer and distinct N-terminus. Human CD39 isoform 4, available under accession numbers NM_001164179.1 and NP_001157651.1, uses an alternate in-frame splice site as compared with transcript variant 1 resulting in a shorter isoform. Human CD39 isoform 5, available under accession numbers NM_001164181.1 and NP_001157653.1, uses an alternate exon in the 5' region that results in a distinct 5' UTR and translation initiation at a downstream start codon relative to transcript variant 1 resulting in a shorter isoform. Human CD39 isoform 6, available under accession numbers NM_001164182.1 and NP_001157654.1, lacks an alternate exon that results in a distinct 5' UTR and causes translation initiation at a downstream start codon relative to transcript variant 1 resulting in a shorter isoform. Human CD39 isoform 6 is also encoded by another transcript variant, available under accession numbers NM_001164183.1 and NP_001157655.1, which lacks two alternate internal exons that results in a distinct 5' UTR and causes translation initiation at a downstream start codon relative to transcript variant 1 resulting in a shorter isoform.

Nucleic acid and polypeptide sequences of CD39 orthologs in organisms other than humans are well known and include, for example, mouse CD39 (NM_009848.3 and NP_033978.1), rat CD39 (NM_022587.1 and NP_072109.1), cow CD39 (NM_174536.2 and NP_776961.1), frog CD39 (NM_001006795.1 and NP_001006796.1), and zebrafish CD39 (NM_001003545.1 and NP_001003545.1).

The extensive glycosylation of CD39 is associated with its cell surface expression and activity such that deletion of glycosylated residues or mutations to non-glycosylatable residues results in significantly reduced CD39 activity (see, for example, deletion or mutation of glycosylatable residues 73 at the N terminus, 333 in the middle, and/or 429 and/or 458 at the C terminus of rat CD39 or corresponding residues in orthologs thereof; Wu et al. (2005) *Mol. Biol. Cell.* 16:1661-1672). Similarly, mutations of conserved residues in the apyrase conserved region (ACR) of any one or more of ACRs 1-5 causes a reduction in CD39 activity (Schulte am Esch et al. (1999) *Biochem.* 38:2248-2258; Yang et al. (2001) *Biochem.* 40:3943-4940; Wang and Guidotti (1998) *J. Biol. Chem.* 273:11392-11399).

The modulation (e.g., decrease) in CD39 activity can be measured in any number of ways (e.g., according to measures described herein, including using controls, ratios, comparisons to baselines, and the like). For example, a CD39 activity modulator can decrease the catalytic activity of the ectonucleotidase or overall CD39 activity as compared to the level of such ectonucleotidase in the presence of a test agent. In one embodiment, CD39 activity is determined by analyzing the concentration of adenosine in a sample. The concentration can be assessed over time. In another embodiment, ATP is added in the sample tested and the concentration of remaining ATP, AMP or adenosine is determined or assessed. A modulation in this context, such as a decrease, can mean a decrease of 1%, 5%, 10%>, 20%, 25%, 30%, 35%, 40%, 45%, 50%, 55%, 60%, 65%, 70%, 75%, 80%, 85%, 90%, 95%, 100%, 120%, 150%, 200%, 500%, 1000%, or more. In an embodiment, said increase is detected over time.

A "CD39 Antibody" (alternatively an "anti-CD39 antibody") refers to an antibody that selectively binds to one or more epitopes of the NTPDase1 protein, and includes monoparatopic antibodies, as well as biparatopic and other multiparatopic format antibodies.

a. Antibodies and Other Polypeptides The term "antibody" as used herein refers to an immunoglobulin molecule that recognizes and specifically binds a target, such as a protein, polypeptide, peptide, carbohydrate, polynucleotide, lipid, or a combination of any of the foregoing, through at least one antigen-binding site wherein the antigen-binding site is usually within the variable region of the immunoglobulin molecule. As used herein, the term encompasses intact polyclonal antibodies, intact monoclonal antibodies, antibody fragments (such as Fab, Fab', F(ab')2, and Fv fragments), single chain Fv (scFv) antibodies provided those fragments have been formatted to include an Fc or other FcγRIII binding domain, multispecific antibodies, bispecific antibodies, monospecific antibodies, monovalent antibodies, chimeric antibodies, humanized antibodies, human antibodies, fusion proteins comprising an antigen-binding site of an antibody (formatted to include an Fc or other FcγRIII binding domain), and any other modified immunoglobulin molecule comprising an antigen-binding site as long as the antibodies exhibit the desired biological activity.

"Antibody-mediated target cytosis" in the context of the present invention refers to antibody-mediated depletion of CD39 from the surface of CD45+ immune cells without a substantial decrease in the number of CD45+ immune cells, i.e., through a process other than induction of CD45+ cell death.

The term "antigen-binding portion" or antigen-binding fragment" of an antibody, as used herein, refers to one or more fragments of an antibody that retain the ability to specifically bind to an antigen (e.g., human CD39). It has been shown that the antigen-binding function of an antibody can be performed by fragments of a full-length antibody. Examples of binding fragments encompassed within the term "antigen-binding portion" of an antibody, e.g., an anti-CD39 antibody described herein, include (i) a Fab fragment, a monovalent fragment consisting of the $V_L$, $V_H$, CL and CH1 domains; (ii) a F(ab')$_2$ fragment, a bivalent fragment comprising two Fab fragments linked by a disulfide bridge at the hinge region; (iii) a Fd fragment consisting of the $V_H$ and CH1 domains; (iv) a Fv fragment consisting of the $V_L$ and $V_H$ domains of a single arm of an antibody, (v) a dAb fragment (Ward et al., (1989) *Nature* 341:544-546), which consists of a $V_H$ domain; and (vi) an isolated complementarity determining region (CDR) or (vii) a combination of two or more isolated CDRs which may optionally be joined by a synthetic linker. Such single chain antibodies are also intended to be encompassed within the term "antigen-binding portion" of an antibody. These and other potential constructs are described at Chan & Carter (2010) *Nat. Rev. Immunol.* 10:301. These antibody fragments are obtained using conventional techniques known to those with skill in the art, and the fragments are screened for utility in the same manner as are intact antibodies. Antigen-binding portions can be produced by recombinant DNA techniques, or by enzymatic or chemical cleavage of intact immunoglobulins.

The term "variable region" of an antibody refers to the variable region of an antibody light chain, or the variable region of an antibody heavy chain, either alone or in combination. Generally, the variable region of heavy and light chains each consist of four framework regions (FR) and three complementarity determining regions (CDRs), also known as "hypervariable regions". The CDRs in each chain are held together in close proximity by the framework regions and, with the CDRs from the other chain, contribute to the formation of the antigen-binding sites of the antibody. There are at least two techniques for determining CDRs: (1) an approach based on cross-species sequence variability (i.e., Kabat et al., 1991, *Sequences of Proteins of Immunological Interest*, 5th Edition, National Institutes of Health, Bethesda Md.), and (2) an approach based on crystallographic studies of antigen-antibody complexes (Al Lazikani et al., 1997, *J. Mol. Biol.*, 273:927-948). In addition, combinations of these two approaches are sometimes used in the art to determine CDRs.

While the antibody can be any of the five major classes of immunoglobulins: IgA, IgD, IgE, IgG, and IgM, or subclasses (isotypes) thereof (e.g., IgG1, IgG2, IgG3, IgG4, IgA1 and IgA2), based on the identity of their heavy-chain constant domains referred to as alpha, delta, epsilon, gamma, and mu, respectively, the preferred CD39 antibody is an IgG1 and IgG3 isotype in order to engage FcγRIII most effectively (i.e., with a Kd of $10^{-7}$ or smaller).

In certain embodiments, the antibody is "hypofucosylated" and may even be "afucosylated". A "hypofucosylated" antibody preparation refers to an antibody preparation in which less than 50% of the oligosaccharide chains contain α-1,6-fucose. Typically, less than about 40%, less than about 30%, less than about 20%, less than about 10%, or less than 5% or less than 1% of the oligosaccharide chains contain α-1,6-fucose in a "hypofucosylated" antibody preparation. An "afucosylated" antibody lacks α-1,6-fucose in the carbohydrate attached to the CH2 domain of the IgG heavy chain.

The term "monoclonal antibody," as used herein, refers to an antibody that displays a single binding specificity and affinity for a particular epitope or a composition of antibodies in which all antibodies display a single binding specificity and affinity for a particular epitope. Typically such monoclonal antibodies will be derived from a single cell or nucleic acid encoding the antibody, and will be propagated without intentionally introducing any sequence alterations. Accordingly, the term "human monoclonal antibody" refers to a monoclonal antibody that has variable and optional constant regions derived from human germline immunoglobulin sequences. In one embodiment, human monoclonal antibodies are produced by a hybridoma, for example, obtained by fusing a B cell obtained from a transgenic or transchromosomal non-human animal (e.g., a transgenic mouse having a genome comprising a human heavy chain transgene and a light chain transgene), to an immortalized cell.

The term "humanized antibody" as used herein refers to forms of non-human (e.g., murine) antibodies that are specific immunoglobulin chains, chimeric immunoglobulins, or fragments thereof that contain minimal non-human sequences. Typically, humanized antibodies are human immunoglobulins in which residues of the CDRs are replaced by residues from the CDRs of a non-human species (e.g., mouse, rat, rabbit, or hamster) that have the desired specificity, affinity, and/or binding capability. In some instances, the Fv framework region residues of a human immunoglobulin are replaced with the corresponding residues in an antibody from a non-human species. The humanized antibody can be further modified by the substitution of additional residues either in the Fv framework region and/or within the replaced non-human residues to refine and optimize antibody specificity, affinity, and/or binding capability. The humanized antibody may comprise variable domains containing all or substantially all of the CDRs that correspond to the non-human immunoglobulin whereas all or substantially all of the framework regions are those of a human immunoglobulin sequence. In some embodiments, the variable domains comprise the framework regions of a human immunoglobulin sequence. In some embodiments, the variable domains comprise the framework regions of a human immunoglobulin consensus sequence. The humanized antibody can also comprise at least a portion of an immunoglobulin constant region or domain (Fc), typically that of a human immunoglobulin. A humanized antibody is usually considered distinct from a chimeric antibody. The term "human antibody" as used herein refers to an antibody produced by a human or an antibody having an amino acid sequence corresponding to an antibody produced by a human made using any of the techniques known in the art.

The term "chimeric antibody" as used herein refers to an antibody wherein the amino acid sequence of the immunoglobulin molecule is derived from two or more species. Typically, the variable region of both light and heavy chains corresponds to the variable region of antibodies derived from one species of mammals (e.g., mouse, rat, rabbit, etc.) with the desired specificity, affinity, and/or binding capability, while the constant regions are homologous to the sequences in antibodies derived from another species (usually human) to avoid eliciting an immune response in that species.

An "Fc receptor" or "FcR" is a receptor that binds to the Fc region of an immunoglobulin. FcRs that bind to an IgG antibody comprise receptors of the FcγR family, including allelic variants and alternatively spliced forms of these receptors. The FcγR family consists of three activating (FcγRI, FcγRIII, and FcγRIV in mice; FcγRIA, FcγRIIA, and FcγRIIIA in humans) and one inhibitory (FcγRIIB) receptor.

An "FcγRIII binding moiety" is a peptide, protein, nucleic acid or other moiety which, when associated with an antigen binding site of an anti-CD39 antibody, is able to bind to FcγRIII (CD16) and mediate antibody-dependent cellular cytotoxicity (ADCC). The heavy chain Fc fragment containing the CH2 and CH3 domains of IgG1 and IgG3 isotypes are FcγRIII binding moiety.

The terms "epitope" and "antigenic determinant" are used interchangeably herein and refer to that portion of an antigen capable of being recognized and specifically bound by a particular antibody. When the antigen is a polypeptide, epitopes can be formed both from contiguous amino acids and noncontiguous amino acids juxtaposed by tertiary folding of a protein. Epitopes formed from contiguous amino acids (also referred to as linear epitopes) are typically retained upon protein denaturing, whereas epitopes formed by tertiary folding (also referred to as conformational epitopes) are typically lost upon protein denaturing. An epitope typically includes at least 3, and more usually, at least 5, 6, 7, or 8-10 amino acids in a unique spatial conformation. As used herein, the term "specifically binds to" or is "specific for" refers to measurable and reproducible interactions such as binding between a target and an antibody, which is determinative of the presence of the target in the presence of a heterogeneous population of molecules including biological molecules. For example, an antibody that specifically binds to a target (which can be an epitope) is an antibody that binds this target with greater affinity, avidity, more readily, and/or with greater duration than it binds to other targets. In one embodiment, the extent of binding of an antibody to an unrelated target is less than about 10% of the binding of the antibody to the target as measured, e.g., by a radioimmunoassay (RIA). In certain embodiments, an antibody that specifically binds to a target has a dissociation constant (Kd) of less than or equal to 1 µM, 100 nM, 10 nM, 1 nM, or even 0.1 nM. In certain embodiments, an antibody specifically binds to an epitope on a protein that is conserved among the protein from different species. In another embodiment, specific binding can include, but does not require exclusive binding.

The terms "polypeptide" and "peptide" and "protein" are used interchangeably herein and refer to polymers of amino acids of any length. The polymer may be linear or branched, it may comprise modified amino acids, and it may be interrupted by non-amino acids. The terms also encompass an amino acid polymer that has been modified naturally or by intervention; for example, disulfide bond formation, glycosylation, lipidation, acetylation, phosphorylation, or any other manipulation or modification, such as conjugation with a labeling component. Also included within the definition are, for example, polypeptides containing one or more analogs of an amino acid (including, for example, unnatural amino acids), as well as other modifications known in the art. It is understood that, because the polypeptides encompassed by the present invention may be based upon antibodies or other members of the immunoglobulin superfamily, in certain embodiments, the polypeptides can occur as single chains or as associated chains.

The terms "identical" or percent "identity" in the context of two or more nucleic acids or polypeptides, refer to two or more sequences or subsequences that are the same or have a specified percentage of nucleotides or amino acid residues that are the same, when compared and aligned (introducing gaps, if necessary) for maximum correspondence, not considering any conservative amino acid substitutions as part of the sequence identity. The percent identity may be measured using sequence comparison software or algorithms or by visual inspection. Various algorithms and software that may be used to obtain alignments of amino acid or nucleotide sequences are well-known in the art. These include, but are not limited to, BLAST, ALIGN, Megalign, BestFit, GCG Wisconsin Package, and variants thereof. In some embodiments, two nucleic acids or polypeptides encompassed by the invention are substantially identical, meaning they have at least 70%, at least 75%, at least 80%, at least 85%, at least 90%, and in some embodiments at least 95%, 96%, 97%, 98%, 99% nucleotide or amino acid residue identity, when compared and aligned for maximum correspondence, as measured using a sequence comparison algorithm or by visual inspection. In some embodiments, identity exists over a region of the amino acid sequences that is at least about 10 residues, at least about 20 residues, at least about 40-60 residues, at least about 60-80 residues in length or any integral value there between. In some embodiments, identity exists over a longer region than 60-80 residues, such as at least about 80-100 residues, and in some embodiments the sequences are substantially identical over the full length of the sequences being compared, such as the coding region of a target protein or an antibody. In some embodiments, identity exists over a region of the nucleotide sequences that is at least about 10 bases, at least about 20 bases, at least about 40-60 bases, at least about 60-80 bases in length or any integral value there between. In some embodiments, identity exists over a longer region than 60-80 bases, such as at least about 80-1000 bases or more, and in some embodiments the sequences are substantially identical over the full length of the sequences being compared, such as a nucleotide sequence encoding a protein of interest.

A "conservative amino acid substitution" is one in which one amino acid residue is replaced with another amino acid residue having a similar side chain. Families of amino acid residues having similar side chains have been generally defined in the art, including basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), nonpolar side chains (e.g., alanine, valine, leucine, isoleucine, proline, phenylalanine, methionine, tryptophan), beta-branched side chains (e.g., threonine, valine, isoleucine) and aromatic side chains (e.g., tyrosine, phenylalanine, tryptophan, histidine). For example, substitution of a phenylalanine for a tyrosine is a conservative substitution. Generally, conservative substitutions in the sequences of the polypeptides, soluble proteins, and/or antibodies encompassed by the present invention do not abrogate the binding of the polypeptide, soluble protein, or antibody containing the amino acid sequence, to the target binding site. Methods of identifying amino acid conservative substitutions which do not eliminate binding are well-known in the art.

A polypeptide, soluble protein, antibody, polynucleotide, vector, cell, or composition which is "isolated" is a polypeptide, soluble protein, antibody, polynucleotide, vector, cell, or composition which is in a form not found in nature. Isolated polypeptides, soluble proteins, antibodies, polynucleotides, vectors, cells, or compositions include those which have been purified to a degree that they are no longer in a form in which they are found in nature. In some embodiments, a polypeptide, soluble protein, antibody, polynucleotide, vector, cell, or composition which is isolated is substantially pure.

The term "substantially pure" as used herein refers to material which is at least 50% pure (i.e., free from contaminants), at least 90% pure, at least 95% pure, at least 98% pure, or at least 99% pure.

The term "fusion protein" or "fusion polypeptide" as used herein refers to a hybrid protein expressed by a nucleic acid molecule comprising nucleotide sequences of at least two genes.

The term "linker" or "linker region" as used herein refers to a linker inserted between a first polypeptide (e.g., an anti-CD39 antibody) and a second polypeptide (e.g., an Fc or other FcγRIII binding moiety; an scFV, Vhh domain or the like the binds a different protein to create a bispecific antibody format maintaining the bivalency for CD39). In some embodiments, the linker is a peptide linker. Linkers should not adversely affect the expression, secretion, or bioactivity of the polypeptides. Preferably, linkers are not antigenic and do not elicit an immune response.

b. Nucleic Acids

The terms "polynucleotide" and "nucleic acid" and "nucleic acid molecule" are used interchangeably herein and refer to polymers of nucleotides of any length, and include DNA and RNA. The nucleotides can be deoxyribonucleotides, ribonucleotides, modified nucleotides or bases, and/or their analogs, or any substrate that can be incorporated into a polymer by DNA or RNA polymerase.

As used herein, the term "nucleic acid molecule encoding", "DNA sequence encoding," and "DNA encoding" refer to the order or sequence of nucleotides along a strand of deoxyribonucleic acid deoxyribonucleotides. The order of these deoxyribonucleotides determines the order of amino acids along the polypeptide (protein) chain. Thus, a nucleic acid sequence encoding the amino acid sequence.

When used in reference to nucleotide sequences, "sequence" as used herein, the term grammatical and other forms may comprise DNA or RNA, and may be single or double stranded. Nucleic acid sequences may be mutated.

The term "vector" as used herein means a construct, which is capable of delivering, and usually expressing, one or more gene(s) or sequence(s) of interest in a host cell. Examples of vectors include, but are not limited to, viral vectors, naked DNA or RNA expression vectors, plasmid, cosmid, or phage vectors, DNA or RNA expression vectors associated with cationic condensing agents, and DNA or RNA expression vectors encapsulated in liposomes.

As used herein, the term "transfection" refers to an exogenous nucleic acid into a eukaryotic cell. Transfection can be achieved by various means known in the art, including calcium phosphate-DNA co-precipitation, DEAE-dextran-mediated transfection, polybrene-mediated transfection, electroporation, microinjection, liposome fusion, lipofection, protoplast fusion, retroviral infection, and biolistics technology (biolistics).

The term "carrier" as used herein is an isolated nucleic acid comprising the isolated nucleic acid can be used to deliver a composition to the interior of the cell. It is known in the art a number of carriers including, but not limited to the linear polynucleotides, polynucleotides associated with ionic or amphiphilic compounds, plasmids, and viruses. Thus, the term "vector" includes an autonomously replicating plasmid or virus. The term should also be construed to include facilitate transfer of nucleic acid into cells of the non-plasmid and non-viral compounds, for example, polylysine compounds, liposomes, and the like. Examples of viral vectors include, but are not limited to adenoviral vectors, adeno-associated virus vectors, retroviral vectors and the like.

As used herein, the term "expression vector" refers to a vector comprising a recombinant polynucleotide comprising expression control sequence and a nucleotide sequence to be expressed operably linked. The expression vector comprises sufficient cis-acting elements (cis-acting elements) used for expression; other elements for expression can be supplied by the host cell or in vitro expression system. Expression vectors include all those known in the art, such as cosmids, plasmids (e.g., naked or contained in liposomes) and viruses (e.g., lentivirus, retroviruses, adenoviruses and adeno-associated viruses).

As used herein, the term "operably linked" refers to functional linkage between the regulatory sequence and a heterologous nucleic acid sequence is connected to a connection results in the expression of the latter. For example, when the first nucleic acid sequence and a second nucleic acid sequence is a functional relationship between the first nucleic acid sequence and the second nucleic acid sequence is operably linked. For example, if the promoter affects the transcription or expression of the coding sequence, the promoter is operably linked to a coding sequence.

Typically, DNA sequencing operably linked are contiguous, and to join two protein coding regions in the same reading frame as necessary.

As used herein, the term "promoter" is defined as a promoter DNA sequence recognized by the synthetic machinery required for the synthesis machinery of the cell specific transcription of a polynucleotide sequence or introduced.

The term "constitutive expression" as used herein refers to all expressed under physiological conditions.

The term "inducible expression" as used herein refers to expression under certain conditions, the conditions such as occurs when a T cell antigen binding. How those skilled in the routine "induce expression."

The term "electroporation" refers to the use of a transmembrane electric field pulse to induce microscopic pathways (pores) in a bio-membrane; their presence allows biomolecules such as plasmids or other oligonucleotide to pass from one side of the cellular membrane to the other.

c. Checkpoint Inhibitors, Co-stimulatory Agonists, Innate Immune Inducers and Chemotherapeutics A "checkpoint molecule" refers to proteins that are expressed by tissues and/or immune cells and reduce the efficacy of an immune response in a manner dependent on the level of expression of the checkpoint molecule. When these proteins are blocked, the "brakes" on the immune system are released and, for example, T cells are able to kill cancer cells more effectively. Examples of checkpoint proteins found on T cells or cancer cells include PD-1/PD-L1 and CTLA-4/B7-1/B7-2, PD-L2, NKG2A, KIR, LAG-3, TIM-3, CD96, VISTA, TIGIT and Siglec-15.

A "checkpoint inhibitor" refers to a drug entity that reverses the immunosuppressive signaling from a checkpoint molecule.

A "costimulatory molecule" refers to an immune cell such as a T cell cognate binding partner which specifically binds to costimulatory ligands thereby mediating co-stimulation, such as, but not limited to proliferation. Costimulatory molecules are cell surface molecules other than the antigen receptor or ligand which facilitate an effective immune response. Co-stimulatory molecules include, but are not limited to MHCI molecules, BTLA receptor and Toll ligands, and OX40, CD27, CD28, CDS, ICAM-1, LFA-1 (CD11a/CD18), ICOS (CD278) and 4-1BB (CD137).

Examples of costimulatory molecules include but are not limited to: CDS, ICAM-1, GITR, BAFFR, HVEM (LIGHTR), SLAMF7, NKp80 (KLRF1), NKp44, NKp30, NKp46, CD160, CD19, CD4, CD8α, CD8β, IL2Rβ, IL2Rγ, IL7Rα, ITGA4, VLA1, CD49a, ITGA4, IA4, CD49D, ITGA6, VLA-6, CD49f, ITGAD, CD11d, ITGAE, CD103, ITGAL, CD11a, LFA-1, ITGAM, CD11b, ITGAX, CD11c, ITGB1, CD29, ITGB2, CD18, LFA-1, ITGB7, NKG2D, NKG2C, TNFR2, TRANCE/RANKL, DNAM1 (CD226), SLAMF4 (CD244,2B4), CD84, CD96 (Tactile), CEACAMi, CRTAM, Ly9 (CD229), CD160 (BY55), PSGL1, CD100 (SEMA4D), CD69, SLAMF6 (NTB-A, Ly108), SLAM (SLAMF1, CD150, IPO-3), BLAME (SLAMF8), SELPLG (CD162), LTBR, LAT, GADS, SLP-76, PAG/Cbp, CD19a, and CD83 ligand.

A "costimulatory agonists" refers to a drug entity that activates (agonizes) the costimulatory molecule, such as costimulatory ligand would do, and produces an immunostimulatory signal or otherwise increases the potency or efficacy of an immune response.

An "innate immune inducer" is an agent that mimics the innate immune response, including activation of inflammatory activities and/or deactivation of anti-inflammatory activities of macrophage, NK cells, dendritic cells, monocytes, neutrophils and the like. Innate immune inducers include inhibitors of the CD47-SIRPα axis, such as antibodies or other binding moieties that bind to CD47 or SIRPα and inhibit the interaction of the two molecules in order to promote antitumor macrophage activity. Innate immune inducers include inhibitors of the CD24-Siglec-10 axis, such as antibodies or other binding moieties that bind to CD24 or Siglec-10 and inhibit the interaction of the two molecules in order to promote antitumor macrophage activity. In other embodiments, the innate immune activator can be an NGK2A checkpoint inhibitor that blocks HLA-E driven inhibition of NK and CD8+ cells. Small molecule inducers of innate immunity include such agents STING agonist, TLR7/8 agonists and RIG-1 agonists.

A "chemotherapeutic agent" is a chemical compound useful in the treatment of cancer. Examples of chemotherapeutic agents include alkylating agents such as thiotepa and cyclophosphamide (CYTOXAN); alkyl sulfonates such as busulfan, improsulfan, and piposulfan; aziridines such as benzodopa, carboquone, meturedopa, and uredopa; ethylenimines and methylamelamines including altretamine, triethylenemelamine, trietylenephosphoramide, triethiylenethiophosphoramide and trimethylolomelamine; acetogenins (especially bullatacin and bullatacinone); delta-9-tetrahydrocannabinol (dronabinol, MARINOL); beta-lapachone; lapachol; colchicines; betulinic acid; a camptothecin (including the synthetic analogue topotecan (HYCAMTIN), CPT-11 (irinotecan, CAMPTOSAR), acetylcamptothecin, scopolectin, and 9-aminocamptothecin); bryostatin; pemetrexed; callystatin; CC-1065 (including its adozelesin, carzelesin and bizelesin synthetic analogues); podophyllotoxin; podophyllinic acid; teniposide; cryptophycins (particularly cryptophycin 1 and cryptophycin 8); dolastatin; duocarmycin (including the synthetic analogues, KW-2189 and CB1-TM1); eleutherobin; pancratistatin; TLK-286; CDP323, an oral alpha-4 integrin inhibitor; a sarcodictyin; spongistatin; nitrogen mustards such as chlorambucil, chlornaphazine, cholophosphamide, estramustine, ifosfamide, mechlorethamine, mechlorethamine oxide hydrochloride, melphalan, novembichin, phenesterine, prednimustine, trofosfamide, uracil mustard; nitrosureas such as carmustine, chlorozotocin, fotemustine, lomustine, nimustine, and ranimnustine; antibiotics such as the enediyne antibiotics (e.g., calicheamicin, especially calicheamicin gamma1I and calicheamicin omega1I (see, e.g., Nicolaou et al., Angew. Chem Intl. Ed. Engl., 33: 183-186 (1994)); dynemicin, including dynemicin A; an esperamicin; as well as neocarzinostatin chromophore and related chromoprotein enediyne antibiotic chromophores), aclacinomysins, actinomycin, authramycin, azaserine, bleomycins, cactinomycin, carabicin, carminomycin, carzinophilin, chromomycins, dactinomycin, daunorubicin, detorubicin, 6-diazo-5-oxo-L-norleucine, doxorubicin (including ADRIAMYCIN, morpholino-doxorubicin, cyanomorpholino-doxorubicin, 2-pyrrolino-doxorubicin, doxorubicin HCl liposome injection (DOXIL) and deoxydoxorubicin), epirubicin, esorubicin, idarubicin, marcellomycin, mitomycins such as mitomycin C, mycophenolic acid, nogalamycin, olivomycins, peplomycin, potfiromycin, puromycin, quelamycin, rodorubicin, streptonigrin, streptozocin, tubercidin, ubenimex, zinostatin, zorubicin; anti-metabolites such as methotrexate, gemcitabine (GEMZAR), tegafur (UFTORAL), capecitabine (XELODA), an epothilone, and 5-fluorouracil (5-FU); folic acid analogues such as denopterin, methotrexate, pteropterin, trimetrexate; purine analogs such as fludarabine, 6-mercaptopurine, thiamiprine, thioguanine; pyrimidine analogs such as ancitabine, azacitidine, 6-azauridine, carmofur, cytarabine, dideoxyuridine, doxifluridine, enocitabine, floxuridine, and imatinib (a 2-phenylaminopyrimidine derivative), as well as other c-Kit inhibitors; anti-adrenals such as aminoglutethimide, mitotane, trilostane; folic acid replenisher such as folinic acid; aceglatone; aldophosphamide glycoside; aminolevulinic acid; eniluracil; amsacrine; bestrabucil; bisantrene; edatraxate; defofamine; demecolcine; diaziquone; elfornithine; elliptinium acetate; etoglucid; gallium nitrate; hydroxyurea; lentinan; lonidainine; maytansinoids such as maytansine and ansamitocins; mitoguazone; mitoxantrone; mopidanmol; nitraerine; pentostatin; phenamet; pirarubicin; losoxantrone; 2-ethylhydrazide; procarbazine; PSK polysaccharide complex (JHS Natural Products, Eugene, Oreg.); razoxane; rhizoxin; sizofiran; spirogermanium; tenuazonic acid; triaziquone; 2,2',2''-trichlorotriethylamine; trichothecenes (especially T-2 toxin, verracurin A, roridin A and anguidine); urethan; vindesine (ELDISINE, FILDESIN); dacarbazine; mannomustine; mitobronitol; mitolactol; pipobroman; gacytosine; arabinoside ("Ara-C"); thiotepa; taxoids, e.g., paclitaxel (TAXOL), albumin-engineered nanoparticle formulation of paclitaxel (ABRAXANE), and doxetaxel (TAXOTERE); chlorambucil; 6-thioguanine; mercaptopurine; methotrexate; platinum analogs such as cisplatin and carboplatin; vinblastine (VELBAN); platinum; etoposide (VP-16); ifosfamide; mitoxantrone; vincristine (ONCOVIN); oxaliplatin; leucovovin; vinorelbine (NAVELBINE); novantrone; edatrexate; daunomycin; aminopterin; ibandronate; topoisomerase inhibitor RFS 2000; difluorometlhylornithine (DMFO); retinoids such as retinoic acid; pharmaceutically acceptable salts, acids or derivatives of any of the above; as well as combinations of two or more of the above such as CHOP, an abbreviation for a combined therapy of cyclophosphamide, doxorubicin, vincristine, and prednisolone, and FOLFOX, an abbreviation for a treatment regimen with oxaliplatin (ELOXATIN) combined with 5-FU and leucovovin.

Also included in this definition are anti-hormonal agents that act to regulate, reduce, block, or inhibit the effects of hormones that can promote the growth of cancer, and are often in the form of systemic, or whole-body treatment. They may be hormones themselves. Examples include anti-estrogens and selective estrogen receptor modulators (SERMs), including, for example, tamoxifen (including NOLVADEX tamoxifen), raloxifene (EVISTA), droloxifene, 4-hydroxytamoxifen, trioxifene, keoxifene, LY117018, onapristone, and toremifene (FARESTON); anti-progesterones; estrogen receptor down-regulators (ERDs); estrogen receptor antagonists such as fulvestrant (FASLODEX); agents that function to suppress or shut down the ovaries, for example, leutinizing hormone-releasing hormone (LHRH) agonists such as leuprolide acetate (LUPRON and ELIGARD), goserelin acetate, buserelin acetate and tripterelin; anti-androgens such as flutamide, nilutamide and bicalutamide; and aromatase inhibitors that inhibit the enzyme aromatase, which regulates estrogen production in the adrenal glands, such as, for example, 4(5)-imidazoles, aminoglutethimide, megestrol acetate (MEGASE), exemestane (AROMASIN), formestanie, fadrozole, vorozole (RIVISOR), letrozole (FEMARA), and anastrozole (ARIMIDEX). In addition, such definition of chemotherapeutic agents includes bisphosphonates such as clodronate (for example, BONEFOS or OSTAC), etidronate (DIDROCAL), NE-58095, zoledronic acid/zoledronate (ZOMETA), alendronate (FOSAMAX), pamidronate (AREDIA), tiludronate (SKELID), or risedronate (ACTONEL); as well as troxacitabine (a 1,3-dioxolane nucleoside cytosine analog); anti-sense oligonucleotides, particularly those that inhibit expression of genes in signaling pathways implicated in abherant cell proliferation, such as, for example, PKC-alpha, Raf, H-Ras, and epidermal growth factor receptor (EGF-R); vaccines such as THERATOPE vaccine and gene therapy vaccines, for example, ALLOVECTIN vaccine, LEUVECTIN vaccine, and VAXID vaccine; topoisomerase 1 inhibitor (e.g., LURTOTECAN); an anti-estrogen such as fulvestrant; a Kit inhibitor such as imatinib or EXEL-0862 (a tyrosine kinase inhibitor); EGFR inhibitor such as erlotinib or cetuximab; an anti-VEGF inhibitor such as bevacizumab; arinotecan; rmRH (e.g., ABARELIX); lapatinib and lapatinib ditosylate (an ErbB-2 and EGFR dual tyrosine kinase small-molecule inhibitor also known as GW572016); 17AAG (geldanamycin derivative that is a heat shock protein (Hsp) 90 poison), and pharmaceutically acceptable salts, acids or derivatives of any of the above.

As used herein, the term "cytokine" refers generically to proteins released by one cell population that act on another cell as intercellular mediators or have an autocrine effect on the cells producing the proteins. Examples of such cytokines include lymphokines, monokines; interleukins ("ILs") such as IL-1, IL-1α, IL-2, IL-3, IL-4, IL-5, IL-6, IL-7, IL-8, IL-9, IL10, IL-11, IL-12, IL-13, IL-15, IL-17A-F, IL-18 to IL-29 (such as IL-23), IL-31, including PROLEUKIN rIL-2; a tumor-necrosis factor such as TNF-α or TNF-β, TGF-β1-3; and other polypeptide factors including leukemia inhibitory factor ("LIF"), ciliary neurotrophic factor ("CNTF"), CNTF-like cytokine ("CLC"), cardiotrophin ("CT"), and kit ligand ("KL").

As used herein, the term "chemokine" refers to soluble factors (e.g., cytokines) that have the ability to selectively induce chemotaxis and activation of leukocytes. They also trigger processes of angiogenesis, inflammation, wound healing, and tumorigenesis. Example chemokines include IL-8, a human homolog of murine keratinocyte chemoattractant (KC).

d. Treatments

The term "dysfunction" in the context of immune dysfunction, refers to a state of reduced immune responsiveness to antigenic stimulation. The term includes the common elements of both exhaustion and/or anergy in which antigen recognition may occur, but the ensuing immune response is ineffective to control infection or tumor growth.

The term "dysfunctional", as used herein, also includes refractory or unresponsive to antigen recognition, specifically, impaired capacity to translate antigen recognition into down-stream T-cell effector functions, such as proliferation, cytokine production (e.g., IL-2) and/or target cell killing.

The term "anergy" refers to the state of unresponsiveness to antigen stimulation resulting from incomplete or insufficient signals delivered through the T-cell receptor (e.g. increase in intracellular $Ca^{+2}$ in the absence of ras-activation). T cell anergy can also result upon stimulation with antigen in the absence of co-stimulation, resulting in the cell becoming refractory to subsequent activation by the antigen even in the context of costimulation. The unresponsive state can often be overridden by the presence of Interleukin-2. Anergic T-cells do not undergo clonal expansion and/or acquire effector functions.

The term "exhaustion" refers to T cell exhaustion as a state of T cell dysfunction that arises from sustained TCR signaling that occurs during many chronic infections and cancer. It is distinguished from anergy in that it arises not through incomplete or deficient signaling, but from sustained signaling. It is defined by poor effector function, sustained expression of inhibitory receptors and a transcriptional state distinct from that of functional effector or memory T cells. Exhaustion prevents optimal control of infection and tumors.

"Enhancing T-cell function" means to induce, cause or stimulate a T-cell to have a sustained or amplified biological function, or renew or reactivate exhausted or inactive T-cells. Examples of enhancing T-cell function include: increased secretion of γ-interferon from CD8+ T-cells, increased proliferation, increased antigen responsiveness (e.g., viral, pathogen, or tumor clearance) relative to such levels before the intervention. In one embodiment, the level of enhancement is as least 50%, alternatively 60%, 70%, 80%, 90%, 100%, 120%, 150%, 200%. The manner of measuring this enhancement is known to one of ordinary skill in the art.

A "T cell dysfunctional disorder" is a disorder or condition of T-cells characterized by decreased responsiveness to antigenic stimulation. In a particular embodiment, a T-cell dysfunctional disorder is a disorder that is specifically associated with inappropriate increased levels of CD39.

In another embodiment, a T-cell dysfunctional disorder is one in which T-cells are anergic or have decreased ability to secrete cytokines, proliferate, or execute cytolytic activity. In a specific aspect, the decreased responsiveness results in ineffective control of a pathogen or tumor expressing an immunogen. Examples of T cell dysfunctional disorders characterized by T-cell dysfunction include unresolved acute infection, chronic infection and tumor immunity.

"Tumor immunity" refers to the process in which tumors evade immune recognition and clearance. Thus, as a therapeutic concept, tumor immunity is "treated" when such evasion is attenuated, and the tumors are recognized and attacked by the immune system. Examples of tumor recognition include tumor binding, tumor shrinkage and tumor clearance.

"Sustained response" refers to the sustained effect on reducing tumor growth after cessation of a treatment. For example, the tumor size may remain to be the same or smaller as compared to the size at the beginning of the administration phase. In some embodiments, the sustained response has a duration at least the same as the treatment duration, at least 1.5×, 2.0×, 2.5×, or 3.0× length of the treatment duration.

The terms "cancer" and "cancerous" as used herein refer to or describe the physiological condition in mammals in which a population of cells are characterized by unregulated cell growth. Examples of cancer include, but are not limited to, carcinoma, blastoma, sarcoma, and hematologic cancers such as lymphoma and leukemia.

The terms "tumor" and "neoplasm" as used herein refer to any mass of tissue that results from excessive cell growth or proliferation, either benign (noncancerous) or malignant (cancerous) including pre-cancerous lesions. Tumor growth is generally uncontrolled and progressive, does not induce or inhibit the proliferation of normal cells. Tumor can affect a variety of cells, tissues or organs, including but not limited to selected from bladder, bone, brain, breast, cartilage, glial cells, esophagus, fallopian tube, gall bladder, heart, intestine, kidney, liver, lung, lymph node, neural tissue, ovary, pancreas, prostate, skeletal muscle, skin, spinal cord, spleen, stomach, testis, thymus, thyroid, trachea, urethra, ureter, urethra, uterus, vagina organ or tissue or the corresponding cells. Tumors include cancers, such as sarcoma, carcinoma, plasmacytoma or (malignant plasma cells). Tumors encompassed by the present invention, may include, but are not limited to leukemias (e.g., acute leukemia, acute lymphoblastic leukemia, acute myeloid leukemia, acute myeloid leukemia, acute promyelocytic leukemia, acute myeloid-monocytic leukemia, acute monocytic leukemia, acute leukemia, chronic leukemia, chronic myeloid leukemia, chronic lymphocytic leukemia, polycythemia vera), lymphomas (Hodgkin's disease, non-Hodgkin's disease), primary macroglobulinemia disease, heavy chain disease, and solid tumors such as sarcomas cancer (e.g., fibrosarcoma, myxosarcoma, liposarcoma, chondrosarcoma, osteosarcoma, chordoma, endothelium sarcoma, lymphangiosarcoma, angiosarcoma, lymphangioendothelio sarcoma, synovioma vioma, mesothelioma, Ewing's tumor, leiomyosarcoma, rhabdomyosarcoma, colon carcinoma, pancreatic cancer, breast cancer, ovarian cancer, prostate cancer, squamous cell carcinoma, basal cell carcinoma, adenocarcinoma, sweat gland carcinoma, sebaceous gland carcinoma, papillary carcinoma, papillary adenocarcinoma, carcinoma, bronchogenic carcinoma, medullary carcinoma, renal cell carcinoma, hepatoma, Nile duct carcinoma, choriocarcinoma, spermatogonia Tumor, embryonal carcinoma, Wilms' tumor, cervical cancer, uterine cancer, testicular cancer, lung carcinoma, small cell lung carcinoma, bladder carcinoma, epithelial carcinoma, glioma, astrocytoma, medulloblastoma, craniopharyngioma, ependymoma, pinealoma, hemangioblastoma, acoustic neuroma, oligodendroglioma, schwannoma, meningioma, melanoma, neuroblastoma, retinoblastoma), esophageal cancer, gallbladder, kidney cancer, multiple myeloma. Preferably, a "tumor" includes, but is not limited to: pancreatic cancer, liver cancer, lung cancer, stomach cancer, esophageal cancer, head and neck squamous cell carcinoma, prostate cancer, colon cancer, breast cancer, lymphoma, gallbladder cancer, renal cancer, leukemia, multiple myeloma, ovarian cancer, cervical cancer and glioma.

The term "metastasis" as used herein refers to the process by which a cancer spreads or transfers from the site of origin to other regions of the body with the development of a similar cancerous lesion at the new location. A "metastatic" or "metastasizing" cell is one that loses adhesive contacts with neighboring cells and migrates via the bloodstream or lymph from the primary site of disease to invade neighboring body structures.

The terms "cancer cell" and "tumor cell" refer to the total population of cells derived from a cancer or tumor or pre-cancerous lesion, including both non-tumorigenic cells, which comprise the bulk of the cancer cell population, and tumorigenic stem cells (cancer stem cells). As used herein, the terms "cancer cell" or "tumor cell" will be modified by the term "non-tumorigenic" when referring solely to those cells lacking the capacity to renew and differentiate to distinguish those tumor cells from cancer stem cells.

The term "effective amount" as used herein refers to an amount to provide therapeutic or prophylactic benefit.

As used herein, "complete response" or "CR" refers to disappearance of all target lesions; "partial response" or "PR" refers to at least a 30% decrease in the sum of the longest diameters (SLD) of target lesions, taking as reference the baseline SLD; and "stable disease" or "SD" refers to neither sufficient shrinkage of target lesions to qualify for PR, nor sufficient increase to qualify for PD, taking as reference the smallest SLD since the treatment started.

As used herein, "progressive disease" or "PD" refers to at least a 20% increase in the SLD of target lesions, taking as reference the smallest SLD recorded since the treatment started or the presence of one or more new lesions.

As used herein, "progression free survival" (PFS) refers to the length of time during and after treatment during which the disease being treated (e.g., cancer) does not get worse. Progression-free survival may include the amount of time patients have experienced a complete response or a partial response, as well as the amount of time patients have experienced stable disease.

As used herein, "overall response rate" (ORR) refers to the sum of complete response (CR) rate and partial response (PR) rate.

As used herein, "overall survival" refers to the percentage of individuals in a group who are likely to be alive after a particular duration of time.

The term "treatment" as used herein refers to the individual trying to change the process or treatment of a clinical disease caused by intervention of a cell, may be either preventive intervention course of clinical pathology. Including but not limited to treatment to prevent the occurrence or recurrence of disease, alleviation of symptoms, reducing the direct or indirect pathological consequences of any disease, preventing metastasis, slow the rate of disease progression, amelioration or remission of disease remission or improved prognosis.

The term "subject" refers to any animal (e.g., a mammal), including, but not limited to, humans, non-human primates, canines, felines, rodents, and the like, which is to be the recipient of a particular treatment. Typically, the terms "subject" and "patient" are used interchangeably herein in reference to a human subject.

The terms "agonist" and "agonistic" as used herein refer to or describe a therapeutic moiety that is capable of, directly or indirectly, substantially inducing, activating, promoting, increasing, or enhancing the biological activity of a target and/or a pathway. The term "agonist" is used herein to include any agent that partially or fully induces, activates, promotes, increases, or enhances the activity of a protein or other target of interest.

The terms "antagonist" and "antagonistic" as used herein refer to or describe a therapeutic moiety that is capable of, directly or indirectly, partially or fully blocking, inhibiting, reducing, or neutralizing a biological activity of a target and/or pathway. The term "antagonist" is used herein to include any agent that partially or fully blocks, inhibits, reduces, or neutralizes the activity of a protein or other target of interest.

The terms "modulation" and "modulate" as used herein refer to a change or an alteration in a biological activity. Modulation includes, but is not limited to, stimulating an activity or inhibiting an activity. Modulation may be an increase in activity or a decrease in activity, a change in binding characteristics, or any other change in the biological, functional, or immunological properties associated with the activity of a protein, a pathway, a system, or other biological targets of interest.

The term "immune response" as used herein includes responses from both the innate immune system and the adaptive immune system. It includes both cell-mediated and/or humoral immune responses. It includes both T-cell and B-cell responses, as well as responses from other cells of the immune system such as natural killer (NK) cells, monocytes, macrophages, etc.

The term "pharmaceutically acceptable" refers to a substance approved or approvable by a regulatory agency of the Federal government or a state government or listed in the U.S. Pharmacopeia or other generally recognized pharmacopeia for use in animals, including humans.

The terms "pharmaceutically acceptable excipient, carrier or adjuvant" or "acceptable pharmaceutical carrier" refer to an excipient, carrier or adjuvant that can be administered to a subject, together with at least one agent of the present disclosure, and which does not destroy the pharmacological activity thereof and is nontoxic when administered in doses sufficient to deliver a therapeutic effect. In general, those of skill in the art and the U.S. FDA consider a pharmaceutically acceptable excipient, carrier, or adjuvant to be an inactive ingredient of any formulation.

The terms "effective amount" or "therapeutically effective amount" or "therapeutic effect" refer to an amount of an anti-CD39 antibody effective to "treat" a disease or disorder in a subject such as, a mammal. In the case of cancer or a tumor, the therapeutically effective amount of an anti-CD39 antibody has a therapeutic effect and as such can boost the immune response, boost the anti-tumor response, increase cytolytic activity of immune cells, increase killing of tumor cells by immune cells, reduce the number of tumor cells; decrease tumorigenicity, tumorigenic frequency or tumorigenic capacity; reduce the number or frequency of cancer stem cells; reduce the tumor size; reduce the cancer cell population; inhibit or stop cancer cell infiltration into peripheral organs including, for example, the spread of cancer into soft tissue and bone; inhibit and stop tumor or cancer cell metastasis; inhibit and stop tumor or cancer cell growth; relieve to some extent one or more of the symptoms associated with the cancer; reduce morbidity and mortality; improve quality of life; or a combination of such effects.

The terms "treating" or "treatment" or "to treat" or "alleviating" or "to alleviate" refer to both (1) therapeutic measures that cure, slow down, lessen symptoms of, and/or halt progression of a diagnosed pathologic condition or disorder and (2) prophylactic or preventative measures that prevent or slow the development of a targeted pathologic condition or disorder. Thus those in need of treatment include those already with the disorder; those prone to have the disorder; and those in whom the disorder is to be prevented. In the case of cancer or a tumor, a subject is successfully "treated" according to the methods encompassed by the present invention if the patient shows one or more of the following: an increased immune response, an increased anti-tumor response, increased cytolytic activity of immune cells, increased killing of tumor cells by immune cells, a reduction in the number of or complete absence of cancer cells; a reduction in the tumor size; inhibition of or an absence of cancer cell infiltration into peripheral organs including the spread of cancer cells into soft tissue and bone; inhibition of or an absence of tumor or cancer cell metastasis; inhibition or an absence of cancer growth; relief of one or more symptoms associated with the specific cancer; reduced morbidity and mortality; improvement in quality of life; reduction in tumorigenicity; reduction in the number or frequency of cancer stem cells; or some combination of effects.

e. Miscellaneous

It is understood that wherever embodiments are described herein with the language "comprising" otherwise analogous embodiments described in terms of "consisting of" and/or "consisting essentially of" are also provided. It is also understood that wherever embodiments are described herein with the language "consisting essentially of" otherwise analogous embodiments described in terms of "consisting of" are also provided.

As used herein, reference to "about" or "approximately" a value or parameter includes (and describes) embodiments that are directed to that value or parameter. For example, description referring to "about X" includes description of "X".

The term "and/or" as used in a phrase such as "A and/or B" herein is intended to include both A and B; A or B; A (alone); and B (alone). Likewise, the term "and/or" as used in a phrase such as "A, B, and/or C" is intended to encompass each of the following embodiments: A, B, and C; A, B, or C; A or C; A or B; B or C; A and C; A and B; B and C; A (alone); B (alone); and C (alone).

III. Anti-CD39 Antibodies a. Monoclonal Antibodies

The anti-CD39 antibodies may be monoclonal antibodies. Monoclonal antibodies may be prepared using hybridoma methods, such as those described by Kohler and Milstein, Nature, 256:495 (1975). In a hybridoma method, a mouse, hamster, or other appropriate host animal, is typically immunized with an immunizing agent to elicit lymphocytes that produce or are capable of producing antibodies that will specifically bind to the immunizing agent. Alternatively, the lymphocytes may be immunized in vitro.

The immunizing agent will typically include the CD39 polypeptide or a fusion protein thereof. Generally, either peripheral blood lymphocytes ("PBLs") are used if cells of human origin are desired, or spleen cells or lymph node cells are used if non-human mammalian sources are desired. The lymphocytes are then fused with an immortalized cell line using a suitable fusing agent, such as polyethylene glycol, to form a hybridoma cell [*Goding, Monoclonal Antibodies: Principles and Practice*, Academic Press, (1986) pp. 59-103]. Immortalized cell lines are usually transformed mammalian cells, particularly myeloma cells of rodent, bovine and human origin. Usually, rat or mouse myeloma cell lines are employed. The hybridoma cells may be cultured in a suitable culture medium that preferably contains one or more substances that inhibit the growth or survival of the unfused, immortalized cells. For example, if the parental cells lack the enzyme hypoxanthine guanine phosphoribosyl transferase (HGPRT or HPRT), the culture medium for the hybridomas typically will include hypoxanthine, aminopterin, and thymidine ("HAT medium"), which substances prevent the growth of HGPRT-deficient cells.

Preferred immortalized cell lines are those that fuse efficiently, support stable high level expression of antibody by the selected antibody-producing cells, and are sensitive to a medium such as HAT medium. More preferred immortalized cell lines are murine myeloma lines, which can be obtained, for instance, from the Salk Institute Cell Distribution Center, San Diego, Calif. and the American Type Culture Collection, Manassas, Va. Human myeloma and mouse-human heteromyeloma cell lines also have been described for the production of human monoclonal antibodies [Kozbor, J. Immunol., 133:3001 (1984); Brodeur et al., Monoclonal Antibody Production Techniques and Applications, Marcel Dekker, Inc., New York, (1987) pp. 51-63].

The culture medium in which the hybridoma cells are cultured can then be assayed for the presence of monoclonal antibodies directed against the polypeptide. Preferably, the binding specificity of monoclonal antibodies produced by the hybridoma cells is determined by immunoprecipitation or by an in vitro binding assay, such as radioimmunoassay (RIA) or enzyme-linked immunoabsorbent assay (ELISA). Such techniques and assays are known in the art. The binding affinity of the monoclonal antibody can, for example, be determined by the Scatchard analysis of Munson and Pollard, Anal. Biochem., 107:220 (1980).

After the desired hybridoma cells are identified, the clones may be subcloned by limiting dilution procedures and grown by standard methods [Goding, supra]. Suitable culture media for this purpose include, for example, Dulbecco's Modified Eagle's Medium and RPMI-1640 medium. Alternatively, the hybridoma cells may be grown in vivo as ascites in a mammal.

The monoclonal antibodies secreted by the subclones may be isolated or purified from the culture medium or ascites fluid by conventional immunoglobulin purification procedures such as, for example, protein A-Sepharose, hydroxylapatite chromatography, gel electrophoresis, dialysis, or affinity chromatography.

The monoclonal antibodies may also be made by recombinant DNA methods, such as those described in U.S. Pat. No. 4,816,567. DNA encoding the monoclonal antibodies encompassed by the invention can be readily isolated and sequenced using conventional procedures (e.g., by using oligonucleotide probes that are capable of binding specifically to genes encoding the heavy and light chains of murine antibodies). The hybridoma cells encompassed by the present invention serve as a preferred source of such DNA. Once isolated, the DNA may be placed into expression vectors, which are then transfected into host cells such as simian COS cells, Chinese hamster ovary (CHO) cells, or myeloma cells that do not otherwise produce immunoglobulin protein, to obtain the synthesis of monoclonal antibodies in the recombinant host cells. The DNA also may be modified, for example, by substituting the coding sequence for human heavy and light chain constant domains in place of the homologous murine sequences [U.S. Pat. No. 4,816,567; Morrison et al., supra] or by covalently joining to the immunoglobulin coding sequence all or part of the coding sequence for a non-immunoglobulin polypeptide. Such a non-immunoglobulin polypeptide can be substituted for the constant domains of an antibody encompassed by the present invention, or can be substituted for the variable domains of one antigen-combining site of an antibody encompassed by the present invention to create a chimeric bivalent antibody.

b. Human and Humanized Antibodies

The anti-CD39 antibodies encompassed by the present invention may further comprise humanized antibodies or human antibodies. Humanized forms of non-human (e.g., murine) antibodies are chimeric immunoglobulins, immunoglobulin chains or fragments thereof (such as Fv, Fab, Fab', F(ab')$_2$ or other antigen-binding subsequences of antibodies) which contain minimal sequence derived from non-human immunoglobulin. Humanized antibodies include human immunoglobulins (recipient antibody) in which residues from a complementary determining region (CDR) of the recipient are replaced by residues from a CDR of a non-human species (donor antibody) such as mouse, rat or rabbit having the desired specificity, affinity and capacity. In some instances, Fv framework residues of the human immunoglobulin are replaced by corresponding non-human residues. Humanized antibodies may also comprise residues which are found neither in the recipient antibody nor in the imported CDR or framework sequences. In general, the humanized antibody will comprise substantially all of at least one, and typically two, variable domains, in which all or substantially all of the CDR regions correspond to those of a non-human immunoglobulin and all or substantially all of the FR regions are those of a human immunoglobulin consensus sequence. The humanized antibody optimally also will comprise at least a portion of an immunoglobulin constant region (Fc), typically that of a human immunoglobulin [Jones et al., Nature, 321:522-525 (1986); Riechmann et al., Nature, 332:323-329 (1988); and Presta, Curr. Op. Struct. Biol., 2:593-596 (1992)].

Methods for humanizing non-human antibodies are well known in the art. Generally, a humanized antibody has one or more amino acid residues introduced into it from a source which is non-human. These non-human amino acid residues are often referred to as "import" residues, which are typically taken from an "import" variable domain. Humanization can be essentially performed following the method of Winter and co-workers [Jones et al., Nature, 321:522-525 (1986); Riechmann et al., Nature, 332:323-327 (1988); Verhoeyen et al., Science, 239:1534-1536 (1988)], by substituting rodent CDRs or CDR sequences for the corresponding sequences of a human antibody. Accordingly, such "humanized" antibodies are chimeric antibodies (U.S. Pat. No. 4,816,567), wherein substantially less than an intact human variable domain has been substituted by the corresponding sequence from a non-human species. In practice, humanized antibodies are typically human antibodies in which some CDR residues and possibly some FR residues are substituted by residues from analogous sites in rodent antibodies.

Human antibodies can also be produced using various techniques known in the art, including phage display libraries [Hoogenboom and Winter, J. Mol. Biol., 227:381 (1991); Marks et al., J. Mol. Biol., 222:581 (1991)]. The techniques of Cole et al. and Boerner et al. are also available for the preparation of human monoclonal antibodies (Cole et al., Monoclonal Antibodies and Cancer Therapy, Alan R. Liss, p. 77 (1985) and Boerner et al., J. Immunol., 147(1):86-95 (1991)]. Similarly, human antibodies can be made by introducing of human immunoglobulin loci into transgenic animals, e.g., mice in which the endogenous immunoglobulin genes have been partially or completely inactivated. Upon challenge, human antibody production is observed, which closely resembles that seen in humans in all respects, including gene rearrangement, assembly, and antibody repertoire. This approach is described, for example, in U.S. Pat. Nos. 5,545,807; 5,545,806; 5,569,825; 5,625,126; 5,633, 425; 5,661,016, and in the following scientific publications: Marks et al., Bio/Technology 10, 779-783 (1992); Lonberg et al., Nature 368 856-859 (1994); Morrison, Nature 368, 812-13 (1994); Fishwild et al., Nature Biotechnology 14, 845-51 (1996); Neuberger, Nature Biotechnology 14, 826 (1996); Lonberg and Huszar, Intern. Rev. Immunol. 13 65-93 (1995).

The antibodies may also be affinity matured using known selection and/or mutagenesis methods as described above. Preferred affinity matured antibodies have an affinity which is five times, more preferably 10 times, even more preferably 20 or 30 times greater than the starting antibody (generally murine, humanized or human) from which the matured antibody is prepared.

c. Bispecific Antibodies

Anti-CD39 antibodies described herein include bispecific molecules. An anti-CD39 antibody, or antigen-binding portions thereof, can be derivatized or linked to another functional molecule, e.g., another peptide or protein (e.g., another antibody or ligand for a receptor) to generate a bispecific molecule that binds to at least two different binding sites or target molecules. The antibody described herein may in fact be derivatized or linked to more than one other functional molecule to generate multispecific molecules that bind to more than two different binding sites and/or target molecules; such multispecific molecules are also intended to be encompassed by the term "bispecific molecule" as used herein. To create a bispecific molecule described herein, an antibody described herein can be functionally linked (e.g., by chemical coupling, genetic fusion, noncovalent association or otherwise) to one or more other binding molecules, such as another antibody, antibody fragment, peptide or binding mimetic, such that a bispecific molecule results.

Accordingly, provided herein are bispecific molecules comprising at least one first binding specificity for CD39 and a second binding specificity for a second target epitope. In an embodiment described herein in which the bispecific molecule is multi-specific, the molecule can further include a third binding specificity.

In certain embodiments, the subject bispecific (or multi-specific as the case may be) includes one or more binding domains for immune checkpoints, e.g., which are checkpoint inhibitors, such as PD-1, PD-L1, CTLA-4/B7-1/B7-2, PD-L2, KIR, LAG-3, TIM-3, CD96, VISTA, TIGIT and/or Siglec-15. In certain embodiments, the multi-specific includes binding domains that bind checkpoint proteins on T-cells, especially checkpoints associated with T-cell exhaustion such as LAG-3, TIM-3 or TIGIT. In certain embodiments, the multi-specific binds to CD39 and one or more other T-cell associated checkpoints and leads to antibody-dependent cellular cytotoxicity of cells expressing each or both of CD39 and the other checkpoint proteins to which it binds.

In certain embodiments, the subject bispecific (or multi-specific as the case may be) includes one or more binding domains for immune costimulatory receptors, e.g., which are costimulatory agonists (activators), such as agonists of MHCI molecules, BTLA receptor and Toll ligands, and OX40, CD27, CD28, CDS, ICAM-1, LFA-1 (CD11a/CD18), ICOS (CD278) and 4-1BB (CD137). Examples of costimulatory molecules that can be included in the multi-specific include but are not limited to: CDS, ICAM-1, GITR, BAFFR, HVEM (LIGHTR), SLAMF7, NKp80 (KLRF1), NKp44, NKp30, NKp46, CD160, CD19, CD4, CD8α, CD8β, IL2Rβ, IL2Rγ, IL7Rα, ITGA4, VLA1, CD49a, ITGA4, IA4, CD49D, ITGA6, VLA-6, CD49f, ITGAD, CD11d, ITGAE, CD103, ITGAL, CD11a, LFA-1, ITGAM, CD11b, ITGAX, CD11c, ITGB1, CD29, ITGB2, CD18, LFA-1, ITGB7, NKG2D, NKG2C, TNFR2, TRANCE/RANKL, DNAM1 (CD226), SLAMF4 (CD244,2B4), CD84, CD96 (Tactile), CEACAMi, CRTAM, Ly9 (CD229), CD160 (BY55), PSGL1, CD100 (SEMA4D), CD69, SLAMF6 (NTB-A, Ly108), SLAM (SLAMFi, CD150, IPO-3), BLAME (SLAMF8), SELPLG (CD162), LTBR, LAT, GADS, SLP-76, PAG/Cbp, CD19a, and CD83 ligand.

In certain embodiments, the subject bispecific (or multi-specific as the case may be) includes one or more binding domains which serve as innate immune activators, such as binding moieties for CD47, SIRPα, CD24, Siglec-10 or NKG2A.

In one embodiment, the bispecific molecules described herein comprise as a binding specificity at least one antibody, or an antibody fragment thereof, including, e.g., an Fab, Fab', F(ab')$_2$, Fv, or a single chain Fv. The antibody may also be a light chain or heavy chain dimer, or any minimal fragment thereof such as a Fv or a single chain (scFv) construct.

Binding of the bispecific molecules to their specific targets can be confirmed using art-recognized methods, such as enzyme-linked immunosorbent assay (ELISA), radioimmunoassay (RIA), FACS analysis, bioassay (e.g., growth inhibition), or Western Blot assay. Each of these assays generally detects the presence of protein-antibody complexes of particular interest by employing a labeled reagent (e.g., an antibody) specific for the complex of interest.

Methods for making bispecific antibodies are known in the art. Traditionally, the recombinant production of bispecific antibodies is based on the co-expression of two immunoglobulin heavy-chain/light-chain pairs, where the two heavy chains have different specificities [Milstein and Cuello, Nature, 305:537-539 (1983)]. Because of the random assortment of immunoglobulin heavy and light chains, these hybridomas (quadromas) produce a potential mixture of ten different antibody molecules, of which only one has the correct bispecific structure. The purification of the correct molecule is usually accomplished by affinity chromatography steps. Similar procedures are disclosed in WO 93/08829, published 13 May 1993, and in Traunecker et al., EMBO J., 10:3655-3659 (1991).

Antibody variable domains with the desired binding specificities (antibody-antigen combining sites) can be fused to immunoglobulin constant domain sequences. The fusion preferably is with an immunoglobulin heavy-chain constant domain, comprising at least part of the hinge, CH2, and CH3 regions. It is preferred to have the first heavy-chain constant region (CH1) containing the site necessary for light-chain binding present in at least one of the fusions. DNAs encoding the immunoglobulin heavy-chain fusions and, if desired, the immunoglobulin light chain, are inserted into separate expression vectors, and are co-transfected into a suitable host organism. For further details of generating bispecific antibodies see, for example, Suresh et al., Methods in Enzymology, 121:210 (1986).

According to another approach described in WO 96/27011, the interface between a pair of antibody molecules can be engineered to maximize the percentage of heterodimers which are recovered from recombinant cell culture. The preferred interface comprises at least a part of the CH3 region of an antibody constant domain. In this method, one or more small amino acid side chains from the interface of the first antibody molecule are replaced with larger side chains (e.g. tyrosine or tryptophan). Compensatory "cavities" of identical or similar size to the large side chain(s) are created on the interface of the second antibody molecule by replacing large amino acid side chains with smaller ones (e.g. alanine or threonine). This provides a mechanism for increasing the yield of the heterodimer over other unwanted end-products such as homodimers.

Bispecific antibodies can be prepared as full length antibodies or antibody fragments (e.g. F(ab')$_2$ bispecific antibodies). Techniques for generating bispecific antibodies from antibody fragments have been described in the literature. For example, bispecific antibodies can be prepared can be prepared using chemical linkage. Brennan et al., Science 229:81 (1985) describe a procedure wherein intact antibodies are proteolytically cleaved to generate F(ab')$_2$ fragments. These fragments are reduced in the presence of the dithiol complexing agent sodium arsenite to stabilize vicinal dithiols and prevent intermolecular disulfide formation. The Fab' fragments generated are then converted to thionitrobenzoate (TNB) derivatives. One of the Fab'-TNB derivatives is then reconverted to the Fab'-thiol by reduction with mercaptoethylamine and is mixed with an equimolar amount of the other Fab'-TNB derivative to form the bispecific antibody. The bispecific antibodies produced can be used as agents for the selective immobilization of enzymes.

Fab' fragments may be directly recovered from *E. coli* and chemically coupled to form bispecific antibodies. Shalaby et al. *J. Exp. Med.* 175:217-225 (1992) describe the production of a fully humanized bispecific antibody F(ab')$_2$ molecule. Each Fab' fragment was separately secreted from *E. coli* and subjected to directed chemical coupling in vitro to form the bispecific antibody. The bispecific antibody thus formed was able to bind to cells overexpressing the ErbB2 receptor and normal human T cells, as well as trigger the lytic activity of human cytotoxic lymphocytes against human breast tumor targets.

Various technique for making and isolating bispecific antibody fragments directly from recombinant cell culture have also been described. For example, bispecific antibodies have been produced using leucine zippers (Kostelny et al., *J. Immunol.* 148(5):1547-1553 (1992)). The leucine zipper peptides from the Fos and Jun proteins were linked to the Fab' portions of two different antibodies by gene fusion. The antibody homodimers were reduced at the hinge region to form monomers and then re-oxidized to form the antibody heterodimers. This method can also be utilized for the production of antibody homodimers. The "diabody" technology described by Hollinger et al., *Proc. Natl. Acad. Sci. USA* 90:6444-6448 (1993) has provided an alternative mechanism for making bispecific antibody fragments. The fragments comprise a heavy-chain variable domain ($V_H$) connected to a light-chain variable domain ($V_L$) by a linker which is too short to allow pairing between the two domains on the same chain. Accordingly, the $V_H$ and $V_L$ domains of one fragment are forced to pair with the complementary $V_L$ and $V_H$ domains of another fragment, thereby forming two antigen-binding sites. Another strategy for making bispecific antibody fragments by the use of single-chain Fv (sFv) dimers has also been reported. See, Gruber et al., *J. Immunol.* 152:5368 (1994).

Antibodies with more than two valencies are contemplated. As one nonlimiting example, trispecific antibodies can be prepared. See, e.g., Tutt et al., *J. Immunol.* 147:60 (1991).

d. Heteroconjugate Antibodies

Heteroconjugate antibodies are also within the scope of the present invention. Heteroconjugate antibodies are composed of two covalently joined antibodies. Such antibodies have, for example, been proposed to target immune system cells to unwanted cells [U.S. Pat. No. 4,676,980], and for treatment of HIV infection [WO 91/00360; WO 92/200373; EP 03089]. It is contemplated that the antibodies may be prepared in vitro using known methods in synthetic protein chemistry, including those involving crosslinking agents. For example, immunotoxins may be constructed using a disulfide exchange reaction or by forming a thioether bond. Examples of suitable reagents for this purpose include iminothiolate and methyl-4-mercaptobutyrimidate and those disclosed, for example, in U.S. Pat. No. 4,676,980.

e. Effector Function Engineering

It may be desirable to modify the antibody encompassed by the present invention with respect to effector function, so as to enhance, e.g., the effectiveness of the anti-CD39 antibody in treating cancer. For example, cysteine residue(s) may be introduced into the Fc region, thereby allowing interchain disulfide bond formation in this region. The homodimeric antibody thus generated may have improved internalization capability and/or increased complement-mediated cell killing and antibody-dependent cellular cytotoxicity (ADCC). See Caron et al., *J. Exp Med.*, 176: 1191-1195 (1992) and Shopes, J. Immunol., 148: 2918-2922 (1992). In certain preferred embodiments, the effector function being engineered is the ability of the anti-CD39 antibody to induce FcγRIII binding-dependent removal (such as by anti-CD39 antibody mediated target cytosis) of CD39 from immune cells, i.e., without depleting the immune cell population by way of cell killing.

Homodimeric antibodies with enhanced anti-tumor activity may also be prepared using heterobifunctional crosslinkers as described in Wolff et al. Cancer Research, 53: 2560-2565 (1993). Alternatively, an antibody can be engineered that has dual Fc regions and may thereby have enhanced CD39 trogocytosis capabilities. See Stevenson et al., Anti-Cancer Drug Design, 3: 219-230 (1989).

f. Representative Anti-CD39 Antibody Sequences

In certain embodiments, the anti-CD39 antibody is a fully human antibody, such as generated from a human antibody library. An exemplary fully human anti-CD39 antibody is clone Ig39-21, the heavy and light variable domains (VH and VL) sequences provided as follows:

|  | Nucleic Acid Sequence | Amino Acid Sequence |
| --- | --- | --- |
| VH domain | SEQ ID No. 1 (VH) | SEQ ID No. 2 (VH) |
| VL domain | SEQ ID No. 3 (VL) | SEQ ID No. 4 (VL) |

For the Ig39-21 clone, the CDRs for each of the VH and VL domains are:

|  | CDR1 | CDR2 | CDR3 |
| --- | --- | --- | --- |
| VH | SEQ ID No. 29 | SEQ ID No. 30 | SEQ ID No. 31 |
| VL | SEQ ID No. 32 | SEQ ID No. 33 | SEQ ID No. 34 |

The sequences for an exemplary full-length antibody and an exemplary single chain antibody (scFV) utilizing the VH and VL domains above are provided as follows:

|  | Nucleic Acid Sequence | Amino Acid Sequence |
| --- | --- | --- |
| Full Length Heavy Chain | SEQ ID No. 35 | SEQ ID No. 36 |
| Full Length Light Chain | SEQ ID No. 37 | SEQ ID No. 38 |
| scFV | SEQ ID No. 39 | SEQ ID No. 40 |

In some embodiments, the anti-CD39 antibody or antigen-binding fragment thereof comprises at least one heavy chain variable domain that is at least 60% identical to a VH domain sequence described herein, such as SEQ ID No. 2, and even more preferably at least 65%, 70%, 75%, 80%, 85% or even 90% identical to a VH domain sequence described herein, such as SEQ ID No. 2, and able to specifically bind human CD39.

In some embodiments, the anti-CD39 antibody or antigen-binding fragment thereof comprises at least one light chain variable domain that is at least 60% identical to a VL domain sequence described herein, such as SEQ ID No. 4, and even more preferably at least 65%, 70%, 75%, 80%, 85% or even 90% identical to a VL domain sequence described herein, such as SEQ ID No. 4, and able to specifically bind human CD39.

In certain embodiments, the anti-CD39 antibody is a humanized antibody comprising a VH domain having human framework sequences associated with CDRs of a VH domain shown in SEQ ID Nos. 29, 30 and 31, and the CDRs of the corresponding VL domain shown in SEQ ID Nos. 32, 33 and 34. CDRs of anti-CD39 antibodies described herein are preferably identical to CDRs described herein, but may vary by 1, 2 or 3 amino acids across each CDR so long as the resulting antibody specifically binds human CD39.

In certain embodiments, the heavy and light chains of the anti-CD39 antibody have variable domains that can be encoded by a nucleic acid which is identical to, or hybridizes under stringent conditions (such as the 6× sodium chloride/sodium citrate (SSC) at 45° C., and washing in 0.2×SSC/0.1% SDS at 50-65C) to VH and VL domain (correspondingly) coding sequences described herein, such as those shown in SEQ ID No. 1 (VH) and SEQ ID No. 3 (VL).

In some embodiments, anti-CD39 antibodies were generated in rabbits, and the variable domains of the heavy and light chains of these antibodies are rabbit sequence while the constant domains are human sequence. Exemplary sequences for the VH and VL domains of rabbit anti-CD39 antibodies are:

| Clone | Nucleic Acid Sequence | Amino Acid Sequence | CDR Sequences |
|---|---|---|---|
| 9B6 | SEQ ID No. 5 (VH)<br>SEQ ID No. 7 (VL) | SEQ ID No. 6 (VH)<br>SEQ ID No. 8 (VL) | SEQ ID NO. 6 (VH) CDRs<br>CDR1: GFSLSAYG<br>CDR2: XYSSGRT<br>CDR3: ARSRAGISSGDGFDS<br>SEQ ID No. 8 (VL) CDRs<br>CDR1: QNIYSN<br>CDR2: RAS<br>CDR3: QQGFDSSNIDNT |
| 8C11 | SEQ ID No. 9 (VH)<br>SEQ ID No. 11 (VL) | SEQ ID No. 10 (VH)<br>SEQ ID No. 12 (VL) | SEQ ID No. 10 (VH) CDRS<br>CDR1: GFSLSKSI<br>CDR2: IGSSGST<br>CDR3: ARGLLYSGNKS<br>SEQ ID No. 12 (VL) CDRs<br>CDR1: QSVLLNNQ<br>CDR2: DAS<br>CDR3: LGGYSGNLYA |
| 8D8 | SEQ ID No. 13 (VH)<br>SEQ ID No. 15 (VL) | SEQ ID No. 14 (VH)<br>SEQ ID No. 16 (VL) | SEQ ID No. 14 (VH) CDRs<br>CDR1: GFSLSSYA<br>CDR2: INSYGTT<br>CDR3: ARGDSYGSGVGLGL<br>SEQ ID No. 16 (VL) CDRs<br>CDR1: QNIYSN<br>CDR2: RAS<br>CDR3: QQGFSSNNVDNT |
| 9C10 | SEQ ID No. 17 (VH)<br>SEQ ID No. 19 (VL) | SEQ ID No. 18 (VH)<br>SEQ ID No. 20 (VL) | SEQ ID No. 18 (VH) CDRs<br>CDR1: GFSLSSYA<br>CDR2: ISSSGST<br>CDR3: ARDRVIYSIGPYYFNL<br>SEQ ID No. 20 (VL) CDRs<br>CDR1: EIIYSN<br>CDR2: GAS<br>CDR3: QQSFSSNNVGNI |
| 65H5 | SEQ ID No. 21 (VH)<br>SEQ ID No. 23 (VL) | SEQ ID No. 22 (VH)<br>SEQ ID No. 24 (VL) | SEQ ID No. 22 (VH) CDRs<br>CDR1: GFSLSTHA<br>CDR2: TYASGRT<br>CDR3: ARNGADETFYYFDL<br>SEQ ID No. 24 (VL) CDRs<br>CDR1: QNINTW<br>CDR2: RAS<br>CDR3: QQYDASINIDNA |
| 2G12 | SEQ ID No. 25 (VH)<br>SEQ ID No. 27 (VL) | SEQ ID No. 26 (VH)<br>SEQ ID No. 28 (VL) | SEQ ID No. 26 (VH) CDRs<br>CDR1: GIDLSSNA<br>CDR2: IRNNDIT<br>CDR3: ARGGGSYSIVFWNL<br>SEQ ID No. 28 (VL) CDRs<br>CDR1: ERIYSN<br>CDR2: YAS<br>CDR3: QQGYSNNNVDNT |
| 48F10 | SEQ ID No. 41 (VH)<br>SEQ ID No. 43 (VL) | SEQ ID No. 42 (VH)<br>SEQ ID No. 44 (VL) | SEQ ID NO. 42 (VH) CDRS<br>CDR1: GIDLSNNA<br>CDR2: IRSSGST<br>CDR3: ARGGGSYSIVFWNL<br>SEQ ID No. 44 (VL) CDRs<br>CDR1: ERIYSN<br>CDR2: YTS<br>CDR3: QQGYSSSNVDNT |

In some embodiments, anti-CD39 antibodies were generated in rabbits, and then humanized by CDR grafting. Exemplary sequences for the VH and VL domains of humanized rabbit anti-CD39 antibodies are:

| Clone | Nucleic Acid Sequence | Amino Acid Sequence | CDR Sequences |
|---|---|---|---|
| Humanized 8D8 | SEQ ID No. 45 (VH) SEQ ID No. 47 (VL) | SEQ ID No. 46 (VH) SEQ ID No. 48 (VL) | SEQ ID No. 46 (VH) CDRs<br>CDR1: GFSLSSYA<br>CDR2: INSYGTT<br>CDR3: ARGDSYGSGVGLGL<br>SEQ ID No. 48 (VL) CDRs<br>CDR1: QNIYSN<br>CDR2: RAS<br>CDR3: QQGFSSNNVDNT |
| Humanized 8C11 | SEQ ID No. 49 (VH) SEQ ID No. 51 (VL) | SEQ ID No. 50 (VH) SEQ ID No. 52 (VL) | SEQ ID No. 50 (VH) CDRs<br>CDR1: GFSLSKSI<br>CDR2: IGSSGST<br>CDR3: ARGLLYSGNKS<br>SEQ ID No. 52 (VL) CDRs<br>CDR1: QSVLLNNQ<br>CDR2: DAS<br>CDR3: LGGYSGNLYA |
| Humanized 9C10 | SEQ ID No. 53 (VH) SEQ ID No. 55 (VL) | SEQ ID No. 54 (VH) SEQ ID No. 56 (VL) | SEQ ID No. 54 (VH) CDRs<br>CDR1: GFSLSSYA<br>CDR2: ISSSGST<br>CDR3: ARDRVIYSIGPYYFNL<br>SEQ ID No. 56 (VL) CDRs<br>CDR1: EIIYSN<br>CDR2: GAS<br>CDR3: QQSFSSNNVGNI |

Figure 33:
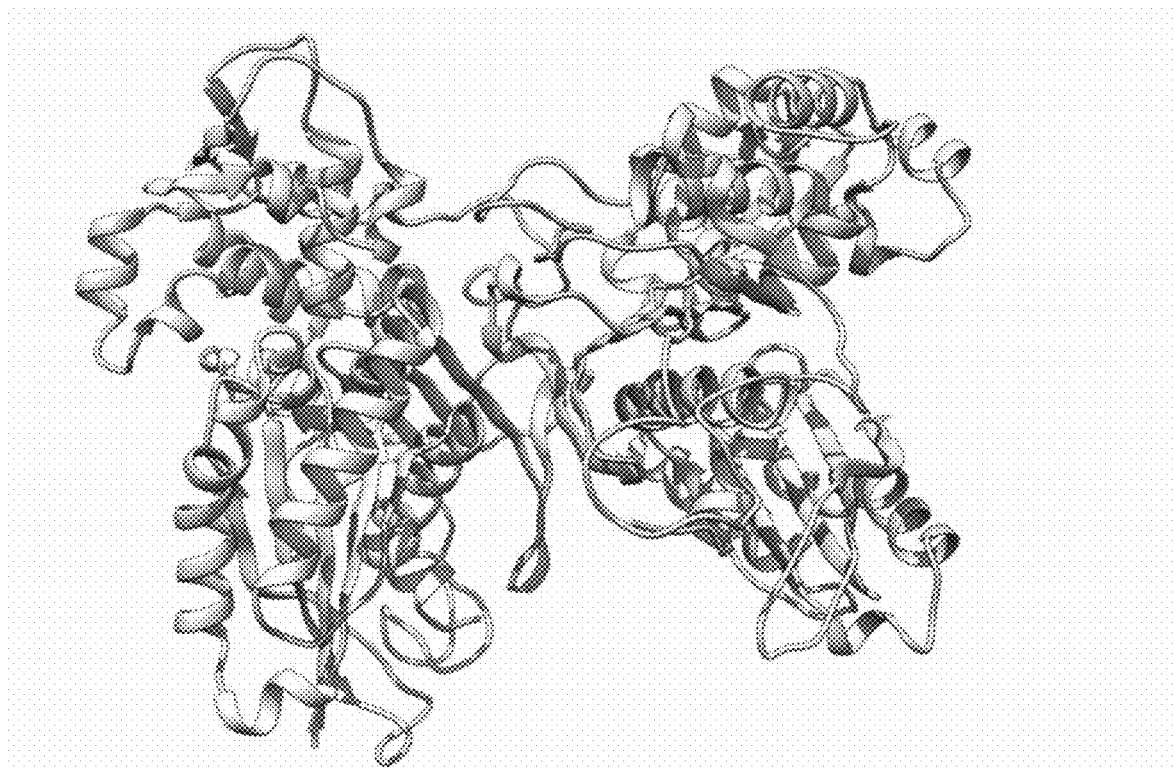
FIG. 33. Conformational epitope mapping. List of main putative CD39 epitope candidates are shown: IYLTDCMERAR (SEQ ID NO: 57), LRMESEELADR (SEQ ID NO: 58), RVKGPGISKFV (SEQ ID NO: 59), DCMERAREVIPR (SEQ ID NO: 60), LTDCMERAREVIPR (SEQ ID NO: 61), SLSNYPFDFQGAR (SEQ ID NO: 62), CRVKGPGISKF (SEQ ID NO: 63), GAYGWITINYLLGKFSQK (SEQ ID NO: 64), ILRDPCFHPGYKK (SEQ ID NO: 65). An exemplary, representative CD39 extracellular domain sequence (SEQ ID NO 66) is provided for reference of CD39 epitope sequences, as well as a homology model of a dimer of human CD39 for data visulization.

In some embodiments, anti anti-CD39 antibodies provided herein promote: (i) stable immune complex formation when incubated with HCC1739BL cells as characterized by loss of less than 30% of the immune complex after 24 hours, optionally wherein the immune complex formation is detected by fluorescent intensity using a fluorescently labeled secondary antibody; (ii) complement dependent cytotoxicity (CDC) activity against CD39+ cells; (iii) antibody-mediated target cytosis of CD39 on CD45+ immune cells; (iv) antibody-mediated target cytosis of CD39 from tumor vascular endothelium disruption or vasculature network collapse in a tumor; (v) (optionally) binding to a CD39 epitope having a sequence selected from the group of CD39 amino acid epitope sequences listed in FIG. 33 (for example, binding one or more linear or conformational CD39 epitopes, such as selected from the group consisting of 1) IYLTDCMERAR (SEQ ID NO: 57), 2) LRMESEELADR (SEQ ID NO: 58), 3) RVKGPGISKFV (SEQ ID NO: 59), 4) DCMERAREVIPR (SEQ ID NO: 60), 5) LTDCMER-AREVIPR (SEQ ID NO: 61), 6) SLSNYPFDFQGAR (SEQ ID NO: 62), 7) CRVKGPGISKF (SEQ ID NO: 63), 8) GAYGWITINYLLGKFSQK (SEQ ID NO: 64), 9) ILRDPCFHPGYKK (SEQ ID NO: 65), and any combination thereof, such as RVKGPGISKFV (SEQ ID NO: 59) and DCMERAREVIPR (SEQ ID NO: 60), LTDCMER-AREVIPR (SEQ ID NO: 61) and SLSNYPFDFQGAR (SEQ ID NO: 62), or CRVKGPGISKF (SEQ ID NO: 63), GAYGWITINYLLGKFSQK (SEQ ID NO: 64), and/or ILRDPCFHPGYKK (SEQ ID NO: 65)); and/or (vi) (optionally) binding to CD39 in a manner that is non-competitive or only partially competitive with monoclonal antibody clone A1 binding to CD39.

Representative anti-CD39 antibody sequences described above according to sequence identification number correspond to the following:

```
(Clone IG39-21vH nucleic acid sequence)
                                                        SEQ ID No. 1
gag gtg caa ctg gtg gag tct ggg gga ggt gtg gta agg cct ggg ggg    48
Glu Val Gln Leu Val Glu Ser Gly Gly Gly Val Val Arg Pro Gly Gly
1               5                   10                  15 tcc ctg aga ctc tcc tgt gca gcc tct gga ttc acc ttc agt agc tat    96
Ser Leu Arg Leu Ser Cys Ala Ala Ser Gly Phe Thr Phe Ser Ser Tyr
                20                  25                  30 gct atg cac tgg gtc cgc cag gct cca ggc aag ggg ctg gag tgg gtg   144
Ala Met His Trp Val Arg Gln Ala Pro Gly Lys Gly Leu Glu Trp Val
                35                  40                  45 gca gtt ata tca tat gat gta agc aat aaa tac tac gca gac tcc gtg   192
Ala Val Ile Ser Tyr Asp Val Ser Asn Lys Tyr Tyr Ala Asp Ser Val
                50                  55                  60
```

-continued

```
aag ggc cga ttc acc atc tcc aga gac aat tcc aag aac acg ctg tat   240
Lys Gly Arg Phe Thr Ile Ser Arg Asp Asn Ser Lys Asn Thr Leu Tyr
 65                  70                  75                  80 ctg caa atg aac agc ctg aga gct gag gac acg gct gtg tat tac tgt   288
Leu Gln Met Asn Ser Leu Arg Ala Glu Asp Thr Ala Val Tyr Tyr Cys
                 85                  90                  95 gcg aga tct tac tac tac tac tac ggt atg gac gtc tgg ggc caa ggg   336
Ala Arg Ser Tyr Tyr Tyr Tyr Tyr Gly Met Asp Val Trp Gly Gln Gly
            100                 105                 110 acc acg gtc acc gtc tcc tca                                       357
Thr Thr Val Thr Val Ser Ser
        115

(Clone IG39-21 vH amino acid sequence)
                                                      SEQ ID No. 2
Glu Val Gln Leu Val Glu Ser Gly Gly Val Val Arg Pro Gly Gly
 1               5                  10                  15

Ser Leu Arg Leu Ser Cys Ala Ala Ser Gly Phe Thr Phe Ser Ser Tyr
                 20                  25                  30

Ala Met His Trp Val Arg Gln Ala Pro Gly Lys Gly Leu Glu Trp Val
             35                  40                  45

Ala Val Ile Ser Tyr Asp Val Ser Asn Lys Tyr Tyr Ala Asp Ser Val
         50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Arg Ser Tyr Tyr Tyr Tyr Tyr Gly Met Asp Val Trp Gly Gln Gly
            100                 105                 110

Thr Thr Val Thr Val Ser Ser
        115

(Clone IG39-21 vL domain nucleic acid sequence)
                                                      SEQ ID No. 3
gat gtt gtg atg acc cag tct cca tcc tcc ctg tct gca tct gta gga    48
Asp Val Val Met Thr Gln Ser Pro Ser Ser Leu Ser Ala Ser Val Gly
 1               5                  10                  15 gac aga gtc acc atc act tgc cgg gca agt cag agc att agc agg tac    96
Asp Arg Val Thr Ile Thr Cys Arg Ala Ser Gln Ser Ile Ser Arg Tyr
                 20                  25                  30 tta gcc tgg tac caa cag aaa cct ggc cag gct ccc agg ctc ctc atc   144
Leu Ala Trp Tyr Gln Gln Lys Pro Gly Gln Ala Pro Arg Leu Leu Ile
             35                  40                  45 tat gat gca tcc aac agg gcc act ggc atc cca gtc agg ttc agt ggc   192
Tyr Asp Ala Ser Asn Arg Ala Thr Gly Ile Pro Val Arg Phe Ser Gly
         50                  55                  60 agt ggg tct ggg aca gac ttc act ctc acc atc agc aga ctg gag cca   240
Ser Gly Ser Gly Thr Asp Phe Thr Leu Thr Ile Ser Arg Leu Glu Pro
 65                  70                  75                  80 gaa gat ttt gca gtg tat tac tgt cag cag ttt ggt agg tca cot cgg   288
Glu Asp Phe Ala Val Tyr Tyr Cys Gln Gln Phe Gly Arg Ser Pro Arg
                 85                  90                  95 acg ttc ggc caa ggg aca cga ctg gag att aaa                       321
Thr Phe Gly Gln Gly Thr Arg Leu Glu Ile Lys
            100                 105

(Clone IG39-21 vL domain amino acid sequence)
                                                      SEQ ID No. 4
Asp Val Val Met Thr Gln Ser Pro Ser Ser Leu Ser Ala Ser Val Gly
 1               5                  10                  15

Asp Arg Val Thr Ile Thr Cys Arg Ala Ser Gln Ser Ile Ser Arg Tyr
                 20                  25                  30
```

```
Leu Ala Trp Tyr Gln Gln Lys Pro Gly Gln Ala Pro Arg Leu Leu Ile
         35                  40                  45

Tyr Asp Ala Ser Asn Arg Ala Thr Gly Ile Pro Val Arg Phe Ser Gly
 50                  55                  60

Ser Gly Ser Gly Thr Asp Phe Thr Leu Thr Ile Ser Arg Leu Glu Pro
65                  70                  75                  80

Glu Asp Phe Ala Val Tyr Tyr Cys Gln Gln Phe Gly Arg Ser Pro Arg
                 85                  90                  95

Thr Phe Gly Gln Gly Thr Arg Leu Glu Ile Lys
                100                 105

(Clone 9B6 vH domain nucleic acid sequence)
                                                       SEQ ID No. 5
cag tca gtg aag gag gcc ggg ggt cgc ctg gta acg cct gga gga tcc   48
Gln Ser Val Lys Glu Ala Gly Gly Arg Leu Val Thr Pro Gly Gly Ser
1               5                   10                  15 ctg aca ctc acc tgc aca gtc tct gga ttc tcc ctc agt gcg tat gga   96
Leu Thr Leu Thr Cys Thr Val Ser Gly Phe Ser Leu Ser Ala Tyr Gly
            20                  25                  30 ata agt tgg gtc cgc cag gct cca ggg aag gga ctg gaa tgg atc gga  144
Ile Ser Trp Val Arg Gln Ala Pro Gly Lys Gly Leu Glu Trp Ile Gly
         35                  40                  45 atc att tat agt agt ggt agg act tac tac gcg aac tgg gcg aaa ggc  192
Ile Ile Tyr Ser Ser Gly Arg Thr Tyr Tyr Ala Asn Trp Ala Lys Gly
 50                  55                  60 cga ttc acc atc tcc aaa acc tcg tcg acc acg gtg gat ctg aaa atg  240
Arg Phe Thr Ile Ser Lys Thr Ser Ser Thr Thr Val Asp Leu Lys Met
65                  70                  75                  80 acc agt ctg aca acc gag gac acg gcc gcc tat ttc tgt gcc aga tca  288
Thr Ser Leu Thr Thr Glu Asp Thr Ala Ala Tyr Phe Cys Ala Arg Ser
                 85                  90                  95 cgg gct ggt att agt agt ggt gat ggt ttt gat tcc tgg ggc cca ggc  336
Arg Ala Gly Ile Ser Ser Gly Asp Gly Phe Asp Ser Trp Gly Pro Gly
                100                 105                 110 acc ctg gtc acc gtc tcc tca  357
Thr Leu Val Thr Val Ser Ser
            115

(Clone 9B6 vH domain amino acid sequence)
                                                       SEQ ID No. 6
Gln Ser Val Lys Glu Ala Gly Gly Arg Leu Val Thr Pro Gly Gly Ser
1               5                   10                  15

Leu Thr Leu Thr Cys Thr Val Ser Gly Phe Ser Leu Ser Ala Tyr Gly
            20                  25                  30

Ile Ser Trp Val Arg Gln Ala Pro Gly Lys Gly Leu Glu Trp Ile Gly
         35                  40                  45

Ile Ile Tyr Ser Ser Gly Arg Thr Tyr Tyr Ala Asn Trp Ala Lys Gly
 50                  55                  60

Arg Phe Thr Ile Ser Lys Thr Ser Ser Thr Thr Val Asp Leu Lys Met
65                  70                  75                  80

Thr Ser Leu Thr Thr Glu Asp Thr Ala Ala Tyr Phe Cys Ala Arg Ser
                 85                  90                  95

Arg Ala Gly Ile Ser Ser Gly Asp Gly Phe Asp Ser Trp Gly Pro Gly
                100                 105                 110

Thr Leu Val Thr Val Ser Ser
            115

(Clone 9B6 vL domain nucleic acid sequence)
                                                       SEQ ID No. 7
gcc aga tgt gcc ctt gtg atg acc cag act cca tcc tcc gtg tct gca   48
Ala Arg Cys Ala Leu Val Met Thr Gln Thr Pro Ser Ser Val Ser Ala
1               5                   10                  15 gct gtg gga ggc aca gtc acc atc aat tgc cag gcc agt cag aac att   96
```

-continued

```
                Ala Val Gly Gly Thr Val Thr Ile Asn Cys Gln Ala Ser Gln Asn Ile
                                20                  25                  30
tac agc aat tta gcc tgg tat cag cag aaa cca ggg cag cgt ccc cag        144
Tyr Ser Asn Leu Ala Trp Tyr Gln Gln Lys Pro Gly Gln Arg Pro Gln
             35                  40                  45
ctc ctg atc tac agg gca tcc act ctg gca tct ggg gtc cca tcg cgg        192
Leu Leu Ile Tyr Arg Ala Ser Thr Leu Ala Ser Gly Val Pro Ser Arg
         50                  55                  60
ttc aaa ggc agt gca tct ggg aca gaa tac act ctc acc atc agc ggt        240
Phe Lys Gly Ser Ala Ser Gly Thr Glu Tyr Thr Leu Thr Ile Ser Gly
 65                  70                  75                  80
gtg cag tgt gac gat gct gcc act tac tat tgt caa cag ggt ttt gat        288
Val Gln Cys Asp Asp Ala Ala Thr Tyr Tyr Cys Gln Gln Gly Phe Asp
                 85                  90                  95
agt agt aac att gat aat act ttc ggc gga ggg acc gag gtg gtg gtc        336
Ser Ser Asn Ile Asp Asn Thr Phe Gly Gly Gly Thr Glu Val Val Val
                100                 105                 110
aca                                                                    339
Thr
```

(Clone 9136 vL domain amino acid sequence)

SEQ ID No. 8

```
Ala Arg Cys Ala Leu Val Met Thr Gln Thr Pro Ser Ser Val Ser Ala
 1               5                  10                  15
Ala Val Gly Gly Thr Val Thr Ile Asn Cys Gln Ala Ser Gln Asn Ile
                20                  25                  30
Tyr Ser Asn Leu Ala Trp Tyr Gln Gln Lys Pro Gly Gln Arg Pro Gln
             35                  40                  45
Leu Leu Ile Tyr Arg Ala Ser Thr Leu Ala Ser Gly Val Pro Ser Arg
         50                  55                  60
Phe Lys Gly Ser Ala Ser Gly Thr Glu Tyr Thr Leu Thr Ile Ser Gly
 65                  70                  75                  80
Val Gln Cys Asp Asp Ala Ala Thr Tyr Tyr Cys Gln Gln Gly Phe Asp
                 85                  90                  95
Ser Ser Asn Ile Asp Asn Thr Phe Gly Gly Gly Thr Glu Val Val Val
                100                 105                 110
Thr
```

(Clone 8C11 vH domain nucleic acid sequence)

SEQ ID No. 9

```
cag tcg gtg gag gag tcc ggg ggt cgc ctg gtc acg cct ggg aca cac         48
Gln Ser Val Glu Glu Ser Gly Gly Arg Leu Val Thr Pro Gly Thr His
 1               5                  10                  15 ctg aca ctc acc tgc aca gtc tct gga ttc tcc ctc agt aag agt ata         96
Leu Thr Leu Thr Cys Thr Val Ser Gly Phe Ser Leu Ser Lys Ser Ile
                20                  25                  30 ata agt tgg gtc cgc cag gct cca ggg aag ggg ctg gaa tac atc gga        144
Ile Ser Trp Val Arg Gln Ala Pro Gly Lys Gly Leu Glu Tyr Ile Gly
             35                  40                  45 atc att ggt agt agt ggt agc aca tac tac gcg aac tgg gcg aaa ggc        192
Ile Ile Gly Ser Ser Gly Ser Thr Tyr Tyr Ala Asn Trp Ala Lys Gly
         50                  55                  60 cga ttc acc atc tcc aaa acc tcg tcg acc acg gtg gat ctg aga atg        240
Arg Phe Thr Ile Ser Lys Thr Ser Ser Thr Thr Val Asp Leu Arg Met
 65                  70                  75                  80 acc agt ctg aca ccc gag gac acg gcc acc tat ttc tgt gcc aga gga        288
Thr Ser Leu Thr Pro Glu Asp Thr Ala Thr Tyr Phe Cys Ala Arg Gly
                 85                  90                  95 ctt ctt tat tct ggt aat aaa tcg tgg ggc ccg ggc acc ctg gtc acc        336
Leu Leu Tyr Ser Gly Asn Lys Ser Trp Gly Pro Gly Thr Leu Val Thr
                100                 105                 110 gtc tcc tca                                                            345
Val Ser Ser
        115
```

(Clone 8C11 vH domain amino acid sequence)

SEQ ID No. 10

```
Gln Ser Val Glu Glu Ser Gly Gly Arg Leu Val Thr Pro Gly Thr His
 1               5                  10                  15

Leu Thr Leu Thr Cys Thr Val Ser Gly Phe Ser Leu Ser Lys Ser Ile
                20                  25                  30

Ile Ser Trp Val Arg Gln Ala Pro Gly Lys Gly Leu Glu Tyr Ile Gly
```

```
                  35                    40                     45
Ile Ile Gly Ser Ser Gly Ser Thr Tyr Tyr Ala Asn Trp Ala Lys Gly
         50                  55                  60

Arg Phe Thr Ile Ser Lys Thr Ser Ser Thr Thr Val Asp Leu Arg Met
65                  70                  75                  80

Thr Ser Leu Thr Pro Glu Asp Thr Ala Thr Tyr Phe Cys Ala Arg Gly
                 85                   90                  95

Leu Leu Tyr Ser Gly Asn Lys Ser Trp Gly Pro Gly Thr Leu Val Thr
            100                 105                 110

Val Ser Ser
        115
```

(Clone 8C11 vL domain nucleic acid sequence)

```
                                                       SEQ ID No. 11
gcc aca ttt gcc att gat atg acc cag act cca tcc tcc gtg tct gca   48
Ala Thr Phe Ala Ile Asp Met Thr Gln Thr Pro Ser Ser Val Ser Ala
1               5                   10                  15 gct gtg gga ggc aca gtc acc atc aac tgc cag tcc agt cag agt gtt   96
Ala Val Gly Gly Thr Val Thr Ile Asn Cys Gln Ser Ser Gln Ser Val
                20                  25                  30 tta ctg aac aac caa tta tcc tgg ttt cag cag aaa cca ggg cag cct  144
Leu Leu Asn Asn Gln Leu Ser Trp Phe Gln Gln Lys Pro Gly Gln Pro
        35                  40                  45 ccc aag ctc ctg atc tat gat gca tcc act ctg gaa tct ggg gtc cca  192
Pro Lys Leu Leu Ile Tyr Asp Ala Ser Thr Leu Glu Ser Gly Val Pro
    50                  55                  60 tct cgg ttc aca ggc agt gga tct ggg aca cag ttc act ctc acc atc  240
Ser Arg Phe Thr Gly Ser Gly Ser Gly Thr Gln Phe Thr Leu Thr Ile
65                  70                  75                  80 agc gac ctg gag tgt gac gat gct gcc act tac tat tgt tta ggc ggt  288
Ser Asp Leu Glu Cys Asp Asp Ala Ala Thr Tyr Tyr Cys Leu Gly Gly
                85                  90                  95 tat agt ggg aac ctt tat gct ttc ggc gga ggg acc gag gtg cta gtc  336
Tyr Ser Gly Asn Leu Tyr Ala Phe Gly Gly Gly Thr Glu Val Leu Val
            100                 105                 110 aaa                                                               339
Lys
```

(Clone 8C11 vL domain amino acid sequence)

```
                                                       SEQ ID No. 12
Ala Thr Phe Ala Ile Asp Met Thr Gln Thr Pro Ser Ser Val Ser Ala
1               5                   10                  15

Ala Val Gly Gly Thr Val Thr Ile Asn Cys Gln Ser Ser Gln Ser Val
                20                  25                  30

Leu Leu Asn Asn Gln Leu Ser Trp Phe Gln Gln Lys Pro Gly Gln Pro
        35                  40                  45

Pro Lys Leu Leu Ile Tyr Asp Ala Ser Thr Leu Glu Ser Gly Val Pro
    50                  55                  60

Ser Arg Phe Thr Gly Ser Gly Ser Gly Thr Gln Phe Thr Leu Thr Ile
65                  70                  75                  80

Ser Asp Leu Glu Cys Asp Asp Ala Ala Thr Tyr Tyr Cys Leu Gly Gly
                85                  90                  95

Tyr Ser Gly Asn Leu Tyr Ala Phe Gly Gly Gly Thr Glu Val Leu Val
            100                 105                 110
Lys
```

(Clone 8D8 vH domain nucleic acid sequence)

```
                                                       SEQ ID No. 13
cag tcg gtg gag gag tcc ggg ggt cgc ctg gtc acg cct ggg aca ccc   48
Gln Ser Val Glu Glu Ser Gly Gly Arg Leu Val Thr Pro Gly Thr Pro
1               5                   10                  15 ctg aca ctc acc tgc aca gtc tct gga ttc tcc ctc agt agc tat gca   96
```

```
                                                        -continued
Leu Thr Leu Thr Cys Thr Val Ser Gly Phe Ser Leu Ser Ser Tyr Ala
            20                  25                  30 ata agt tgg gtc cgc cag gct cca ggg aag ggg ctc gaa tat atc gcg    144
Ile Ser Trp Val Arg Gln Ala Pro Gly Lys Gly Leu Glu Tyr Ile Ala
        35                  40                  45 atc att aat agt tat ggt acc aca tac tac gcg agc tgg gcg aaa ggc    192
Ile Ile Asn Ser Tyr Gly Thr Thr Tyr Tyr Ala Ser Trp Ala Lys Gly
    50                  55                  60 cga gtc acc atc tcc aaa acc tcg agc acg gtg gat ctg aaa atc tcc   240
Arg Val Thr Ile Ser Lys Thr Ser Ser Thr Val Asp Leu Lys Ile Ser
65                  70                  75                  80 agt ccg aca acc gag gac acg gcc acc tat ttc tgt gcc aga ggc gat   288
Ser Pro Thr Thr Glu Asp Thr Ala Thr Tyr Phe Cys Ala Arg Gly Asp
                85                  90                  95 agt tat ggt agt ggt gtt ggt ttg ggc ttg tgg ggc cca ggc acc ctg   336
Ser Tyr Gly Ser Gly Val Gly Leu Gly Leu Trp Gly Pro Gly Thr Leu
                100                 105                 110 gtc acc gtc tcc tca                                                351
Val Thr Val Ser Ser
            115
```

(Clone 8D8 vH domain amino acid sequence)
                                                            SEQ ID No. 14
```
Gln Ser Val Glu Glu Ser Gly Gly Arg Leu Val Thr Pro Gly Thr Pro
1               5                   10                  15

Leu Thr Leu Thr Cys Thr Val Ser Gly Phe Ser Leu Ser Ser Tyr Ala
            20                  25                  30

Ile Ser Trp Val Arg Gln Ala Pro Gly Lys Gly Leu Glu Tyr Ile Ala
        35                  40                  45

Ile Ile Asn Ser Tyr Gly Thr Thr Tyr Tyr Ala Ser Trp Ala Lys Gly
    50                  55                  60

Arg Val Thr Ile Ser Lys Thr Ser Ser Thr Val Asp Leu Lys Ile Ser
65                  70                  75                  80

Ser Pro Thr Thr Glu Asp Thr Ala Thr Tyr Phe Cys Ala Arg Gly Asp
                85                  90                  95

Ser Tyr Gly Ser Gly Val Gly Leu Gly Leu Trp Gly Pro Gly Thr Leu
                100                 105                 110

Val Thr Val Ser Ser
            115
```

(Clone 8D8 vL domain nucleic acid sequence)
                                                            SEQ ID No. 15
```
gcc aga tgt gcc tat gat atg acc cag act cca gcc tct gtg gag gta    48
Ala Arg Cys Ala Tyr Asp Met Thr Gln Thr Pro Ala Ser Val Glu Val
1               5                   10                  15 gct gtg gga ggc aca gtc acc atc aag tgc cag gcc agt cag aac att    96
Ala Val Gly Gly Thr Val Thr Ile Lys Cys Gln Ala Ser Gln Asn Ile
            20                  25                  30 tac agc aat tta gcc tgg tat cag cag aaa cca ggg cag cgt ccc aag   144
Tyr Ser Asn Leu Ala Trp Tyr Gln Gln Lys Pro Gly Gln Arg Pro Lys
        35                  40                  45 ctc ctg atc tac agg gca tcc agt ctg gca tct ggg gtc ccg tcg cgg   192
Leu Leu Ile Tyr Arg Ala Ser Ser Leu Ala Ser Gly Val Pro Ser Arg
    50                  55                  60 ttc agt ggc agt gga tct ggg aca gag ttc act ctc acc atc agc ggt   240
Phe Ser Gly Ser Gly Ser Gly Thr Glu Phe Thr Leu Thr Ile Ser Gly
65                  70                  75                  80 gtg cag tgt gac gat gct gcc act tac tac tgt caa cag ggt ttt agt   288
Val Gln Cys Asp Asp Ala Ala Thr Tyr Tyr Cys Gln Gln Gly Phe Ser
                85                  90                  95 agt aat aat gtt gat aat act ttc ggc gga ggg acc gag gtg gtg gtc   336
Ser Asn Asn Val Asp Asn Thr Phe Gly Gly Gly Thr Glu Val Val Val
```

-continued

```
                     100                 105                 110
aaa                                                                     339
Lys
```

(Clone 8D8 vL domain amino acid sequence)

SEQ ID No. 16

```
Ala Arg Cys Ala Tyr Asp Met Thr Gln Thr Pro Ala Ser Val Glu Val
1               5                   10                  15

Ala Val Gly Gly Thr Val Thr Ile Lys Cys Gln Ala Ser Gln Asn Ile
            20                  25                  30

Tyr Ser Asn Leu Ala Trp Tyr Gln Gln Lys Pro Gly Gln Arg Pro Lys
        35                  40                  45

Leu Leu Ile Tyr Arg Ala Ser Ser Leu Ala Ser Gly Val Pro Ser Arg
    50                  55                  60

Phe Ser Gly Ser Gly Ser Gly Thr Glu Phe Thr Leu Thr Ile Ser Gly
65                  70                  75                  80

Val Gln Cys Asp Asp Ala Ala Thr Tyr Tyr Cys Gln Gln Gly Phe Ser
                85                  90                  95

Ser Asn Asn Val Asp Asn Thr Phe Gly Gly Gly Thr Glu Val Val Val
                100                 105                 110

Lys
```

(Clone 9C10 vH domain nucleic acid sequence)

SEQ ID No. 17

```
cag tcg gtg gag gag tcc ggg ggt cgc ctg gtc acg cct ggg aca ccc    48
Gln Ser Val Glu Glu Ser Gly Gly Arg Leu Val Thr Pro Gly Thr Pro
1               5                   10                  15 ctg aca ctc acc tgc acc gtc tcc gga ttc tcc ctc agt agc tat gca    96
Leu Thr Leu Thr Cys Thr Val Ser Gly Phe Ser Leu Ser Ser Tyr Ala
            20                  25                  30 atg agc tgg gtc cgc cag gct cca ggg aag ggg ctg gaa tac atc gga   144
Met Ser Trp Val Arg Gln Ala Pro Gly Lys Gly Leu Glu Tyr Ile Gly
        35                  40                  45 atc att agt agt agt ggt agc aca tac tac gcg agc tgg gcg aaa ggc   192
Ile Ile Ser Ser Ser Gly Ser Thr Tyr Tyr Ala Ser Trp Ala Lys Gly
    50                  55                  60 cga ttc acc atc tcc aaa acc tcg acc acg gtg gat ctg aaa atc tcc   240
Arg Phe Thr Ile Ser Lys Thr Ser Thr Thr Val Asp Leu Lys Ile Ser
65                  70                  75                  80 agt ccg aca acc gag gac acg gcc acc tat ttc tgt gcc aga gat cgt   288
Ser Pro Thr Thr Glu Asp Thr Ala Thr Tyr Phe Cys Ala Arg Asp Arg
                85                  90                  95 gtt att tat agt att ggt ccg tat tat ttt aat ttg tgg ggc cca ggc   336
Val Ile Tyr Ser Ile Gly Pro Tyr Tyr Phe Asn Leu Trp Gly Pro Gly
                100                 105                 110 acc ctg gtc acc gtc tcc tca                                        357
Thr Leu Val Thr Val Ser Ser
            115
```

(Clone 9C10 vH domain amino acid sequence)

SEQ ID No. 18

```
Gln Ser Val Glu Glu Ser Gly Gly Arg Leu Val Thr Pro Gly Thr Pro
1               5                   10                  15

Leu Thr Leu Thr Cys Thr Val Ser Gly Phe Ser Leu Ser Ser Tyr Ala
            20                  25                  30

Met Ser Trp Val Arg Gln Ala Pro Gly Lys Gly Leu Glu Tyr Ile Gly
        35                  40                  45

Ile Ile Ser Ser Ser Gly Ser Thr Tyr Tyr Ala Ser Trp Ala Lys Gly
    50                  55                  60

Arg Phe Thr Ile Ser Lys Thr Ser Thr Thr Val Asp Leu Lys Ile Ser
65                  70                  75                  80
```

-continued

```
Ser Pro Thr Thr Glu Asp Thr Ala Thr Tyr Phe Cys Ala Arg Asp Arg
                85                  90                  95

Val Ile Tyr Ser Ile Gly Pro Tyr Tyr Phe Asn Leu Trp Gly Pro Gly
            100                 105                 110

Thr Leu Val Thr Val Ser Ser
        115
```

(Clone 9C10 vL domain nucleic acid sequence)

SEQ ID No. 19

```
gcc aga tgt gcc tat gat atg acc cag act cca tcc tcc gtg tct gca   48
Ala Arg Cys Ala Tyr Asp Met Thr Gln Thr Pro Ser Ser Val Ser Ala
1               5                   10                  15 act gtg gga ggc aca gtc acc atc aat tgc cag gcc agt gag atc att   96
Thr Val Gly Gly Thr Val Thr Ile Asn Cys Gln Ala Ser Glu Ile Ile
            20                  25                  30 tat agc aat tta gcc tgg tat cag cag aaa cca ggg cag cct ccc aag  144
Tyr Ser Asn Leu Ala Trp Tyr Gln Gln Lys Pro Gly Gln Pro Pro Lys
        35                  40                  45 ctc ctg atc tat ggc gca tcc act ctg gca tct ggg gtc cca tcg cgg  192
Leu Leu Ile Tyr Gly Ala Ser Thr Leu Ala Ser Gly Val Pro Ser Arg
    50                  55                  60 ttc aaa ggc agt gga tct ggg aca gag tac act ctc acc atc agc gac  240
Phe Lys Gly Ser Gly Ser Gly Thr Glu Tyr Thr Leu Thr Ile Ser Asp
65                  70                  75                  80 ctg cag tgt gac gat gct gcc act tac tac tgt caa cag agt ttt agt  288
Leu Gln Cys Asp Asp Ala Ala Thr Tyr Tyr Cys Gln Gln Ser Phe Ser
                85                  90                  95 agt aat aat gtt ggg aat att ttc ggc gga ggg acc gag gtg gtg gtc  336
Ser Asn Asn Val Gly Asn Ile Phe Gly Gly Gly Thr Glu Val Val Val
            100                 105                 110 aaa                                                              339
Lys
```

(Clone 9C10 vL domain amino acid sequence)

SEQ ID No. 20

```
Ala Arg Cys Ala Tyr Asp Met Thr Gln Thr Pro Ser Ser Val Ser Ala
1               5                   10                  15

Thr Val Gly Gly Thr Val Thr Ile Asn Cys Gln Ala Ser Glu Ile Ile
            20                  25                  30

Tyr Ser Asn Leu Ala Trp Tyr Gln Gln Lys Pro Gly Gln Pro Pro Lys
        35                  40                  45

Leu Leu Ile Tyr Gly Ala Ser Thr Leu Ala Ser Gly Val Pro Ser Arg
    50                  55                  60

Phe Lys Gly Ser Gly Ser Gly Thr Glu Tyr Thr Leu Thr Ile Ser Asp
65                  70                  75                  80

Leu Gln Cys Asp Asp Ala Ala Thr Tyr Tyr Cys Gln Gln Ser Phe Ser
                85                  90                  95

Ser Asn Asn Val Gly Asn Ile Phe Gly Gly Gly Thr Glu Val Val Val
            100                 105                 110

Lys
```

(Clone 651-15 vH domain nucleic acid sequence)

SEQ ID No. 21

```
cag tcg gtg gag gag tcc ggg ggt cgc ctg gtc acg cct ggg aca ccc   48
Gln Ser Val Glu Glu Ser Gly Gly Arg Leu Val Thr Pro Gly Thr Pro
1               5                   10                  15 ctg aca ctc acc tgc aca gcc tct gga ttc tcc ctc agt acc cat gca   96
Leu Thr Leu Thr Cys Thr Ala Ser Gly Phe Ser Leu Ser Thr His Ala
            20                  25                  30 ata aac tgg gtc cgc cag gct cca ggg aag ggg ctg gaa tgg atc ggg  144
Ile Asn Trp Val Arg Gln Ala Pro Gly Lys Gly Leu Glu Trp Ile Gly
        35                  40                  45 atc act tat gct agt ggt agg aca tat tac gcg agc tgg gcg aaa ggc  192
```

```
                                       -continued
Ile Thr Tyr Ala Ser Gly Arg Thr Tyr Tyr Ala Ser Trp Ala Lys Gly
    50                  55                  60 cga ttc acc atc tcc aaa acc tcg acc acg gtg gat ctg aaa atc acc    240
Arg Phe Thr Ile Ser Lys Thr Ser Thr Thr Val Asp Leu Lys Ile Thr
65                  70                  75                  80 agt ccg aca acc gag gac acg gcc acc tat ttc tgt gcc aga aat ggg    288
Ser Pro Thr Thr Glu Asp Thr Ala Thr Tyr Phe Cys Ala Arg Asn Gly
                85                  90                  95 gct gat gaa aca ttt tac tac ttt gac ttg tgg ggc cca ggc acc ctg    336
Ala Asp Glu Thr Phe Tyr Tyr Phe Asp Leu Trp Gly Pro Gly Thr Leu
            100                 105                 110 gtc acc gtc tcc tca                                                351
Val Thr Val Ser Ser
        115

(Clone 65H5 vH domain amino acid sequence)
                                                        SEQ ID No. 22
Gln Ser Val Glu Glu Ser Gly Gly Arg Leu Val Thr Pro Gly Thr Pro
1               5                   10                  15

Leu Thr Leu Thr Cys Thr Ala Ser Gly Phe Ser Leu Ser Thr His Ala
                20                  25                  30

Ile Asn Trp Val Arg Gln Ala Pro Gly Lys Gly Leu Glu Trp Ile Gly
            35                  40                  45

Ile Thr Tyr Ala Ser Gly Arg Thr Tyr Tyr Ala Ser Trp Ala Lys Gly
    50                  55                  60

Arg Phe Thr Ile Ser Lys Thr Ser Thr Thr Val Asp Leu Lys Ile Thr
65                  70                  75                  80

Ser Pro Thr Thr Glu Asp Thr Ala Thr Tyr Phe Cys Ala Arg Asn Gly
                85                  90                  95

Ala Asp Glu Thr Phe Tyr Tyr Phe Asp Leu Trp Gly Pro Gly Thr Leu
            100                 105                 110

Val Thr Val Ser Ser
        115

(Clone 65H5 vL domain nucleic acid sequence)
                                                        SEQ ID No. 23
gcc aga tgt gcc tat gat atg acc cag act cca gcc tcc gtg gag gca     48
Ala Arg Cys Ala Tyr Asp Met Thr Gln Thr Pro Ala Ser Val Glu Ala
1               5                   10                  15 gct gtg gga ggc aca gtc acc atc aag tgc cag gcc agt cag aat att     96
Ala Val Gly Gly Thr Val Thr Ile Lys Cys Gln Ala Ser Gln Asn Ile
                20                  25                  30 aat act tgg tta tcc tgg tat cag cag aag gca ggg cag cct ccc aag    144
Asn Thr Trp Leu Ser Trp Tyr Gln Gln Lys Ala Gly Gln Pro Pro Lys
            35                  40                  45 ctc ctg atc tac agg gca tcc act ctg gca tct ggg gtc tca tcg cgg    192
Leu Leu Ile Tyr Arg Ala Ser Thr Leu Ala Ser Gly Val Ser Ser Arg
    50                  55                  60 ttc aaa ggc agt gga tct ggg aca cag ttc act ctc acc atc agc ggc    240
Phe Lys Gly Ser Gly Ser Gly Thr Gln Phe Thr Leu Thr Ile Ser Gly
65                  70                  75                  80 gtg gag tgt gcc gat gct gcc act tac tac tgt caa caa tat gat gct    288
Val Glu Cys Ala Asp Ala Ala Thr Tyr Tyr Cys Gln Gln Tyr Asp Ala
                85                  90                  95 agt att aat att gat aat gct ttc ggc gga ggg acc gag gtg gtg gtc    336
Ser Ile Asn Ile Asp Asn Ala Phe Gly Gly Gly Thr Glu Val Val Val
            100                 105                 110 aaa                                                                339
Lys (Clone 65H5 vL domain amino acid sequence)
                                                        SEQ ID No. 24
Ala Arg Cys Ala Tyr Asp Met Thr Gln Thr Pro Ala Ser Val Glu Ala
```

-continued

```
1               5                  10                 15
Ala Val Gly Gly Thr Val Thr Ile Lys Cys Gln Ala Ser Gln Asn Ile
            20                  25                 30

Asn Thr Trp Leu Ser Trp Tyr Gln Gln Lys Ala Gly Gln Pro Pro Lys
            35                  40                 45

Leu Leu Ile Tyr Arg Ala Ser Thr Leu Ala Ser Gly Val Ser Ser Arg
50                  55                  60

Phe Lys Gly Ser Gly Ser Gly Thr Gln Phe Thr Leu Thr Ile Ser Gly
65                  70                  75                 80

Val Glu Cys Ala Asp Ala Ala Thr Tyr Tyr Cys Gln Gln Tyr Asp Ala
            85                  90                 95

Ser Ile Asn Ile Asp Asn Ala Phe Gly Gly Thr Glu Val Val Val
                100                 105                110

Lys
```

(Clone 2G12 vH domain nucleic acid sequence)
                                                              SEQ ID No. 25
```
cag tcg gtg gag gag tcc ggg ggt cgc ctg gtc acg cct ggg aca ccc   48
Gln Ser Val Glu Glu Ser Gly Gly Arg Leu Val Thr Pro Gly Thr Pro
1               5                  10                 15 ctg aca ctc acc tgc aca gtc tct gga atc gac ctc agt agc aat gca   96
Leu Thr Leu Thr Cys Thr Val Ser Gly Ile Asp Leu Ser Ser Asn Ala
            20                  25                 30 atg agc tgg gtc cgc cag gct cca ggg aag ggg ctg gaa tat atc gga  144
Met Ser Trp Val Arg Gln Ala Pro Gly Lys Gly Leu Glu Tyr Ile Gly
            35                  40                 45 att att agg aat aat gat atc aca tac tac gcg agc tgg gcg aaa ggc  192
Ile Ile Arg Asn Asn Asp Ile Thr Tyr Tyr Ala Ser Trp Ala Lys Gly
50                  55                  60 cga ttc acc atc tcc aaa acc tcg acc acg gtg gat ctg ata atc acc  240
Arg Phe Thr Ile Ser Lys Thr Ser Thr Thr Val Asp Leu Ile Ile Thr
65                  70                  75                 80 agt ccg aca acc gag gac acg gcc acc tat ttc tgt gcc aga ggg ggt  288
Ser Pro Thr Thr Glu Asp Thr Ala Thr Tyr Phe Cys Ala Arg Gly Gly
            85                  90                 95 ggt tct tac agt att gtc ttc tgg aac tta tgg ggc cca ggc acc ctg  336
Gly Ser Tyr Ser Ile Val Phe Trp Asn Leu Trp Gly Pro Gly Thr Leu
                100                 105                110 gtc acc gtc tcc tca                                              351
Val Thr Val Ser Ser
        115
```

(Clone 2G12 vH domain amino acid sequence)
                                                              SEQ ID No. 26
```
Gln Ser Val Glu Glu Ser Gly Gly Arg Leu Val Thr Pro Gly Thr Pro
1               5                  10                 15

Leu Thr Leu Thr Cys Thr Val Ser Gly Ile Asp Leu Ser Ser Asn Ala
            20                  25                 30

Met Ser Trp Val Arg Gln Ala Pro Gly Lys Gly Leu Glu Tyr Ile Gly
            35                  40                 45

Ile Ile Arg Asn Asn Asp Ile Thr Tyr Tyr Ala Ser Trp Ala Lys Gly
50                  55                  60

Arg Phe Thr Ile Ser Lys Thr Ser Thr Thr Val Asp Leu Ile Ile Thr
65                  70                  75                 80

Ser Pro Thr Thr Glu Asp Thr Ala Thr Tyr Phe Cys Ala Arg Gly Gly
            85                  90                 95

Gly Ser Tyr Ser Ile Val Phe Trp Asn Leu Trp Gly Pro Gly Thr Leu
                100                 105                110

Val Thr Val Ser Ser
        115
```

-continued (Clone 2G12 vL domain nucleic acid sequence)

SEQ ID No. 27

```
gcc aga tgt gcc tat gat atg acc cag act cca gcc tct gtg gag gta   48
Ala Arg Cys Ala Tyr Asp Met Thr Gln Thr Pro Ala Ser Val Glu Val
1               5                   10                  15 gct gtg gga ggc aca gtc acc atc aat tgc cag gcc agt gag agg att   96
Ala Val Gly Gly Thr Val Thr Ile Asn Cys Gln Ala Ser Glu Arg Ile
            20                  25                  30 tat agc aat tta gcc tgg tat cag cag aaa cca ggg cag cgt ccc aaa  144
Tyr Ser Asn Leu Ala Trp Tyr Gln Gln Lys Pro Gly Gln Arg Pro Lys
        35                  40                  45 ctc ctg atc tat tat gca tcc act ctg gca tct ggg gtc tca tcg cgg  192
Leu Leu Ile Tyr Tyr Ala Ser Thr Leu Ala Ser Gly Val Ser Ser Arg
    50                  55                  60 ttc aaa ggc agt gga tct ggg aca cag ttc act ctc acc atc agc ggc  240
Phe Lys Gly Ser Gly Ser Gly Thr Gln Phe Thr Leu Thr Ile Ser Gly
65                  70                  75                  80 gtg cag tgt gcc gat gct gcc act tac tac tgt cag cag ggt tat agt  288
Val Gln Cys Ala Asp Ala Ala Thr Tyr Tyr Cys Gln Gln Gly Tyr Ser
                85                  90                  95 aat aat aat gtt gac aat act ttc ggc gga ggg acc gag gtg gtg gtc  336
Asn Asn Asn Val Asp Asn Thr Phe Gly Gly Gly Thr Glu Val Val Val
            100                 105                 110 aga                                                               339
Arg
```

(Clone 2G12 vL domain amino acid sequence)

SEQ ID No. 28

```
Ala Arg Cys Ala Tyr Asp Met Thr Gln Thr Pro Ala Ser Val Glu Val
1               5                   10                  15

Ala Val Gly Gly Thr Val Thr Ile Asn Cys Gln Ala Ser Glu Arg Ile
            20                  25                  30

Tyr Ser Asn Leu Ala Trp Tyr Gln Gln Lys Pro Gly Gln Arg Pro Lys
        35                  40                  45

Leu Leu Ile Tyr Tyr Ala Ser Thr Leu Ala Ser Gly Val Ser Ser Arg
    50                  55                  60

Phe Lys Gly Ser Gly Ser Gly Thr Gln Phe Thr Leu Thr Ile Ser Gly
65                  70                  75                  80

Val Gln Cys Ala Asp Ala Ala Thr Tyr Tyr Cys Gln Gln Gly Tyr Ser
                85                  90                  95

Asn Asn Asn Val Asp Asn Thr Phe Gly Gly Gly Thr Glu Val Val Val
            100                 105                 110

Arg
```

(Clone IG39-21 vH domain CDR1 amino acid sequence)

SEQ ID No. 29

```
Gly Phe Thr Phe Ser Ser Tyr Ala
1               5
```

(Clone IG39-21 vH domain CDR2 amino acid sequence)

SEQ ID No. 30

```
Ile Ser Tyr Asp Val Ser Asn Lys
1               5
```

(Clone IG39-21 vH domain CDR3 amino acid sequence)

SEQ ID No. 31

```
Ala Arg Ser Tyr Tyr Tyr Tyr Gly Met Asp Val
1               5                   10
```

(Clone IG39-21 vL domain CDR1 amino acid sequence)

SEQ ID No. 32

```
Gln Ser Ile Ser Arg Tyr
1               5
```

(Clone IG39-21 vL domain CDR2 amino acid sequence)

SEQ ID No. 33

-continued

Asp Ala Ser
1

(Clone IG39-21 vL domain CDR3 amino acid sequence)
SEQ ID No. 34
Gln Gln Phe Gly Arg Ser Pro Arg Thr
1               5

(Clone IG39-21 full-length vH chain nucleic acid sequence)
SEQ ID No. 35

```
gag gtg caa ctg gtg gag tct ggg gga ggt gtg gta agg cct ggg ggg   48
Glu Val Gln Leu Val Glu Ser Gly Gly Gly Val Val Arg Pro Gly Gly
1               5                  10                  15 tcc ctg aga ctc tcc tgt gca gcc tct gga ttc acc ttc agt agc tat   96
Ser Leu Arg Leu Ser Cys Ala Ala Ser Gly Phe Thr Phe Ser Ser Tyr
            20                  25                  30 gct atg cac tgg gtc cgc cag gct cca ggc aag ggg ctg gag tgg gtg  144
Ala Met His Trp Val Arg Gln Ala Pro Gly Lys Gly Leu Glu Trp Val
        35                  40                  45 gca gtt ata tca tat gat gta agc aat aaa tac tac gca gac tcc gtg  192
Ala Val Ile Ser Tyr Asp Val Ser Asn Lys Tyr Tyr Ala Asp Ser Val
    50                  55                  60 aag ggc cga ttc acc atc tcc aga gac aat tcc aag aac acg ctg tat  240
Lys Gly Arg Phe Thr Ile Ser Arg Asp Asn Ser Lys Asn Thr Leu Tyr
65                  70                  75                  80 ctg caa atg aac agc ctg aga gct gag gac acg gct gtg tat tac tgt  288
Leu Gln Met Asn Ser Leu Arg Ala Glu Asp Thr Ala Val Tyr Tyr Cys
                85                  90                  95 gcg aga tct tac tac tac tac tac ggt atg gac gtc tgg ggc caa ggg  336
Ala Arg Ser Tyr Tyr Tyr Tyr Tyr Gly Met Asp Val Trp Gly Gln Gly
            100                 105                 110 acc acg gtc acc gtc tcc tca gcc tcc act aag ggc cca tcc gtc ttc  384
Thr Thr Val Thr Val Ser Ser Ala Ser Thr Lys Gly Pro Ser Val Phe
        115                 120                 125 cca ctg gca ccc tct agt aag agc aca tct ggg ggt act gcc gct ctg  432
Pro Leu Ala Pro Ser Ser Lys Ser Thr Ser Gly Gly Thr Ala Ala Leu
    130                 135                 140 gga tgt ctg gtg aag gat tac ttc cca gag cca gtc acc gtg tcc tgg  480
Gly Cys Leu Val Lys Asp Tyr Phe Pro Glu Pro Val Thr Val Ser Trp
145                 150                 155                 160 aac agc ggg gcc ctg act tcc ggt gtc cat acc ttt cca gct gtg ctg  528
Asn Ser Gly Ala Leu Thr Ser Gly Val His Thr Phe Pro Ala Val Leu
                165                 170                 175 cag tca tcc ggc ctg tac agc ctg agc tct gtg gtc acc gtc ccc agt  576
Gln Ser Ser Gly Leu Tyr Ser Leu Ser Ser Val Val Thr Val Pro Ser
            180                 185                 190 tca tcc ctg gga aca cag act tat atc tgc aac gtg aat cac aag cca  624
Ser Ser Leu Gly Thr Gln Thr Tyr Ile Cys Asn Val Asn His Lys Pro
        195                 200                 205 tcc aat aca aaa gtc gac aag aaa gtg gaa ccc aag agc tgt gat aaa  672
Ser Asn Thr Lys Val Asp Lys Lys Val Glu Pro Lys Ser Cys Asp Lys
    210                 215                 220 acc cat aca tgc ccc cct tgt cct gct cca gag ctg ctg gga gga cca  720
Thr His Thr Cys Pro Pro Cys Pro Ala Pro Glu Leu Leu Gly Gly Pro
225                 230                 235                 240 tcc gtg ttc ctg ttt cca ccc aag cct aaa gac act ctg atg att tct  768
Ser Val Phe Leu Phe Pro Pro Lys Pro Lys Asp Thr Leu Met Ile Ser
                245                 250                 255 cga acc ccc gaa gtc aca tgc gtg gtc gtg gac gtg tcc cac gag gat  816
Arg Thr Pro Glu Val Thr Cys Val Val Asp Val Ser His Glu Asp
            260                 265                 270 cct gaa gtc aag ttc aac tgg tac gtg gat ggc gtc gag gtg cat aat  864
Pro Glu Val Lys Phe Asn Trp Tyr Val Asp Gly Val Glu Val His Asn
        275                 280                 285
```

-continued

```
gcc aag aca aaa cca cga gag gaa cag tac aac agt acc tat cgt gtc  912
Ala Lys Thr Lys Pro Arg Glu Glu Gln Tyr Asn Ser Thr Tyr Arg Val
    290             295                 300 gtg tca gtc ctg aca gtg ctg cac cag gac tgg ctg aac ggg aag gaa  960
Val Ser Val Leu Thr Val Leu His Gln Asp Trp Leu Asn Gly Lys Glu
305             310                 315                 320 tat aag tgc aaa gtg agc aat aag gca ctg ccc gcc cct atc gag aaa 1008
Tyr Lys Cys Lys Val Ser Asn Lys Ala Leu Pro Ala Pro Ile Glu Lys
                325                 330                 335 aca att tct aag gct aaa gga cag cct agg gaa cca cag gtg tac act 1056
Thr Ile Ser Lys Ala Lys Gly Gln Pro Arg Glu Pro Gln Val Tyr Thr
            340                 345                 350 ctg cct cca tca cgg gac gag ctg aca aag aac cag gtc agt ctg act 1104
Leu Pro Pro Ser Arg Asp Glu Leu Thr Lys Asn Gln Val Ser Leu Thr
        355                 360                 365 tgt ctg gtg aaa ggg ttc tat cct tct gat atc gcc gtg gag tgg gaa 1152
Cys Leu Val Lys Gly Phe Tyr Pro Ser Asp Ile Ala Val Glu Trp Glu
    370                 375                 380 agt aat ggt cag cca gag aac aat tac aag acc aca ccc cct gtc ctg 1200
Ser Asn Gly Gln Pro Glu Asn Asn Tyr Lys Thr Thr Pro Pro Val Leu
385                 390                 395                 400 gac tct gat ggg agt ttc ttt ctg tat tcc aag ctg acc gtg gat aaa 1248
Asp Ser Asp Gly Ser Phe Phe Leu Tyr Ser Lys Leu Thr Val Asp Lys
                405                 410                 415 agc cgg tgg cag cag ggt aat gtc ttt agt tgt tca gtg atg cac gag 1296
Ser Arg Trp Gln Gln Gly Asn Val Phe Ser Cys Ser Val Met His Glu
            420                 425                 430 gca ctg cac aat cac tac acc cag aaa tca ctg tca ctg tca cca ggt 1344
Ala Leu His Asn His Tyr Thr Gln Lys Ser Leu Ser Leu Ser Pro Gly
        435                 440                 445 aaa tga                                                          1350
Lys (Clone IG39-21 full-length vH chain amino acid sequence)
                                                   SEQ ID No. 36
Glu Val Gln Leu Val Glu Ser Gly Gly Gly Val Val Arg Pro Gly Gly
1               5                   10                  15

Ser Leu Arg Leu Ser Cys Ala Ala Ser Gly Phe Thr Phe Ser Ser Tyr
            20                  25                  30

Ala Met His Trp Val Arg Gln Ala Pro Gly Lys Gly Leu Glu Trp Val
        35                  40                  45

Ala Val Ile Ser Tyr Asp Val Ser Asn Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Ser Tyr Tyr Tyr Tyr Gly Met Asp Val Trp Gly Gln Gly
            100                 105                 110

Thr Thr Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190
```

-continued

```
Ser Ser Leu Gly Thr Gln Thr Tyr Ile Cys Asn Val Asn His Lys Pro
        195                 200                 205

Ser Asn Thr Lys Val Asp Lys Val Glu Pro Lys Ser Cys Asp Lys
        210                 215                 220

Thr His Thr Cys Pro Pro Cys Pro Ala Pro Glu Leu Leu Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
                260                 265                 270

Pro Glu Val Lys Phe Asn Trp Tyr Val Asp Gly Val Glu Val His Asn
                275                 280                 285

Ala Lys Thr Lys Pro Arg Glu Glu Gln Tyr Asn Ser Thr Tyr Arg Val
        290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Thr
                340                 345                 350

Leu Pro Pro Ser Arg Asp Glu Leu Thr Lys Asn Gln Val Ser Leu Thr
                355                 360                 365

Cys Leu Val Lys Gly Phe Tyr Pro Ser Asp Ile Ala Val Glu Trp Glu
370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
                420                 425                 430

Ala Leu His Asn His Tyr Thr Gln Lys Ser Leu Ser Leu Ser Pro Gly
            435                 440                 445
Lys (Clone IG39-21 full-length vi chain nucleic acid sequence)
                                                     SEQ ID No. 37
gat gtt gtg atg acc cag tct cca tcc tcc ctg tct gca tct gta gga   48
Asp Val Val Met Thr Gln Ser Pro Ser Ser Leu Ser Ala Ser Val Gly
1               5                   10                  15 gac aga gtc acc atc act tgc cgg gca agt cag agc att agc agg tac  96
Asp Arg Val Thr Ile Thr Cys Arg Ala Ser Gln Ser Ile Ser Arg Tyr
            20                  25                  30 tta gcc tgg tac caa cag aaa cot ggc cag gct ccc agg ctc ctc atc  144
Leu Ala Trp Tyr Gln Gln Lys Pro Gly Gln Ala Pro Arg Leu Leu Ile
        35                  40                  45 tat gat gca tcc aac agg gcc act ggc atc cca gtc agg ttc agt ggc  192
Tyr Asp Ala Ser Asn Arg Ala Thr Gly Ile Pro Val Arg Phe Ser Gly
    50                  55                  60 agt ggg tct ggg aca gac ttc act ctc acc atc agc aga ctg gag cca  240
Ser Gly Ser Gly Thr Asp Phe Thr Leu Thr Ile Ser Arg Leu Glu Pro
65                  70                  75                  80 gaa gat ttt gca gtg tat tac tgt cag cag ttt ggt agg tca cct cgg  288
Glu Asp Phe Ala Val Tyr Tyr Cys Gln Gln Phe Gly Arg Ser Pro Arg
                85                  90                  95 acg ttc ggc caa ggg aca cga ctg gag att aaa cga act gtg gct gca  336
Thr Phe Gly Gln Gly Thr Arg Leu Glu Ile Lys Arg Thr Val Ala Ala
            100                 105                 110 cca tct gtc ttc atc ttc ccg cca tct gat gag cag ttg aaa tct gga  384
```

```
                Pro Ser Val Phe Ile Phe Pro Ser Asp Glu Gln Leu Lys Ser Gly
                        115                 120                 125 act gcc tct gtt gtg tgc ctg ctg aat aac ttc tat coo aga gag gcc    432
Thr Ala Ser Val Val Cys Leu Leu Asn Asn Phe Tyr Pro Arg Glu Ala
        130                 135                 140 aaa gta cag tgg aag gtg gat aac gcc ctc caa tog ggt aac tcc cag    480
Lys Val Gln Trp Lys Val Asp Asn Ala Leu Gln Ser Gly Asn Ser Gln
145                 150                 155                 160 gag agt gtc aca gag cag gac agc aag gac agc acc tac agc ctc agc    528
Glu Ser Val Thr Glu Gln Asp Ser Lys Asp Ser Thr Tyr Ser Leu Ser
                165                 170                 175 agc acc ctg acg ctg agc aaa gca gac tac gag aaa cac aaa gtc tac    576
Ser Thr Leu Thr Leu Ser Lys Ala Asp Tyr Glu Lys His Lys Val Tyr
        180                 185                 190 gcc tgc gaa gtc acc cat cag ggc ctg agc tog ccc gtc aca aag agc    624
Ala Cys Glu Val Thr His Gln Gly Leu Ser Ser Pro Val Thr Lys Ser
        195                 200                 205 ttc aac agg gga gag tgt tag                                        645
Phe Asn Arg Gly Glu Cys
        210

(Clone IG39-21 full-length vi chain amino acid sequence)
                                                    SEQ ID No. 38
Asp Val Val Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Arg Tyr
            20                  25                  30

Leu Ala Trp Tyr Gln Gln Lys Pro Gly Gln Ala Pro Arg Leu Leu Ile
        35                  40                  45

Tyr Asp Ala Ser Asn Arg Ala Thr Gly Ile Pro Val Arg Phe Ser Gly
    50                  55                  60

Ser Gly Ser Gly Thr Asp Phe Thr Leu Thr Ile Ser Arg Leu Glu Pro
65                  70                  75                  80

Glu Asp Phe Ala Val Tyr Tyr Cys Gln Gln Phe Gly Arg Ser Pro Arg
                85                  90                  95

Thr Phe Gly Gln Gly Thr Arg Leu Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
        130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
        180                 185                 190

Ala Cys Glu Val Thr His Gln Gly Leu Ser Ser Pro Val Thr Lys Ser
        195                 200                 205

Phe Asn Arg Gly Glu Cys
        210

(Clone IG39-21 scFv nucleic acid sequence)
                                                    SEQ ID No. 39
gat gtt gtg atg acc cag tct cca tcc tcc ctg tct gca tct gta gga    48
Asp Val Val Met Thr Gln Ser Pro Ser Ser Leu Ser Ala Ser Val Gly
1               5                   10                  15 gac aga gtc acc atc act tgc cgg gca agt cag agc att agc agg tac    96
Asp Arg Val Thr Ile Thr Cys Arg Ala Ser Gln Ser Ile Ser Arg Tyr
            20                  25                  30
```

```
tta gcc tgg tac caa cag aaa cct ggc cag gct ccc agg ctc ctc atc    144
Leu Ala Trp Tyr Gln Gln Lys Pro Gly Gln Ala Pro Arg Leu Leu Ile
        35                  40                  45 tat gat gca tcc aac agg gcc act ggc atc cca gtc agg ttc agt ggc    192
Tyr Asp Ala Ser Asn Arg Ala Thr Gly Ile Pro Val Arg Phe Ser Gly
 50                  55                  60 agt ggg tct ggg aca gac ttc act ctc acc atc agc aga ctg gag cca    240
Ser Gly Ser Gly Thr Asp Phe Thr Leu Thr Ile Ser Arg Leu Glu Pro
 65                  70                  75                  80 gaa gat ttt gca gtg tat tac tgt cag cag ttt ggt agg tca cct cgg    288
Glu Asp Phe Ala Val Tyr Tyr Cys Gln Gln Phe Gly Arg Ser Pro Arg
                85                  90                  95 acg ttc ggc caa ggg aca cga ctg gag att aaa ggc gga tcc tct agg    336
Thr Phe Gly Gln Gly Thr Arg Leu Glu Ile Lys Gly Gly Ser Ser Arg
            100                 105                 110 tca agt tcc agc ggc ggc ggt ggc agc gga ggc ggc ggt gag gtg caa    384
Ser Ser Ser Ser Gly Gly Gly Gly Ser Gly Gly Gly Gly Glu Val Gln
        115                 120                 125 ctg gtg gag tct ggg gga ggt gtg gta agg cct ggg ggg tcc ctg aga    432
Leu Val Glu Ser Gly Gly Gly Val Val Arg Pro Gly Gly Ser Leu Arg
    130                 135                 140 ctc tcc tgt gca gcc tct gga ttc acc ttc agt agc tat gct atg cac    480
Leu Ser Cys Ala Ala Ser Gly Phe Thr Phe Ser Ser Tyr Ala Met His
145                 150                 155                 160 tgg gtc cgc cag gct cca ggc aag ggg ctg gag tgg gtg gca gtt ata    528
Trp Val Arg Gln Ala Pro Gly Lys Gly Leu Glu Trp Val Ala Val Ile
                165                 170                 175 tca tat gat gta agc aat aaa tac tac gca gac tcc gtg aag ggc cga    576
Ser Tyr Asp Val Ser Asn Lys Tyr Tyr Ala Asp Ser Val Lys Gly Arg
            180                 185                 190 ttc acc atc tcc aga gac aat tcc aag aac acg ctg tat ctg caa atg    624
Phe Thr Ile Ser Arg Asp Asn Ser Lys Asn Thr Leu Tyr Leu Gln Met
        195                 200                 205 aac agc ctg aga gct gag gac acg gct gtg tat tac tgt gcg aga tct    672
Asn Ser Leu Arg Ala Glu Asp Thr Ala Val Tyr Tyr Cys Ala Arg Ser
    210                 215                 220 tac tac tac tac tac ggt atg gac gtc tgg ggc caa ggg acc acg gtc    720
Tyr Tyr Tyr Tyr Tyr Gly Met Asp Val Trp Gly Gln Gly Thr Thr Val
225                 230                 235                 240 acc gtc tcc tca                                                    732
Thr Val Ser Ser (Clone IG39-21 scFv amino acid sequence)
                                                       SEQ ID No. 40
Asp Val Val Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Arg Tyr
            20                  25                  30

Leu Ala Trp Tyr Gln Gln Lys Pro Gly Gln Ala Pro Arg Leu Leu Ile
        35                  40                  45

Tyr Asp Ala Ser Asn Arg Ala Thr Gly Ile Pro Val Arg Phe Ser Gly
 50                  55                  60

Ser Gly Ser Gly Thr Asp Phe Thr Leu Thr Ile Ser Arg Leu Glu Pro
 65                  70                  75                  80

Glu Asp Phe Ala Val Tyr Tyr Cys Gln Gln Phe Gly Arg Ser Pro Arg
                85                  90                  95

Thr Phe Gly Gln Gly Thr Arg Leu Glu Ile Lys Gly Gly Ser Ser Arg
            100                 105                 110

Ser Ser Ser Ser Gly Gly Gly Gly Ser Gly Gly Gly Gly Glu Val Gln
        115                 120                 125
```

-continued

```
Leu Val Glu Ser Gly Gly Gly Val Val Arg Pro Gly Gly Ser Leu Arg
130                 135                 140

Leu Ser Cys Ala Ala Ser Gly Phe Thr Phe Ser Ser Tyr Ala Met His
145                 150                 155                 160

Trp Val Arg Gln Ala Pro Gly Lys Gly Leu Glu Trp Val Ala Ile
                165                 170                 175

Ser Tyr Asp Val Ser Asn Lys Tyr Tyr Ala Asp Ser Val Lys Gly Arg
                180                 185                 190

Phe Thr Ile Ser Arg Asp Asn Ser Lys Asn Thr Leu Tyr Leu Gln Met
            195                 200                 205

Asn Ser Leu Arg Ala Glu Asp Thr Ala Val Tyr Tyr Cys Ala Arg Ser
210                 215                 220

Tyr Tyr Tyr Tyr Gly Met Asp Val Trp Gly Gln Gly Thr Thr Val
225                 230                 235                 240

Thr Val Ser Ser
```

SEQ ID No. 41

```
cag tcg gtg gag gag tcc ggg ggt cgc ctg gtc acg cct ggg aca ccc    48
Gln Ser Val Glu Glu Ser Gly Gly Arg Leu Val Thr Pro Gly Thr Pro
1               5                   10                  15 ctg aca ctc acc tgc aca gtc tct gga atc gac ctc agt aac aat gca    96
Leu Thr Leu Thr Cys Thr Val Ser Gly Ile Asp Leu Ser Asn Asn Ala
                20                  25                  30 atg agc tgg gtc cgc cag gct cca ggg aag ggg ctg gaa tat atc gga   144
Met Ser Trp Val Arg Gln Ala Pro Gly Lys Gly Leu Glu Tyr Ile Gly
            35                  40                  45 atc att agg agt agt ggt agt aca tat tac gcg aac tgg gca aaa ggc   192
Ile Ile Arg Ser Ser Gly Ser Thr Tyr Tyr Ala Asn Trp Ala Lys Gly
        50                  55                  60 cgg ttc acc atc tcc aaa acc tcg acc acg gtg gat ctg ata atc acc   240
Arg Phe Thr Ile Ser Lys Thr Ser Thr Thr Val Asp Leu Ile Ile Thr
65                  70                  75                  80 agt ccg aca acc gag gac acg gcc acc tat ttc tgt gcc aga ggg ggt   288
Ser Pro Thr Thr Glu Asp Thr Ala Thr Tyr Phe Cys Ala Arg Gly Gly
                85                  90                  95 ggt tct tac agt att gtc ttc tgg aac ttg tgg ggc cca ggc acc ctg   336
Gly Ser Tyr Ser Ile Val Phe Trp Asn Leu Trp Gly Pro Gly Thr Leu
            100                 105                 110 gtc acc gtc tcc tca                                                351
Val Thr Val Ser Ser
            115
```

SEQ ID No. 42

```
Gln Ser Val Glu Glu Ser Gly Gly Arg Leu Val Thr Pro Gly Thr Pro
1               5                   10                  15

Leu Thr Leu Thr Cys Thr Val Ser Gly Ile Asp Leu Ser Asn Asn Ala
                20                  25                  30

Met Ser Trp Val Arg Gln Ala Pro Gly Lys Gly Leu Glu Tyr Ile Gly
            35                  40                  45

Ile Ile Arg Ser Ser Gly Ser Thr Tyr Tyr Ala Asn Trp Ala Lys Gly
        50                  55                  60

Arg Phe Thr Ile Ser Lys Thr Ser Thr Thr Val Asp Leu Ile Ile Thr
65                  70                  75                  80

Ser Pro Thr Thr Glu Asp Thr Ala Thr Tyr Phe Cys Ala Arg Gly Gly
                85                  90                  95

Gly Ser Tyr Ser Ile Val Phe Trp Asn Leu Trp Gly Pro Gly Thr Leu
            100                 105                 110

Val Thr Val Ser Ser
            115
```

```
                                                            SEQ ID No. 43
gcc aga tgt gcc tat gat atg acc cag act cca gcc tct gtg gag gta   48
Ala Arg Cys Ala Tyr Asp Met Thr Gln Thr Pro Ala Ser Val Glu Val
1               5                   10                  15 gct gtg gga ggc aca gtc acc atc aat tgc cag gcc agt gag agg att   96
Ala Val Gly Gly Thr Val Thr Ile Asn Cys Gln Ala Ser Glu Arg Ile
                20                  25                  30 tat agc aat tta gcc tgg tat cag cag aaa cca ggg cag cgt ccc aag  144
Tyr Ser Asn Leu Ala Trp Tyr Gln Gln Lys Pro Gly Gln Arg Pro Lys
        35                  40                  45 ctc ctg atc tat tat aca tcc act ctg gca tct ggg gtc tca tcg cgg  192
Leu Leu Ile Tyr Tyr Thr Ser Thr Leu Ala Ser Gly Val Ser Ser Arg
    50                  55                  60 ttc aaa ggc agt gga tct ggg aca cag ttc act ctc acc atc agc ggc  240
Phe Lys Gly Ser Gly Ser Gly Thr Gln Phe Thr Leu Thr Ile Ser Gly
65                  70                  75                  80 gtg gag tgt gcc gat gct gcc act tac tac tgt caa cag ggt tat agt  288
Val Glu Cys Ala Asp Ala Ala Thr Tyr Tyr Cys Gln Gln Gly Tyr Ser
                85                  90                  95 agt agt aat gtt gac aat act ttc ggc gga ggg acc gag gtg gtg gtc  336
Ser Ser Asn Val Asp Asn Thr Phe Gly Gly Gly Thr Glu Val Val Val
                100                 105                 110 aaa ggt                                                          342
Lys Gly

SEQ ID No. 44
Ala Arg Cys Ala Tyr Asp Met Thr Gln Thr Pro Ala Ser Val Glu Val
1               5                   10                  15

Ala Val Gly Gly Thr Val Thr Ile Asn Cys Gln Ala Ser Glu Arg Ile
                20                  25                  30

Tyr Ser Asn Leu Ala Trp Tyr Gln Gln Lys Pro Gly Gln Arg Pro Lys
        35                  40                  45

Leu Leu Ile Tyr Tyr Thr Ser Thr Leu Ala Ser Gly Val Ser Ser Arg
    50                  55                  60

Phe Lys Gly Ser Gly Ser Gly Thr Gln Phe Thr Leu Thr Ile Ser Gly
65                  70                  75                  80

Val Glu Cys Ala Asp Ala Ala Thr Tyr Tyr Cys Gln Gln Gly Tyr Ser
                85                  90                  95

Ser Ser Asn Val Asp Asn Thr Phe Gly Gly Gly Thr Glu Val Val Val
                100                 105                 110

Lys Gly

SEQ ID No. 45
ggc gag cag cag ctg gtg gag agc ggc gga ggc ctg gtg cag cot gga   48
Gly Glu Gln Gln Leu Val Glu Ser Gly Gly Gly Leu Val Gln Pro Gly
1               5                   10                  15 gga agc ctg agg ctg agc tgc gcc gtg tcc ggc ttc agc ctg agc agc   96
Gly Ser Leu Arg Leu Ser Cys Ala Val Ser Gly Phe Ser Leu Ser Ser
                20                  25                  30 tac gcc atc agc tgg gtg agg cag gcc ccc gga aag ggc ctg gag tac  144
Tyr Ala Ile Ser Trp Val Arg Gln Ala Pro Gly Lys Gly Leu Glu Tyr
        35                  40                  45 atc gcc atc atc aac agc tac ggc acc acc tac tac gcc agc tgg gcc  192
Ile Ala Ile Ile Asn Ser Tyr Gly Thr Thr Tyr Tyr Ala Ser Trp Ala
    50                  55                  60 aag ggc aga gtg acc atc tcc aag gat tcc tcc aag aac acc gtg tac  240
Lys Gly Arg Val Thr Ile Ser Lys Asp Ser Ser Lys Asn Thr Val Tyr
65                  70                  75                  80 ctg cag atg ggc tcc ctg aga gcc gag gat atg gcc gtg tac ttt tgc  288
Leu Gln Met Gly Ser Leu Arg Ala Glu Asp Met Ala Val Tyr Phe Cys
                85                  90                  95
```

```
gcc aga ggc gat tcc tac ggc tcc ggc gtg ggc ctg ggc ctg tgg gga   336
Ala Arg Gly Asp Ser Tyr Gly Ser Gly Val Gly Leu Gly Leu Trp Gly
                100                 105                 110 cct gga acc ctg gtg aca gtg tcc tcc                               363
Pro Gly Thr Leu Val Thr Val Ser Ser
        115                 120
```

SEQ ID No. 46

```
Gly Glu Gln Gln Leu Val Glu Ser Gly Gly Leu Val Gln Pro Gly
1               5                   10                  15

Gly Ser Leu Arg Leu Ser Cys Ala Val Ser Gly Phe Ser Leu Ser Ser
                20                  25                  30

Tyr Ala Ile Ser Trp Val Arg Gln Ala Pro Gly Lys Gly Leu Glu Tyr
            35                  40                  45

Ile Ala Ile Ile Asn Ser Tyr Gly Thr Thr Tyr Tyr Ala Ser Trp Ala
        50                  55                  60

Lys Gly Arg Val Thr Ile Ser Lys Asp Ser Ser Lys Asn Thr Val Tyr
65                  70                  75                  80

Leu Gln Met Gly Ser Leu Arg Ala Glu Asp Met Ala Val Tyr Phe Cys
                85                  90                  95

Ala Arg Gly Asp Ser Tyr Gly Ser Gly Val Gly Leu Gly Leu Trp Gly
                100                 105                 110

Pro Gly Thr Leu Val Thr Val Ser Ser
        115                 120
```

SEQ ID No. 47

```
gga gac tac cag atg aca cag tcc cct agc acc ctg tcc gcc tcc gtg   48
Gly Asp Tyr Gln Met Thr Gln Ser Pro Ser Thr Leu Ser Ala Ser Val
1               5                   10                  15 ggc gac aga gtg aca atc acc tgt cag gcc tcc cag aat atc tac agc   96
Gly Asp Arg Val Thr Ile Thr Cys Gln Ala Ser Gln Asn Ile Tyr Ser
                20                  25                  30 aat ctg gcc tgg tac cag cag aag cct ggc aag agg ccc aag ctg ctg   144
Asn Leu Ala Trp Tyr Gln Gln Lys Pro Gly Lys Arg Pro Lys Leu Leu
            35                  40                  45 atc tac aga gcc agc tcc ctg gcc tcc ggc gtg cca tct aga ttt tcc   192
Ile Tyr Arg Ala Ser Ser Leu Ala Ser Gly Val Pro Ser Arg Phe Ser
        50                  55                  60 ggc tcc ggc agc ggc aca gag ttt acc ctg aca atc agc agc ctg cag   240
Gly Ser Gly Ser Gly Thr Glu Phe Thr Leu Thr Ile Ser Ser Leu Gln
65                  70                  75                  80 ccc gat gat ttc gcc acc tac tac tgt cag cag ggc ttc agc agc aat   288
Pro Asp Asp Phe Ala Thr Tyr Tyr Cys Gln Gln Gly Phe Ser Ser Asn
                85                  90                  95 aat gtg gac aat aca ttt ggc ggc ggc aca aag gtg gag atc aag       333
Asn Val Asp Asn Thr Phe Gly Gly Gly Thr Lys Val Glu Ile Lys
                100                 105                 110
```

SEQ ID No. 48

```
Gly Asp Tyr Gln Met Thr Gln Ser Pro Ser Thr Leu Ser Ala Ser Val
1               5                   10                  15

Gly Asp Arg Val Thr Ile Thr Cys Gln Ala Ser Gln Asn Ile Tyr Ser
                20                  25                  30

Asn Leu Ala Trp Tyr Gln Gln Lys Pro Gly Lys Arg Pro Lys Leu Leu
            35                  40                  45

Ile Tyr Arg Ala Ser Ser Leu Ala Ser Gly Val Pro Ser Arg Phe Ser
        50                  55                  60

Gly Ser Gly Ser Gly Thr Glu Phe Thr Leu Thr Ile Ser Ser Leu Gln
65                  70                  75                  80

Pro Asp Asp Phe Ala Thr Tyr Tyr Cys Gln Gln Gly Phe Ser Ser Asn
                85                  90                  95
```

```
                        Asn Val Asp Asn Thr Phe Gly Gly Gly Thr Lys Val Glu Ile Lys
                                        100                 105                 110

SEQ ID No. 49
ggc gag cag cag ctg gtg gag agc ggc gga ggc ctg gtg cag cct gga           48
Gly Glu Gln Gln Leu Val Glu Ser Gly Gly Gly Leu Val Gln Pro Gly
1               5                   10                  15 gga agc ctg agg ctg agc tgc gcc gtg tcc ggc ttt tcc ctg agc aag           96
Gly Ser Leu Arg Leu Ser Cys Ala Val Ser Gly Phe Ser Leu Ser Lys
                20                  25                  30 agc atc atc agc tgg gtg agg cag gcc cct ggc aag ggc ctg gag tac          144
Ser Ile Ile Ser Trp Val Arg Gln Ala Pro Gly Lys Gly Leu Glu Tyr
            35                  40                  45 atc ggc atc atc ggc agc agc ggc tcc acc tac tac gcc aac tgg gcc          192
Ile Gly Ile Ile Gly Ser Ser Gly Ser Thr Tyr Tyr Ala Asn Trp Ala
        50                  55                  60 aag ggc aga ttc aca atc tcc aag gac tcc tcc aag aat acc gtg tac          240
Lys Gly Arg Phe Thr Ile Ser Lys Asp Ser Ser Lys Asn Thr Val Tyr
65                  70                  75                  80 ctg cag atg ggc tcc ctg agg gcc gag gat atg gcc gtg tac ttt tgt          288
Leu Gln Met Gly Ser Leu Arg Ala Glu Asp Met Ala Val Tyr Phe Cys
                85                  90                  95 gcc aga ggc ctg ctg tac tcc ggc aat aag tcc tgg ggc ccc ggc aca          336
Ala Arg Gly Leu Leu Tyr Ser Gly Asn Lys Ser Trp Gly Pro Gly Thr
                100                 105                 110 ctg gtg acc gtg agc tcc                                                  354
Leu Val Thr Val Ser Ser
            115

SEQ ID No. 50
Gly Glu Gln Gln Leu Val Glu Ser Gly Gly Gly Leu Val Gln Pro Gly
1               5                   10                  15

Gly Ser Leu Arg Leu Ser Cys Ala Val Ser Gly Phe Ser Leu Ser Lys
                20                  25                  30

Ser Ile Ile Ser Trp Val Arg Gln Ala Pro Gly Lys Gly Leu Glu Tyr
            35                  40                  45

Ile Gly Ile Ile Gly Ser Ser Gly Ser Thr Tyr Tyr Ala Asn Trp Ala
        50                  55                  60

Lys Gly Arg Phe Thr Ile Ser Lys Asp Ser Ser Lys Asn Thr Val Tyr
65                  70                  75                  80

Leu Gln Met Gly Ser Leu Arg Ala Glu Asp Met Ala Val Tyr Phe Cys
                85                  90                  95

Ala Arg Gly Leu Leu Tyr Ser Gly Asn Lys Ser Trp Gly Pro Gly Thr
                100                 105                 110

Leu Val Thr Val Ser Ser
            115

SEQ ID No. 51
ggc gac atc gtg atg acc cag tcc ccc gat tcc ctg gcc gtg tcc ctg           48
Gly Asp Ile Val Met Thr Gln Ser Pro Asp Ser Leu Ala Val Ser Leu
1               5                   10                  15 ggc gag aga gcc aca atc aat tgt cag tcc tcc cag agc gtg ctg ctg           96
Gly Glu Arg Ala Thr Ile Asn Cys Gln Ser Ser Gln Ser Val Leu Leu
                20                  25                  30 aac aat cag ctg tcc tgg ttc cag cag aag cct ggc cag cct ccc aag          144
Asn Asn Gln Leu Ser Trp Phe Gln Gln Lys Pro Gly Gln Pro Pro Lys
            35                  40                  45 ctg ctg atc tac gac gcc tcc aca ctg gag tcc ggc gtg ccc gat agg          192
Leu Leu Ile Tyr Asp Ala Ser Thr Leu Glu Ser Gly Val Pro Asp Arg
        50                  55                  60 ttc agc ggc tcc ggc agc ggc acc gac ttt acc ctg acc atc tcc agc          240
Phe Ser Gly Ser Gly Ser Gly Thr Asp Phe Thr Leu Thr Ile Ser Ser
65                  70                  75                  80
```

-continued

```
ctg cag gcc gag gat gtg gcc gtg tac tac tgc ctg ggc ggc tac agc    288
Leu Gln Ala Glu Asp Val Ala Val Tyr Tyr Cys Leu Gly Gly Tyr Ser
                85                  90                  95 ggc aac ctg tac gcc ttt ggc ggc ggc acc aag gtg gag atc aag        333
Gly Asn Leu Tyr Ala Phe Gly Gly Gly Thr Lys Val Glu Ile Lys
            100                 105                 110
```

SEQ ID No. 52

Gly Asp Ile Val Met Thr Gln Ser Pro Asp Ser Leu Ala Val Ser Leu
1               5                   10                  15

Gly Glu Arg Ala Thr Ile Asn Cys Gln Ser Ser Gln Ser Val Leu Leu
                20                  25                  30

Asn Asn Gln Leu Ser Trp Phe Gln Gln Lys Pro Gly Gln Pro Pro Lys
            35                  40                  45

Leu Leu Ile Tyr Asp Ala Ser Thr Leu Glu Ser Gly Val Pro Asp Arg
        50                  55                  60

Phe Ser Gly Ser Gly Ser Gly Thr Asp Phe Thr Leu Thr Ile Ser Ser
65                  70                  75                  80

Leu Gln Ala Glu Asp Val Ala Val Tyr Tyr Cys Leu Gly Gly Tyr Ser
                85                  90                  95

Gly Asn Leu Tyr Ala Phe Gly Gly Gly Thr Lys Val Glu Ile Lys
            100                 105                 110

SEQ ID No. 53
```
ggc gag cag cag ctg gtg gag tcc ggc gga ggc ctg gtg cag cca gga    48
Gly Glu Gln Gln Leu Val Glu Ser Gly Gly Gly Leu Val Gln Pro Gly
1               5                   10                  15 gga agc ctg agg ctg tcc tgt gcc gtg agc ggc ttc tcc ctg agc tcc    96
Gly Ser Leu Arg Leu Ser Cys Ala Val Ser Gly Phe Ser Leu Ser Ser
                20                  25                  30 tac gcc atg agc tgg gtg agg cag gcc ccc gga aag ggc ctg gag tac    144
Tyr Ala Met Ser Trp Val Arg Gln Ala Pro Gly Lys Gly Leu Glu Tyr
            35                  40                  45 atc ggc atc atc agc agc agc ggc agc aca tac tac gcc agc tgg gcc    192
Ile Gly Ile Ile Ser Ser Ser Gly Ser Thr Tyr Tyr Ala Ser Trp Ala
        50                  55                  60 aag ggc agg ttc aca atc agc aag gat tcc tcc aag aat aca gtg tac    240
Lys Gly Arg Phe Thr Ile Ser Lys Asp Ser Ser Lys Asn Thr Val Tyr
65                  70                  75                  80 ctg cag atg ggc tcc ctg agg gcc gag gac atg gcc gtg tac ttc tgt    288
Leu Gln Met Gly Ser Leu Arg Ala Glu Asp Met Ala Val Tyr Phe Cys
                85                  90                  95 gcc aga gac agg gtc atc tat tcc atc ggc cct tac tac ttc aac ctg    336
Ala Arg Asp Arg Val Ile Tyr Ser Ile Gly Pro Tyr Tyr Phe Asn Leu
            100                 105                 110 tgg ggc ccc ggc aca ctg gtg aca gtg tcc agc                        369
Trp Gly Pro Gly Thr Leu Val Thr Val Ser Ser
        115                 120
```

SEQ ID No. 54

Gly Glu Gln Gln Leu Val Glu Ser Gly Gly Gly Leu Val Gln Pro Gly
1               5                   10                  15

Gly Ser Leu Arg Leu Ser Cys Ala Val Ser Gly Phe Ser Leu Ser Ser
                20                  25                  30

Tyr Ala Met Ser Trp Val Arg Gln Ala Pro Gly Lys Gly Leu Glu Tyr
            35                  40                  45

Ile Gly Ile Ile Ser Ser Ser Gly Ser Thr Tyr Tyr Ala Ser Trp Ala
        50                  55                  60

Lys Gly Arg Phe Thr Ile Ser Lys Asp Ser Ser Lys Asn Thr Val Tyr
65                  70                  75                  80

Leu Gln Met Gly Ser Leu Arg Ala Glu Asp Met Ala Val Tyr Phe Cys

```
                        85                      90                      95
Ala Arg Asp Arg Val Ile Tyr Ser Ile Gly Pro Tyr Tyr Phe Asn Leu
                100                     105                     110

Trp Gly Pro Gly Thr Leu Val Thr Val Ser Ser
            115                     120
```

```
                                                            SEQ ID No. 55
ggc gat tac cag atg aca cag tcc ccc tcc tcc ctg agc gcc tcc gtg    48
Gly Asp Tyr Gln Met Thr Gln Ser Pro Ser Ser Leu Ser Ala Ser Val
1               5                   10                  15 gga gat agg gtg acc atc aca tgc cag gcc agc gag atc atc tac agc    96
Gly Asp Arg Val Thr Ile Thr Cys Gln Ala Ser Glu Ile Ile Tyr Ser
                20                  25                  30 aat ctg gcc tgg tac cag cag aag ccc ggc aag ccc ccc aag ctg ctg   144
Asn Leu Ala Trp Tyr Gln Gln Lys Pro Gly Lys Pro Pro Lys Leu Leu
            35                  40                  45 atc tac ggc gcc tcc aca ctg gcc agc ggc gtg cct agc aga ttc agc   192
Ile Tyr Gly Ala Ser Thr Leu Ala Ser Gly Val Pro Ser Arg Phe Ser
        50                  55                  60 ggc agc ggc tcc ggc acc gat tac acc ctg aca atc tcc agc ctg cag   240
Gly Ser Gly Ser Gly Thr Asp Tyr Thr Leu Thr Ile Ser Ser Leu Gln
65                  70                  75                  80 cct gag gat ttt gcc aca tac tac tgt cag cag tcc ttc agc tcc aat   288
Pro Glu Asp Phe Ala Thr Tyr Tyr Cys Gln Gln Ser Phe Ser Ser Asn
                85                  90                  95 aac gtg ggc aac atc ttc ggc ggc ggc aca aag gtg gag atc aag       333
Asn Val Gly Asn Ile Phe Gly Gly Gly Thr Lys Val Glu Ile Lys
                100                     105                     110
```

```
                                                            SEQ ID No. 56
Gly Asp Tyr Gln Met Thr Gln Ser Pro Ser Ser Leu Ser Ala Ser Val
1               5                   10                  15

Gly Asp Arg Val Thr Ile Thr Cys Gln Ala Ser Glu Ile Ile Tyr Ser
                20                  25                  30

Asn Leu Ala Trp Tyr Gln Gln Lys Pro Gly Lys Pro Pro Lys Leu Leu
            35                  40                  45

Ile Tyr Gly Ala Ser Thr Leu Ala Ser Gly Val Pro Ser Arg Phe Ser
        50                  55                  60

Gly Ser Gly Ser Gly Thr Asp Tyr Thr Leu Thr Ile Ser Ser Leu Gln
65                  70                  75                  80

Pro Glu Asp Phe Ala Thr Tyr Tyr Cys Gln Gln Ser Phe Ser Ser Asn
                85                  90                  95

Asn Val Gly Asn Ile Phe Gly Gly Gly Thr Lys Val Glu Ile Lys
                100                     105                     110
```

For use in human patients, it will be desirable to humanize these antibodies, replacing both the constant regions of the heavy and light chains with human constant regions, as well as replacing the framework regions of the variable regions with human antibody framework regions. In some embodiments, the anti-CD39 antibody or antigen-binding fragment thereof, is a humanized version of a rabbit antibody.

In some embodiments, the anti-CD39 antibody or antigen-binding fragment thereof comprises at least one heavy chain variable is at least 60% identical to SEQ ID No. 6, 10, 14, 18, 22, 26, 42, 46, 50, or 54, and even more preferably at least 65%, 70%, 75%, 80%, 85% or even 90% identical to SEQ ID No. 6, 10, 14, 18, 22, 26, 42, 46, 50, and 54, and able to specifically bind human CD39.

In some embodiments, the anti-CD39 antibody or antigen-binding fragment thereof comprises at least one light chain variable is at least 60% identical to SEQ ID No. 8, 12, 16, 20, 24, 28, 44, 48, 52, or 56, and even more preferably at least 65%, 70%, 75%, 80%, 85% or even 90% identical to SEQ ID No. 8, 12, 16, 20, 24, 28, 44, 48, 52, or 56, and able to specifically bind human CD39.

In certain embodiments, a chimeric antibody is a humanized antibody. Typically, a non-human antibody is humanized to reduce immunogenicity to humans, while retaining the specificity and affinity of the parental non-human antibody. Generally, a humanized antibody comprises one or more variable domains in which HVRs, e.g., CDRs, (or portions thereof) are derived from a non-human antibody, and FRs (or portions thereof) are derived from human antibody sequences. A humanized antibody optionally will also comprise at least a portion of a human constant region.

In some embodiments, some FR residues in a humanized antibody are substituted with corresponding residues from a non-human antibody (e.g., the antibody from which the HVR residues are derived), e.g., to restore or improve antibody specificity or affinity.

In certain embodiments, the anti-CD39 antibody is a humanized antibody comprising a VH domain having human framework sequences associated with CDRs of a VH domain selected from SEQ ID No. 6, 10, 14, 18, 22, 26, 42, 46, 50, or 54, and the CDRs of the corresponding VL domain selected from SEQ ID No. 8, 12, 16, 20, 24, 28, 44, 48, 52, or 56. The CDRs are preferably identical, but may vary by 1, 2 or 3 amino acids across each CDR so long as the resulting antibody specifically binds human CD39.

Humanized antibodies and methods of making them are reviewed, e.g., in Almagro and Fransson, Front. Biosci. 13:1619-1633 (2008), and are further described, e.g., in Riechmann et al., Nature 332:323-329 (1988); Queen et al., Proc. Nat'l Acad. Sci. USA 86:10029-10033 (1989); U.S. Pat. Nos. 5,821,337, 7,527,791, 6,982,321, and 7,087,409; Kashmiri et al., Methods 36:25-34 (2005) (describing specificity determining region (SDR) grafting); Padlan, Mol. Immunol. 28:489-498 (1991) (describing "resurfacing"); Dall'Acqua et al., Methods 36:43-60 (2005) (describing "FR shuffling"); and Osbourn et al., Methods 36:61-68 (2005) and Klimka et al., Br. J. Cancer, 83:252-260 (2000) (describing the "guided selection" approach to FR shuffling).

Human framework regions that may be used for humanization include but are not limited to: framework regions selected using the "best-fit" method (see, e.g., Sims et al. J. Immunol. 151:2296 (1993)); framework regions derived from the consensus sequence of human antibodies of a particular subgroup of light or heavy chain variable regions (see, e.g., Carter et al. Proc. Natl. Acad. Sci. USA, 89:4285 (1992); and Presta et al. J. Immunol., 151:2623 (1993)); human mature (somatically mutated) framework regions or human germline framework regions (see, e.g., Almagro and Fransson, Front. Biosci. 13:1619-1633 (2008)); and framework regions derived from screening FR libraries (see, e.g., Baca et al., J. Biol. Chem. 272:10678-10684 (1997) and Rosok et al., J Biol. Chem. 271:22611-22618 (1996)).

In certain embodiments, an anti-CD39 antibody provided herein is a human antibody. Human antibodies can be produced using various techniques known in the art. Human antibodies are described generally in van Dijk and van de Winkel, Curr. Opin. Pharmacol. 5: 368-74 (2001) and Lonberg, Curr. Opin. Immunol. 20:450-459 (2008).

For instance, human antibodies may be prepared by administering an immunogen to a transgenic animal that has been modified to produce intact human antibodies or intact antibodies with human variable regions in response to antigenic challenge. Such animals typically contain all or a portion of the human immunoglobulin loci, which replace the endogenous immunoglobulin loci, or which are present extrachromosomally or integrated randomly into the animal's chromosomes. In such transgenic mice, the endogenous immunoglobulin loci have generally been inactivated. For review of methods for obtaining human antibodies from transgenic animals, see Lonberg, Nat. Biotech. 23:1117-1125 (2005). See also, e.g., U.S. Pat. Nos. 6,075,181 and 6,150,584 describing XENOMOUSE technology; U.S. Pat. No. 5,770,429 describing HuMAB technology; U.S. Pat. No. 7,041,870 describing K-M MOUSE technology, and U.S. Patent Application Publication No. US 2007/0061900, describing VELOCIMOUSE technology). Human variable regions from intact antibodies generated by such animals may be further modified, e.g., by combining with a different human constant region.

Human antibodies can also be made by hybridoma-based methods. Human myeloma and mouse-human heteromyeloma cell lines for the production of human monoclonal antibodies have been described. (See, e.g., Kozbor J. Immunol., 133: 3001 (1984); Brodeur et al., Monoclonal Antibody Production Techniques and Applications, pp. 51-63 (Marcel Dekker, Inc., New York, 1987); and Boerner et al., J. Immunol., 147: 86 (1991).) Human antibodies generated via human B-cell hybridoma technology are also described in Li et al., Proc. Natl. Acad. Sci USA, 103:3557-3562 (2006). Additional methods include those described, for example, in U.S. Pat. No. 7,189,826 (describing production of monoclonal human IgM antibodies from hybridoma cell lines) and Ni, Xiandai Mianyixue, 26(4):265-268 (2006) (describing human-human hybridomas). Human hybridoma technology (Trioma technology) is also described in Vollmers and Brandlein, Histology and Histopathology, 20(3):927-937 (2005) and Vollmers and Brandlein, Methods and Findings in Experimental and Clinical Pharmacology, 27(3):185-91 (2005).

Human antibodies may also be generated by isolating Fv clone variable domain sequences selected from human-derived phage, yeast or bacterial display libraries. Such variable domain sequences may then be combined with a desired human constant domain. Techniques for selecting human antibodies from antibody libraries are described below.

To illustrate, anti-CD39 antibodies encompassed by the present invention may be isolated by screening combinatorial libraries for antibodies with the desired activity or activities. For example, a variety of methods are known in the art for generating phage or yeast display libraries and screening such libraries for antibodies possessing the desired binding characteristics. Such methods are reviewed, e.g., in Hoogenboom et al. in Methods in Molecular Biology 178: 1-37 (O'Brien et al., ed., Human Press, Totowa, N.J., 2001) and further described, e.g., in the McCafferty et al., Nature 348:552-554; Clackson et al., Nature 352: 624-628 (1991); Marks et al., J. Mol. Biol. 222: 581-597 (1992); Marks and Bradbury, in Methods in Molecular Biology 248:161-175 (Lo, ed., Human Press, Totowa, N.J., 2003); Sidhu et al., J. Mol. Biol. 338(2): 299-310 (2004); Lee et al., J. Mol. Biol. 340(5): 1073-1093 (2004); Fellouse, Proc. Natl. Acad. Sci. USA 101(34): 12467-12472 (2004); and Lee et al., J. Immunol. Methods 284(1-2): 119-132(2004).

As an example of phage display methods, repertoires of VH and VL genes are separately cloned by polymerase chain reaction (PCR) and recombined randomly in phage libraries, which can then be screened for antigen-binding phage as described in Winter et al., Ann. Rev. Immunol., 12: 433-455 (1994). Phage typically display antibody fragments, either as single-chain Fv (scFv) fragments or as Fab fragments. Libraries from immunized sources provide high-affinity antibodies to the immunogen without the requirement of constructing hybridomas. Alternatively, the naive repertoire can be cloned (e.g., from human) to provide a single source of antibodies to a wide range of non-self and also self-antigens without any immunization as described by Griffiths et al., EMBO J, 12: 725-734 (1993). Finally, naive libraries can also be made synthetically by cloning unrearranged V-gene segments from stem cells, and using PCR primers containing random sequence to encode the highly variable CDR3 regions and to accomplish rearrangement in vitro, as described by Hoogenboom and Winter, J. Mol. Biol., 227: 381-388 (1992). Patent publications describing human antibody phage libraries include, for example: U.S. Pat. No. 5,750,373, and US Patent Publication Nos. 2005/0079574, 2005/0119455, 2005/0266000, 2007/0117126, 2007/0160598, 2007/0237764, 2007/0292936, and 2009/0002360.

Antibodies or antibody fragments isolated from human antibody libraries are considered human antibodies or human antibody fragments herein.

FcγRIII binding can also be increased by methods according to the state of the art, e.g. by modifying the amino acid sequence of the Fc part or the glycosylation of the Fc part of the antibody (see e.g. EP2235061). In certain embodiments, the subject antibodies are produced by cells in which, when glycosylated, less than 50% of the oligosaccharide chains on the antibody contain α-1,6-fucose. Typically, less than about 40%, less than about 30%, less than about 20%, less than about 10%, or less than 5% or less than 1% of the oligosaccharide chains contain α-1,6-fucose in a "hypofucosylated" antibody preparation. An "afucosylated" antibody lacks α-1,6-fucose in the carbohydrate attached to the CH2 domain of the IgG heavy chain. Mori, K et al., Cytotechnology 55 (2007)109 and Satoh M, et al., Expert Opin Biol Ther. 6 (2006) 1161-1173 relate to a FUT8 ((α-1,6-fucosyltransferase) gene knockout CHO line for the generation of afucosylated antibodies.

IV. Expression Vectors

In certain embodiments, a recombinant expression vector is used to amplify and express DNA encoding the anti-CD39 antibody described herein. For example, a recombinant expression vector can be a replicable DNA construct which has synthetic or cDNA-derived DNA fragments encoding the polypeptide chains of the anti-CD39 antibody operatively linked to suitable transcriptional and/or translational regulatory elements derived from mammalian, microbial, viral or insect genes. A transcriptional unit generally comprises an assembly of (1) a genetic element or elements having a regulatory role in gene expression, for example, transcriptional promoters or enhancers, (2) a structural or coding sequence which is transcribed into mRNA and translated into protein, and (3) appropriate transcription and translation initiation and termination sequences. Regulatory elements can include an operator sequence to control transcription. The ability to replicate in a host, usually conferred by an origin of replication, and a selection gene to facilitate recognition of transformants can additionally be incorporated. DNA regions are "operatively linked" when they are functionally related to each other. For example, DNA for a signal peptide (secretory leader) is operatively linked to DNA for a polypeptide if it is expressed as a precursor which participates in the secretion of the polypeptide; a promoter is operatively linked to a coding sequence if it controls the transcription of the sequence; or a ribosome binding site is operatively linked to a coding sequence if it is positioned so as to permit translation. In some embodiments, structural elements intended for use in yeast expression systems include a leader sequence enabling extracellular secretion of translated protein by a host cell. In other embodiments, where recombinant protein is expressed without a leader or transport sequence, it can include an N-terminal methionine residue. This residue can optionally be subsequently cleaved from the expressed recombinant protein to provide a final product.

The choice of an expression control sequence and an expression vector depends upon the choice of host cell. A wide variety of expression host/vector combinations can be employed. Useful expression vectors for eukaryotic hosts include, for example, vectors comprising expression control sequences from SV40, bovine papilloma virus, adenovirus, and cytomegalovirus. Useful expression vectors for bacterial hosts include known bacterial plasmids, such as plasmids from *E. coli*, including pCR1, pBR322, pMB9 and their derivatives, and wider host range plasmids, such as M13 and other filamentous single-stranded DNA phages.

Suitable host cells for expression of the polypeptide chains of the anti-CD39 antibody (or a protein to use as a target) include prokaryotes, yeast cells, insect cells, or higher eukaryotic cells under the control of appropriate promoters. Prokaryotes include gram-negative or gram-positive organisms, for example *E. coli* or *Bacillus*. Higher eukaryotic cells include established cell lines of mammalian origin as described below. Cell-free translation systems may also be employed. Appropriate cloning and expression vectors for use with bacterial, fungal, yeast, and mammalian cellular hosts are well known by those skilled in the art.

Various mammalian cell culture systems are used to express recombinant polypeptides. Expression of recombinant proteins in mammalian cells can be preferred because such proteins are generally correctly folded, appropriately modified, and biologically functional. Examples of suitable mammalian host cell lines include COS-7 (monkey kidney-derived), L-929 (murine fibroblast-derived), C127 (murine mammary tumor-derived), 3T3 (murine fibroblast-derived), CHO (Chinese hamster ovary-derived), HeLa (human cervical cancer-derived), BHK (hamster kidney fibroblast-derived), and HEK-293 (human embryonic kidney-derived) cell lines and variants thereof. Mammalian expression vectors can comprise non-transcribed elements such as an origin of replication, a suitable promoter and enhancer linked to the gene to be expressed, and other 5' or 3' flanking non-transcribed sequences, and 5' or 3' non-translated sequences, such as necessary ribosome binding sites, a polyadenylation site, splice donor and acceptor sites, and transcriptional termination sequences.

Expression of recombinant proteins in insect cell culture systems (e.g., baculovirus) also offers a robust method for producing correctly folded and biologically functional proteins. Baculovirus systems for production of heterologous proteins in insect cells are well-known to those of skill in the art.

In certain embodiments, the polynucleotide comprises a polynucleotide encoding an antibody light chain comprising a variable region at least 60% identical to SEQ ID No. 1, and even more preferably at least 65%, 70%, 75%, 80%, 85% or even 90% identical to SEQ ID No. 1, and able to specifically bind human CD39.

In certain embodiments, the polynucleotide comprises a polynucleotide encoding an antibody heavy chain comprising a variable region at least 60% identical to SEQ ID No. 2, and even more preferably at least 65%, 70%, 75%, 80%, 85% or even 90% identical to SEQ ID No. 2, and able to specifically bind human CD39.

V. Encoded Anti-CD39 Antibodies for In Vivo Delivery

Therapeutic vectors for delivering the coding sequence for an anti-CD39 antibody to be expressed in the patient can be viral, non-viral, or physical. See, for example, Rosenberg et al., Science, 242:1575-1578, 1988, and Wolff et al., Proc. Natl. Acad. Sci. USA 86:9011-9014 (1989). Discussion of methods and compositions for use in gene therapy include Eck et al., in Goodman & Gilman's The Pharmacological Basis of Therapeutics, Ninth Edition, Hardman et al., eds., McGraw-Hill, New York, (1996), Chapter 5, pp. 77-101; Wilson, Clin. Exp. Immunol. 107 (Suppl. 1):31-32, 1997; Wivel et al., Hematology/Oncology Clinics of North America, Gene Therapy, S. L. Eck, ed., 12(3):483-501, 1998; Romano et al., Stem Cells, 18:19-39, 2000, and the references cited therein. U.S. Pat. No. 6,080,728 also provides a discussion of a wide variety of gene delivery methods and compositions. The routes of delivery include, for example, systemic administration and administration in situ. Well-known viral delivery techniques include the use of adenovirus, retrovirus, lentivirus, foamy virus, herpes simplex virus, vaccinia virus and adeno-associated virus vectors.

a. Viral Vectors

Preferred viral vectors are based on non-cytopathic eukaryotic viruses in which non-essential genes have been replaced with the nucleic acid construct carrying the nucleic acid sequences encoding the epitopes and targeting sequences of interest. Preferred viruses for certain embodiments encompassed by the present invention are the adenoviruses and adeno-associated (AAV) viruses, which are double-stranded DNA viruses that have already been approved for human use in gene therapy. In addition, preferred vectors for tolerizing do not include immune-stimulating sequences.

Adenovirus Vectors

One illustrative method for in vivo delivery of one or more nucleic acid sequences involves the use of an adenovirus expression vector. "Adenovirus expression vector" is meant to include those constructs containing adenovirus sequences sufficient to (a) support packaging of the construct and (b) to express a polynucleotide that has been cloned therein in a sense or antisense orientation. Of course, in the context of an antisense construct, expression does not require that the gene product be synthesized. In a specific embodiment, the delivery vector pertains to commercially available ORF of cytochrome b5 reductase 3 (CYB5R3), transcript variant 1 in adenoviral vector pAd, with C terminal Flag and His tag, (Vigene Biosciences Product code AH889428). WIPO Patent Application WO/2015/050364 also teaches vectors with expression constructs including a Cyb5r3 gene.

Adenoviral vectors are highly immunogenic and therefore are less preferred for administration to induce tolerance by presenting antigens, or in the case of autoimmune diseases. These vectors can be used, however to induce immunity, for example in treatment of infectious diseases and the like, include, for example, influenza, HBV, HCV and HIV.

Adeno-Associated Virus Vectors (AAV)

AAV is a good choice of delivery vehicles due to its safety, i.e., genetically engineered (recombinant) does not integrate into the host genome. Likewise, AAV is not pathogenic and not associated with any disease. The removal of viral coding sequences minimizes immune reactions to viral gene expression, and therefore, rAAV does not evoke an inflammatory response. According to a specific embodiment, an AAV vector containing an epitope sequence containing nucleic acid construct described herein is useful for transducing APCs.

Typically, viral vectors containing an epitope containing nucleic acid construct are assembled from polynucleotides encoding the desired epitopes, suitable regulatory elements and elements necessary for epitope expression which mediate cell transduction. In one embodiment, adeno-associated viral (AAV) vectors are employed. In a more specific embodiment, the AAV vector is an AAV1, AAV6, or AAV8.

The AAV expression vector which harbors the DNA molecule of interest bounded by AAV ITRs, can be constructed by directly inserting the selected sequence(s) into an AAV genome which has had the major AAV open reading frames ("ORFs") excised therefrom. Examples of constitutive promoters which may be included in the AAV of this invention include, without limitation, the exemplified CMV immediate early enhancer/chicken β-actin (CBA) promoter.

For eukaryotic cells, expression control sequences typically include a promoter, an enhancer, such as one derived from an immunoglobulin gene, SV40, cytomegalovirus, etc., and a polyadenylation sequence which may include splice donor and acceptor sites. The polyadenylation sequence generally is inserted following the transgene sequences and before the 3' ITR sequence. In one embodiment, the bovine growth hormone polyA may be used.

Selection of these and other common vector and regulatory elements are conventional, and many such sequences are available. See, e.g., Sambrook et al., and references cited therein at, for example, pages 3.18-3.26 and 16.17-16.27 and Ausubel et al., Current Protocols in Molecular Biology, John Wiley & Sons, New York, 1989). Of course, not all vectors and expression control sequences will function equally well to express all of the transgenes of this invention. However, one of skill in the art may make a selection among these expression control sequences without departing from the scope of this invention. Suitable promoter/enhancer sequences may be selected by one of skill in the art using the guidance provided by this application. Such selection is a routine matter and is not a limitation of the molecule or construct.

Retrovirus Vectors

In a certain embodiments, the viral vector may be a retroviral vector. "Retroviruses" are viruses having an RNA genome. In particular embodiments, a retroviral vector contains all of the cis-acting sequences necessary for the packaging and integration of the viral genome, i.e., (a) a long terminal repeat (LTR), or portions thereof, at each end of the vector; (b) primer binding sites for negative and positive strand DNA synthesis; and (c) a packaging signal, necessary for the incorporation of genomic RNA into virions. More detail regarding retroviral vectors can be found in Boesen, et al., 1994, Biotherapy 6:291-302; Clowes, et al, 1994, J. Clin. Invest. 93:644-651; Kiem, et al., 1994, Blood 83: 1467-1473; Salmons and Gunzberg, 1993, Human Gene Therapy 4: 129-141; Miller, et al., 1993, Meth. Enzymol. 217:581-599; and Grossman and Wilson, 1993, Curr. Opin. in Genetics and Devel. 3: 110-114.

"Gammaretroviruses" refers to a genus of the retroviridae family. Exemplary gammaretroviruses include mouse stem cell virus, murine leukemia virus, feline leukemia virus, feline sarcoma virus, and avian reticuloendotheliosis viruses.

Widely used retroviral vectors include those based upon murine leukemia virus (MuLV), gibbon ape leukemia virus (GaLV), simian immunodeficiency virus (SIV), human immunodeficiency virus (HIV), and combinations thereof (see, e.g., Buchscher et al., J. Virol. 66:2731-2739, 1992; Johann et al., J. Virol. 66: 1635-1640, 1992; Sommerfelt et al., Virol. 176:58-59, 1990; Wilson et al., J. Virol. 63:2374-2378, 1989; Miller et al., J. Virol. 65:2220-2224, 1991; and PCT/US94/05700).

Lentiviral vectors refer to a genus of retroviruses that are capable of infecting dividing and non-dividing cells and typically produce high viral titers. Several examples of lentiviruses include HIV (human immunodeficiency virus: including HIV type 1, and HIV type 2); equine infectious anemia virus; feline immunodeficiency virus (FIV); bovine immune deficiency virus (BIV); and simian immunodeficiency virus (SIV).

In particular embodiments, other retroviral vectors can be used. These include, e.g., vectors based on human foamy virus (HFV) or other viruses in the Spumavirus genera. Foamy viruses (FVes) are the largest retroviruses known today and are widespread among different mammals, including all non-human primate species, however are absent in humans. This complete apathogenicity qualifies FV vectors as ideal gene transfer vehicles for genetic therapies in humans and clearly distinguishes FV vectors as gene delivery system from HIV-derived and also gammaretrovirus-derived vectors.

Non-cytopathic viruses include retroviruses (e.g., lentivirus), the life cycle of which involves reverse transcription of genomic viral RNA into DNA with subsequent proviral integration into host cellular DNA. Retroviruses have been approved for human gene therapy trials. Most useful are those retroviruses that are replication-deficient (i.e., capable of directing synthesis of the desired proteins, but incapable of manufacturing an infectious particle). Such genetically altered retroviral expression vectors have general utility for the high-efficiency transduction of genes in vivo. Standard protocols for producing replication-deficient retroviruses (including the steps of incorporation of exogenous genetic material into a plasmid, transfection of a packaging cell lined with plasmid, production of recombinant retroviruses by the packaging cell line, collection of viral particles from tissue culture media, and infection of the target cells with viral particles) are known to those of skill in the art.

The retroviral genome contains three genes, gag, pol, and env that code for capsid proteins, polymerase enzyme, and envelope components, respectively. A sequence found upstream from the gag gene contains a signal for packaging of the genome into virions. Retroviral vectors are gene transfer plasmids wherein the heterologous nucleic acid resides between two retroviral LTRs. Retroviral vectors typically contain appropriate packaging signals that enable the retroviral vector, or RNA transcribed using the retroviral vector as a template, to be packaged into a viral virion in an appropriate packaging cell line (see, e.g., U.S. Pat. No. 4,650,764). These two long terminal repeat (LTR) sequences are present at the 5' and 3' ends of the viral genome. These contain strong promoter and enhancer sequences and are also required for integration in the host cell genome (Coffin, 1990). In order to construct a retroviral vector, a nucleic acid encoding one or more oligonucleotide or polynucleotide sequences of interest is inserted into the viral genome in the place of certain viral sequences to produce a virus that is replication-defective.

Also included are episomal or non-integrating forms of retroviral vectors based on lentiviruses (e.g., a type of retrovirus).

Lentiviral vectors are useful when stable expression is needed, but lentiviral vectors can be immunogenic, and possibly have other undesirable effects. Therefore, although lentiviral vectors are convenient for research, care should be taken when using them for human administration, particularly where it is desired to induce tolerance rather than immunity. Lentiviruses are suitable for engineering T cells or dendritic cells or other antigen presenting cells ex vivo for cancer therapy, although mRNA electroporation is more safe. However, two recent advances have made the use of lentiviruses safer and more clinically translatable. First, the coexpression of a suicide gene along with the antigens whose products become functional when a drug is administered. A typical example is Herpes simplex virus thymidine kinase (HSV-Tk). Cells that express these genes can metabolize the drug ganciclovir into a cytotoxic product that induces cell death. Thus, in case some transduced cells become malignant, they can be eradicated. About a dozen such systems exist (Duarte et al., Cancer Letters, 324:160-170, 2012). Second, there are now non-integrating lentiviral vectors being developed that are therefore non-oncogenic (Nightingale et al., 2006, Mol. Ther., 13:1121-1132). These methods can be used with the invention according to the judgement of the person of skill in the art.

Suitable retroviral vectors for use herein are described, for example, in U.S. Pat. Nos. 5,399,346 and 5,252,479; and in WIPO publications WO 92/07573, WO 90/06997, WO 89/05345, WO 92/05266 and WO 92/14829, which provide a description of methods for efficiently introducing nucleic acids into human cells using such retroviral vectors. Other retroviral vectors include, for example, mouse mammary tumor virus vectors (e.g., Shackleford et al., Proc. Natl. Acad. Sci. U.S.A. 85:9655-9659, 1998), lentiviruses, and the like. An exemplary viral vector is plentilox-IRES-GFP.

Additional retroviral viral delivery systems that can be readily adapted for delivery of a transgene encoding a Anti-CD39 antibody Agent include, merely to illustrate Published PCT Applications WO/2010/045002, WO/2010/148203, WO/2011/126864, WO/2012/058673, WO/2014/066700, WO/2015/021077, WO/2015/148683, WO/2017/040815—the specifications and figures of each of which are incorporated by reference herein.

In certain embodiments, the retrovirus is a recombinant replication competent retrovirus comprising: a nucleic acid sequence encoding a retroviral GAG protein; a nucleic acid sequence encoding a retroviral POL protein; a nucleic acid sequence encoding a retroviral envelope; an oncoretroviral polynucleotide sequence comprising Long-Terminal Repeat (LTR) sequences at the 5' and 3' end of the oncoretroviral polynucleotide sequence; a cassette comprising an internal ribosome entry site (IRES) operably linked to a coding sequence for an Anti-CD39 antibody Agent, wherein the cassette is positioned 5' to the U3 region of the 3' LTR and 3' to the sequence encoding the retroviral envelope; and cis-acting sequences for reverse transcription, packaging and integration in a target cell.

In certain embodiments, the retrovirus is a recombinant replication competent retrovirus comprising: a retroviral GAG protein; a retroviral POL protein; a retroviral envelope; a retroviral polynucleotide comprising Long-Terminal Repeat (LTR) sequences at the 3' end of the retroviral polynucleotide sequence, a promoter sequence at the 5' end of the retroviral polynucleotide, the promoter being suitable for expression in a mammalian cell, a gag nucleic acid domain, a pol nucleic acid domain and an env nucleic acid domain; a cassette comprising an Anti-CD39 antibody Agent coding sequence operably linked to a heterologous polynucleotide, wherein the cassette is positioned 5' to the 3' LTR and is operably linked and 3' to the env nucleic acid domain encoding the retroviral envelope; and cis-acting sequences necessary for reverse transcription, packaging and integration in a target cell.

In certain preferred embodiments of the recombinant replication competent retrovirus, the envelope is chosen from one of amphotropic, polytropic, xenotropic, 10A1, GALV, Baboon endogenous virus, RD114, rhabdovirus, alphavirus, measles or influenza virus envelopes.

In certain preferred embodiments of the recombinant replication competent retrovirus, the retroviral polynucleotide sequence is engineered from a virus selected from the group consisting of murine leukemia virus (MLV), Moloney murine leukemia virus (MoMLV), Feline leukemia virus (FeLV), Baboon endogenous retrovirus (BEV), porcine endogenous virus (PERV), the cat derived retrovirus RD114, squirrel monkey retrovirus, Xenotropic murine leukemia virus-related virus (XMRV), avian reticuloendotheliosis virus (REV), or Gibbon ape leukemia virus (GALV).

In certain preferred embodiments of the recombinant replication competent retrovirus, retrovirus is a gammaretrovirus.

In certain preferred embodiments of the recombinant replication competent retrovirus, there is a second cassette comprising a coding sequence for a second therapeutic protein, such as another checkpoint inhibitor polypeptide, a co-stimulatory polypeptide and/or a immunostimulatory cytokine (merely as examples), e.g., downstream of the cassette. In certain instances, the second cassette can include an internal ribosome entry site (IRES) or a minipromoter or a polIII promoter operably linked to the coding sequence for the second therapeutic protein.

In certain preferred embodiments of the recombinant replication competent retrovirus, it is a nonlytic, amphotropic retroviral replicating vector which, preferably, selectively infects and replicates in the cells of the tumor microenvironment.

Other Viral Vectors as Expression Constructs

Other viral vectors may be employed as expression constructs in the present invention for the delivery of oligonucleotide or polynucleotide sequences to a host cell. Vectors derived from viruses such as vaccinia virus, polioviruses and herpes viruses may be employed. They offer several attractive features for various mammalian cells. Also included are hepatitis B viruses.

b. Non-Viral Vectors

Plasmid Vectors

Other vectors include plasmid vectors. Plasmid vectors have been extensively described in the art and are well known to those of skill in the art. See e.g. Sambrook et al., 1989, cited above. In the last few years, plasmid vectors have been used as DNA vaccines for delivering antigen-encoding genes to cells in vivo. They are particularly advantageous for this because they do not have the same safety concerns as with many of the viral vectors. These plasmids, however, having a promoter compatible with the host cell, can express a peptide epitope encoded by nucleic acid within the plasmid. Other plasmids are well known to those of ordinary skill in the art. Additionally, plasmids may be custom designed using restriction enzymes and ligation reactions to remove and add specific fragments of DNA. Plasmids may be delivered by a variety of parenteral, mucosal and topical routes. For example, the DNA plasmid can be injected by intramuscular, intradermal, subcutaneous, or other routes. It may also be administered by intranasal sprays or drops, rectal suppository and orally. It may also be administered into the epidermis or a mucosal surface using a gene-gun. The plasmids may be given in an aqueous solution, dried onto gold particles or in association with another DNA delivery system including but not limited to liposomes, dendrimers, cochleate and microencapsulation.

Thus, in one aspect, a plasmid is provided for expression of the epitope containing nucleic acid construct which includes an expression cassette; also referred to as a transcription unit. When a plasmid is placed in an environment suitable for epitope expression, the transcriptional unit will express the polynucleotide including a sequence encoding the epitopes, ETS and MHCII activator sequence, or sequence encoding the epitopes and secretion signal sequence, and anything else encoded in the construct. The transcription unit includes a transcriptional control sequence, which is transcriptionally linked with a cellular immune response element coding sequence. Transcriptional control sequence may include promoter/enhancer sequences such as cytomegalovirus (CMV) promoter/enhancer sequences. However, those skilled in the art will recognize that a variety of other promoter sequences suitable for expression in eukaryotic cells are known and can similarly be used in the constructs disclosed herein. The level of expression of the nucleic acid product will depend on the associated promoter and the presence and activation of an associated enhancer element.

In certain embodiments, a sequence encoding the desired epitopes and targeting sequence can be cloned into an expression plasmid which contains the regulatory elements for transcription, translation, RNA stability and replication (i.e., including a transcriptional control sequence). Such expression plasmids are well known in the art and one of ordinary skill would be capable of designing an appropriate expression construct with a polynucleotide including a sequence encoding a cellular immune response element or fragment thereof in such a manner that the cellular immune response element is expressible. There are numerous examples of suitable expression plasmids into which a polynucleotide including a sequence could be cloned such as pCI-neo, pUMVC or pcDNA3.

Large quantities of a bacterial host harboring a plasmid for expression of cellular immune response element or fragment thereof may be fermented and the plasmid can be purified for subsequent use. Current human clinical trials using plasmids utilize this approach. Recombinant DNA Advisory Committee Data Management Report, Human Gene Therapy 6: 535-548, 1994. Current DNA isolation methods known in the art include removal of lipopolysaccharides (endotoxins) that are contaminants from the bacteria used to propagate the plasmids. This step is most preferably taken for use of tolerogenic DNA vaccines as endotoxins act as strong adjuvants and can produce undesired immune stimulation.

The purpose of the plasmid is the efficient delivery of nucleic acid sequences to and expression of therapeutic epitopes in a cell or tissue. In particular, the purpose of the plasmid may be to achieve high copy number, avoid potential causes of plasmid instability and provide a means for plasmid selection. As for expression, the nucleic acid cassette contains the necessary elements for expression of the nucleic acid within the cassette. Expression includes the efficient transcription of an inserted gene, nucleic acid sequence, or nucleic acid cassette with the plasmid. Expression products may be proteins, polypeptides or RNA. The nucleic acid sequence can be contained in a nucleic acid cassette. Expression of the nucleic acid can be continuous or regulated.

Minicircle

Embodiments of nucleic acid constructs described herein may be processed in the form of minicircle DNA. Minicircle DNA pertains to small (2-4 kb) circular plasmid derivatives that have been freed from all prokaryotic vector parts. Since minicircle DNA vectors contain no bacterial DNA sequences, they are less likely to be perceived as foreign and destroyed. (Typical transgene delivery methods involve plasmids, which contain foreign DNA.) As a result, these vectors can be expressed for longer periods of time (in order of weeks or months) compared to conventional plasmids (days to weeks). The smaller size of minicircles also extends their cloning capacity and facilitates their delivery into cells. Kits for producing minicircle DNA are known in the art and are commercially available (System Biosciences, Inc., Palo Alto, Calif.). Information on minicircle DNA is provided in Dietz et al., Vector Engineering and Delivery Molecular Therapy (2013); 218, 1526-1535 and Hou et al., Molecular Therapy-Methods & Clinical Development, Article number: 14062 (2015) doi:10.1038/mtm.2014.62. More information on Minicircles is provided in Chen Z Y, He C Y, Ehrhardt A, Kay M A. Mol Ther. 2003 September; 8(3):495-500 and Minicircle DNA vectors achieve sustained expression reflected by active chromatin and transcriptional level. Gracey Maniar L E, Maniar J M, Chen Z Y, Lu J, Fire A Z, Kay M A. Mol Ther. 2013 January; 21(1):131-8

As an initial step in the process of ultimately obtaining expression of a product encoded by a nucleic acid, is to effect the uptake of the nucleic acid by cells. Uptake of nucleic acid by cells is dependent on a number of factors, one of which is the length of time during which a nucleic acid is in proximity to a cellular surface. For instance, after intramuscular (i.m.) administration of plasmid DNA in buffer, a marked reduction in gene expression was observed if the muscle is massaged, presumably due to DNA leakage out of the muscle either directly or via lymphatic vessels (Human Gene Therapy 4:151-159; 1993). Accordingly, it may be desirable to formulate nucleic acids with compounds which would retard the rate at which nucleic acids diffuse or are carried away from a site at which cellular uptake of the nucleic acid is desired. Further, these compounds could be suitable for administration to an organism by means such as injection while maintaining or regaining the physical characteristics necessary to increase cellular uptake of nucleic acids.

In order to effect expression of oligonucleotide or polynucleotide sequences, the expression construct must be delivered into a cell. In certain embodiments encompassed by the present invention, an expression construct comprising one or more oligonucleotide or polynucleotide sequences may simply consist of naked recombinant DNA or plasmids.

To prime immunity, DNA vaccine vectors of any type preferably are engineered to be CpG-rich (to stimulate TLR9 on immune cells) or conversely are engineered to remove CpG, and when possible, replace CpG motifs with GpG motifs (Ho et al., J. Immunol. 71(9):4920-6, 2003; Ho et al., J. Immunol. 175(9):6226-34, 2005). DNA vaccines can be engineered to contain the antigen(s)/epitope(s), and also can contain additional genes for co-expression with the antigens to act as adjuvants or immunomodulators (multiple promoter vectors). These DNA vaccines have been found to be safe clinically, for example in T1D patients (Roep et al., Sci. Transl. Med. 5(191):191ra82, 2013).

Mechanical Delivery Systems

Additional non-viral delivery methods include but are not limited to mechanical delivery systems that can be used in vitro such as the approach described in Woffendin et al., Proc. Natl. Acad. Sci. USA 91(24):11581, 1994; deposition of photopolymerized hydrogel materials or use of ionizing radiation (see, e.g., U.S. Pat. No. 5,206,152 and WO 92/11033); the use of a hand-held gene transfer particle gun (see, e.g., U.S. Pat. No. 5,149,655); and the use of ionizing radiation for activating transferred gene (see, e.g., U.S. Pat. No. 5,206,152 and WO 92/11033). Delivery devices can also be biocompatible, and may also be biodegradable. The formulation preferably provides a relatively constant level of active component release. On the other hand, a more rapid rate of release immediately upon administration may be desired. The formulation of such compositions is well within the level of ordinary skill in the art using known techniques.

Physical methods to enhance delivery include electroporation (where short pulses of high voltage carries the nucleic acid across the membrane), a gene gun (where DNA is loaded onto gold particles and forced to achieve penetration of the DNA into the cells), sonoporation, magnetofection, hydrodynamic delivery and the like, all of which are known to those of skill in the art. DNA also can be encapsulated in liposomes, preferably cationic liposomes, or polymersomes (synthetic liposomes) which can interact with the cell membrane and fuse or undergo endocytosis to effect DNA transfer into the cell. The DNA also can be formed into complexes with polymers (polyplexes) or with dendrimers which can directly release there load into the cytoplasm of a cell.

Illustrative carriers useful in this regard include microparticles of poly(lactide-co-glycolide), polyacrylate, latex, starch, cellulose, dextran and the like. Other illustrative delayed-release carriers include supramolecular biovectors, which comprise a non-liquid hydrophilic core (e.g., a cross-linked polysaccharide or oligosaccharide) and, optionally, an external layer comprising an amphiphilic compound, such as a phospholipid (see e.g., U.S. Pat. No. 5,151,254 and PCT applications WO 94/20078, WO/94/23701 and WO 96/06638). The amount of active agent contained within a sustained release formulation depends upon the site of implantation, the rate and expected duration of release and the nature of the condition to be treated or prevented.

Biodegradable microspheres (e.g., polylactate polyglycolate) may be employed as carriers for compositions. Suitable biodegradable microspheres are disclosed, for example, in U.S. Pat. Nos. 4,897,268; 5,075,109; 5,928,647; 5,811,128; 5,820,883; 5,853,763; 5,814,344, 5,407,609 and 5,942,252. Modified hepatitis B core protein carrier systems such as described in WO/99 40934, and references cited therein, will also be useful for many applications. Another illustrative carrier/delivery system employs a carrier comprising particulate-protein complexes, such as those described in U.S. Pat. No. 5,928,647, which can have the added benefit when used intratumorally to deliver the coding sequence for a Anti-CD39 antibody Agent of being capable of inducing an MHC I-restricted cytotoxic T lymphocyte responses targeted tumor tissues of the patient.

Biodegradable polymeric nanoparticles facilitate nonviral nucleic acid transfer to cells. Small (approximately 200 nm), positively charged (approximately 10 mV) particles are formed by the self-assembly of cationic, hydrolytically degradable poly(beta-amino esters) and plasmid DNA.

Polynucleotides may also be administered to cells by direct microinjection, temporary cell permeabilizations (e.g., co-administration of repressor and/or activator with a cell permeabilizing agent), fusion to membrane translocating peptides, and the like.

In certain particular embodiments of the present disclosure, the gene construct is introduced into target cells via electroporation. Electroporation involves the exposure of cells (or tissues) and DNA (or a DNA complex) to a high-voltage electric discharge. In vivo electroporation is a gene delivery technique that has been used successfully for efficient delivery of plasmid DNA to many different tissues. Studies have reported the administration of in vivo electroporation for delivery of plasmid DNA to B16 melanomas and other tumor tissues. Systemic and local expression of a gene or cDNA encoded by a plasmid can be obtained with administration of in vivo electroporation. Use of in vivo electroporation enhances plasmid DNA uptake in tumor tissue, resulting in expression within the tumor, and delivers plasmids to muscle tissue, resulting in systemic expression of secreted proteins, such as cytokines (see, e.g., U.S. Pat. No. 8,026,223). Exemplary techniques, vectors and devices for electroporating Anti-CD39 antibody Agent transgenes into cells in vivo include PCT Publications WO/2017/

106795, WO/2016/161201, WO/2016/154473, WO/2016/112359 and WO/2014/066655.

U.S. Pat. No. 7,245,963 describes modular electrode systems and their use for facilitating the introduction of a biomolecule into cells of a selected tissue in a body or plant. The modular electrode systems comprise a plurality of needle electrodes; a hypodermic needle; an electrical connector that provides a conductive link from a programmable constant-current pulse controller to the plurality of needle electrodes; and a power source. An operator can grasp the plurality of needle electrodes that are mounted on a support structure and firmly insert them into the selected tissue in a body or plant. The biomolecules are then delivered via the hypodermic needle into the selected tissue. The programmable constant-current pulse controller is activated and constant-current electrical pulse is applied to the plurality of needle electrodes.

The applied constant-current electrical pulse facilitates the introduction of the biomolecule into the ceil between the plurality of electrodes. The entire content of U.S. Pat. No. 7,245,963 is hereby incorporated by reference.

U.S. Patent Pub. 2005/0052630 describes an electroporation device which may be used to effectively facilitate the introduction of a biomolecule into ceils of a selected tissue in a body or plant. The electroporation device comprises an electro-kinetic device ("EKD device") whose operation is specified by software or firmware. The EKD device produces a series of programmable constant-current pulse patterns between electrodes in an array based on user control and input of the pulse parameters, and allows the storage and acquisition of current waveform data. The electroporation device also comprises a replaceable electrode disk having an array of needle electrodes, a central injection channel for an injection needle, and a removable guide disk (see, e.g., U.S. Patent Pub. 2005/0052630) is hereby incorporated by reference.

The electrode arrays and methods described in U.S. Pat. No. 7,245,963 and U.S. Patent Pub. 2005/0052630 are adapted for deep penetration into not only tissues such as muscle, but also other tissues or organs. Because of the configuration of the electrode array, the injection needle (to deliver the biomolecule of choice) is also inserted completely into the target organ, and the injection is administered perpendicular to the target issue, in the area that is pre-delineated by the electrodes.

Typically, the electric fields needed for in vivo cell electroporation are generally similar in magnitude to the fields required for cells in vitro. In one embodiment, the magnitude of the electric field range from approximately, 10 V/cm to about 1500 V/cm, preferably from about 300 V/cm to 1500 V/cm and preferably from about 1000 V/cm to 1500 V/cm. Alternatively, lower field strengths (from about 10 V/cm to 100 V/cm, and more preferably from about 25 V/cm to 75 V/cm) the pulse length is long. For example, when the nominal electric field is about 25-75 V/cm, if is preferred that the pulse length is about 10 msec.

The pulse length can be about 10 s to about 100 ms. There can be any desired number of pulses, typically one to 100 pulses per second. The delay between pulses sets can be any desired time, such as one second. The waveform, electric field strength and pulse duration may also depend upon the type of cells and the type of molecules that are to enter the cells via electroporation.

Also encompassed are electroporation devices incorporating electrochemical impedance spectroscopy ("EIS"). Such devices provide real-time information on in vivo, in particular, intratumoral electroporation efficiency, allowing for the optimization of conditions. Examples of electroporation devices incorporating EIS can be found, e.g., in WO2016/161201, which is hereby incorporated by reference.

Uptake of the non-viral delivery vectors encompassed by the present invention may also be enhanced by plasma electroporation also termed avalanche transfection. Briefly, microsecond discharges create cavitation microbubbles at electrode surface. The mechanical force created by the collapsing microbubbles combined with the magnetic field serve to increase transport efficiency across the cell membrane as compared with the diffusion mediated transport associated with conventional electroporation. The technique of plasma electroporation is described in U.S. Pat. Nos. 7,923,251 and 8,283,171. This technique may also be employed in vivo for the transformation of cells. Chaiberg, et al (2006) Investigative Ophthalmology & Visual Science 47:4083-4090; Chaiberg, et al U.S. Pat. No. 8,101,169 Issued Jan. 24, 2012.

Other alternative electroporation technologies are also contemplated. In vivo plasmid delivery can also be performed using cold plasma. Plasma is one of the four fundamental states of matter, the others being solid, liquid, and gas. Plasma is an electrically neutral medium of unbound positive and negative particles (i.e. the overall charge of a plasma is roughly zero). A plasma can be created by heating a gas or subjecting it to a strong electromagnetic field, applied with a laser or microwave generator. This decreases or increases the number of electrons, creating positive or negative charged particles called ions (Luo, et al. (1998) Phys. Plasma 5:2868-2870) and is accompanied by the dissociation of molecular bonds, if present.

Cold plasmas (i.e., non-thermal plasmas) are produced by the delivery of pulsed high voltage signals to a suitable electrode. Cold plasma devices may take the form of a gas jet device or a dielectric barrier discharge (DBD) device. Cold temperature plasmas have attracted a great deal of enthusiasm and interest by virtue of their provision of plasmas at relatively low gas temperatures. The provision of plasmas at such a temperature is of interest to a variety of applications, including wound healing, anti-bacterial processes, various other medical therapies and sterilization. As noted earlier, cold plasmas (i.e., non-thermal plasmas) are produced by the delivery of pulsed high voltage signals to a suitable electrode. Cold plasma devices may take the form of a gas jet device, a dielectric barrier discharge (DBD) device or multi-frequency harmonic-rich power supply.

Dielectric barrier discharge device relies on a different process to generate the cold plasma. A dielectric barrier discharge (DBD) device contains at least one conductive electrode covered by a dielectric layer. The electrical return path is formed by the ground that can be provided by the target substrate undergoing the cold plasma treatment or by providing an in-built ground for the electrode. Energy for the dielectric barrier discharge device can be provided by a high voltage power supply, such as that mentioned above. More generally, energy is input to the dielectric barrier discharge device in the form of pulsed DC electrical voltage to form the plasma discharge.

By virtue of the dielectric layer, the discharge is separated from the conductive electrode and electrode etching and gas heating is reduced. The pulsed DC electrical voltage can be varied in amplitude and frequency to achieve varying regimes of operation. Any device incorporating such a principle of cold plasma generation (e.g., a DBD electrode device) falls within the scope of various embodiments encompassed by the present invention.

Cold plasma has been employed to transfect cells with foreign nucleic acids. In particular, transfection of tumor cells (see, e.g., Connolly, et al. (2012) Human Vaccines & Immune-therapeutics 8: 1729-1733; and Connolly et al (2015) Bioelectrochemistry 103: 15-21).

In certain illustrative embodiments, the transgene construct encoding the anti-CD39 antibody agent encompassed by the present invention is delivered using an electroporation device comprising: an applicator; a plurality of electrodes extending from the applicator, the electrodes being associated with a cover area; a power supply in electrical communication with the electrodes, the power supply configured to generate one or more electroporating signals to cells within the cover area; and a guide member coupled to the electrodes, wherein the guide member is configured to adjust the cover area of the electrodes. At least a portion of the electrodes can be positioned within the applicator in a conical arrangement. The one or more electroporating signals may be each associated with an electric field. The device may further comprise a potentiometer coupled to the power supply and electrodes. The potentiometer may be configured to maintain the electric field substantially within a predetermined range.

The one or more electroporating signals may be each associated with an electric field. The device may further comprise a potentiometer coupled to the power supply and the electrodes. The potentiometer may be configured to maintain the electric field within a predetermined range so as to substantially prevent permanent damage in the cells within the cover area and/or substantially minimize pain. For instance, potentiometer may be configured to maintain the electric field to about 1300 V/cm.

The power supply may provide a first electrical signal to a first electrode and a second electrical signal to a second electrode. The first and second electrical signals may combine to produce a wave having a beat frequency. The first and second electrical signals may each have at least one of a unipolar waveform and a bipolar waveform. The first electrical signal may have a first frequency and a first amplitude. The second electrical signal may have a second frequency and a second amplitude. The first frequency may be different from or the same as the second frequency. The first amplitude may be different from or the same as the second amplitude.

In certain embodiments, the present invention provides a method for treating a subject having a tumor, the method comprising: injecting the tumor with an effective dose of plasmid coding for a Anti-CD39 antibody Agent; and administering electroporation therapy to the tumor. In certain embodiments, the electroporation therapy further comprises the administration of at least one voltage pulse of about 200 V/cm to about 1500 V/cm over a pulse width of about 100 microseconds to about 20 milliseconds.

In certain embodiments, the plasmid (or a second electroporated plasmid) further encodes at least one immunostimulatory cytokine, such as selected from the group encoding IL-12, IL-15, and a combination of IL-12 and IL-15.

Lipids and Polycationic Molecules for Delivering Anti-CD39 antibody Encoding Nucleic Constructs Lipid-mediated nucleic acid delivery and expression of foreign nucleic acids, including mRNA, in vitro and in vivo has been very successful. Lipid based non-viral formulations provide an alternative to adenoviral gene therapies. Current in vivo lipid delivery methods use subcutaneous, intradermal, intratumoral, or intracranial injection. Advances in lipid formulations have improved the efficiency of gene transfer in vivo (see PCT Application WO 98/07408). For instance, a lipid formulation composed of an equimolar ratio of 1,2-bis(oleoyloxy)-3-(trimethyl ammonio)propane (DOTAP) and cholesterol can significantly enhances systemic in vivo gene transfer. The DOTAP:cholesterol lipid formulation forms unique structure termed a "sandwich liposome". This formulation is reported to "sandwich" DNA between an invaginated bi-layer or 'vase' structure. Beneficial characteristics of these lipid structures include a positive p, colloidal stabilization by cholesterol, two dimensional nucleic acid packing and increased serum stability.

Cationic liposome technology is based on the ability of amphipathic lipids, possessing a positively charged head group and a hydrophobic lipid tail, to bind to negatively charged DNA or RNA and form particles that generally enter cells by endocytosis. Some cationic liposomes also contain a neutral co-lipid, thought to enhance liposome uptake by mammalian cells. Similarly, other polycations, such as poly-l-lysine and polyethylene-imine, complex with nucleic acids via charge interaction and aid in the condensation of DNA or RNA into nanoparticles, which are then substrates for endosome-mediated uptake.[8] Several of these cationic-nucleic acid complex technologies have been developed as potential clinical products, including complexes with plasmid DNA (pDNA), oligodeoxynucleotides, and various forms of synthetic RNA.

The nucleic acid constructs disclosed herein may be associated with polycationic molecules that serve to enhance uptake into cells. Complexing the nucleic acid construct with polycationic molecules also helps in packaging the construct such their size is reduced, which is believed to assist with cellular uptake. Once in the endosome, the complex dissociates due to the lower pH, and the polycationic molecules can disrupt the endosome's membrane to facilitate DNA escape into the cytoplasm before it can be degraded. Preliminary data shows that the nucleic acid construct embodiments had enhanced uptake into SCs over DCs when complexed with the polycationic molecules polylysine or polyethyleneimine.

One example of polycationic molecules useful for complexing with nucleic acid constructs includes cell penetrating peptides (CPP), examples include polylysine (described above), polyarginine and Tat peptides. Cell penetrating peptides (CPP) are small peptides which can bind to DNA and, once released, penetrate cell membranes to facilitate escape of the DNA from the endosome to the cytoplasm. Another example of a CPP pertains to a 27 residue chimeric peptide, termed MPG, was shown some time ago to bind ss- and ds-oligonucleotides in a stable manner, resulting in a non-covalent complex that protected the nucleic acids from degradation by DNase and effectively delivered oligonucleotides to cells in vitro (Mahapatro A, et al., J Nanobiotechnol, 2011, 9:55). The complex formed small particles of approximately 150 nm to 1 um when different peptide:DNA ratios were examined, and the 10:1 and 5:1 ratios (150 nm and 1 um respectively). Another CPP pertains to a modified tetrapeptide [tetralysine containing guanidinocarbonylpyrrole (GCP) groups (TL-GCP)], which was reported to bind with high affinity to a 6.2 kb plasmid DNA resulting in a positive charged aggregate of 700-900 nm Li et al., Agnew Chem Int Ed Enl 2015; 54(10):2941-4). RNA can also be complexed by such polycationic molecules for in vivo delivery.

Other examples of polycationic molecules that may be complexed with the nucleic acid constructs described herein include polycationic polymers commercially available as JETPRIME® and In Vivo JET (Polypus-transfection, S.A., Illkirch, France).

VI. Methods of Use and Pharmaceutical Compositions

The anti-CD39 antibodies encompassed by the present invention are useful in a variety of applications including, but not limited to, therapeutic treatment methods, such as immunotherapy for cancer. In certain embodiments, an anti-CD39 antibody described herein is useful for activating, promoting, increasing, and/or enhancing an immune response, inhibiting tumor growth, reducing tumor volume, inducing tumor regression, increasing tumor cell apoptosis, and/or reducing the tumorigenicity of a tumor. In certain embodiments, the anti-CD39 antibody encompassed by the present invention are also useful for immunotherapy against pathogens, such as viruses. In certain embodiments, an anti-CD39 antibody described herein is useful for inhibiting viral infection, reducing viral infection, increasing virally-infected cell apoptosis, and/or increasing killing of virus-infected cells. The methods of use may be in vitro, ex vivo, or in vivo methods.

The present invention provides methods for activating an immune response in a subject using an anti-CD39 antibody described herein. In some embodiments, the invention provides methods for promoting an immune response in a subject using an anti-CD39 antibody described herein. In some embodiments, the invention provides methods for increasing an immune response in a subject using an anti-CD39 antibody described herein. In some embodiments, the invention provides methods for enhancing an immune response in a subject using an anti-CD39 antibody described herein. In some embodiments, the activating, promoting, increasing, and/or enhancing of an immune response comprises increasing cell-mediated immunity. In some embodiments, the activating, promoting, increasing, and/or enhancing of an immune response comprises increasing Th1-type responses. In some embodiments, the activating, promoting, increasing, and/or enhancing of an immune response comprises increasing T-cell activity. In some embodiments, the activating, promoting, increasing, and/or enhancing of an immune response comprises increasing CD4+ T-cell activity. In some embodiments, the activating, promoting, increasing, and/or enhancing of an immune response comprises increasing CD8+ T-cell activity. In some embodiments, the activating, promoting, increasing, and/or enhancing of an immune response comprises increasing CTL activity. In some embodiments, the activating, promoting, increasing, and/or enhancing of an immune response comprises increasing NK cell activity. In some embodiments, the activating, promoting, increasing, and/or enhancing of an immune response comprises increasing T-cell activity and increasing NK cell activity. In some embodiments, the activating, promoting, increasing, and/or enhancing of an immune response comprises increasing CU activity and increasing NK cell activity. In some embodiments, the activating, promoting, increasing, and/or enhancing of an immune response comprises inhibiting or decreasing the suppressive activity of Treg cells. In some embodiments, the activating, promoting, increasing, and/or enhancing of an immune response comprises inhibiting or decreasing the suppressive activity of MDSCs. In some embodiments, the activating, promoting, increasing, and/or enhancing of an immune response comprises increasing the number of the percentage of memory T-cells. In some embodiments, the activating, promoting, increasing, and/or enhancing of an immune response comprises increasing long-term immune memory function. In some embodiments, the activating, promoting, increasing, and/or enhancing of an immune response comprises increasing long-term memory. In some embodiments, the activating, promoting, increasing, and/or enhancing of an immune response comprises no evidence of substantial side effects and/or immune-based toxicities. In some embodiments, the activating, promoting, increasing, and/or enhancing of an immune response comprises no evidence of cytokine release syndrome (CRS) or a cytokine storm. In some embodiments, the immune response is a result of antigenic stimulation. In some embodiments, the antigenic stimulation is a tumor cell. In some embodiments, the antigenic stimulation is cancer. In some embodiments, the antigenic stimulation is a pathogen. In some embodiments, the antigenic stimulation is a virally-infected cell.

In vivo and in vitro assays for determining whether an anti-CD39 antibody modulates, activates, or inhibits an immune response are known in the art or are being developed.

In certain embodiments of the methods described herein, a method of inducing a persistent or long-term immunity which inhibits tumor relapse or tumor regrowth comprises administering to a subject a therapeutically effective amount of an anti-CD39 antibody.

In some embodiments, the tumor is a solid tumor. In certain embodiments, the tumor is a tumor selected from the group consisting of: colorectal tumor, pancreatic tumor, lung tumor, ovarian tumor, liver tumor, breast tumor, kidney tumor, prostate tumor, neuroendocrine tumor, gastrointestinal tumor, melanoma, cervical tumor, bladder tumor, glioblastoma, lymphoma and head and neck tumor. In certain embodiments, the tumor is a colorectal tumor. In certain embodiments, the tumor is an ovarian tumor. In some embodiments, the tumor is a lung tumor.

In certain embodiments, the tumor is a pancreatic or pancreatic islet tumor. In certain embodiments, the tumor is a melanoma tumor. In some embodiments, the tumor is a bladder or urothelial tumor.

In some embodiments, the tumor is a liquid tumor. In certain embodiments, the tumor is a leukemia, such as myelogenous or granulocytic leukemia, lymphatic, lymphocytic, or lymphoblastic leukemia, and polycythemia vera or erythremia.

In some embodiments, the tumor expresses or overexpresses a tumor antigen targeted by the anti-CD39 antibody, such as a bispecific agent which comprises an antigen-binding site that specifically binds the tumor antigen.

The present invention further provides methods for treating cancer in a subject comprising administering to the subject a therapeutically effective amount of an anti-CD39 antibody described herein. In some embodiments, the anti-CD39 antibody and inhibits or reduces growth of the cancer.

The present invention provides for methods of treating cancer comprising administering to a subject (e.g., a subject in need of treatment) a therapeutically effective amount of an anti-CD39 antibody described herein. In certain embodiments, the subject is a human. In certain embodiments, the subject has a cancerous tumor. In certain embodiments, the subject has had a tumor removed.

In certain embodiments, the cancer is a cancer selected from the group consisting of colorectal cancer, pancreatic cancer, lung cancer, ovarian cancer, liver cancer, breast cancer, kidney cancer, prostate cancer, gastrointestinal cancer, melanoma, cervical cancer, neuroendocrine cancer, bladder cancer, brain cancer, glioblastoma, and head and neck cancer. In certain embodiments, the cancer is pancreatic cancer. In certain embodiments, the cancer is ovarian cancer. In certain embodiments, the cancer is colorectal cancer. In certain embodiments, the cancer is breast cancer.

In certain embodiments, the cancer is prostate cancer. In certain embodiments, the cancer is lung cancer. In certain embodiments, the cancer is melanoma. In some embodiments, the cancer is bladder cancer.

The present invention provides compositions comprising an anti-CD39 antibody described herein. The present invention also provides pharmaceutical compositions comprising an anti-CD39 antibody described herein and a pharmaceutically acceptable vehicle. In some embodiments, the pharmaceutical compositions find use in immunotherapy. In some embodiments, the pharmaceutical compositions find use in immuno-oncology. In some embodiments, the compositions find use in inhibiting tumor growth. In some embodiments, the pharmaceutical compositions find use in inhibiting tumor growth in a subject (e.g., a human patient). In some embodiments, the compositions find use in treating cancer. In some embodiments, the pharmaceutical compositions find use in treating cancer in a subject (e.g., a human patient).

Formulations are prepared for storage and use by combining a purified agent encompassed by the present invention with a pharmaceutically acceptable vehicle (e.g., a carrier or excipient). Those of skill in the art generally consider pharmaceutically acceptable carriers, excipients, and/or stabilizers to be inactive ingredients of a formulation or pharmaceutical composition.

In some embodiments, the anti-CD39 antibody is lyophilized and/or stored in a lyophilized form. In some embodiments, a formulation comprising an anti-CD39 antibody described herein is lyophilized.

Suitable pharmaceutically acceptable vehicles include, but are not limited to, nontoxic buffers such as phosphate, citrate, and other organic acids; salts such as sodium chloride; antioxidants including ascorbic acid and methionine; preservatives such as octadecyldimethylbenzyl ammonium chloride, hexamethonium chloride, benzalkonium chloride, benzethonium chloride, phenol, butyl or benzyl alcohol, alkyl parabens, such as methyl or propyl paraben, catechol, resorcinol, cyclohexanol, 3-pentanol, and m-cresol; low molecular weight polypeptides (e.g., less than about 10 amino acid residues); proteins such as serum albumin, gelatin, or immunoglobulins; hydrophilic polymers such as polyvinylpyrrolidone; amino acids such as glycine, glutamine, asparagine, histidine, arginine, or lysine; carbohydrates such as monosaccharides, disaccharides, glucose, mannose, or dextrins; chelating agents such as EDTA; sugars such as sucrose, mannitol, trehalose or sorbitol; salt-forming counter-ions such as sodium; metal complexes such as Zn-protein complexes; and non-ionic surfactants such as TWEEN or polyethylene glycol (PEG). (Remington: The Science and Practice of Pharmacy, 22.sup.nd Edition, 2012, Pharmaceutical Press, London.).

The pharmaceutical compositions encompassed by the present invention can be administered in any number of ways for either local or systemic treatment. Administration can be topical by epidermal or transdermal patches, ointments, lotions, creams, gels, drops, suppositories, sprays, liquids and powders; pulmonary by inhalation or insufflation of powders or aerosols, including by nebulizer, intratracheal, and intranasal; oral; or parenteral including intravenous, intraarterial, intratumoral, subcutaneous, intraperitoneal, intramuscular (e.g., injection or infusion), or intracranial (e.g., intrathecal or intraventricular).

The therapeutic formulation can be in unit dosage form. Such formulations include tablets, pills, capsules, powders, granules, solutions or suspensions in water or non-aqueous media, or suppositories. In solid compositions such as tablets the principal active ingredient is mixed with a pharmaceutical carrier. Conventional tableting ingredients include corn starch, lactose, sucrose, sorbitol, talc, stearic acid, magnesium stearate, dicalcium phosphate or gums, and diluents (e.g., water). These can be used to form a solid preformulation composition containing a homogeneous mixture of a compound encompassed by the present invention, or a non-toxic pharmaceutically acceptable salt thereof. The solid preformulation composition is then subdivided into unit dosage forms of a type described above. The tablets, pills, etc. of the formulation or composition can be coated or otherwise compounded to provide a dosage form affording the advantage of prolonged action. For example, the tablet or pill can comprise an inner composition covered by an outer component. Furthermore, the two components can be separated by an enteric layer that serves to resist disintegration and permits the inner component to pass intact through the stomach or to be delayed in release. A variety of materials can be used for such enteric layers or coatings, such materials include a number of polymeric acids and mixtures of polymeric acids with such materials as shellac, cetyl alcohol and cellulose acetate.

The anti-CD39 antibody can also be entrapped in microcapsules. Such microcapsules are prepared, for example, by coacervation techniques or by interfacial polymerization, for example, hydroxymethylcellulose or gelatin-microcapsules and poly-(methylmethacylate) microcapsules, respectively, in colloidal drug delivery systems (for example, liposomes, albumin microspheres, microemulsions, nanoparticles and nanocapsules) or in macroemulsions as described in Remington: The Science and Practice of Pharmacy, 22.sup.nd Edition, 2012, Pharmaceutical Press, London.

In certain embodiments, pharmaceutical formulations include an anti-CD39 antibody complexed with liposomes. Methods to produce liposomes are known to those of skill in the art. For example, some liposomes can be generated by reverse phase evaporation with a lipid composition comprising phosphatidylcholine, cholesterol, and PEG-derivatized phosphatidylethanolamine (PEG-PE). Liposomes can be extruded through filters of defined pore size to yield liposomes with the desired diameter.

In certain embodiments, sustained-release preparations comprising the anti-CD39 antibody can be produced. Suitable examples of sustained-release preparations include semi-permeable matrices of solid hydrophobic polymers containing an anti-CD39 antibody, where the matrices are in the form of shaped articles (e.g., films or microcapsules). Examples of sustained-release matrices include polyesters, hydrogels such as poly(2-hydroxyethyl-methacrylate) or poly(vinyl alcohol), polylactides, copolymers of L-glutamic acid and 7 ethyl-L-glutamate, non-degradable ethylene-vinyl acetate, degradable lactic acid-glycolic acid copolymers such as the LUPRON DEPOT (injectable microspheres composed of lactic acid-glycolic acid copolymer and leuprolide acetate), sucrose acetate isobutyrate, and poly-D-(−)-3-hydroxybutyric acid.

In certain embodiments, in addition to administering an anti-CD39 antibody, the method or treatment further comprises administering at least one additional immune response stimulating agent. In some embodiments, the additional immune response stimulating agent includes, but is not limited to, a colony stimulating factor (e.g., granulocyte-macrophage colony stimulating factor (GM-CSF), macrophage colony stimulating factor (M-CSF), granulocyte colony stimulating factor (G-CSF), stem cell factor (SCF)), an interleukin (e.g., IL-1, IL2, IL-3, IL-7, IL-12, IL-15, IL-18), a checkpoint inhibitor, an antibody that blocks immunosuppressive functions (e.g., an anti-CTLA-4 antibody, anti-CD28 antibody, anti-CD3 antibody), a toll-like receptor (e.g., TLR4, TLR7, TLR9), or a member of the B7 family (e.g., CD80, CD86). An additional immune response stimulating agent can be administered prior to, concurrently with, and/or subsequently to, administration of the anti-CD39 antibody. Pharmaceutical compositions comprising an anti-CD39 antibody and the immune response stimulating agent(s) are also provided. In some embodiments, the immune response stimulating agent comprises 1, 2, 3, or more immune response stimulating agents.

In certain embodiments, in addition to administering an anti-CD39 antibody, the method or treatment further comprises administering at least one additional therapeutic agent. An additional therapeutic agent can be administered prior to, concurrently with, and/or subsequently to, administration of the anti-CD39 antibody. Pharmaceutical compositions comprising an anti-CD39 antibody and the additional therapeutic agent(s) are also provided. In some embodiments, the at least one additional therapeutic agent comprises 1, 2, 3, or more additional therapeutic agents.

Combination therapy with two or more therapeutic agents often uses agents that work by different mechanisms of action, although this is not required. Combination therapy using agents with different mechanisms of action may result in additive or synergetic effects. Combination therapy may allow for a lower dose of each agent than is used in monotherapy, thereby reducing toxic side effects and/or increasing the therapeutic index of the anti-CD39 antibody. Combination therapy may decrease the likelihood that resistant cancer cells will develop. In some embodiments, combination therapy comprises a therapeutic agent that affects the immune response (e.g., enhances or activates the response) and a therapeutic agent that affects (e.g., inhibits or kills) the tumor/cancer cells.

In some embodiments of the methods described herein, the combination of an anti-CD39 antibody and at least one additional therapeutic agent results in additive or synergistic results. In some embodiments, the combination therapy results in an increase in the therapeutic index of the anti-CD39 antibody. In some embodiments, the combination therapy results in an increase in the therapeutic index of the additional therapeutic agent(s). In some embodiments, the combination therapy results in a decrease in the toxicity and/or side effects of the anti-CD39 antibody. In some embodiments, the combination therapy results in a decrease in the toxicity and/or side effects of the additional therapeutic agent(s).

Useful classes of therapeutic agents include, for example, anti-tubulin agents, auristatins, DNA minor groove binders, DNA replication inhibitors, alkylating agents (e.g., platinum complexes such as cisplatin, mono(platinum), bis(platinum) and tri-nuclear platinum complexes and carboplatin), anthracyclines, antibiotics, anti-folates, anti-metabolites, chemotherapy sensitizers, duocarmycins, etoposides, fluorinated pyrimidines, ionophores, lexitropsins, nitrosoureas, platinols, purine antimetabolites, puromycins, radiation sensitizers, steroids, taxanes, topoisomerase inhibitors, *vinca* alkaloids, or the like. In certain embodiments, the second therapeutic agent is an alkylating agent, an antimetabolite, an antimitotic, a topoisomerase inhibitor, or an angiogenesis inhibitor.

Therapeutic agents that may be administered in combination with the anti-CD39 antibody described herein include chemotherapeutic agents. Thus, in some embodiments, the method or treatment involves the administration of an anti-CD39 antibody in combination with a chemotherapeutic agent or in combination with a cocktail of chemotherapeutic agents. Treatment with an anti-CD39 antibody can occur prior to, concurrently with, or subsequent to administration of chemotherapies. Combined administration can include co-administration, either in a single pharmaceutical formulation or using separate formulations, or consecutive administration in either order but generally within a time period such that all active agents can exert their biological activities simultaneously. Preparation and dosing schedules for such chemotherapeutic agents can be used according to manufacturers' instructions or as determined empirically by the skilled practitioner. Preparation and dosing schedules for such chemotherapy are also described in The Chemotherapy Source Book, 4.sup.th Edition, 2008, M. C. Perry, Editor, Lippincott, Williams & Wilkins, Philadelphia, Pa.

Chemotherapeutic agents useful in the present invention include, but are not limited to, alkylating agents such as thiotepa and cyclosphosphamide (CYTOXAN); alkyl sulfonates such as busulfan, improsulfan and piposulfan; aziridines such as benzodopa, carboquone, meturedopa, and uredopa; ethylenimines and methylamelamines including altretamine, triethylenemelamine, trietylenephosphoramide, triethylenethiophosphaoramide and trimethylolomelamime; nitrogen mustards such as chlorambucil, chlornaphazine, cholophosphamide, estramustine, ifosfamide, mechlorethamine, mechlorethamine oxide hydrochloride, melphalan, novembichin, phenesterine, prednimustine, trofosfamide, uracil mustard; nitrosureas such as carmustine, chlorozotocin, fotemustine, lomustine, nimustine, ranimustine; antibiotics such as aclacinomysins, actinomycin, authramycin, azaserine, bleomycins, cactinomycin, calicheamicin, carabicin, caminomycin, carzinophilin, chromomycins, dactinomycin, daunorubicin, detorubicin, 6-diazo-5-oxo-L-norleucine, doxorubicin, epirubicin, esorubicin, idarubicin, marcellomycin, mitomycins, mycophenolic acid, nogalamycin, olivomycins, peplomycin, potfiromycin, puromycin, quelamycin, rodorubicin, streptonigrin, streptozocin, tubercidin, ubenimex, zinostatin, zorubicin; anti-metabolites such as methotrexate and 5-fluorouracil (5-FU); folic acid analogues such as denopterin, methotrexate, pteropterin, trimetrexate; purine analogs such as fludarabine, 6-mercaptopurine, thiamiprine, thioguanine; pyrimidine analogs such as ancitabine, azacitidine, 6-azauridine, carmofur, cytosine arabinoside, dideoxyuridine, doxifluridine, enocitabine, floxuridine, 5-FU; androgens such as calusterone, dromostanolone propionate, epitiostanol, mepitiostane, testolactone; anti-adrenals such as aminoglutethimide, mitotane, trilostane; folic acid replenishers such as folinic acid; aceglatone; aldophosphamide glycoside; aminolevulinic acid; amsacrine; bestrabucil; bisantrene; edatraxate; defofamine; demecolcine; diaziquone; elformithine; elliptinium acetate; etoglucid; gallium nitrate; hydroxyurea; lentinan; lonidamine; mitoguazone; mitoxantrone; mopidamol; nitracrine; pentostatin; phenamet; pirarubicin; podophyllinic acid; 2-ethylhydrazide; procarbazine; PSK; razoxane; sizofuran; spirogermanium; tenuazonic acid; triaziquone; 2,2', 2"-trichlorotriethylamine; urethan; vindesine; dacarbazine; mannomustine; mitobronitol; mitolactol; pipobroman; gacytosine; arabinoside (Ara-C); taxoids, e.g. paclitaxel (TAXOL) and docetaxel (TAXOTERE); chlorambucil; gemcitabine; 6-thioguanine; mercaptopurine; platinum analogs such as cisplatin and carboplatin; vinblastine; platinum; etoposide (VP-16); ifosfamide; mitomycin C; mitoxantrone; vincristine; vinorelbine; navelbine; novantrone; teniposide; daunomycin; aminopterin; ibandronate; CPT11; topoisomerase inhibitor RFS 2000; difluoromethylornithine (DMFO); retinoic acid; esperamicins; capecitabine (XE- LODA); and pharmaceutically acceptable salts, acids or derivatives of any of the above. Chemotherapeutic agents also include anti-hormonal agents that act to regulate or inhibit hormone action on tumors such as anti-estrogens including for example tamoxifen, raloxifene, aromatase inhibiting 4(5)-imidazoles, 4-hydroxytamoxifen, trioxifene, keoxifene, LY117018, onapristone, and toremifene (FARESTON); and anti-androgens such as flutamide, nilutamide, bicalutamide, leuprolide, and goserelin; and pharmaceutically acceptable salts, acids or derivatives of any of the above. In certain embodiments, the additional therapeutic agent is cisplatin. In certain embodiments, the additional therapeutic agent is carboplatin.

In certain embodiments of the methods described herein, the chemotherapeutic agent is a topoisomerase inhibitor. Topoisomerase inhibitors are chemotherapy agents that interfere with the action of a topoisomerase enzyme (e.g., topoisomerase I or II). Topoisomerase inhibitors include, but are not limited to, doxorubicin HCl, daunorubicin citrate, mitoxantrone HCl, actinomycin D, etoposide, topotecan HCl, teniposide (VM-26), and irinotecan, as well as pharmaceutically acceptable salts, acids, or derivatives of any of these.

In certain embodiments, the chemotherapeutic agent is an anti-metabolite. An anti-metabolite is a chemical with a structure that is similar to a metabolite required for normal biochemical reactions, yet different enough to interfere with one or more normal functions of cells, such as cell division. Anti-metabolites include, but are not limited to, gemcitabine, fluorouracil, capecitabine, methotrexate sodium, raltitrexed, pemetrexed, tegafur, cytosine arabinoside, thioguanine, 5-azacytidine, 6-mercaptopurine, azathioprine, 6-thioguanine, pentostatin, fludarabine phosphate, and cladribine, as well as pharmaceutically acceptable salts, acids, or derivatives of any of these.

In certain embodiments of the methods described herein, the chemotherapeutic agent is an antimitotic agent, including, but not limited to, agents that bind tubulin. In some embodiments, the agent is a taxane. In certain embodiments, the agent is paclitaxel or docetaxel, or a pharmaceutically acceptable salt, acid, or derivative of paclitaxel or docetaxel. In certain embodiments, the agent is paclitaxel (TAXOL), docetaxel (TAXOTERE), albumin-bound paclitaxel (nab-paclitaxel; ABRAXANE), DHA-paclitaxel, or PG-paclitaxel. In certain alternative embodiments, the antimitotic agent comprises a *vinca* alkaloid, such as vincristine, vinblastine, vinorelbine, or vindesine, or pharmaceutically acceptable salts, acids, or derivatives thereof. In some embodiments, the antimitotic agent is an inhibitor of kinesin Eg5 or an inhibitor of a mitotic kinase such as Aurora A or Plk1.

In certain embodiments of the methods described herein, it is anticipated that the subject anti-CD39 antibody will have a greater combinatorial effect (perhaps even synergy) with those chemotherapeutic agents that induce the release of ATP in the tumor and/or cause upregulation of CD39 or CD73 intratumorally. There are a wide range of chemotherapeutic agents that cause the release of ATP into the extracellular space as they induce tumor cell death, such as (but not limited to) anthracyclines (such as doxorubicin, daunorubicin, epirubicin and idarubicin), platinum-based drugs (such as cisplatin, carboplatin, and oxaliplatin), and proteasome inhibitors (such as bortezomib). Radiotherapy and photodynamic therapy (PDT) may also result in ATP release and/or upregulation of intratumoral levels of CD39 and/or CD73.

In some embodiments of the methods described herein, an additional therapeutic agent comprises an agent such as a small molecule. For example, treatment can involve the combined administration of an anti-CD39 antibody with a small molecule that acts as an inhibitor against tumor-associated antigens including, but not limited to, EGFR, HER2 (ErbB2), and/or VEGF. In some embodiments, an anti-CD39 antibody is administered in combination with a protein kinase inhibitor selected from the group consisting of: gefitinib (IRESSA), erlotinib (TARCEVA), sunitinib (SUTENT), lapatanib, vandetanib (ZACTIMA), AEE788, CI-1033, cediranib (RECENTIN), sorafenib (NEXAVAR), and pazopanib (GW786034B). In some embodiments, an additional therapeutic agent comprises an mTOR inhibitor.

In certain embodiments of the methods described herein, the additional therapeutic agent is a small molecule that inhibits a cancer stem cell pathway. In some embodiments, the additional therapeutic agent is an inhibitor of the Notch pathway. In some embodiments, the additional therapeutic agent is an inhibitor of the Wnt pathway. In some embodiments, the additional therapeutic agent is an inhibitor of the BMP pathway. In some embodiments, the additional therapeutic agent is an inhibitor of the Hippo pathway. In some embodiments, the additional therapeutic agent is an inhibitor of the mTOR/AKR pathway. In some embodiments, the additional therapeutic agent is an inhibitor of the RSPO/LGR pathway.

In some embodiments of the methods described herein, an additional therapeutic agent comprises a biological molecule, such as an antibody. For example, treatment can involve the combined administration of an anti-CD39 antibody with antibodies against tumor-associated antigens including, but not limited to, antibodies that bind EGFR, HER2/ErbB2, and/or VEGF. In certain embodiments, the additional therapeutic agent is an antibody specific for a cancer stem cell marker. In some embodiments, the additional therapeutic agent is an antibody that binds a component of the Notch pathway. In some embodiments, the additional therapeutic agent is an antibody that binds a component of the Wnt pathway. In certain embodiments, the additional therapeutic agent is an antibody that inhibits a cancer stem cell pathway. In some embodiments, the additional therapeutic agent is an inhibitor of the Notch pathway. In some embodiments, the additional therapeutic agent is an inhibitor of the Wnt pathway. In some embodiments, the additional therapeutic agent is an inhibitor of the BMP pathway. In some embodiments, the additional therapeutic agent is an antibody that inhibits β-catenin signaling. In certain embodiments, the additional therapeutic agent is an antibody that is an angiogenesis inhibitor (e.g., an anti-VEGF or VEGF receptor antibody). In certain embodiments, the additional therapeutic agent is bevacizumab (AVASTIN), ramucirumab, trastuzumab (HERCEPTIN), pertuzumab (OMNITARG), panitumumab (VECTIBIX), nimotuzumab, zalutumumab, or cetuximab (ERBITUX).

I/O Combinations—Representative Checkpoint Inhibitors and Co-Stimulatory Agonists In some embodiments of the methods described herein, the additional therapeutic agent is an antibody that modulates the immune response. In some embodiments, the additional therapeutic agent is an anti-PD-1 antibody, an anti-PD-L1 antibody, an anti-CTLA-4 antibody, an anti-LAG-3 antibody, an anti-TIM-3 antibody, an anti-TIGIT antibody and/or an anti-Siglec-15 antibody.

For instance, the therapy can further include administering an inhibitor of immune checkpoint molecule or an activator of a costimulatory molecule, or a combination thereof. Exemplary inhibitors of immune checkpoints include inhibitors of one or more of PD-1, CTLA-4, TIM-3, LAG-3, CEACAM, VISTA, BTLA, TIGIT, LAIR1, CD160, 2B4, NLRP1, NRLP3, STING, TGFRbeta or Siglec-15. Exemplary activators of costimulatory molecules include agonists of one or more of OX40, CD2, CD27, CDS, ICAM-1, LFA-1 (CD11a/CD18), ICOS (CD278), 4-1BB (CD137), GITR, CD30, CD40, BAFFR, HVEM, CD7, LIGHT, NKG2C, SLAMF7, NKp80, CD160, B7-H3 or CD83 ligand. Exemplary inhibitor of immune checkpoints and exemplary activators of costimulatory molecules can be found in PCT Publication WO 2016/054555, which is incorporated by reference herein.

PD-1 Antagonists

The PD-1 gene is a 55 kDa type I transmembrane protein that is part of the Ig gene superfamily (Agata et al. (1996) Int Immunol 8:765-72). PD-1 contains a membrane proximal immunoreceptor tyrosine inhibitory motif (ITIM) and a membrane distal tyrosine-based switch motif (ITSM) (Thomas, M. L. (1995) J Exp Med 181:1953-6; Vivier, E and Daeron, M (1997) Immunol Today 18:286-91). Two ligands for PD-1 have been identified, PD-L1 and PD-L2, that have been shown to downregulate T cell activation upon binding to PD-1 (Freeman et al. (2000) J Exp Med 192: 1027-34; Latchman et al. (2001) Nat Immunol 2:261-8; Carter et al. (2002) Eur J Immunol 32:634-43). Both PD-L1 and PD-L2 are B7 homologs that bind to PD-1, but do not bind to other CD28 family members. PD-LI is abundant in a variety of human cancers (Dong et al. (2002) Nat. Med. 8:787-9). The interaction between PD-1 and PD-L1 results in a decrease in tumor infiltrating lymphocytes, a decrease in T-cell receptor mediated proliferation, and immune evasion by the cancerous cells (Dong et al. (2003) J. Mol. Med. 81:281-7; Blank et al. (2005) Cancer Immunol. Immunother. 54:307-314; Konishi et al. (2004) Clin. Cancer Res. 10:5094-100). Immune suppression can be reversed by inhibiting the local interaction of PD-1 with PD-L1, and the effect is additive when the interaction of PD-1 with PD-L2 is blocked as well (Iwai et al. (2002) Proc. Nat'l. Acad. Sci. USA 99:12293-7; Brown et al. (2003) J. Immunol. 170: 1257-66)

As used herein, the terms "Programmed Death 1," "Programmed Cell Death 1," "Protein PD-1," "PD-1," PD1," "PDCD1," "hPD-1" and "hPD-I" are used interchangeably, and include variants, isoforms, species homologs of human PD-1, and analogs having at least one common epitope with human PD-1. The complete human PD-1 sequence can be found under GenBank Accession No. U64863.

As used herein, the terms "Programmed Cell Death 1 Ligand 1", "PD-L1", "PDL1", "PDCDiLi", "PDCD1LG1", "CD274", "B7 homolog 1", "B7-H1", "B7-H", and "B7H1" are used interchangeably, and include variants, isoforms, species homologs of human PDL-1, and analogs having at least one common epitope with human PDL-1. The complete human PD-L1 amino acid sequence—isoform a precursor—can be found under GenBank Accession No. NP_054862.1. The complete human PD-Li amino acid sequence—isoform b precursor—can be found under GenBank Accession No. NP_001254635.1.

fencodeThe term "PD-1 axis binding antagonist" is a molecule that inhibits the interaction of a PD-1 axis binding partner with either one or more of its binding partner, so as to remove T-cell dysfunction resulting from signaling on the PD-1 signaling axis with a result being to restore or enhance T-cell function (e.g., proliferation, cytokine production, target cell killing). As used herein, a PD-1 axis binding antagonist includes a PD-1 binding antagonist, a PD-L1 binding antagonist and a PD-L2 binding antagonist.

The term "PD-1 binding antagonists" is a molecule that decreases, blocks, inhibits, abrogates or interferes with signal transduction resulting from the interaction of PD-1 with one or more of its binding partners, such as PD-L1, PD-L2. In some embodiments, the PD-1 binding antagonist is a molecule that inhibits the binding of PD-1 to its binding partners. In a specific aspect, the PD-1 binding antagonist inhibits the binding of PD-1 to PD-L1 and/or PD-L2. For example, PD-1 binding antagonists include anti-PD-1 antibodies, antigen binding fragments thereof, immunoadhesins, fusion proteins, oligopeptides and other molecules that decrease, block, inhibit, abrogate or interfere with signal transduction resulting from the interaction of PD-1 with PD-L1 and/or PD-L2. In one embodiment, a PD-1 binding antagonist reduces the negative co-stimulatory signal mediated by or through cell surface proteins expressed on T lymphocytes mediated signaling through PD-1 so as render a dysfunctional T-cell less dysfunctional (e.g., enhancing effector responses to antigen recognition). In some embodiments, the PD-1 binding antagonist is an anti-PD-1 antibody. In a specific aspect, a PD-1 binding antagonist is MDX-1106 described herein. In another specific aspect, a PD-1 binding antagonist is Merck 3745 described herein. In another specific aspect, a PD-1 binding antagonist is CT-011 described herein.

The term "PD-L1 binding antagonists" is a molecule that decreases, blocks, inhibits, abrogates or interferes with signal transduction resulting from the interaction of PD-L1 with either one or more of its binding partners, such as PD-1, B7-1. In some embodiments, a PD-L1 binding antagonist is a molecule that inhibits the binding of PD-L1 to its binding partners. In a specific aspect, the PD-L1 binding antagonist inhibits binding of PD-L1 to PD-1 and/or B7-1. In some embodiments, the PD-L1 binding antagonists include anti-PD-L1 antibodies, antigen binding fragments thereof, immunoadhesins, fusion proteins, oligopeptides and other molecules that decrease, block, inhibit, abrogate or interfere with signal transduction resulting from the interaction of PD-L1 with one or more of its binding partners, such as PD-1, B7-1. In one embodiment, a PD-L1 binding antagonist reduces the negative co-stimulatory signal mediated by or through cell surface proteins expressed on T lymphocytes mediated signaling through PD-L1 so as to render a dysfunctional T-cell less dysfunctional (e.g., enhancing effector responses to antigen recognition). In some embodiments, a PD-L1 binding antagonist is an anti-PD-L1 antibody. In a specific aspect, an anti-PD-L1 antibody is YW243.55.S70 described herein. In another specific aspect, an anti-PD-L1 antibody is MDX-1105 described herein. In still another specific aspect, an anti-PD-L1 antibody is MPDL3280A described herein.

The term "PD-L2 binding antagonists" is a molecule that decreases, blocks, inhibits, abrogates or interferes with signal transduction resulting from the interaction of PD-L2 with either one or more of its binding partners, such as PD-1. In some embodiments, a PD-L2 binding antagonist is a molecule that inhibits the binding of PD-L2 to its binding partners. In a specific aspect, the PD-L2 binding antagonist inhibits binding of PD-L2 to PD-1. In some embodiments, the PD-L2 antagonists include anti-PD-L2 antibodies, antigen binding fragments thereof, immunoadhesins, fusion proteins, oligopeptides and other molecules that decrease, block, inhibit, abrogate or interfere with signal transduction resulting from the interaction of PD-L2 with either one or more of its binding partners, such as PD-1. In one embodiment, a PD-L2 binding antagonist reduces the negative co-stimulatory signal mediated by or through cell surface proteins expressed on T lymphocytes mediated signaling through PD-L2 so as render a dysfunctional T-cell less dysfunctional (e.g., enhancing effector responses to antigen recognition). In some embodiments, a PD-L2 binding antagonist is an immunoadhesin.

PD-1 pathway: Members of the PD-1 pathway are all proteins which are associated with PD-1 signaling. On the one hand these might be proteins which induce PD-1 signaling upstream of PD-1 as e.g., the ligands of PD-1 PD-L1 and PD-L2 and the signal transduction receptor PD-1. On the other hand, these might be signal transduction proteins downstream of PD-1 receptor. Particularly preferred as members of the PD-1 pathway in the context encompassed by the present invention are PD-1, PD-L1 and PD-L2.

PD-1 pathway inhibitor: In the context encompassed by the present invention, a PD-1 pathway inhibitor is preferably defined herein as a compound capable to impair the PD-1 pathway signaling, preferably signaling mediated by the PD-1 receptor. Therefore, the PD-1 pathway inhibitor may be any inhibitor directed against any member of the PD-1 pathway capable of antagonizing PD-1 pathway signaling. In this context, the inhibitor may be an antagonistic antibody as defined herein, targeting any member of the PD-1 pathway, preferably directed against PD-1 receptor, PD-L1 or PD-L2. This antagonistic antibody may also be encoded by a nucleic acid. Such encoded antibodies are also called "intrabodies" as defined herein. Also, the PD-1 pathway inhibitor may be a fragment of the PD-1 receptor or the PD1-receptor blocking the activity of PD1 ligands. B7-1 or fragments thereof may act as PD1-inhibiting ligands as well. Furthermore, the PD-1 pathway inhibitor may be siRNA (small interfering RNA) or antisense RNA directed against a member of the PD-1 pathway, preferably PD-1, PD-L1 or PD-L2. Additionally, a PD-1 pathway inhibitor may be a protein comprising (or a nucleic acid coding for) an amino acid sequence capable of binding to PD-1 but preventing PD-1 signaling, e.g., by inhibiting PD-1 and B7-H1 or B7-DL interaction. Additionally, a PD-1 pathway inhibitor may be a small molecule inhibitor capable of inhibiting PD-1 pathway signaling, e.g., a PD-1 binding peptide or a small organic molecule.

In certain embodiments, PD-1 antagonists encompassed by the present invention include agents that bind to ligands of PD-1 and interfere with, reduce, or inhibit the binding of one or more ligands to the PD-1 receptor, or bind directly to the PD-1 receptor, without engaging in signal transduction through the PD-1 receptor. In one embodiment, the PD-1 antagonist binds directly to PD-1 and blocks PD-1 inhibitory signal transduction. In another embodiment, the PD-1 antagonist binds to one or more ligands of PD-1 (e.g., PD-L1 and PD-L2) and reduces or inhibits the ligand(s) from triggering inhibitory signal transduction through the PD-1. In one embodiment, the PD-1 antagonist binds directly to PD-LI, inhibiting or preventing PD-L1 from binding to PD-1, thereby blocking PD-1 inhibitory signal transduction.

PD-1 antagonists used in the methods and compositions encompassed by the present invention include PD-1 binding scaffold proteins and include, but are not limited to, PD-ligands, antibodies and multivalent agents. In a particular embodiment, the antagonist is a fusion protein, such as AMP-224. In another embodiment, the antagonist is an anti-PD-1 antibody ("PD-1 antibody"). Anti-human-PD-1 antibodies (or VH and/or VL domains derived therefrom) suitable for use in the invention can be generated using methods well known in the art. Alternatively, art recognized anti-PD-1 antibodies can be used. For example, antibodies MK-3475 or CT-011 can be used. Additionally, monoclonal antibodies 5C4, 17D8, 2D3, 4H1, 4A11, 7D3, and 5F4, described in WO 2006/121168, the teachings of which are hereby incorporated by reference, can be used. Antibodies that compete with any of these art-recognized antibodies for binding to PD-1 also can be used.

In another embodiment, the PD-1 antagonist is an anti-PD-L1 antibody. Anti-human-PD-L1 antibodies (or VH and/or VL domains derived therefrom) suitable for use in the invention can be generated using methods well known in the art. Alternatively, art recognized anti-PD-L1 antibodies can be used. For example, MED14736 (also known as Anti-B7-HI) or MPDL3280A (also known as RG7446) can be used. Additionally, monoclonal antibodies 12A4, 3G10, 10A5, 5F8, 10H10, 1B12, 7H1, 11E6, 12B7, and 13G4 described in WO 2007/005874 and U.S. Pat. No. 7,943,743, the teachings of which are hereby incorporated by reference, can be used. Antibodies that compete with any of these art-recognized antibodies for binding to PD-L1 also can be used.

An exemplary anti-PD-L1 antibody is 12A4 which is described in WO 2007/005874 and U.S. Pat. No. 7,943,743. In one embodiment, the antibody comprises the heavy and light chain CDRs or VRs of 12A4. In another embodiment, the antibody competes for binding with, and/or binds to the same epitope on PD-L1 as, the above-mentioned antibodies. In another embodiment, the antibody has at least about 90% variable region amino acid sequence identity with the above-mentioned antibodies.

Anti-PD-1 or anti-PD-L1 antibodies may bind to PD-1 or PD-L1, respectively, with a KD of $10^{-7}$ M, $5\times10^{-8}$ M, $10^{-8}$ M, $5\times10^{-9}$ M, $10^{-9}$ M, $5\times10^{-10}$ M, $10^{-10}$ M or less.

In one embodiment, the PD-1 inhibitor is an anti-PD-1 antibody chosen from Nivolumab, Pembrolizumab or Pidilizumab. A preferred PD-1 inhibitor is Nivolumab.

In some embodiments, the anti-PD-1 antibody is Nivolumab. Alternative names for Nivolumab include MDX-1106, MDX-1106-04, ONO-4538, or BMS-936558. In some embodiments, the anti-PD-1 antibody is Nivolumab (CAS Registry Number: 946414-94-4). Nivolumab is a fully human IgG4 monoclonal antibody which specifically blocks PDI. Nivolumab (clone 5C4) and other human monoclonal antibodies that specifically bind to PDI are disclosed in U.S. Pat. No. 8,008,449 (incorporated by reference) and WO 2006/121168 (incorporated by reference). In other embodiments, the anti-PD-1 antibody is Pembrolizumab. Pembrolizumab (Trade name KEYTRUDA® formerly Lambrolizumab, also known as Merck 3745, MK-3475 or SCH-900475) is a humanized IgG4 monoclonal antibody that binds to PD1. Pembrolizumab is disclosed, e.g., in Hamid, O. et al. (2013) New England Journal of Medicine 369 (2): 134-44, WO 2009/114335 (incorporated by reference), and U.S. Pat. No. 8,354,509 (incorporated by reference).

In some embodiments, the anti-PD-1 antibody is Pidilizumab. Pidilizumab (CT-011; Cure Tech) is a humanized IgGlk monoclonal antibody that binds to PD1. Pidilizumab and other humanized anti-PD-1 monoclonal antibodies are disclosed in WO2009/101611. Other anti-PD1 antibodies are disclosed in U.S. Pat. No. 8,609,089, US 2010028330, and/or US 20120114649. Other anti-PDI antibodies include AMP 514 (Amplimmune).

In some embodiments, the PD-1 inhibitor is an immunoadhesin {e.g., an immunoadhesin comprising an extracellular or PD-1 binding portion of PD-L1 or PD-L2 fused to a constant region {e.g., an Fc region of an immunoglobulin sequence). In some embodiments, the PD-1 inhibitor is AMP-224. In some embodiments, the PD-L1 inhibitor is anti-PD-L1 antibody. In some embodiments, the anti-PD-L1 inhibitor is YW243.55.S70, MPDL3280A, MEDI-4736, MSB-0010718C, or MDX-1105.

In one embodiment, the PD-L1 inhibitor is MDX-1105. MDX-1105, also known as BMS-936559, is an anti-PD-L1 antibody described in WO 2007/005874. In one embodiment, the PD-L1 inhibitor is YW243.55.S70. The YW243.55.S70 antibody is an anti-PD-L1 described in WO 2010/077634 (incorporated by reference) (heavy and light chain variable region sequences shown in SEQ ID Nos. 20 and 21, respectively, in WO 2010/077634).

In one embodiment, the PD-L1 inhibitor is MDPL3280A (Genentech/Roche). MDPL3280A is a human Fc optimized IgGI monoclonal antibody that binds to PD-L1. MDPL3280A and other human monoclonal antibodies to PD-L1 are disclosed in U.S. Pat. No. 7,943,743 (incorporated by reference) and U.S Publication No.: 2012/0039906 (incorporated by reference). In other embodiments, the PD-L2 inhibitor is AMP-224. AMP-224 is a PD-L2 Fc fusion soluble receptor that blocks the interaction between PD1 and B7-H1 (B7-DCIg; Amplimmune; e.g., disclosed in WO 2010/027827 (incorporated by reference) and WO 2011/066342 (incorporated by reference)).

In certain embodiments, the PD-1 pathway inhibitor is a small molecule antagonist of PD-1 pathway signaling. Such small molecule antagonists include those agents that bind to one or more of PD-1, PD-1L and/or PD-1L2 and inhibits the interaction of PD-1 with PD-1L1 and/or PD-1L2.

Exemplary small molecule antagonist of PD-1 pathway signaling can be found in, inter alia, published US applications 2014/0294898 and 2014/0199334, and published PCT Applications WO 2013/132317 and WO 2012/168944, each of which is incorporated by reference herein.

Merely to illustrate, the subject combination therapy can be practiced with small molecule antagonist selected from the group consisting of

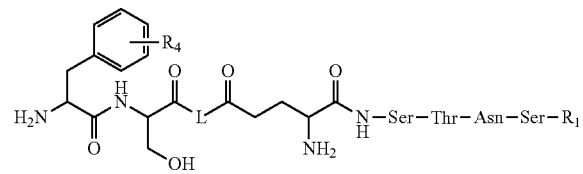

In other embodiments, the small molecule antagonist is represented in the general formula

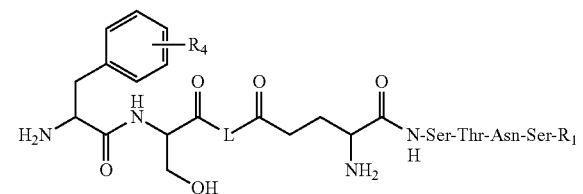

wherein,
R1 is free C-terminal or amidated C-terminal of Ser;
L is a linker selected from —NH(CH$_2$)$_n$NH— or —NH(CH$_2$CH$_2$O)$_n$NH—;
R4 is selected from hydrogen, amino(C$_1$-C$_{20}$)alkyl, —NHCOCH$_3$ or —NHCONH$_2$;
or retro analogue or a pharmaceutically acceptable stereoisomer or a pharmaceutically acceptable salt thereof.

In still other embodiments, the small molecule antagonist is represented in the general formula

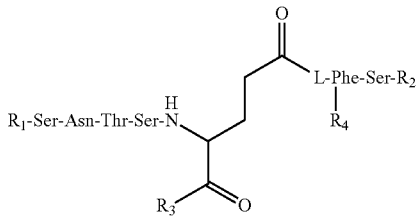

wherein,
R$_1$ is N-terminal of Ser; or (C$_1$-C$_{20}$)acyl substituted with either hydroxyl group or amino group of Ser;
L is a linker selected from —NH(CH$_2$)$_n$NH—, —NH(CH$_2$)$_n$CH(NH$_2$)CO—, —OOC(CH$_2$)$_m$COO—, —NH(CH$_2$)$_n$CO—, —NH(CH$_2$CH$_2$O)$_n$NH—, —NH(CH$_2$CH$_2$O)$_n$CO— or —CO(CH$_2$CH$_2$O)$_n$CO—;
R$_2$ is free C-terminal, amidated C-terminal or N-terminal of Am$_2$; or Y—R$_5$;
Y is an optional linker selected from —OOC(CH$_2$)$_m$COO—, —CO(CH$_2$)$_n$NH—, —CO(CH$_2$CH$_2$O)$_n$NH— or —COCH$_2$(OCH$_2$CH$_2$)$_n$NH—;
R$_5$ is an albumin binding moiety such as maleimido propionic acid;
R$_3$ is OH or NH$_2$;
R$_4$ is a substituent on phenyl group of Phe and is selected from hydrogen, amino(C$_1$-C$_{20}$)alkyl, —NHCOCH$_3$ or —NHCONH$_2$;
n is an integer having values selected from 2 to 10, both inclusive;
m is an integer having values selected from 0 to 8, both inclusive; and
one of the peptide bond (—CONH—) of Ser-Asn, Asn-Thr or Thr-Ser may be replaced with a modified peptide bond of

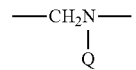

wherein Q is hydrogen, —CO(C$_1$-C$_{20}$)alkyl or —COO(C$_1$-C$_{20}$)alkyl group; wherein one or more or all amino acids may be in the D-configuration;
or retro analogue or a pharmaceutically acceptable stereoisomer or a pharmaceutically acceptable salt thereof.

For instance, the small molecule antagonist can be selected from the group consisting of

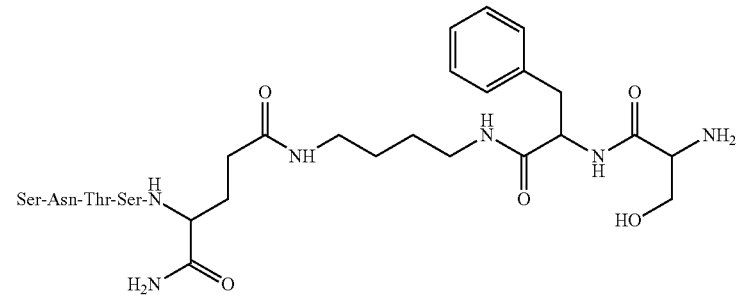

-continued
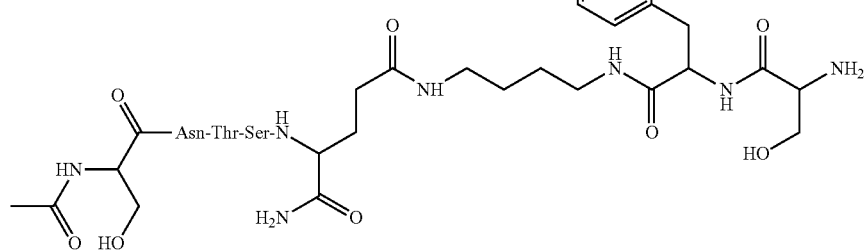
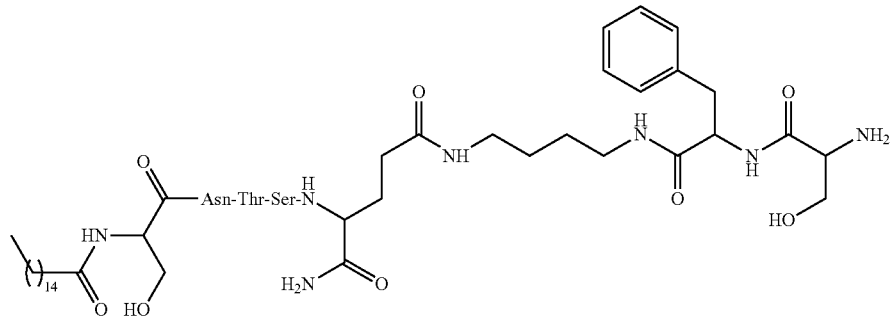
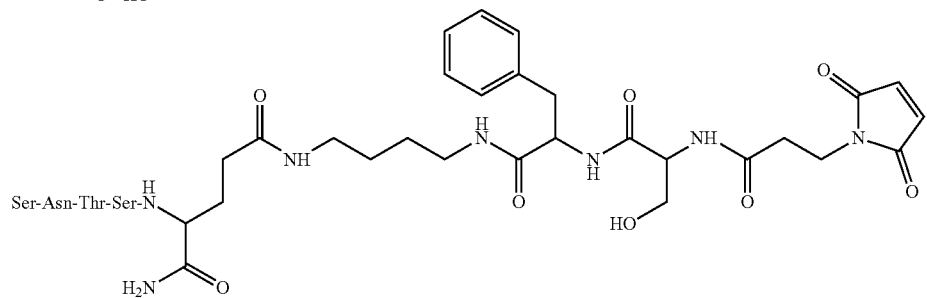
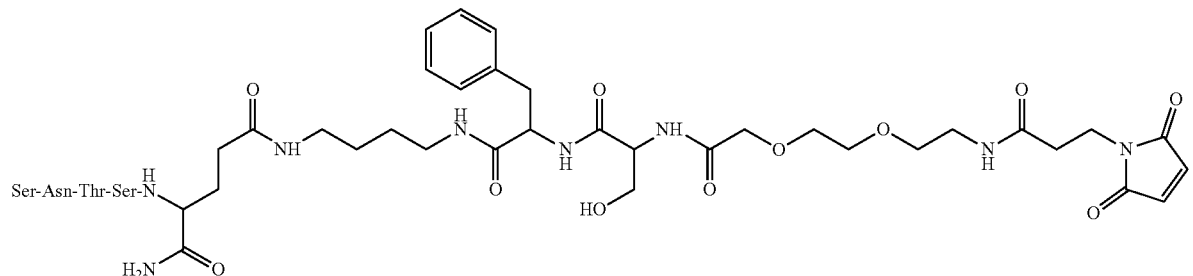
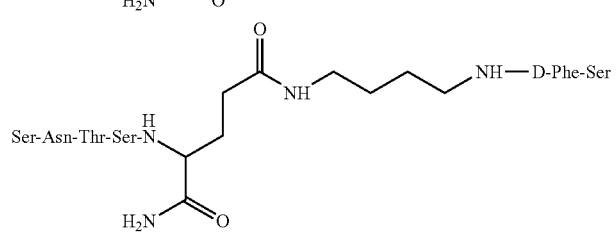
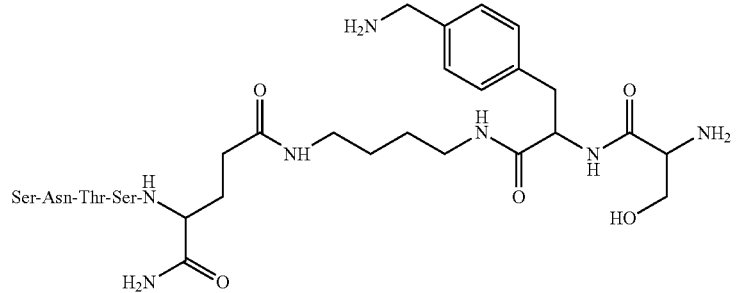

-continued
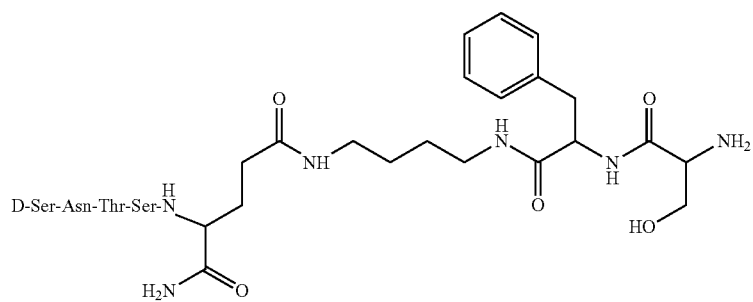
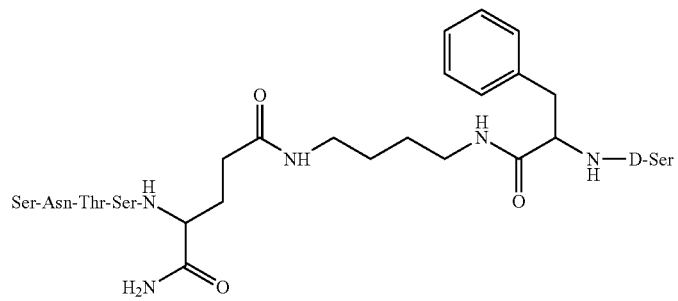
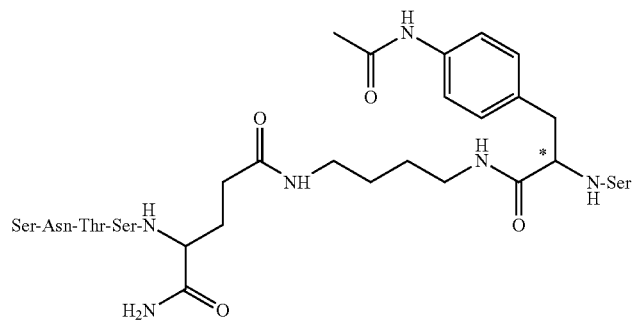
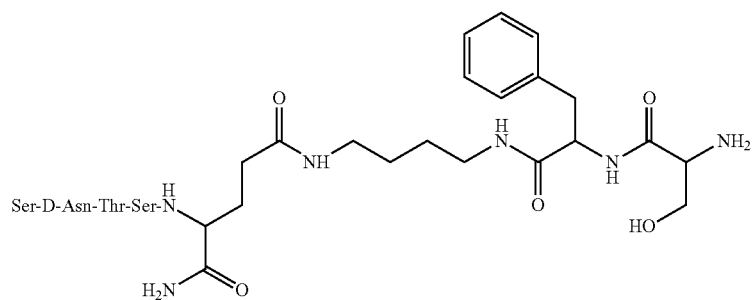
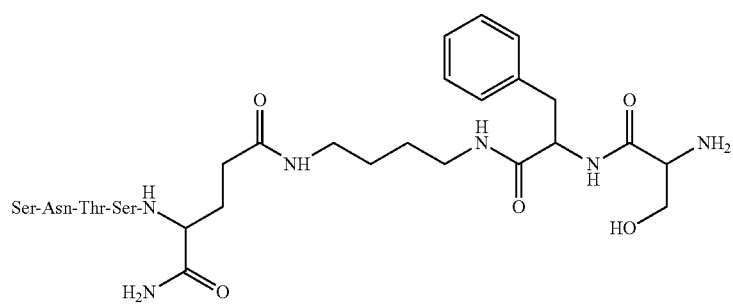

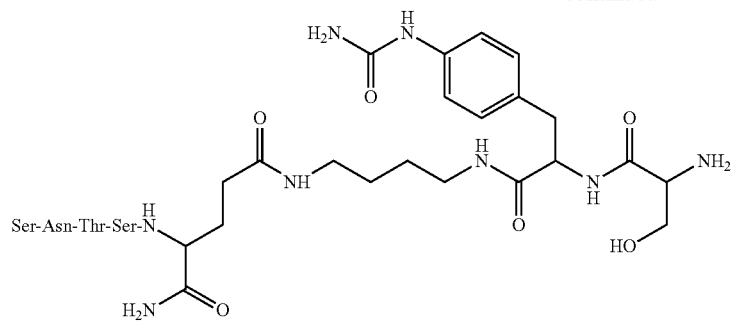
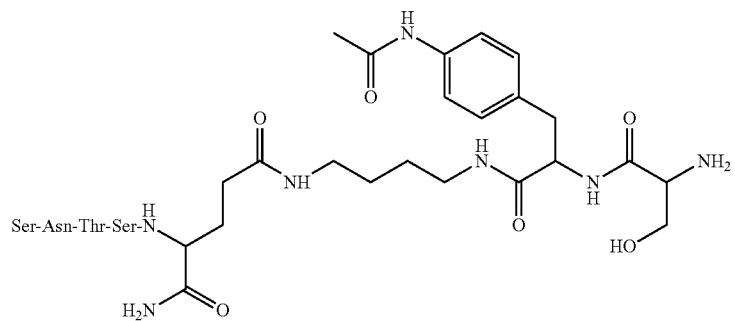
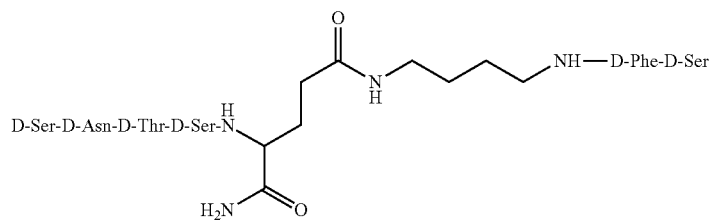
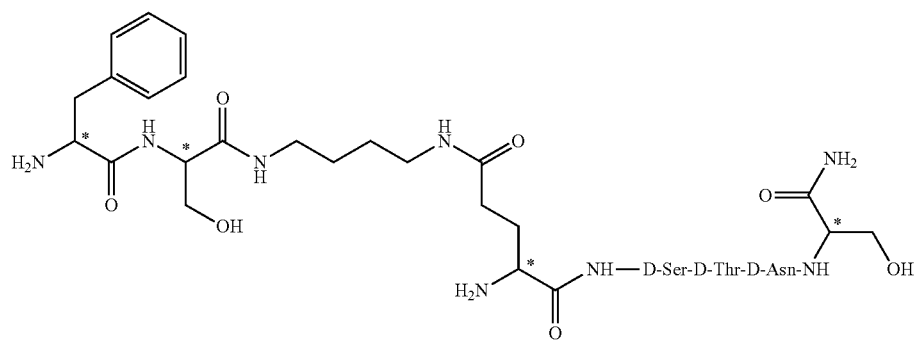
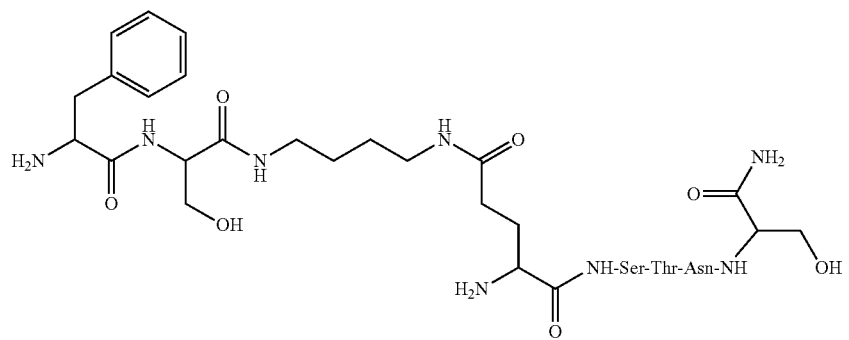

-continued
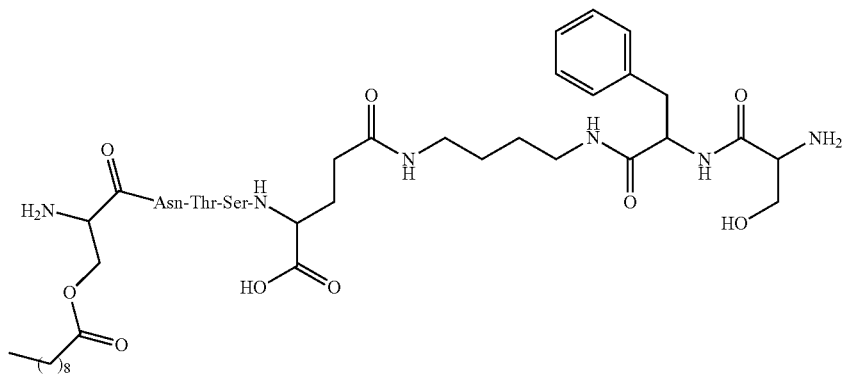
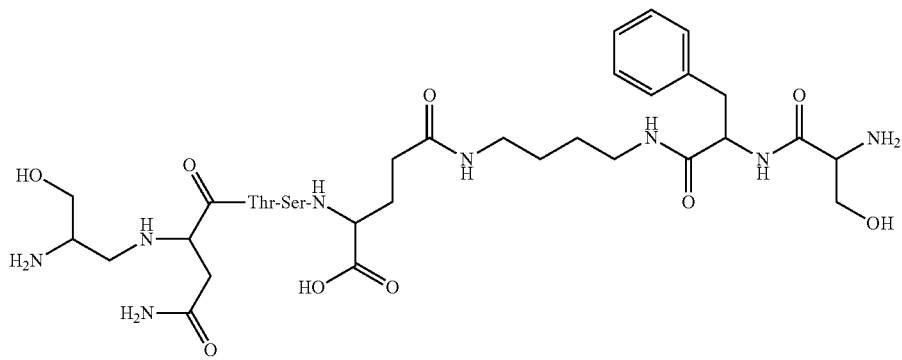
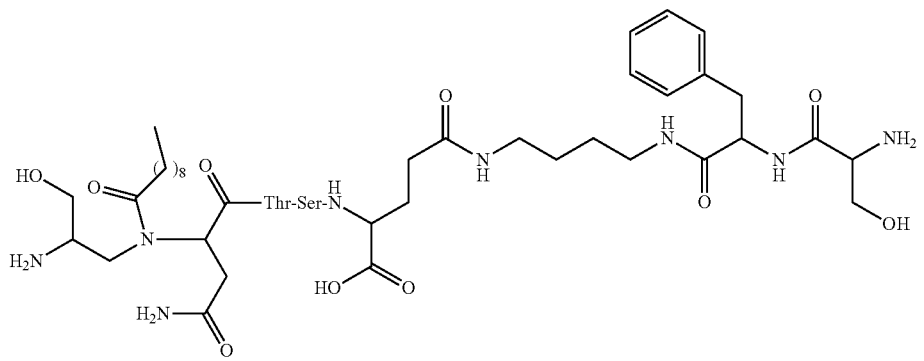
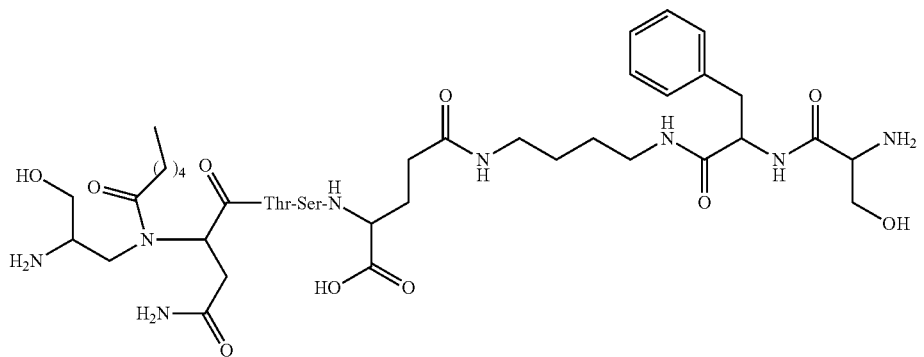

-continued
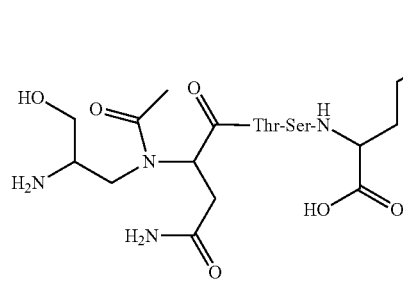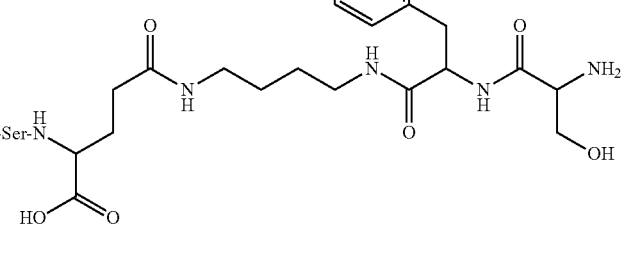
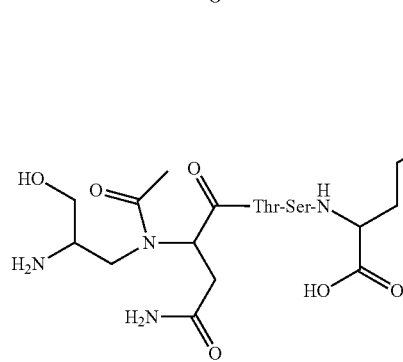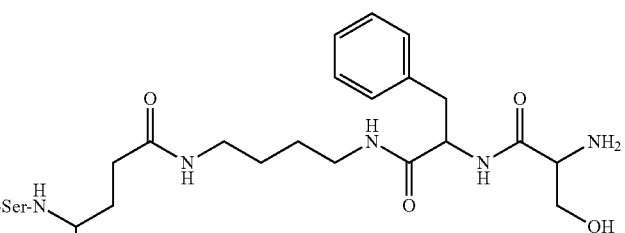
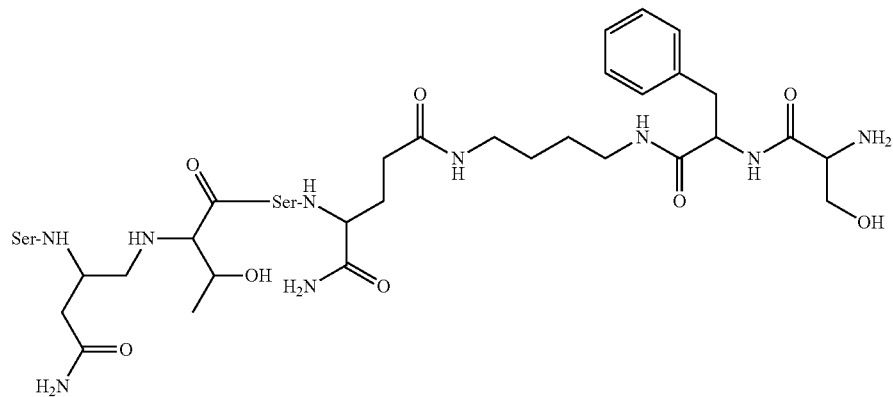
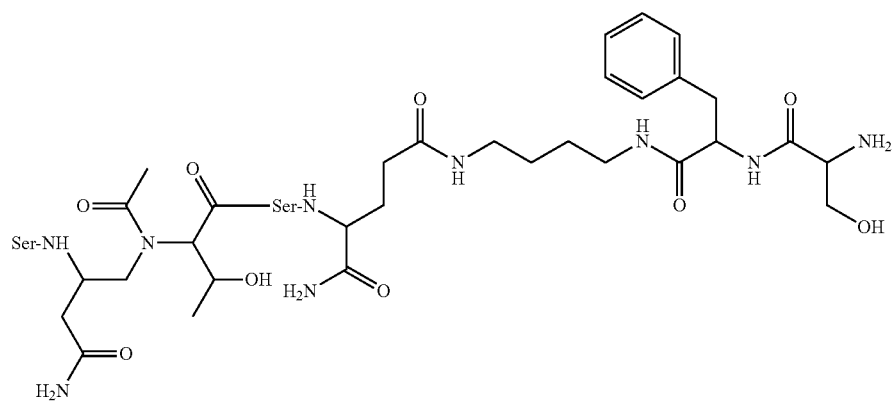

-continued
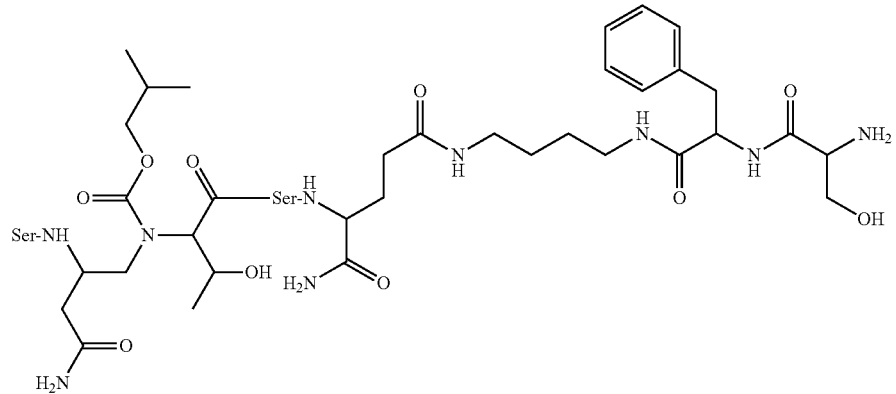
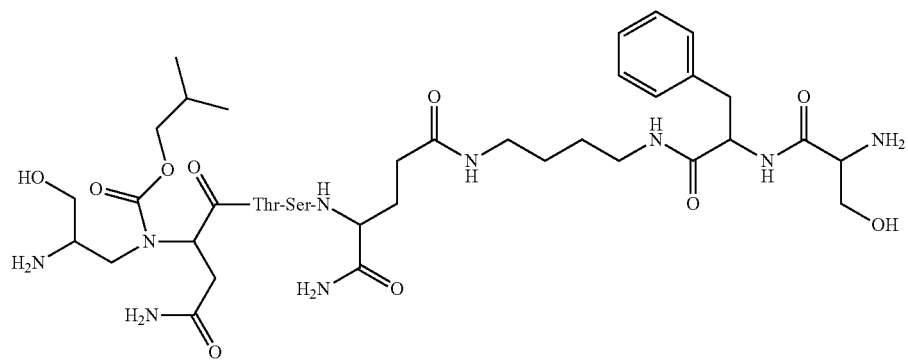
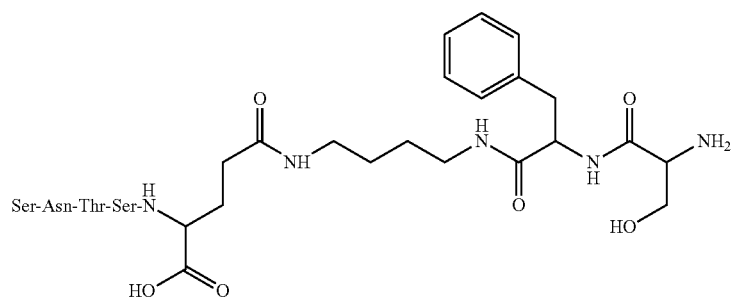
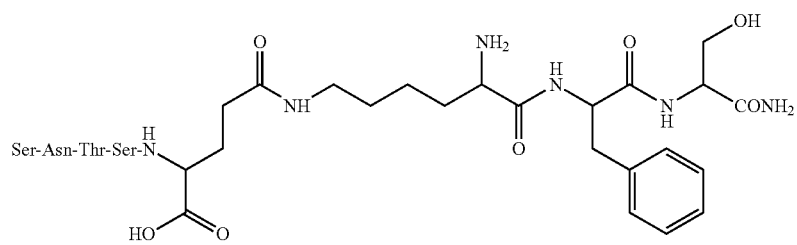
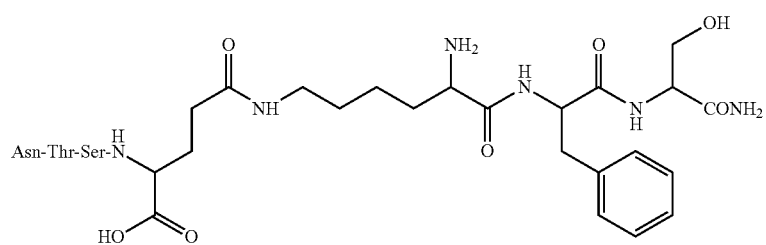

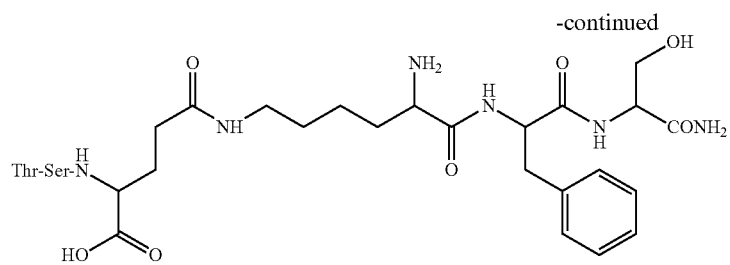

CTLA-4 Antagonists

In certain embodiments, a combination described herein also includes a CTLA-4 inhibitor. Exemplary anti-CTLA-4 antibodies include Tremelimumab (IgG2 monoclonal antibody available from Pfizer, formerly known as ticilimumab, CP-675,206); and Ipilimumab (CTLA-4 antibody, also known as MDX-010, CAS No. 477202-00-9).

Information regarding tremelimumab (or antigen-binding fragments thereof) for use in the methods provided herein can be found in U.S. Pat. No. 6,682,736 (incorporated by reference) (where it is referred to as 11.2.1), the disclosure of which is incorporated herein by reference in its entirety. Tremelimumab (also known as CP-675,206, CP-675, CP-675206, and ticilimumab) is a human IgG2 monoclonal antibody that is highly selective for CTLA-4 and blocks binding of CTLA-4 to CD80 (B7.1) and CD86 (B7.2). It has been shown to result in immune activation in vitro and some patients treated with tremelimumab have shown tumor regression.

Tremelimumab for use in the methods provided herein comprises a heavy chain and a light chain or a heavy chain variable region and a light chain variable region. In a specific aspect, tremelimumab or an antigen-binding fragment thereof for use in the methods provided herein comprises a light chain variable region comprising the amino acid sequences shown herein above and a heavy chain variable region comprising the amino acid sequence shown herein above. In a specific aspect, tremelimumab or an antigen-binding fragment thereof for use in the methods provided herein comprises a heavy chain variable region and a light chain variable region, wherein the heavy chain variable region comprises the Kabat-defined CDR1, CDR2, and CDR3 sequences shown herein above, and wherein the light chain variable region comprises the Kabat-defined CDR1, CDR2, and CDR3 sequences shown herein above. Those of ordinary skill in the art would easily be able to identify Chothia-defined, Abm-defined or other CDR definitions known to those of ordinary skill in the art. In a specific aspect, tremelimumab or an antigen-binding fragment thereof for use in the methods provided herein comprises the variable heavy chain and variable light chain CDR sequences of the antibody as disclosed in U.S. Pat. No. 6,682,736, which is herein incorporated by reference in its entirety.

The present invention also contemplates utilizing small molecule inhibitors of CTLA-4, such as described by Huxley et al. 2004 Cell Chemical Biology 11:1651-1658, which includes compounds of the formula:

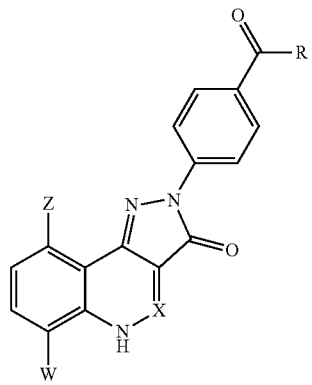

| Compound | W | Z | X  | R |
|---|---|---|---|---|
| 1 | F | H | CH | OH |
| 2 | F | H | CH | NHCH$_2$CH$_2$CH$_2$NMe$_2$ |
| 3 | H | H | N  | 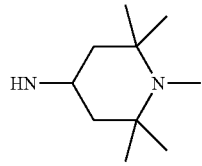 |
| 4 | F | H | N  | 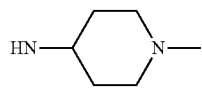 |
| 5 | F | H | N  | 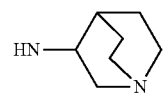 |
| 6 | F | F | N  | 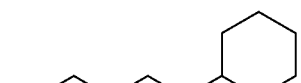 |

Other small molecule CTLA-4 antagonists include

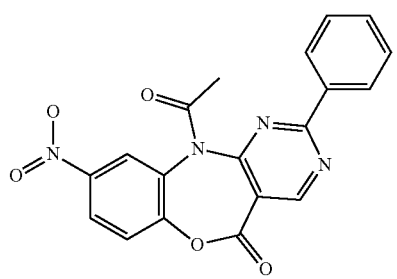

-continued

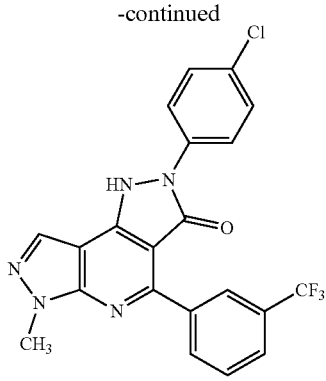

In one embodiment, the combination includes an immuno-DASH inhibitor, an anti-PD-1 antibody molecule, e.g., as described herein, and an anti-CTLA-4 antibody, e.g., ipilimumab. Exemplary doses that can be use include a dose of anti-PD-1 antibody molecule of about 1 to 10 mg/kg, e.g., 3 mg/kg, and a dose of an anti-CTLA-4 antibody, e.g., ipilimumab, of about 3 mg/kg.

Other exemplary anti-CTLA-4 antibodies are disclosed, e.g., in U.S. Pat. No. 5,811,097. In some embodiments of the methods described herein, the additional therapeutic agent is an antibody that modulates the immune response. In some embodiments, the additional therapeutic agent is an anti-PD-1 antibody, an anti-LAG-3 antibody, an anti-CTLA-4 antibody, an anti-TIM-3 antibody, an anti-TIGIT antibody, or an anti-Siglec-15 antibody.

In some embodiments, the LAG3 antibody is IMP701, IMP731, BMS-986016, LAG525, and GSK2831781. In some embodiments, the LAG3 antagonist includes a soluble LAG3 receptor, for example, IMP321.

In some embodiments, an immune response stimulating agent is selected from the group consisting of: a CD28 agonist, a 4-1BB agonist, an OX40 agonist, a CD27 agonist, a CD80 agonist, a CD86 agonist, a CD40 agonist, and a GITR agonist. In some embodiments, the OX40 agonist includes OX40 ligand, or an OX40-binding portion thereof. For example, the OX40 agonist may be MED16383. In some embodiments, the OX40 agonist is an antibody that specifically binds OX40. In some embodiments, the antibody that binds OX40 is MED16469, MED10562, or MOXR0916 (RG7888). In some embodiments, the OX40 agonist is a vector (e.g., an expression vector or virus, such as an adenovirus) capable of expressing OX40 ligand. In some embodiments the OX40-expressing vector is Delta-24-RG-DOX or DNX2401.

In some embodiments, the 4-1BB (CD137) agonist is a binding molecule, such as an anticalin. In some embodiments, the anticalin is PRS-343. In some embodiments, the 4-1BB agonist is an antibody that specifically binds 4-1BB. In some embodiments, antibody that binds 4-1BB is PF-2566 (PF-05082566) or urelumab (BMS-663513).

In some embodiments, the CD27 agonist is an antibody that specifically binds CD27. In some embodiments, the antibody that binds CD27 is varlilumab (CDX-1127).

In some embodiments, the GITR agonist comprises GITR ligand or a GITR-binding portion thereof.

In some embodiments, the GITR agonist is an antibody that specifically binds GITR. In some embodiments, the antibody that binds GITR is TRX518, MK-4166, or INBRX-110.

In certain embodiments, an anti-CD39 antibody is combined with STING agonist, preferably as part of a pharmaceutical composition. The cyclic-di-nucleotides (CDNs) cyclic-di-AMP (produced by Listeria monocytogenes and other bacteria) and its analogs cyclic-di-GMP and cyclic-GMP-AMP are recognized by the host cell as a pathogen associated molecular pattern (PAMP), which bind to the pathogen recognition receptor (PRR) known as Stimulator of INterferon Genes (STING). STING is an adaptor protein in the cytoplasm of host mammalian cells which activates the TANK binding kinase (TBK1)-IRF3 and the NF-κB signaling axis, resulting in the induction of IFN-3 and other gene products that strongly activate innate immunity. It is now recognized that STING is a component of the host cytosolic surveillance pathway (Vance et al., 2009), that senses infection with intracellular pathogens and in response induces the production of IFN-β, leading to the development of an adaptive protective pathogen-specific immune response consisting of both antigen-specific CD4+ and CD8+ T cells as well as pathogen-specific antibodies. U.S. Pat. Nos. 7,709,458 and 7,592,326; PCT Publication Nos. WO2007/054279, WO2014/093936, WO2014/179335, WO2014/189805, WO2015/185565, WO2016/096174, WO2016/145102, WO2017/027645, WO2017/027646, and WO2017/075477; and Yan et al., Bioorg. Med. Chem Lett. 18:5631-4, 2008.

Exemplary Combinations

In a preferred embodiment, the invention is directed to the combination of an anti-CD39 antibody with an antitumor platinum coordination complex in the treatment of cancer, and more particularly in the treatment of a cancer selected from lung cancer, sarcoma, malignant melanoma, prostate cancer, pancreas carcinoma, gastric carcinoma, ovarian cancer, hepatoma, breast cancer, colorectal cancer, kidney cancer, brain cancer and lymphoma. This chemotherapeutic group includes, but is not limited to cisplatin, oxaliplatin, carboplatin, triplatin tetranitrate (BBR3464), satraplatin, tetraplatin, ormiplatin, iproplatin, nedaplatin and lobaplatin.

Particularly preferred is the combination of an anti-CD39 antibody with cisplatin, oxaliplatin, carboplatin, triplatin tetranitrate, satraplatin, tetraplatin, ormiplatin, iproplatin, nedaplatin and lobaplatin, and even more preferred is the combination with cisplatin and oxaliplatin in the treatment of cancer, and more particularly in the treatment of a cancer selected from lung cancer, sarcoma, malignant melanoma, prostate cancer, pancreas carcinoma, gastric carcinoma, ovarian cancer, hepatoma, breast cancer, colorectal cancer, kidney cancer and brain cancer. In another preferred embodiment, the invention is directed to the combination of an anti-CD39 antibody with an antimetabolite in the treatment of cancer, and more particularly in the treatment of a cancer selected from lung cancer, sarcoma, malignant melanoma, bladder carcinoma, prostate cancer, pancreas carcinoma, gastric carcinoma, ovarian cancer, hepatoma, breast cancer, colorectal cancer, kidney cancer, esophageal cancer, brain cancer, anal cancer, leukaemia and lymphoma. This chemotherapeutic group includes, but is not limited to 5-fluorouracil, gemcitabine, cytarabine, capecitabine, decitabine, floxuridine, fludarabine, aminopterin, methotrexate, pemetrexed, raltitrexed, cladribine, clofarabine, mercaptopurine, pentostatin, and thioguanine. Particularly preferred is the combination of an anti-CD39 antibody with 5-fluorouracil, gemcitabine, cytarabine, capecitabine, decitabine, floxuridine, fludarabine, aminopterin, methotrexate, pemetrexed, raltitrexed, cladribine, clofarabine, mercaptopurine, pentostatin, and thioguanine, and even more preferred is the combination with 5-fluorouracil, gemcitabine, cytarabine and methotrexate in the treatment of cancer, and more particularly in the treatment of a cancer selected from lung cancer, sarcoma, malignant melanoma, prostate cancer, pancreas carcinoma, gastric carcinoma, ovarian cancer, hepatoma, breast cancer, colorectal cancer, kidney cancer, brain cancer, leukemia and lymphoma.

In another preferred embodiment, the invention is directed to the combination of an anti-CD39 antibody with a mitotic inhibitor in the treatment of cancer, and more particularly in the treatment of a cancer selected from lung cancer, sarcoma, prostate cancer, gastric carcinoma, ovarian cancer, hepatoma, breast cancer, colorectal cancer, kidney cancer, brain cancer, leukemia, and lymphoma. This chemotherapeutic group includes, but is not limited to paclitaxel, docetaxel, vinblastine, vincristine, vindesine, and vinorelbine. Particularly preferred is the combination of an anti-CD39 antibody with paclitaxel, docetaxel, vinblastine, vincristine, vindesine, and vinorelbine, and even more preferred is the combination with paclitaxel, docetaxel, vincristine and vinorelbine in the treatment of cancer, and more particularly in the treatment of a cancer selected from lung cancer, sarcoma, prostate cancer, gastric carcinoma, ovarian cancer, hepatoma, breast cancer, colorectal cancer, kidney cancer and brain cancer.

In another preferred embodiment, the invention is directed to the combination of anti-CD39 antibody with an anticancer antibiotic in the treatment of cancer, and more particularly in the treatment of lung cancer, sarcoma, malignant melanoma, bladder carcinoma, prostate cancer, pancreas carcinoma, thyroid cancer, gastric carcinoma, ovarian cancer, hepatoma, breast cancer, colorectal cancer, kidney cancer, neuroblastoma, brain cancer, anal cancer, testicular cancer, leukemia, multiple myeloma and lymphoma. This chemotherapeutic group includes, but is not limited to daunorubicin, doxorubicin, epirubicin, idarubicin, mitoxantrone, pixantrone, valrubicin, mitomycin C, bleomycin, actinomycin A and mithramycin. Particularly preferred is the combination of an anti-CD39 antibody with daunorubicin, doxorubicin, epirubicin, idarubicin, mitoxantrone, pixantrone, valrubicin, mitomycin C, bleomycin, actinomycin D and mithramycin, and even more preferred is the combination with daunorubicin, doxorubicin, mitomycin C and actinomycin D in the treatment of cancer, and more particularly in the treatment of lung cancer, sarcoma, malignant melanoma, prostate cancer, pancreas carcinoma, gastric carcinoma, ovarian cancer, hepatoma, breast cancer, colorectal cancer, kidney cancer, brain cancer, leukemia and lymphoma.

In another preferred embodiment, the invention is directed to the combination of anti-CD39 antibody with a topoisomerase I and/or II inhibitor in the treatment of cancer, and more particularly in the treatment of lung cancer, sarcoma, malignant melanoma, prostate cancer, pancreas carcinoma, gastric carcinoma, ovarian cancer, hepatoma, breast cancer, colorectal cancer, kidney cancer, neuroblastoma, brain cancer, cervical cancer, testicular cancer, leukemia and lymphoma. This chemotherapeutic group includes, but is not limited to topotecan, SN-38, irinotecan, camptothecin, rubitecan, etoposide, amsacrine and teniposide. Particularly preferred is the combination of PM00104, or a pharmaceutically acceptable salt thereof, with topotecan, SN-38, irinotecan, camptothecin, rubitecan, etoposide, amsacrine and teniposide, and even more preferred is the combination with topotecan, irinotecan and etoposide in the treatment of cancer, and more particularly in the treatment of lung cancer, sarcoma, malignant melanoma, prostate cancer, pancreas carcinoma, gastric carcinoma, ovarian cancer, hepatoma, breast cancer, colorectal cancer, kidney cancer, and brain cancer.

In another preferred embodiment, the invention is directed to the combination of an anti-CD39 antibody with a proteosome inhibitor in the treatment of cancer, and more particularly in the treatment of lung cancer, prostate cancer, pancreas carcinoma, gastric carcinoma, hepatoma, colorectal cancer, brain cancer, multiple myeloma and lymphoma. This chemotherapeutic group includes, but is not limited to bortezomib, disulfiram, epigallocatechin gallate, and salinosporamide A. Particularly preferred is the combination of an anti-CD39 antibody with bortezomib, disulfiram, epigallocatechin gallate, and salinosporamide A, and even more preferred is the combination with bortezomib in the treatment of cancer, and more particularly in the treatment of lung cancer, prostate cancer, pancreas carcinoma, gastric carcinoma, hepatoma, colorectal cancer and brain cancer.

In another preferred embodiment, the invention is directed to the combination of an anti-CD39 antibody with a histone deacetylase inhibitor in the treatment of cancer, and more particularly in the treatment of lung cancer, sarcoma, prostate cancer, pancreas carcinoma, gastric carcinoma, ovarian cancer, breast cancer, colorectal cancer, kidney cancer, brain cancer and lymphoma. This chemotherapeutic group includes, but is not limited to romidepsin, panobinostat, vorinostat, mocetinostat, belinostat, entinostat, resminostat, PCI-24781, AR-42, CUDC-101, and valproic acid. Particularly preferred is the combination of an anti-CD39 antibody with romidepsin, panobinostat, vorinostat, mocetinostat, belinostat, entinostat, resminostat, PCI-24781, AR-42, CUDC-101, and valproic acid, and even more preferred is the combination with vorinostat in the treatment of cancer, and more particularly in the treatment of lung cancer, sarcoma, prostate cancer, pancreas carcinoma, gastric carcinoma, ovarian cancer, breast cancer, colorectal cancer, kidney cancer and brain cancer.

In another preferred embodiment, the invention is directed to the combination of an anti-CD39 antibody with a nitrogen mustard alkylating agent in the treatment of cancer, and more particularly in the treatment of lung cancer, sarcoma, bladder carcinoma, gastric carcinoma, ovarian cancer, hepatoma, breast cancer, colorectal cancer, kidney cancer, leukemia, multiple myeloma and lymphoma. This chemotherapeutic group includes, but is not limited to melphalan, ifosfamide, chlorambucil, cyclophosphamide, mechlorethamine, uramustine, estramustine and bendamustine. Particularly preferred is the combination of an anti-CD39 antibody with melphalan, ifosfamide, chlorambucil, cyclophosphamide, mechlorethamine, uramustine, estramustine and bendamustine, and even more preferred is the combination with cyclophosphamide in the treatment of cancer, and more particularly in the treatment of lung cancer, sarcoma, gastric carcinoma, ovarian cancer, hepatoma, breast cancer, colorectal cancer and kidney cancer. In another preferred embodiment, the invention is directed to the combination of an anti-CD39 antibody with a nitrosourea alkylating agent in the treatment of cancer, and more particularly in the treatment of lung cancer, ovarian cancer, breast cancer, brain cancer, multiple myeloma and lymphoma. This chemotherapeutic group includes, but is not limited to lomustine, semustine, carmustine, fotemustine and streptozotocin. Particularly preferred is the combination of an anti-CD39 antibody with lomustine, semustine, carmustine, fotemustine and streptozotocin, and even more preferred is the combination with carmustine in the treatment of cancer, and more particularly in the treatment of lung cancer, ovarian cancer and breast cancer.

In another preferred embodiment, the invention is directed to the combination of an anti-CD39 antibody with a nonclassical alkylating agent in the treatment of cancer, and more particularly in the treatment of lung cancer, sarcoma, malignant melanoma, pancreas carcinoma, gastric carcinoma, ovarian cancer, breast cancer, colorectal cancer, kidney cancer, brain cancer, leukemia and lymphoma. This chemotherapeutic group includes, but is not limited to procarbazine, dacarbazine, temozolomide and altretamine. Particularly preferred is the combination of an anti-CD39 antibody with procarbazine, dacarbazine, temozolomide and altretamine, and even more preferred is the combination with dacarbazine and tezolomide in the treatment of lung cancer, sarcoma, malignant melanoma, gastric carcinoma, ovarian cancer, breast cancer, colorectal cancer, kidney cancer and brain cancer. In another preferred embodiment, the invention is directed to the combination of an anti-CD39 antibody with an estrogen antagonist in the treatment of cancer, and more particularly in the treatment of breast cancer. This chemotherapeutic group includes, but is not limited to toremifene, fulvestrant, tamoxifen and nafoxidine. Particularly preferred is the combination of an anti-CD39 antibody with toremifene, fulvestrant, tamoxifen and nafoxidine, and even more preferred is the combination with tamoxifen in the treatment of breast cancer.

In another preferred embodiment, the invention is directed to the combination of an anti-CD39 antibody with an androgen antagonist in the treatment of cancer, and more particularly in the treatment of prostate cancer. This chemotherapeutic group includes, but is not limited to bicalutamide, flutamide, MDV3100 and nilutamide. Particularly preferred is the combination of an anti-CD39 antibody with bicalutamide, flutamide, MDV3100 and nilutamide, and even more preferred is the combination with flutamide in the treatment of prostate cancer.

In another preferred embodiment, the invention is directed to the combination of an anti-CD39 antibody with a mTOR inhibitor in the treatment of cancer, and more particularly in the treatment of lung cancer, sarcoma, malignant melanoma, prostate cancer, pancreas carcinoma, gastric carcinoma, ovarian cancer, breast cancer, colorectal cancer, kidney cancer and brain cancer. This chemotherapeutic group includes, but is not limited to sirolimus, temsirolimus, everolimus, ridaforolimus, KU-0063794 and WYE-354. Particularly preferred is the combination of an anti-CD39 antibody with sirolimus, temsirolimus, everolimus, ridaforolimus, KU-0063794 and WYE-354, and even more preferred is the combination with temsirolimus in the treatment of lung cancer, sarcoma, malignant melanoma, prostate cancer, pancreas carcinoma, gastric carcinoma, ovarian cancer, breast cancer, colorectal cancer and brain cancer.

In another preferred embodiment, the invention is directed to the combination of an anti-CD39 antibody with a tyrosine kinase inhibitor in the treatment of cancer, and more particularly in the treatment of a cancer selected from lung cancer, sarcoma, prostate cancer, pancreas carcinoma, gastric carcinoma, ovarian cancer, hepatoma, breast cancer, colorectal cancer, kidney cancer and brain cancer. This chemotherapeutic group includes, but is not limited to erlotinib, sorafenib, axitinib, bosutinib, cediranib, crizotinib, dasatinib, gefitinib, imatinib, canertinib, lapatinib, lestaurtinib, neratinib, nilotinib, semaxanib, sunitinib, vatalanib and vandetanib. Particularly preferred is the combination of an anti-CD39 antibody with erlotinib, sorafenib, axitinib, bosutinib, cediranib, crizotinib, dasatinib, gefitinib, imatinib, canertinib, lapatinib, lestaurtinib, neratinib, nilotinib, semaxanib, sunitinib, vatalanib and vandetanib, and even more preferred is the combination with erlotinib in the treatment of cancer, and more particularly in the treatment of a cancer selected from lung cancer, sarcoma, prostate cancer, pancreas carcinoma, gastric carcinoma, ovarian cancer, hepatoma, breast cancer, colorectal cancer, kidney cancer and brain cancer.

Another aspect encompassed by the present invention relates to any one of the foregoing methods, further comprising administering to the patient a MAP kinase pathway inhibitor or a WNT pathway inhibitor.

In some embodiments, the MAP kinase pathway inhibitor is selected from the group consisting of a BRAF inhibitor, a MEK inhibitor, a PI3K inhibitor and a c-KIT inhibitor.

In some embodiments, the BRAF inhibitor is selected from the group consisting of GDC-0879, PLX-4720, sorafenib tosylate, dabrafenib and LGX818.

In some embodiments, the MEK inhibitor is selected from the group consisting of GSK1120212, selumetinib and MEK162.

In some embodiments, the WNT pathway inhibitor is a β-catenin inhibitor or a frizzled inhibitor.

In some embodiments, the β-catenin inhibitor is selected from the group consisting of niclosamide, XAV-939, FH 535 and ICG 001.

Another aspect encompassed by the present invention relates to any one of the foregoing methods, further comprising administering to the patient a cancer vaccine. In some embodiments, the cancer vaccine is a dendritic cell vaccine.

Another aspect encompassed by the present invention relates to any one of the foregoing methods, further comprising administering to the patient an adoptive cell transfer.

In some embodiments, the adoptive cell transfer is a CAR-T cell therapy.

Another aspect encompassed by the present invention relates to any one of the foregoing methods, further comprising administering to the patient an antibody therapy.

Another aspect encompassed by the present invention relates to any one of the foregoing methods, wherein administration of the anti-CD39 antibody enhances antibody-dependent cell-mediated cytotoxicity of the antibody therapy.

In some embodiment, the antibody therapy is selected from the group consisting of trastuzamab, cetuximab, bevacizumab, and rituximab.

Furthermore, treatment with anti-CD39 antibody can include combination treatment with other biologic molecules, such as one or more cytokines (e.g., lymphokines, interleukins, tumor necrosis factors, and/or growth factors) or can be accompanied by surgical removal of tumors, removal of cancer cells, or any other therapy deemed necessary by a treating physician. In some embodiments, the additional therapeutic agent is an immune response stimulating agent.

In some embodiments of the methods described herein, the anti-CD39 antibody can be combined with a growth factor selected from the group consisting of: adrenomedullin (AM), angiopoietin (Ang), BMPs, BDNF, EGF, erythropoietin (EPO), FGF, GDNF, G-CSF, GM-CSF, GDF9, HGF, HDGF, IGF, migration-stimulating factor, myostatin (GDF-8), NGF, neurotrophins, PDGF, thrombopoietin, TGF-α, TGF-β, TNF-α, VEGF, P1GF, IL-1, IL-2, IL-3, IL-4, IL-5, IL-6, IL-7, IL-12, IL-15, and IL-18.

In some embodiments of the methods described herein, the additional therapeutic agent is an immune response stimulating agent. In some embodiments, the immune response stimulating agent is selected from the group consisting of granulocyte-macrophage colony stimulating factor (GM-CSF), macrophage colony stimulating factor (M-CSF), granulocyte colony stimulating factor (G-CSF), interleukin 3 (IL-3), interleukin 12 (IL-12), interleukin 1 (IL-1) or interleukin 2 (IL-2).

Administration Scheduling

In certain embodiments of the methods described herein, the treatment involves the administration of an anti-CD39 antibody in combination with radiation therapy. Treatment with an anti-CD39 antibody can occur prior to, concurrently with, or subsequent to administration of radiation therapy. Dosing schedules for such radiation therapy can be determined by the skilled medical practitioner.

In certain embodiments of the methods described herein, the treatment involves the administration of an anti-CD39 antibody in combination with anti-viral therapy. Treatment with an anti-CD39 antibody can occur prior to, concurrently with, or subsequent to administration of antiviral therapy. The anti-viral drug used in combination therapy will depend upon the virus the subject is infected with.

Combined administration can include co-administration, either in a single pharmaceutical formulation or using separate formulations, or consecutive administration in either order but generally within a time period such that all active agents can exert their biological activities simultaneously.

It will be appreciated that the combination of an anti-CD39 antibody and at least one additional therapeutic agent may be administered in any order or concurrently. In some embodiments, the anti-CD39 antibody will be administered to patients that have previously undergone treatment with a second therapeutic agent. In certain other embodiments, the anti-CD39 antibody and a second therapeutic agent will be administered substantially simultaneously or concurrently. For example, a subject may be given an anti-CD39 antibody while undergoing a course of treatment with a second therapeutic agent (e.g., chemotherapy). In certain embodiments, an anti-CD39 antibody will be administered within 1 year of the treatment with a second therapeutic agent. In certain alternative embodiments, an anti-CD39 antibody will be administered within 10, 8, 6, 4, or 2 months of any treatment with a second therapeutic agent. In certain other embodiments, an anti-CD39 antibody will be administered within 4, 3, 2, or 1 weeks of any treatment with a second therapeutic agent. In some embodiments, an anti-CD39 antibody will be administered within 5, 4, 3, 2, or 1 days of any treatment with a second therapeutic agent. It will further be appreciated that the two (or more) agents or treatments may be administered to the subject within a matter of hours or minutes (i.e., substantially simultaneously).

For the treatment of a disease, the appropriate dosage of an anti-CD39 antibody depends on the type of disease to be treated, the severity and course of the disease, the responsiveness of the disease, whether the anti-CD39 antibody is administered for therapeutic or preventative purposes, previous therapy, the patient's clinical history, and so on, all at the discretion of the treating physician. The anti-CD39 antibody can be administered one time or over a series of treatments lasting from several days to several months, or until a cure is effected or a diminution of the disease state is achieved (e.g., reduction in tumor size). Optimal dosing schedules can be calculated from measurements of drug accumulation in the body of the patient and will vary depending on the relative potency of an individual agent. The administering physician can determine optimum dosages, dosing methodologies, and repetition rates. In certain embodiments, dosage is from 0.01 μg to 100 mg/kg of body weight, from 0.1 μg to 100 mg/kg of body weight, from 1 μg to 100 mg/kg of body weight, from 1 mg to 100 mg/kg of body weight, 1 mg to 80 mg/kg of body weight from 10 mg to 100 mg/kg of body weight, from 10 mg to 75 mg/kg of body weight, or from 10 mg to 50 mg/kg of body weight. In certain embodiments, the dosage of the anti-CD39 antibody is from about 0.1 mg to about 20 mg/kg of body weight. In some embodiments, the dosage of the anti-CD39 antibody is about 0.1 mg/kg of body weight. In some embodiments, the dosage of the anti-CD39 antibody is about 0.25 mg/kg of body weight. In some embodiments, the dosage of the anti-CD39 antibody is about 0.5 mg/kg of body weight. In some embodiments, the dosage of the anti-CD39 antibody is about 1 mg/kg of body weight. In some embodiments, the dosage of the anti-CD39 antibody is about 1.5 mg/kg of body weight. In some embodiments, the dosage of the anti-CD39 antibody is about 2 mg/kg of body weight. In some embodiments, the dosage of the anti-CD39 antibody is about 2.5 mg/kg of body weight. In some embodiments, the dosage of the anti-CD39 antibody is about 5 mg/kg of body weight. In some embodiments, the dosage of the anti-CD39 antibody is about 7.5 mg/kg of body weight. In some embodiments, the dosage of the anti-CD39 antibody is about 10 mg/kg of body weight. In some embodiments, the dosage of the anti-CD39 antibody is about 12.5 mg/kg of body weight. In some embodiments, the dosage of the anti-CD39 antibody is about 15 mg/kg of body weight. In certain embodiments, the dosage can be given once or more daily, weekly, monthly, or yearly. In certain embodiments, the anti-CD39 antibody is given once every week, once every two weeks, once every three weeks, or once every four weeks.

In some embodiments, an anti-CD39 antibody may be administered at an initial higher "loading" dose, followed by one or more lower doses. In some embodiments, the frequency of administration may also change. In some embodiments, a dosing regimen may comprise administering an initial dose, followed by additional doses (or "maintenance" doses) once a week, once every two weeks, once every three weeks, or once every month. For example, a dosing regimen may comprise administering an initial loading dose, followed by a weekly maintenance dose of, for example, one-half of the initial dose. Or a dosing regimen may comprise administering an initial loading dose, followed by maintenance doses of, for example one-half of the initial dose every other week. Or a dosing regimen may comprise administering three initial doses for 3 weeks, followed by maintenance doses of, for example, the same amount every other week.

As is known to those of skill in the art, administration of any therapeutic agent may lead to side effects and/or toxicities. In some cases, the side effects and/or toxicities are so severe as to preclude administration of the particular agent at a therapeutically effective dose. In some cases, drug therapy must be discontinued, and other agents may be tried. However, many agents in the same therapeutic class often display similar side effects and/or toxicities, meaning that the patient either has to stop therapy, or if possible, suffer from the unpleasant side effects associated with the therapeutic agent.

In some embodiments, the dosing schedule may be limited to a specific number of administrations or "cycles". In some embodiments, the anti-CD39 antibody is administered for 3, 4, 5, 6, 7, 8, or more cycles. For example, the anti-CD39 antibody is administered every 2 weeks for 6 cycles, the anti-CD39 antibody is administered every 3 weeks for 6 cycles, the anti-CD39 antibody is administered every 2 weeks for 4 cycles, the anti-CD39 antibody is administered every 3 weeks for 4 cycles, etc. Dosing schedules can be decided upon and subsequently modified by those skilled in the art.

Thus, the present invention provides methods of administering to a subject the anti-CD39 antibody described herein comprising using an intermittent dosing strategy for administering one or more agents, which may reduce side effects and/or toxicities associated with administration of an anti-CD39 antibody, chemotherapeutic agent, etc. In some embodiments, a method for treating cancer in a human subject comprises administering to the subject a therapeutically effective dose of an anti-CD39 antibody in combination with a therapeutically effective dose of a chemotherapeutic agent, wherein one or both of the agents are administered according to an intermittent dosing strategy. In some embodiments, the intermittent dosing strategy comprises administering an initial dose of an anti-CD39 antibody to the subject, and administering subsequent doses of the anti-CD39 antibody about once every 2 weeks. In some embodiments, the intermittent dosing strategy comprises administering an initial dose of an anti-CD39 antibody to the subject, and administering subsequent doses of the anti-CD39 antibody about once every 3 weeks. In some embodiments, the intermittent dosing strategy comprises administering an initial dose of an anti-CD39 antibody to the subject, and administering subsequent doses of the anti-CD39 antibody about once every 4 weeks. In some embodiments, the anti-CD39 antibody is administered using an intermittent dosing strategy and the chemotherapeutic agent is administered weekly.

Anti-infective Therapeutic Combinations

In an embodiment, the invention provides methods for treating subjects using an anti-CD39 antibody, wherein the subject suffers from a viral infection. In one embodiment, the viral infection is infection with a virus selected from the group consisting of human immunodeficiency virus (HIV), hepatitis virus (A, B, or C), herpes virus (e.g., VZV, HSV-I, HAV-6, HSV-II, and CMV, Epstein Barr virus), adenovirus, influenza virus, flaviviruses, echovirus, rhinovirus, coxsackie virus, coronavirus, respiratory syncytial virus, mumps virus, rotavirus, measles virus, rubella virus, parvovirus, vaccinia virus, HTLV virus, dengue virus, papillomavirus, molluscum virus, poliovirus, rabies virus, JC virus or arboviral encephalitis virus.

In an embodiment, the invention provides methods for treating subjects using an anti-CD39 antibody, wherein the subject suffers from a bacterial infection. In one embodiment, the bacterial infection is infection with a bacterium selected from the group consisting of *Chlamydia*, rickettsial bacteria, mycobacteria, staphylococci, streptococci, pneumonococci, meningococci and gonococci, *klebsiella, proteus, serratia, pseudomonas, Legionella, Corynebacterium diphtheriae, Salmonella*, bacilli, *Vibrio cholerae, Clostridium tetan, Clostridium botulinum, Bacillus anthricis, Yersinia pestis, Mycobacterium leprae, Mycobacterium lepromatosis*, and Borriella.

In an embodiment, the invention provides methods for treating subjects using an anti-CD39 antibody, wherein the subject suffers from a fungal infection. In one embodiment, the fungal infection is infection with a fungus selected from the group consisting of *Candida (albicans, krusei, glabrata, tropicalis*, etc.), *Cryptococcus neoformans, Aspergillus (fumigatus, niger*, etc.), Genus Mucorales (*mucor, absidia, rhizopus*), *Sporothrix schenkii, Blastomyces dermatitidis, Paracoccidioides brasiliensis, Coccidioides immitis* and *Histoplasma capsulatum*.

In an embodiment, the invention provides methods for treating subjects using an anti-CD39 antibody, wherein the subject suffers from a parasitic infection. In one embodiment, the parasitic infection is infection with a parasite selected from the group consisting of *Entamoeba histolytica, Balantidium coli, Naegleria fowleri, Acanthamoeba, Giardia lambia, Cryptosporidium, Pneumocystis carinii, Plasmodium vivax, Babesia microti, Trypanosoma brucei, Trypanosoma cruzi, Leishmania donovani, Toxoplasma gondii* and *Nippostrongylus brasiliensis*.

VII. Anti-CD39 Antibody Conjugates

The anti-CD39 antibodies disclosed herein may also be conjugated to a chemical moiety. The chemical moiety may be, inter alia, a polymer, a radionuclide or a cytotoxic factor.

For instance, the present invention provides an anti-CD39 antibody conjugated to a therapeutic moiety, i.e. a drug. The therapeutic moiety can be, e.g., a cytotoxin, a chemotherapeutic agent, a cytokine, an immunosuppressant, an immune stimulator, a lytic peptide, or a radioisotope. Such conjugates are referred to herein as an "antibody-drug conjugates" or "ADCs". Accordingly, in one aspect, the anti-CD39 antibody according to any above-described aspect or embodiment is conjugated to a therapeutic moiety. Exemplary therapeutic moieties include a cytotoxic moiety, a radioisotope, a cytokine, and a lytic peptide.

In certain embodiments, the anti-CD39 antibody is capable of inducing cytotoxicity in a CD39-expressing cells by internalization of the antibody conjugated to or associated with a cytotoxic moiety. The cytotoxic moiety may, for example, be selected from the group consisting of taxol; cytochalasin B; gramicidin D; ethidium bromide; emetine; mitomycin; etoposide; tenoposide; vincristine; vinblastine; colchicin; doxorubicin; daunorubicin; dihydroxy anthracin dione; a tubulin-inhibitor such as maytansine or an analog or derivative thereof; an antimitotic agent such as monomethyl auristatin E or F or an analog or derivative thereof; dolastatin 10 or 15 or an analogue thereof; irinotecan or an analogue thereof; mitoxantrone; mithramycin; actinomycin D; 1-dehydrotestosterone; a glucocorticoid; procaine; tetracaine; lidocaine; propranolol; puromycin; calicheamicin or an analog or derivative thereof; an antimetabolite such as methotrexate, 6 mercaptopurine, 6 thioguanine, cytarabine, fludarabin, 5 fluorouracil, decarbazine, hydroxyurea, asparaginase, gemcitabine, or cladribine; an alkylating agent such as mechlorethamine, thioepa, chlorambucil, melphalan, carmustine (BSNU), lomustine (CCNU), cyclophosphamide, busulfan, dibromomannitol, streptozotocin, dacarbazine (DTIC), procarbazine, mitomycin C; a platinum derivative such as cisplatin or carboplatin; duocarmycin A, duocarmycin SA, rachelmycin (CC-1065), or an analog or derivative thereof; an antibiotic such as dactinomycin, bleomycin, daunorubicin, doxorubicin, idarubicin, mithramycin, mitomycin, mitoxantrone, plicamycin, anthramycin (AMC)); pyrrolo[2,1-c][1,4]-benzodiazepines (PDB); diphtheria toxin and related molecules such as diphtheria A chain and active fragments thereof and hybrid molecules, ricin toxin such as ricin A or a deglycosylated ricin A chain toxin, cholera toxin, a Shiga-like toxin such as SLT I, SLT II, SLT IIV, LT toxin, C3 toxin, Shiga toxin, pertussis toxin, tetanus toxin, soybean Bowman-Birk protease inhibitor, *Pseudomonas* exotoxin, alorin, saporin, modeccin, gelanin, abrin A chain, modeccin A chain, alpha-sarcin, *Aleurites fordii* proteins, dianthin proteins, *Phytolacca americana* proteins such as PAPI, PAPII, and PAP-S, *Momordica charantia* inhibitor, curcin, crotin, *Sapaonaria officinalis* inhibitor, gelonin, mitogellin, restrictocin, phenomycin, and enomycin toxins; ribonuclease (RNase); DNase I, Staphylococcal enterotoxin A; pokeweed antiviral protein; diphtherin toxin; and *Pseudomonas* endotoxin.

In one embodiment, the anti-CD39 antibody is conjugated to an auristatin or a peptide analog, derivative or prodrug thereof. Auristatins have been shown to interfere with microtubule dynamics, GTP hydrolysis and nuclear and cellular division (Woyke et al (2001) Antimicrob. Agents and Chemother. 45(12): 3580-3584) and have anti-cancer (U.S. Pat. No. 5,663,149) and anti-fungal activity (Pettit et al., (1998) Antimicrob. Agents and Chemother. 42:2961-2965. For example, auristatin E can be reacted with para-acetyl benzoic acid or benzoylvaleric acid to produce AEB and AEVB, respectively. Other typical auristatin derivatives include AFP, MMAF (monomethyl auristatin F), and MMAE (monomethyl auristatin E). Suitable auristatins and auristatin analogs, derivatives and prodrugs, as well as suitable linkers for conjugation of auristatins to Abs, are described in, e.g., U.S. Pat. Nos. 5,635,483, 5,780,588 and 6,214,345 and in International patent application publications WO02088172, WO2004010957, WO2005081711, WO2005084390, WO2006132670, WO03026577, WO2005082023.

In another embodiment, the anti-CD39 antibody is conjugated to pyrrolo[2,1-c][1,4]-benzodiazepine (PDB) or an analog, derivative or prodrug thereof. Suitable PDBs and PDB derivatives, and related technologies are described in, e.g., Hartley J. A. et al., Cancer Res 2010; 70(17): 6849-6858; Antonow D. et al., Cancer J 2008; 14(3):154-169; Howard P. W. et al., Bioorg Med Chem Lett 2009; 19: 6463-6466 and Sagnou et al., Bioorg Med Chem Lett 2000; 10(18): 2083-2086.

In another embodiment, the anti-CD39 antibody is conjugated to a cytotoxic moiety selected from the group consisting of an anthracycline, maytansine, calicheamicin, duocarmycin, rachelmycin (CC-1065), dolastatin 10, dolastatin 15, irinotecan, monomethyl auristatin E, monomethyl auristatin F, a PDB, or an analog, derivative, or prodrug of any thereof.

In a particular embodiment, the anti-CD39 antibody is conjugated to an anthracycline or an analog, derivative or prodrug thereof. In another particular embodiment, the antibody is conjugated to maytansine or an analog, derivative or prodrug thereof. In another particular embodiment, the antibody is conjugated to calicheamicin or an analog, derivative or prodrug thereof. In another particular embodiment, the antibody is conjugated to duocarmycin or an analog, derivative or prodrug thereof. In another particular embodiment, the antibody is conjugated to rachelmycin (CC-1065) or an analog, derivative or prodrug thereof. In another particular embodiment, the antibody is conjugated to dolastatin 10 or an analog, derivative or prodrug thereof. In another particular embodiment, the antibody is conjugated to dolastatin 15 or an analog, derivative or prodrug thereof. In another particular embodiment, the antibody is conjugated to monomethyl auristatin E or an analog, derivative or prodrug thereof. In another particular embodiment, the antibody is conjugated to monomethyl auristatin F or an analog, derivative or prodrug thereof. In another particular embodiment, the antibody is conjugated to pyrrolo[2,1-c][1,4]-benzodiazepine or an analog, derivative or prodrug thereof. In another particular embodiment, the antibody is conjugated to irinotecan or an analog, derivative or prodrug thereof.

In one embodiment, an anti-CD39 antibody encompassed by the present invention is conjugated to a nucleic acid or nucleic acid-associated molecule. In one such embodiment, the conjugated nucleic acid is a cytotoxic ribonuclease (RNase) or deoxy-ribonuclease (e.g., DNase I), an antisense nucleic acid, an inhibitory RNA molecule (e.g., a siRNA molecule) or an immunostimulatory nucleic acid (e.g., an immunostimulatory CpG motif-containing DNA molecule). In another embodiment, a CD39-specific antibody encompassed by the present invention is conjugated to an aptamer or a ribozyme.

In one embodiment, an anti-CD39 antibody encompassed by the present invention is conjugated, e.g., as a fusion protein, to a lytic peptide such as CLIP, Magainin 2, mellitin, Cecropin and P18.

In one embodiment, the anti-CD39 antibody is conjugated to a cytokine, such as, e.g., IL-2, IL-4, IL-6, IL-7, IL-10, IL-12, IL-13, IL-15, IL-18, IL-23, IL-24, IL-27, IL-28a, IL-28b, IL-29, KGF, IFNα, IFNβ, IFNγ, GM-CSF, CD40L, Flt3 ligand, stem cell factor, ancestim, and TNFα.

In certain embodiments, the chemical moiety is a polymer which increases the half-life of the antibody or fragment in the body of a subject. Suitable polymers include, but are not limited to, hydrophilic polymers which include but are not limited to polyethylene glycol (PEG) (e.g., PEG with a molecular weight of 2 kDa, 5 kDa, 10 kDa, 12 kDa, 20 kDa, 30 kDa or 40 kDa), dextran and monomethoxypolyethylene glycol (mPEG). Lee, et al., (1999) (Bioconj. Chem. 10:973-981) discloses PEG conjugated single-chain antibodies. Wen, et al., (2001) (Bioconj. Chem. 12:545-553) disclose conjugating antibodies with PEG which is attached to a radiometal chelator (diethylenetriaminpentaacetic acid (DTPA)).

The anti-CD39 antibodies may also be conjugated with labels such as $^{99}$Tc, $^{90}$Y, $^{111}$In, $^{32}$P, $^{14}$C, $^{125}$I, $^3$H, 1311, $^{11}$C, 150, $^{13}$N, $^{18}$F, $^{35}$S, $^{51}$Cr, $^{57}$To, $^{226}$Ra, $^{60}$Co, $^{59}$Fe, $^{57}$Se, $^{152}$Eu, $^{67}$CU, $^{217}$Ci, $^{211}$At, $^{212}$Pb, $^{47}$Sc, $^{109}$Pd, $^{234}$Th, $^{40}$K, $^{157}$Gd, $^{55}$Mn, $^{52}$Tr, and $^{56}$Fe.

The anti-CD39 antibodies may also be conjugated with fluorescent or chemilluminescent labels, including fluorophores such as rare earth chelates, fluorescein and its derivatives, rhodamine and its derivatives, isothiocyanate, phycoerythrin, phycocyanin, allophycocyanin, o-phthaladehyde, fluorescamine, $^{152}$Eu, dansyl, umbelliferone, luciferin, luminal label, isoluminal label, an aromatic acridinium ester label, an imidazole label, an acridimium salt label, an oxalate ester label, an aequorin label, 2,3-dihydrophthalazinediones, biotin/avidin, spin labels and stable free radicals.

Any method known in the art for conjugating the antibodies and antigen-binding fragments thereof encompassed by the present invention to the various moieties may be employed, including those methods described by Hunter, et al., (1962) Nature 144:945; David, et al., (1974) Biochemistry 13:1014; Pain, et al., (1981) J. Immunol. Meth. 40:219; and Nygren, J., (1982) Histochem. and Cytochem. 30:407. Methods for conjugating antibodies and fragments are conventional and very well known in the art.

VIII. Pharmaceutical Compositions

Anti-CD39 antibodies, antibody fragments, nucleic acids, or vectors encompassed by the present invention can be formulated in compositions, especially pharmaceutical compositions. Such compositions comprise a therapeutically or prophylactically effective amount of an anti-CD39 antibody, antibody fragment, nucleic acid, or vector encompassed by the present invention in admixture with a suitable carrier, e.g., a pharmaceutically acceptable agent. Typically, anti-CD39 antibodies, antibody fragments, nucleic acids, or vectors encompassed by the present invention are sufficiently purified for administration to an animal before formulation in a pharmaceutical composition.

Pharmaceutically acceptable agents for use in the present pharmaceutical compositions include carriers, excipients, diluents, antioxidants, preservatives, coloring, flavoring and diluting agents, emulsifying agents, suspending agents, solvents, fillers, bulking agents, buffers, delivery vehicles, tonicity agents, cosolvents, wetting agents, complexing agents, buffering agents, antimicrobials, and surfactants.

Neutral buffered saline or saline mixed with serum albumin are exemplary appropriate carriers. The pharmaceutical compositions can include antioxidants such as ascorbic acid; low molecular weight polypeptides; proteins, such as serum albumin, gelatin, or immunoglobulins; hydrophilic polymers such as polyvinylpyrrolidone; amino acids such as glycine, glutamine, asparagine, arginine or lysine; monosaccharides, disaccharides, and other carbohydrates including glucose, mannose, or dextrins; chelating agents such as EDTA; sugar alcohols such as mannitol or sorbitol; salt-forming counterions such as sodium; and/or nonionic surfactants such as Tween, pluronics, or polyethylene glycol (PEG). Also by way of example, suitable tonicity enhancing agents include alkali metal halides (preferably sodium or potassium chloride), mannitol, sorbitol, and the like. Suitable preservatives include benzalkonium chloride, thimerosal, phenethyl alcohol, methylparaben, propylparaben, chlorhexidine, sorbic acid and the like. Hydrogen peroxide also can be used as preservative. Suitable cosolvents include glycerin, propylene glycol, and PEG. Suitable complexing agents include caffeine, polyvinylpyrrolidone, beta-cyclodextrin or hydroxy-propyl-beta-cyclodextrin. Suitable surfactants or wetting agents include sorbitan esters, polysorbates such as polysorbate 80, tromethamine, lecithin, cholesterol, tyloxapal, and the like. The buffers can be conventional buffers such as acetate, borate, citrate, phosphate, bicarbonate, or Tris-HCl. Acetate buffer may be about pH 4-5.5, and Tris buffer can be about pH 7-8.5. Additional pharmaceutical agents are set forth in Remington's Pharmaceutical Sciences, 18th Edition, A. R. Gennaro, ed., Mack Publishing Company, 1990.

The composition can be in liquid form or in a lyophilized or freeze-dried form and may include one or more lyoprotectants, excipients, surfactants, high molecular weight structural additives and/or bulking agents (see for example U.S. Pat. Nos. 6,685,940, 6,566,329, and 6,372,716). In one embodiment, a lyoprotectant is included, which is a non-reducing sugar such as sucrose, lactose or trehalose. The amount of lyoprotectant generally included is such that, upon reconstitution, the resulting formulation will be isotonic, although hypertonic or slightly hypotonic formulations also may be suitable. In addition, the amount of lyoprotectant should be sufficient to prevent an unacceptable amount of degradation and/or aggregation of the protein upon lyophilization.

Exemplary lyoprotectant concentrations for sugars (e.g., sucrose, lactose, trehalose) in the pre-lyophilized formulation are from about 10 mM to about 400 mM. In another embodiment, a surfactant is included, such as for example, nonionic surfactants and ionic surfactants such as polysorbates (e.g. polysorbate 20, polysorbate 80); poloxamers (e.g. poloxamer 188); poly (ethylene glycol) phenyl ethers (e.g. Triton); sodium dodecyl sulfate (SDS); sodium laurel sulfate; sodium octyl glycoside; lauryl-, myristyl-, linoleyl-, or stearyl-sulfobetaine; lauryl-, myristyl-, linoleyl- or stearyl-sarcosine; linoleyl-, myristyl-, or cetyl-betaine; lauroami-dopropyl-, cocamidopropyl-, Hnoleamidopropyl-, myristamidopropyl-, palmidopropyl-, or isostearamidopropyl-betaine (e.g. lauroamidopropyl); myristamidopropyl-, palmidopropyl-, or isostearamidopropyl-dimethylamine; sodium methyl cocoyl-, or disodium methyl ofeyl-taurate; and the MONAQUAT™. series (Mona Industries, Inc., Paterson, NJ.), polyethyl glycol, polypropyl glycol, and copolymers of ethylene and propylene glycol (e.g. Pluronics, PF68 etc.). Exemplary amounts of surfactant that may be present in the pre-lyophilized formulation are from about 0.001-0.5%. High molecular weight structural additives (e.g. fillers, binders) may include for example, acacia, albumin, alginic acid, calcium phosphate (dibasic), cellulose, carboxymethylcellulose, carboxymethylcellulose sodium, hydroxyethylcellulose, hydroxypropylcellulose, hydroxypropylmethylcellulose, microcrystalline cellulose, dextran, dextrin, dextrates, sucrose, tylose, pregelatinized starch, calcium sulfate, amylose, glycine, bentonite, maltose, sorbitol, ethylcellulose, disodium hydrogen phosphate, disodium phosphate, disodium pyrosulfite, polyvinyl alcohol, gelatin, glucose, guar gum, liquid glucose, compressible sugar, magnesium aluminum silicate, maltodextrin, polyethylene oxide, polymethacrylates, povidone, sodium alginate, tragacanth microcrystalline cellulose, starch, and zein. Exemplary concentrations of high molecular weight structural additives are from 0.1% to 10% by weight. In other embodiments, a bulking agent (e.g., mannitol, glycine) may be included.

Compositions can be suitable for parenteral administration. Exemplary compositions are suitable for injection or infusion into an animal by any route available to the skilled worker, such as intraarticular, subcutaneous, intravenous, intramuscular, intraperitoneal, intracerebral (intraparenchymal), intracerebroventricular, intramuscular, intraocular, intraarterial, or intralesional routes. A parenteral formulation typically will be a sterile, pyrogen-free, isotonic aqueous solution, optionally containing pharmaceutically acceptable preservatives.

Examples of non-aqueous solvents are propylene glycol, polyethylene glycol, vegetable oils such as olive oil, and injectable organic esters such as ethyl oleate. Aqueous carriers include water, alcoholic/aqueous solutions, emulsions or suspensions, including saline and buffered media. Parenteral vehicles include sodium chloride solution, Ringers' dextrose, dextrose and sodium chloride, lactated Ringer's, or fixed oils. Intravenous vehicles include fluid and nutrient replem'shers, electrolyte replenishers, such as those based on Ringer's dextrose, and the like. Preservatives and other additives may also be present, such as, for example, anti-microbials, anti-oxidants, chelating agents, inert gases and the like. See generally, Remington's Pharmaceutical Science, 16th Ed., Mack Eds., 1980, which is incorporated herein by reference.

Pharmaceutical compositions described herein can be formulated for controlled or sustained delivery in a manner that provides local concentration of the product (e.g., bolus, depot effect) and/or increased stability or half-life in a particular local environment. The compositions can include the formulation of anti-CD39 antibodies, antibody fragments, nucleic acids, or vectors encompassed by the present invention with particulate preparations of polymeric compounds such as polylactic acid, polyglycolic acid, etc., as well as agents such as a biodegradable matrix, injectable microspheres, microcapsular particles, microcapsules, bioerodible particles beads, liposomes, and implantable delivery devices that provide for the controlled or sustained release of the active agent which then can be delivered as a depot injection. Techniques for formulating such sustained- or controlled-delivery means are known and a variety of polymers have been developed and used for the controlled release and delivery of drugs. Such polymers are typically biodegradable and biocompatible. Polymer hydrogels, including those formed by complexation of enantiomeric polymer or polypeptide segments, and hydrogels with temperature or pH sensitive properties, may be desirable for providing drug depot effect because of the mild and aqueous conditions involved in trapping bioactive protein agents (e.g., antibodies). See, for example, the description of controlled release porous polymeric microparticles for the delivery of pharmaceutical compositions in PCT Application Publication WO 93/15722.

Suitable materials for this purpose include polylactides (see, e.g., U.S. Pat. No. 3,773,919), polymers of poly-(a-hydroxycarboxylic acids), such as poly-D-(-)-3-hydroxybutyric acid (EP 133,988A), copolymers of L-glutamic acid and gamma ethyl-L-glutamate (Sidman et al., Biopolymers, 22: 547-556 (1983)), poly (2-hydroxyethyl-methacrylate) (Langer et al., J. Biomed. Mater. Res., 15: 167-277 (1981), and Langer, Chem. Tech., 12: 98-105 (1982)), ethylene vinyl acetate, or poly-D(~)~3-hydroxybutyric acid. Other biodegradable polymers include poly(lactones), poly(acetals), poly(orthoesters), and poly(orthocarbonates). Sustained-release compositions also may include liposomes, which can be prepared by any of several methods known in the art (see, e.g., Eppstein et al, Proc. Natl. Acad. Sci. USA, 82: 3688-92 (1985)). The carrier itself, or its degradation products, should be nontoxic in the target tissue and should not further aggravate the condition. This can be determined by routine screening in animal models of the target disorder or, if such models are unavailable, in normal animals. [00196] Microencapsulation of recombinant proteins for sustained release has been performed successfully with human growth hormone (rhGH), interferon-(rhIFN—), interleukin-2, and MNrgpl20. Johnson et al., Nat. Med., 2:795-799 (1996); Yasuda, Biomed. Ther., 27:1221-1223 (1993); Hora et al., Bio/Technologv. 8:755-758 (1990); Cleland, "Design and Production of Single Immunization Vaccines Using Polylactide Polyglycolide Microsphere Systems," in Vaccine Design: The Subunit and Adjuvant Approach, Powell and Newman, eds, (Plenum Press: New York, 1995), pp. 439-462; WO 97/03692, WO 96/40072, WO 96/07399; and U.S. Pat. No. 5,654,010. The sustained-release formulations of these proteins were developed using poly-lactic-coglycolic acid (PLGA) polymer due to its biocompatibility and wide range of biodegradable properties. The degradation products of PLGA, lactic and glycolic acids can be cleared quickly within the human body. Moreover, the degradability of this polymer can be depending on its molecular weight and composition. Lewis, "Controlled release of bioactive agents from lactide/glycolide polymer," in: M. Chasin and R. Langer (Eds.), Biodegradable Polymers as Drug Delivery Systems (Marcel Dekker: New York, 1990), pp. 1-41. Additional examples of sustained release compositions include, for example, EP 58,48 IA, U.S. Pat. No. 3,887,699, EP 158,277A, Canadian Patent No. 1176565, U. Sidman et al., Biopolymers 22, 547 [1983], R. Langer et al., Chem. Tech. 12, 98 [1982], Sinha et al., J. Control. Release 90, 261 [2003], Zhu et al., Nat. Biotechnol. 18, 24 [2000], and Dai et al., Colloids Surf B Biointerfaces 41, 117 [2005].

Bioadhesive polymers are also contemplated for use in or with compositions encompassed by the present invention. Bioadhesives are synthetic and naturally occurring materials able to adhere to biological substrates for extended time periods. For example, Carbopol and polycarbophil are both synthetic cross-linked derivatives of poly (acrylic acid). Bioadhesive delivery systems based on naturally occurring substances include for example hyaluronic acid, also known as hyaluronan. Hyaluronic acid is a naturally occurring mucopolysaccharide consisting of residues of D-glucuronic and N-acetyl-D-glucosamine. Hyaluronic acid is found in the extracellular tissue matrix of vertebrates, including in connective tissues, as well as in synovial fluid and in the vitreous and aqueous humour of the eye. Esterified derivatives of hyaluronic acid have been used to produce microspheres for use in delivery that are biocompatible and biodegrable (see for example, Cortivo et al., Biomaterials (1991) 12:727-730; European Publication No. 517,565; International Publication No. WO 96/29998; Ilium et al., J. Controlled Rel. (1994) 29:133-141). Exemplary hyaluronic acid containing compositions encompassed by the present invention comprise a hyaluronic acid ester polymer in an amount of approximately 0.1% to about 40% (w/w) of an IL-1/3 binding antibody or fragment to hyaluronic acid polymer.

Both biodegradable and non-biodegradable polymeric matrices can be used to deliver compositions encompassed by the present invention, and such polymeric matrices may comprise natural or synthetic polymers. Biodegradable matrices are preferred. The period of time over which release occurs is based on selection of the polymer. Typically, release over a period ranging from between a few hours and three to twelve months is most desirable. Exemplary synthetic polymers which can be used to form the biodegradable delivery system include: polymers of lactic acid and glycolic acid, polyamides, polycarbonates, polyalkylenes, polyalkylene glycols, polyalkylene oxides, polyalkylene terepthalates, polyvinyl alcohols, polyvinyl ethers, polyvinyl esters, poly-vinyl halides, polyvinylpyrrolidone, polyglycolides, polysiloxanes, polyanhydrides, polyurethanes and co-polymers thereof, poly(butic acid), poly(valeric acid), alkyl cellulose, hydroxyalkyl celluloses, cellulose ethers, cellulose esters, nitro celluloses, polymers of acrylic and methacrylic esters, methyl cellulose, ethyl cellulose, hydroxypropyl cellulose, hydroxy-propyl methyl cellulose, hydroxybutyl methyl cellulose, cellulose acetate, cellulose propionate, cellulose acetate butyrate, cellulose acetate phthalate, carboxylethyl cellulose, cellulose triacetate, cellulose sulphate sodium salt, poly(methyl methacrylate), poly (ethyl methacrylate), poly(butylmethacrylate), poly(isobutyl methacrylate), poly(hexylmethacrylate), poly(isodecyl methacrylate), poly(lauryl methacrylate), poly(phenyl methacrylate), poly(methyl acrylate), poly(isopropyl acrylate), poly(isobutyl acrylate), poly(octadecyl acrylate), polyethylene, polypropylene, poly(ethylene glycol), polyethylene oxide), polyethylene terephthalate), poly(vinyl alcohols), polyvinyl acetate, poly vinyl chloride, polystyrene and polyvinylpyrrolidone. Exemplary natural polymers include alginate and other polysaccharides including dextran and cellulose, collagen, chemical derivatives thereof (substitutions, additions of chemical groups, for example, alkyl, alkylene, hydroxylations, oxidations, and other modifications routinely made by those skilled in the art), albumin and other hydrophilic proteins, zein and other prolamines and hydrophobic proteins, copolymers and mixtures thereof. In general, these materials degrade either by enzymatic hydrolysis or exposure to water in vivo, by surface or bulk erosion. The polymer optionally is in the form of a hydrogel (see for example WO 04/009664, WO 05/087201, Sawhney, et al., Macromolecules, 1993, 26, 581-587,) that can absorb up to about 90% of its weight in water and further, optionally is cross-linked with multi-valent ions or other polymers. Delivery systems also include non-polymer systems that are lipids including sterols such as cholesterol, cholesterol esters and fatty acids or neutral fats such as mono-di- and triglycerides; hydrogel release systems; silastic systems; peptide based systems; wax coatings; compressed tablets using conventional binders and excipients; partially fused implants; and the like. Specific examples include, but are not limited to: (a) erosional systems in which the product is contained in a form within a matrix such as those described in U.S. Pat. Nos. 4,452,775, 4,675,189 and 5,736,152 and (b) diffusional systems in which a product permeates at a controlled rate from a polymer such as described in U.S. Pat. Nos. 3,854,480, 5,133,974 and 5,407,686. Liposomes containing the product may be prepared by methods known methods, such as for example (DE 3,218,121; Epstein et al., Proc. Natl. Acad. Sci. USA, 82: 3688-3692 (1985); Hwang et al., Proc. Natl. Acad. Sci. USA, 77: 4030-4034 (1980); EP 52,322; EP 36,676; EP 88,046; EP 143,949; EP 142,641; Japanese patent application 83-118008; U.S. Pat. Nos. 4,485,045 and 4,544,545; and EP 102,324).

Alternatively or additionally, the compositions can be administered locally via implantation into the affected area of a membrane, sponge, or other appropriate material on to which an anti-CD39 antibody, antibody fragment, nucleic acid, or vector encompassed by the present invention has been absorbed or encapsulated. Where an implantation device is used, the device can be implanted into any suitable tissue or organ, and delivery of an anti-CD39 antibody, antibody fragment, nucleic acid, or vector encompassed by the present invention can be directly through the device via bolus, or via continuous administration, or via catheter using continuous infusion.

A pharmaceutical composition comprising an anti-CD39 antibody, antibody fragment, nucleic acid, or vector encompassed by the present invention can be formulated for inhalation, such as for example, as a dry powder. Inhalation solutions also can be formulated in a liquefied propellant for aerosol delivery. In yet another formulation, solutions may be nebulized. Additional pharmaceutical composition for pulmonary administration include, those described, for example, in PCT Application Publication WO 94/20069, which discloses pulmonary delivery of chemically modified proteins. For pulmonary delivery, the particle size should be suitable for delivery to the distal lung. For example, the particle size can be from 1 μm to 5 μm; however, larger particles may be used, for example, if each particle is fairly porous.

Certain formulations containing anti-CD39 antibody, antibody fragments, nucleic acids, or vectors encompassed by the present invention can be administered orally. Formulations administered in this fashion can be formulated with or without those carriers customarily used in the compounding of solid dosage forms such as tablets and capsules. For example, a capsule can be designed to release the active portion of the formulation at the point in the gastrointestinal tract when bioavailability is maximized and pre-systemic degradation is minimized. Additional agents can be included to facilitate absorption of a selective binding agent. Diluents, flavorings, low melting point waxes, vegetable oils, lubricants, suspending agents, tablet disintegrating agents, and binders also can be employed.

Another preparation can involve an effective quantity of an anti-CD39 antibody, antibody fragment, nucleic acid, or vector encompassed by the present invention in a mixture with non-toxic excipients which are suitable for the manufacture of tablets. By dissolving the tablets in sterile water, or another appropriate vehicle, solutions can be prepared in unit dose form. Suitable excipients include, but are not limited to, inert diluents, such as calcium carbonate, sodium carbonate or bicarbonate, lactose, or calcium phosphate; or binding agents, such as starch, gelatin, or acacia; or lubricating agents such as magnesium stearate, stearic acid, or talc.

IX. Exemplary Methods

Materials and Methods

Reagents

All chemical reagents were purchased from Sigma-Aldrich (St. Louis, MO), cell culture media from Life Technologies (Carlsbad, CA), cell culture consumables from CELLTREAT® Scientific Products (Shirley, MA), and commercial antibodies from Biolegend (San Diego, CA), unless otherwise stated. Secondary antibodies including Alexa Fluor® 488-conjugated AffiniPure Donkey anti-human IgG (Fc specific) (#709-545-098) and Alexa Fluor® 488-conjugated anti-rabbit IgG (H+L) (#711-545-152) were obtained from Jackson ImmunoResearch (West Grove, PA), CellTiter-Glo® (#G7571) and Bio-Glo™ (#G7941) from Promega (Madison, WI). 2-Deoxy-2-fluoro-L-fucose was purchased from BIOSYNTH Carbosynth (#MD06089) and Normal Human Serum (#A113) from Quidel Corporation (San Diego, CA). The anti-human CD39 reference antibody (hCD39 Ref) was produced by transient transfection using ExpiCHO™ Expression System Kit (#A29133; Thermo Fisher Scientific, Waltham, MA) and antibody sequences were obtained as published (Perrot et al., *Cell Reports* 27:2411-2425 (2019)). Both hCD39 Ref antibody and our fully human anti-CD39 monoclonal antibody (Ig39-21) contain the same human IgG1 Fc fraction.

The hCD39 Ref antibody shares the antigen binding sites with an antibody in the art. However, that prior art antibody, unlike the Ref antibody used in the current examples, was generated with an Fc portion specifically designed to have an abrogated ADCC function (i.e., was taught to have been generated specifically to bind CD39 and inhibit NTPase activity without invoking CD39 dependent ADCC cell killing).

Cell culture Human CD39 stably transfected Chinese Hamster Ovary cells (CHO-hCD39) were maintained in F12K supplemented with 10% fetal bovine serum (FBS), 1% penicillin-streptomycin. Human B lymphoblastoid cells (HCC1739BL, ATCC #CRL-2334), Raji cells (Raji-hCD39neg), and human CD39 stably transfected Raji cells (Raji-hCD39hi) were cultured in RPMI 1640 supplemented with 10% FBS, 1% penicillin-streptomycin. Human melanoma cells (SK-MEL-28, ATCC #HTB-72) were grown in EMEM plus 10% FBS, 1% penicillin-streptomycin. Human natural killer cells (NK-92-CD16 V/V) (ATCC #PTA-6967) were cultured in MEM-Alpha medium with IL-2 (10 ng/ml). Human umbilical vein endothelial cells (HUVEC), Single Donor, EGM™-2 (Lonza #C2517A, Basel, Switzerland) were grown in EGM™ Endothelial Cell Growth Medium BulletKit (Lonza #CC-3124). All cell lines were maintained in culture flasks at 37° C. in a 5% $CO_2$ atmosphere at 100% humidity, except for Jurkat cells/NFAT-luc+FcγRIIIA (Promega Cat #: G7011), which were thawed in water bath at 37° C. prior to use for experiments.

Production and Afucosylation of Our Fully Human Anti-CD39 Antibodies

Fully human anti-CD39 antibody Ig39-21 was produced by transient transfection using FreeStyle™ 293-F cells (Thermo Fisher Scientific #R79007) either in the absence (Ig39-21 WT) or presence of fucosylation inhibitor 2-Deoxy-2-fluoro-L-fucose (Ig39-21 AF). Optimized Ig39-21 (identified as clone NP501-BK) was produced by stably transfected CHO cells.

Monoclonal Antibody Affinity to Cell Lines Expressing Human CD39

CHO-hCD39 cells or HCC1739BL cells (endogenously expressing high level of hCD39) ($1\times10^5$ cells) were incubated with serially diluted monoclonal antibodies for 30 minutes at 4° C. After two washes with cell staining buffer, cells were incubated with anti-human IgG (Fc specific) Alexa Fluor® 488 (1:5000) for 30 minutes at 4° C. Cells were then washed twice with cell staining buffer and analyzed by Cytek™ Aurora flow cytometry (Cytek Biosciences, Fremont, CA). Alexa Fluor® 488 median fluorescence intensity (MFI) was detected and data was analyzed by FCS Express 7 software (De Novo Software, Los Angeles, CA).

Inhibition of Human CD39 Enzyme Activity on Intact Cells

CHO-hCD39 cells ($8\times10^4$ cells/well) were trypsinized, counted and plated in a 96-well plate-U bottom, followed by two washes with Modified Ringer Buffer (RB) (120 mM NaCl, 5 mM KCl, 2.5 mM CaCl2, 1.2 mM MgSO4, 25 mM NaHCO$_3$, 10 mM dextrose, 80 mM Tris-HCl, pH 7.4) and incubation with monoclonal antibodies for 30 minutes at 37° C. CHO-hCD39 cells were then exposed to ATP (250 µM) for 15 minutes at room temperature. Supernatants were finally collected to a 96-well opaque-walled multiwell plate (BRANDplates #781968) and ATP levels were detected by luminescence using CellTiter-Glo®. Luminescence values were read on a Synergy™ Neo2 Multi-Mode Reader (BioTeK Instruments Inc., Winooski, VT) that are directly correlated to ATP levels. Cells with no antibody (Cells+ATP) or ATP alone in the absence of cells served as controls. Results were expressed as % of enzyme activity inhibition calculated by: [(Cells+ATP+Ab)−(Cells+ATP)/(ATP)−(Cells+ATP)]×100. All steps were performed in RB.

NK Cell-Mediated Antibody-Dependent Cellular Cytotoxicity (NK Cytotoxicity Assay)

Target cells (expressing hCD39) were pre-labeled with CFSE (0.025 µM) for 5 minutes at 37° C. in water bath. After two washes with 1×PBS, cells were incubated in MEM-Alpha medium (Thermo Fisher Scientific #32561037) containing 4% ultra-low IgG FBS (Thermo Fisher Scientific #A3381901) with or without monoclonal antibodies for 30 minutes at 37° C. in 5% CO$_2$. Target cells were then co-cultured with NK-92-CD16 V/V effector cells in different proportions for 6 hours at 37° C. in 5% CO$_2$. After incubation, cells were stained with Propidium Iodide (P/I) (200 ng/mL) for 10 minutes at room temperature and target cell death was analyzed by Cytek™ Aurora flow cytometry (Cytek Biosciences). Results were expressed as % of CFSE$^+$ P/I$^+$ cells or % of cytotoxicity.

NFAT Luciferase Reporter Jurkat System (ADCC Assay)

Attached target cells (SK-MEL-28 melanoma cells endogenously expressing hCD39 at an intermediate level or HUVEC cells endogenously expressing low level of hCD39) were seeded in a 96-well plate ($8\times10^3$ cells/100 µl/well) (BRANDplates #781965) and grown for 24 hours, while suspension target cells (HCC1739BL) were seeded right before the experiment ($5\times10^5$ cells/ml). Cells were then washed twice with ADCC assay buffer (DMEM or RPMI 1640 medium supplemented with 4% ultra-low IgG serum) and incubated with serially diluted monoclonal antibodies for 30 minutes at 37° C. Effector cells (Jurkat cells/NFAT-luc+FcγRIIIA) ($3\times10^6$ cells/ml) were then added to the wells and the mixture (E:T=1:6) was incubated for 6 hours at 37° C. Bio-Glo™ was finally added into wells and luminescence values were read at 5, 15, and 30 minutes using a Synergy™ Neo2 Multi-Mode Reader (BioTeK Instruments Inc.). ADCC activity was indicated by an increase of luciferase activity over background.

Complement-Dependent Cytotoxicity (CDC) Assay

Target Raji cells overexpressing human CD39 cells (Raji-CD39hi) were washed twice with serum-free RPMI 1640 medium, resuspended in CDC assay buffer (RPMI 1640 medium with 4% ultra-low IgG FBS) at the final concentration of $2\times10^6$/ml and rested on ice for 2-3 hours. Cells were then incubated with serially diluted monoclonal antibodies for 30 minutes at 37° C. in 5% CO$_2$. Normal Human Serum (NHS 10%) were then added to the cells and incubated for 2 hours at 37° C. in 5% CO$_2$. After incubation, cells were stained with Propidium Iodide (P/I) (200 ng/mL) for 10 minutes at room temperature and target cell death was analyzed by Cytek™ Aurora flow cytometry (Cytek Biosciences). Results were expressed as % of cytotoxicity (P/I$^+$ cells).

Epitope Competition Assay

Figure 27:
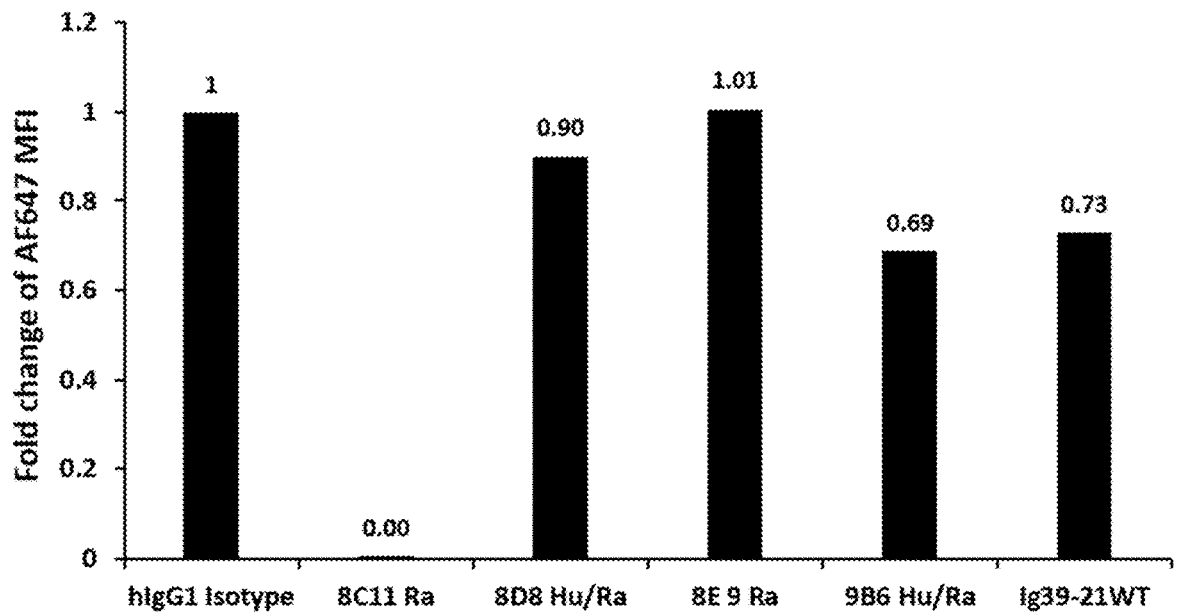
FIG. 27. Epitope competition matrix-I against anti-hCD39 reference antibody (hCD39 Ref) on HCC1739BL cells. HCC1739BL cells were incubated with 10 µg/ml of unconjugated human IgG1 isotype Ultra-LEAF antibody or hCD39 Ref antibody, at 4° C. for 30 minutes. Cells were then exposed to Alexa Fluor® 647-conjugated antibodies (8C11, 8D8, 8E9, 9B6, and Ig39-21 WT) or PE-conjugated Clone A1 for 30 minutes at 4° C., followed by two washes and flow cytometry analysis. Fold change in AF647 or PE MFI detection in relation to Isotype control was calculated (No epitope overlap=1). Ra: rabbit antibody; Hu/Ra: Human/Rabbit chimeric antibody.
Figure 27:
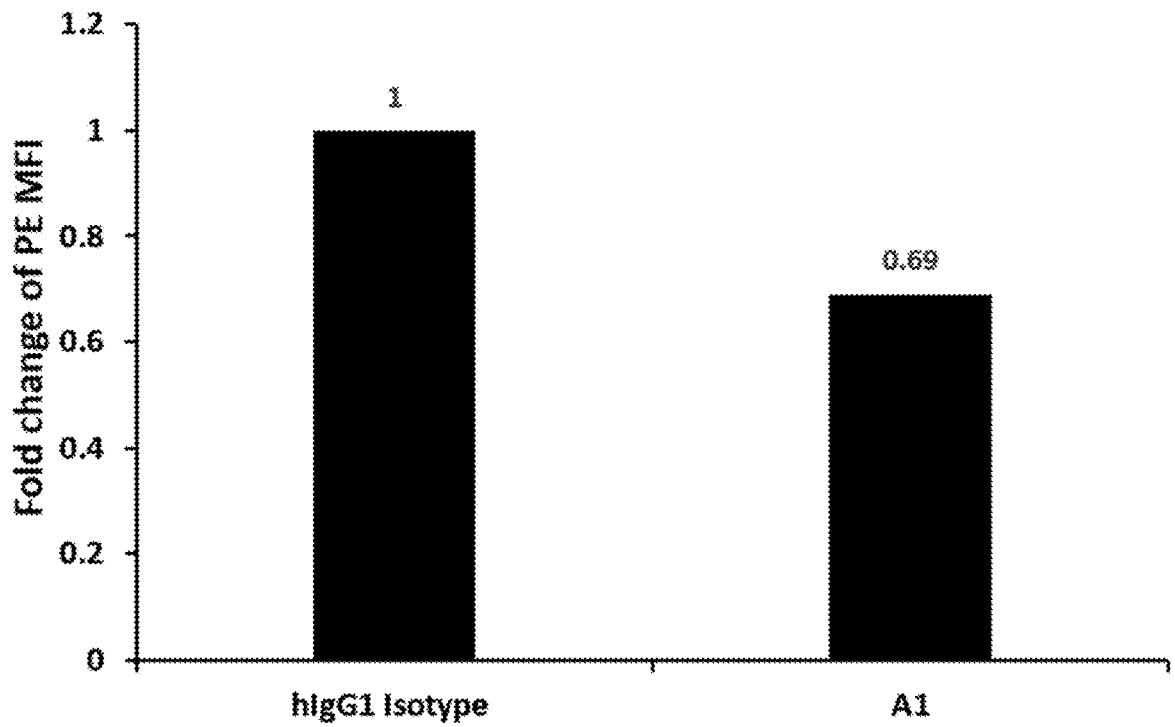

Epitope competition matrix-I (FIG. 27): anti-human CD39 monoclonal antibodies (clones 8C11, 8D8, 8E9, 9B6 and Ig39-21 WT) were conjugated with Alexa Fluor® 647 using Antibody Labeling Kit according to the manufacturer's instructions (Thermo Fisher Scientific #A20186). Mouse anti-human CD39 clone A1-PE was purchased from Biolegend (#328208). Unconjugated human IgG1 isotype Ultra-LEAF antibody (Biolegend #403502) or anti-human CD39 monoclonal antibodies (10 µg/mL) were incubated with HCC1739BL cells ($1\times10^5$ cells) for 30 minutes at 4° C. Next, Alexa Fluor® 647-conjugated (1 µg/mL) or PE-conjugated (0.25 µg/mL) anti-human CD39 monoclonal antibodies were added to each well and incubated for 30 minutes at 4° C. Cells were then washed twice with cell staining buffer and analyzed by Cytek™ Aurora flow cytometry. Alexa Fluor® 647 (AF647) or PE median fluorescence intensity (MFI) was detected and data was analyzed by FCS Express 7 software (De Novo Software). Fold change in AF647 or PE MFI detection in relation to isotype control was calculated (No epitope overlap=1).

Figure 28:
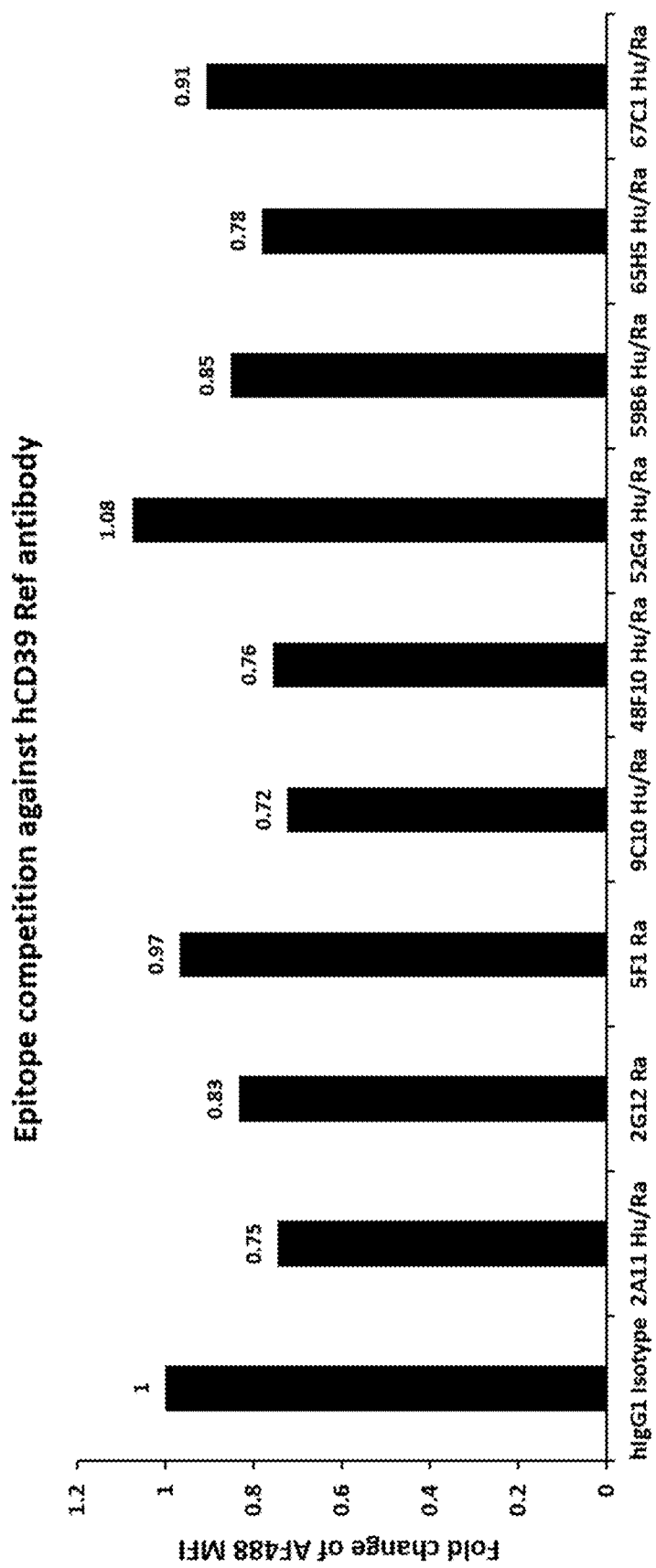
FIG. 28. Epitope competition matrix-II against anti-hCD39 reference antibody (hCD39 Ref) on HCC1739BL cells. HCC1739BL cells were incubated with 10 µg/ml of unconjugated human IgG1 isotype Ultra-LEAF antibody or hCD39 Ref antibody, at 4° C. for 30 minutes. Cells were then exposed to unconjugated rabbit or Human/Rabbit chimeric antibodies (2A11, 2G12, 5F1, 9C10, 48F10, 52G4, 59B6, 65H5, and 67C1) for 30 minutes at 4° C., washed twice and stained with secondary antibody (anti-rabbit IgG (H+L), Alexa Fluor® 488) for 30 minutes at 4° C. Lastly, cells were washed and analyzed by flow cytometry. Fold change in AF488 MFI detection in relation to Isotype control was calculated (No epitope overlap=1).

Epitope competition matrix-II (FIG. 28): unconjugated human IgG1 isotype control or hCD39 Ref monoclonal antibody (10 µg/mL) were incubated with HCC1739BL cells ($1\times10^5$ cells) for 30 minutes at 4° C. Next, rabbit or human/rabbit chimeric clones (1 µg/mL) were added to each well and incubated for 30 minutes at 4° C. Cells were then washed twice with cell staining buffer and stained with Alexa Fluor® 488-conjugated anti-rabbit IgG (H+L) (1:5000) for 30 minutes at 4° C. Cells were washed twice again with cell staining buffer and analyzed by Cytek™ Aurora flow cytometry. Alexa Fluor® 488 (AF488) MFI was detected, and data was analyzed by FCS Express 7 software (De Novo Software). Fold change in AF488 MFI detection in relation to isotype control was calculated (No epitope overlap=1).

Conformational Epitope Mapping

This was done using a proprietary CLIPS technology by Pepscan (Lelystad, The Netherlands). Results of epitope mapping are visualized using a homology model created by Swiss-model using template PDB entry 3ZX3.pdb.

Stable Immune Complex Assay

HCC1739BL cells ($5\times10^5$ cells/mL) were incubated with anti-human CD39 antibodies (2 µg/ml) or left untreated for 24 hours at 37° C. in 5% CO$_2$. The following day, untreated cells were exposed to the same panel of monoclonal antibodies (2 µg/ml) but for 20 minutes at 4° C. to obtain the basal level of CD39 expression. Cells were then washed twice with cell staining buffer and stained with anti-human IgG (Fc specific) Alexa Fluor® 488 (1:2000) for 30 minutes at 4° C., followed by two additional washes and fixation with paraformaldehyde (PFA, 2%) for 10 minutes at room temperature. Lastly, cells were washed twice and analyzed by Cytek™ Aurora flow cytometry (Cytek Biosciences). Alexa Fluor® 488 (AF488) MFI was detected, and data were analyzed by FCS Express 7 software (De Novo Software). The percentage of human CD39 loss on cell membrane at 24 hours was calculated as: [(20 min MFI−24 h MFI/20 min MFI)]X100.

Purification of Lymphocytes from Tumors and Spleen

Spleen and tumors from tumor-bearing mice were excised at the time of study termination. Single cell suspension from spleen was obtained by mechanically meshing the spleen through a 70 µM cell strainer, followed by red cell lysis (#555899; BD Biosciences, San Jose, CA). Tumor-infiltrating lymphocytes were obtained by digesting tumor using Mouse Tumor Dissociation Kit (#130-096-730) on the gentleMACS™ Dissociator (#130-096-427) following the manufacturer's instructions (Miltenyi Biotec, Bergisch Gladbach, Germany). Immunophenotyping was performed using Cytek™ Aurora flow cytometry. Detection antibodies were listed in Table 1.

Animal Studies

Immunocompetent syngeneic mouse model: C57BL6 hCD39 KI mice wherein extracellular domain of mouse CD39 was replaced with a human counterpart were licensed from Beth Israel Deaconess Medical Center. Six to 8-week-old female mice were used for tumor inoculation. Syngeneic murine MC38 colorectal cancer cells were maintained in RPMI 1640 medium supplemented with 10% FBS, penicillin (100 units/mL) and streptomycin (100 µg/mL). $1 \times 10^5$ of MC38 cells were harvested by trypsinization and resuspended with 150 µl of RPMI 1640 supplemented with 10% FBS for injection. MC38 cells were injected subcutaneously into the right flank of mice. Mice were then randomized into three groups (n=5 per group). At days 8, 11, 14 and 17, tumor-bearing mice received 5 mg/kg of human IgG1 isotype control antibody (KLH-hIgG1), or fully human anti-CD39 monoclonal antibodies (Ig39-21 AF or NP501-BK) via i.p.

Xenograft tumor model: homozygous athymic nude mice (#002019; NU/J) were purchased from The Jackson Laboratory (Bar Harbor, ME). Five-week-old female mice were used for tumor inoculation. SK-MEL-28 xenografts were prepared by s.c. injecting $4 \times 10^6$ of SK-MEL-28 cells suspended in 200 µl of EMEM mixed 1:1 with BD Matrigel Matrix High Concentration (BD Biosciences #354262) into the right flank of mice. When tumors reached an average volume of approximately 500 mm$^3$ (considered as day 0 of treatment), mice were randomized into two groups (n=6-7 per group), and treated with two doses of 300 µl of saline or 10 mg/kg of NP501-BK on days 0 and 3 via i.p.

Tumor length (L) and width (W) were measured using a digital caliper twice weekly. Tumor volume (mm$^3$) was determined as L*W*W*0.52.

Statistical Analyses

Statistical analyses were performed using GraphPad Prism 8 (GraphPad Software, San Diego, CA).

TABLE 1

Detection antibodies

| Name | Vendor/Cat# | Concentration/Dilution |
| --- | --- | --- |
| AffiniPure Donkey Anti-human IgG (Fc specific) Alexa Fluor ® 488 | Jackson ImmunoResearch #709-545-098 | 1:2000-1:5000 |
| AffiniPure Donkey Anti-rabbit IgG (H + L) Alexa Fluor ® 488 | Jackson ImmunoResearch #711-545-152 | 1:5000 |
| Mouse anti-human CD39 Clone A1-PE | Biolegend #328208 | 0.25 µg/mL |
| Zombie NIR | Biolegend #423106 | 1:20,000 |
| CD11b-AF700 | Biolegend #101222 | 1:400 |
| CD45-BV510 | Biolegend #103138 | 1:400 |
| F4/80-PE Cy7 | Biolegend #123114 | 1:400 |
| CD3-PE Cy5 | BD Biosciences #555276 | 1:200 |
| Gr-1-BV480 | BD Biosciences #746614 | 1:800 |
| Rabbit Anti-human CD39 Clone 8C11 Alexa Fluor ® 647 | Purinomia Biotech Inc. | 1-2 µg/mL |
| Human/Rabbit Anti-human CD39 Clone 8D8 Alexa Fluor ® 647 | Purinomia Biotech Inc. | 1 µg/mL |
| Rabbit Anti-human CD39 Clone 8E9 Alexa Fluor ® 647 | Purinomia Biotech Inc. | 1 µg/mL |
| Human/Rabbit Anti-human CD39 Clone 9B6 Alexa Fluor ® 647 | Purinomia Biotech Inc. | 1 µg/mL |
| Human Anti-human CD39 Clone Ig39-21 Alexa Fluor ® 647 | Purinomia Biotech Inc. | 1 µg/mL |

INCORPORATION BY REFERENCE

All publications, patents, and patent applications mentioned herein are hereby incorporated by reference in their entirety as if each individual publication, patent or patent application was specifically and individually indicated to be incorporated by reference. In case of conflict, the present application, including any definitions herein, will control.

Also incorporated by reference in their entirety are any polynucleotide and polypeptide sequences which reference an accession number correlating to an entry in a public database, such as those maintained by The Institute for Genomic Research (TIGR) on the World Wide Web and/or the National Center for Biotechnology Information (NCBI) on the World Wide Web.

EQUIVALENTS AND SCOPE

The details of one or more embodiments encompassed by the present invention are set forth in the description above.

Although the preferred materials and methods have been described above, any materials and methods similar or equivalent to those described herein may be used in the practice or testing of embodiments encompassed by the present invention. Other features, objects and advantages related to the present invention are apparent from the description.

Unless defined otherwise, all technical and scientific terms used herein have the same meaning as commonly understood by one of ordinary skill in the art to which this invention belongs. In the case of conflict, the present description provided above will control.

Those skilled in the art will recognize or be able to ascertain using no more than routine experimentation, many equivalents to the specific embodiments encompassed by the present invention described herein. The scope encompassed by the present invention is not intended to be limited to the description provided herein and such equivalents are intended to be encompassed by the appended claims.

The articles "a" and "an" are used herein to refer to one or to more than one (i.e. to at least one) of the grammatical object of the article unless indicated to the contrary or otherwise evident from the context. By way of example, "an element" means one element or more than one element. Claims or descriptions that include "or" between one or more members of a group are considered satisfied if one, more than one, or all of the group members are present in, employed in, or otherwise relevant to a given product or process unless indicated to the contrary or otherwise evident from the context. The present invention includes embodiments in which exactly one member of the group is present in, employed in, or otherwise relevant to a given product or process. The present invention also includes embodiments in which more than one, or the entire group members are present in, employed in, or otherwise relevant to a given product or process.

It is also noted that the term "comprising" is intended to be open and permits but does not require the inclusion of additional elements or steps. When the term "comprising" is used herein, the term "consisting of" is thus also encompassed and disclosed.

Where ranges are given, endpoints are included. Furthermore, it is to be understood that unless otherwise indicated or otherwise evident from the context and understanding of one of ordinary skill in the art, values that are expressed as ranges may assume any specific value or subrange within the stated ranges in different embodiments encompassed by the present invention, to the tenth of the unit of the lower limit of the range, unless the context clearly dictates otherwise.

In addition, it is to be understood that any particular embodiment encompassed by the present invention that falls within the prior art may be explicitly excluded from any one or more of the claims. Since such embodiments are deemed to be known to one of ordinary skill in the art, they may be excluded even if the exclusion is not set forth explicitly herein. Any particular embodiment of the compositions encompassed by the present invention (e.g., any antibiotic, therapeutic or active ingredient; any method of production; any method of use; etc.) may be excluded from any one or more claims, for any reason, whether or not related to the existence of prior art.

It is to be understood that the words which have been used are words of description rather than limitation, and that changes may be made within the purview of the appended claims without departing from the true scope and spirit encompassed by the present invention in its broader aspects.

While the present invention has been described at some length and with some particularity with respect to several described embodiments, it is not intended that it should be limited to any such particulars or embodiments or any particular embodiment, but it is to be construed with references to the appended claims so as to provide the broadest possible interpretation of such claims in view of the prior art and, therefore, to effectively encompass the intended scope encompassed by the present invention.

The invention claimed is:

1. An anti-CD39 antibody, or antigen-binding fragment thereof, comprising
   i) a light chain variable domain comprising complementarity determining region (CDR) L1 having the sequence of SEQ ID NO: 32, CDRL2 having the sequence of SEQ ID NO: 33, and CDRL3 having the sequence of SEQ ID NO: 34; and
   ii) a heavy chain variable domain comprising CDRH1 having the sequence of SEQ ID NO: 29, CDRH2 having the sequence of SEQ ID NO: 30, and CDRH3 having the sequence of SEQ ID NO: 31.

2. The anti-CD39 antibody, or antigen-binding fragment thereof, of claim 1, comprising
   a) a light chain variable domain comprising the sequence of SEQ ID NO: 4; and
   b) a heavy chain variable domain comprising the sequence of SEQ ID NO: 2.

3. The anti-CD39 antibody, or antigen-binding fragment thereof, of claim 2, comprising a) a light chain comprising the sequence of SEQ ID NO: 38; and
b) a heavy chain comprising the sequence of SEQ ID NO: 36.

4. The anti-CD39 antibody, or antigen-binding fragment thereof, of claim 1, further comprising an FcγRIIIa binding moiety that binds FcγRIIIa receptor and confers antibody-dependent cellular cytotoxicity (ADCC) activity against CD39+ cells to the anti-CD39 antibody.

5. The anti-CD39 antibody, or antigen-binding fragment thereof, of claim 4, wherein the FcγRIIIa binding moiety is selected from the group consisting of an Fc domain, an antibody or fragment thereof that binds to FcγRIIIa, and an FcγRIIIa binding peptide.

6. The anti-CD39 antibody, or antigen-binding fragment thereof, of claim 5, comprising an Fc domain of an IgG1 or IgG3 isotype.

7. The anti-CD39 antibody, or antigen-binding fragment thereof, of claim 5, wherein the Fc domain is human.

8. The anti-CD39 antibody, or antigen-binding fragment thereof, of claim 5, wherein the anti-CD39 antibody, or antigen-binding fragment thereof, is hypo-fucosylated or afucosylated.

9. The anti-CD39 antibody, or antigen-binding fragment thereof, of claim 5, wherein the anti-CD39 antibody, or antigen-binding fragment thereof, is human or is humanized.

10. The anti-CD39 antibody, or antigen-binding fragment thereof, of claim 5, wherein the anti-CD39 antibody, or antigen-binding fragment thereof promotes one or more of:
   i) stable immune complex formation when incubated with HCC1739BL cells as characterized by loss of less than 30% of the immune complex after 24 hours, optionally wherein the immune complex formation is detected by fluorescent intensity using a fluorescently labeled secondary antibody;
   ii) complement dependent cytotoxicity (CDC) activity against CD39+ cells;
   iii) antibody-mediated target cytosis of CD39 on CD45+ immune cells;
   iv) antibody-mediated target cytosis of CD39 from tumor vascular endothelium disruption or vasculature network collapse in a tumor;
   v) binding to a CD39 epitope having a sequence selected from the group of CD39 amino acid epitope sequences listed in FIG. 33; and
   vi) binding to CD39 in a manner that is non-competitive or only partially competitive with monoclonal antibody clone A1 binding to CD39.

11. The anti-CD39 antibody, or antigen-binding fragment thereof, of claim 4, comprising an Fc domain of an IgG1 or IgG3 isotype.

12. The anti-CD39 antibody, or antigen-binding fragment thereof, of claim 4, wherein the Fc domain is human.

13. The anti-CD39 antibody, or antigen-binding fragment thereof, of claim 4, wherein the anti-CD39 antibody, or antigen-binding fragment thereof, is hypo-fucosylated or afucosylated.

14. The anti-CD39 antibody, or antigen-binding fragment thereof, of claim 4, wherein the anti-CD39 antibody, or antigen-binding fragment thereof, is human or is humanized.

15. The anti-CD39 antibody, or antigen-binding fragment thereof, of claim 1, comprising an Fc domain of an IgG1 or IgG3 isotype.

16. The anti-CD39 antibody, or antigen-binding fragment thereof, of claim 1, wherein the Fc domain is human.

17. The anti-CD39 antibody, or antigen-binding fragment thereof, of claim 1, wherein the anti-CD39 antibody, or antigen-binding fragment thereof, is hypo-fucosylated or afucosylated.

18. The anti-CD39 antibody, or antigen-binding fragment thereof, of claim 1, wherein the anti-CD39 antibody, or antigen-binding fragment thereof, is human or is humanized.

19. The anti-CD39 antibody, or antigen-binding fragment thereof, of claim 1, wherein the antigen-binding fragment thereof is selected from the group consisting of a Fab, Fab', F(ab')2, Fv or single chain Fv (scFv), disulfide-linked variable fragment (dsFv), single-chain variable $(Fv)_2$ $(sc(Fv)_2)$, sdFv, and diabodies fragments, optionally wherein the antigen-binding fragment thereof is an scFV comprising the sequence of SEQ ID NO: 40.

20. The anti-CD39 antibody, or antigen-binding fragment thereof, of claim 1, wherein the anti-CD39 antibody, or antigen-binding fragment thereof, is conjugated to a binding protein, an enzyme, a drug, a chemotherapeutic agent, a biologic agent, a toxin, a radionuclide, an immunomodulatory agent, a detectable moiety, and a tag.

21. The anti-CD39 antibody, or antigen-binding fragment thereof, of claim 1, wherein the anti-CD39 antibody, or antigen-binding fragment thereof, is a bispecific antibody including at least one additional antigen binding site for a tumor antigen, immune checkpoint, or costimulatory receptor, wherein if the additional antigen binding site is for an immune checkpoint it functions as a checkpoint inhibitor and wherein if the additional antigen binding site is for a costimulatory receptor it functions as a costimulatory agonist.

22. The anti-CD39 antibody, or antigen-binding fragment thereof, of claim 21, wherein the additional binding site binds to one or more of
   i) a checkpoint protein selected from the group consisting of PD-1, PD-L1, CTLA-4/B7-1/B7-2, PD-L2, NKG2A, KIR, LAG-3, TIM-3, CD96, VISTA, TIGIT and Siglec-15;
   ii) a checkpoint protein upregulated on T-cells and associated with T-cell exhaustion;
   iii) an immune costimulatory receptors selected from the group consisting of MHCI molecules, BTLA receptor, OX40, CD27, CD28, CD5, ICAM-1, LFA-1 (CD11a/CD18), ICOS (CD278) and 4-1BB (CD137); or
   iv) CD47, SIRPα, CD24 or Siglec-10.

23. A pharmaceutical preparation comprising a therapeutically effective amount of the anti-CD39 antibody, or antigen-binding fragment thereof, of claim 1, and one or more pharmaceutically acceptable excipients, buffers or solutions.

24. The pharmaceutical preparation of claim 23 for improving anti-tumor T cell immunity and suitable for administration to a subject having a tumor, comprising an effective amount of the anti-CD39 antibody, or antigen-binding fragment thereof, and one or more pharmaceutically acceptable excipients, buffers or solutions, wherein administration of the anti-CD39 antibody to the subject results in a reduction in numbers of intratumoral CD39high cells and enhances T-cell infiltration into the tumor or decreases T-cell exhaustion in the tumor or both.

25. An isolated nucleic acid molecule that encodes an immunoglobulin heavy and/or light chain polypeptide of the anti-CD39 antibody, or antigen-binding fragment thereof, of claim 1.

26. A vector comprising the isolated nucleic acid of claim 25.

27. The vector of claim 26, wherein the vector is an expression vector.

28. A host cell which comprises the isolated nucleic acid of claim 25.

29. The host cell of claim 28, wherein the host cell
   a) expresses the anti-CD39 antibody, or antigen-binding fragment thereof, of claim 1;
   b) comprises anti-CD39 antibody, or antigen-binding fragment thereof, of claim 1;
   and/or
   c) comprises the vector of claim 26.

30. A method of producing at least one anti-CD39 antibody, or antigen-binding fragment thereof, of claim 1, which method comprises the steps of: (i) culturing a transformed host cell which has been transformed by a nucleic acid comprising a sequence encoding at least one anti-CD39 antibody, or antigen-binding fragment thereof, under conditions suitable to allow expression of said anti-CD39 antibody, or antigen-binding fragment thereof; and (ii) recovering the expressed anti-CD39 antibody, or antigen-binding fragment thereof.

* * * * *